(12) United States Patent
Xie et al.

(10) Patent No.: US 12,351,599 B2
(45) Date of Patent: Jul. 8, 2025

(54) ANTIVIRAL APPLICATION OF NUCLEOSIDE ANALOG OR COMBINATION FORMULATION CONTAINING NUCLEOSIDE ANALOG

(71) Applicants: Shanghai Institute of Materia Medica, Chinese Academy of Sciences, Shanghai (CN); Wuhan Institute of Virology, Chinese Academy of Science, Wuhan (CN); Xinjiang Technical Institute of Physics and Chemistry, Chinese Academy of Science, Urumqi (CN); Vigonvita Life Sciences Co., Ltd., Suzhou (CN)

(72) Inventors: Yuanchao Xie, Shanghai (CN); Gengfu Xiao, Wuhan (CN); Yang He, Shanghai (CN); Leike Zhang, Wuhan (CN); Haji Akber Aisa, Xinjiang (CN); Hualiang Jiang, Shanghai (CN); Jingshan Shen, Shanghai (CN)

(73) Assignees: Shanghai Institute of Materia Medica, Chines Academy of Sciences, Shanghai (CN); Wuhan Institute of Virology, Chinese Academy of Science, Hubei (CN); Xinjiang Technical Institute of Physics and Chimestry, Chinese Academy of Sciences, Xinjiang (CN); Vigonvita Life Sciences Co., Ltd., Jiangsu (CN)

( * ) Notice: Subject to any disclaimer, the term of this patent is extended or adjusted under 35 U.S.C. 154(b) by 0 days.

(21) Appl. No.: 18/519,408

(22) Filed: Nov. 27, 2023

(65) Prior Publication Data
US 2024/0140975 A1 May 2, 2024

Related U.S. Application Data

(63) Continuation of application No. 17/996,430, filed as application No. PCT/CN2021/087928 on Apr. 16, 2021, now Pat. No. 11,919,923.

(30) Foreign Application Priority Data

Apr. 20, 2020 (CN) .......................... 202010313870.X
Jun. 19, 2020 (CN) .......................... 202010568329.3
Sep. 27, 2020 (CN) .......................... 202011035065.1

(51) Int. Cl.
*C07H 7/06* (2006.01)
*A61P 31/14* (2006.01)
*A61P 31/16* (2006.01)

(52) U.S. Cl.
CPC ................ *C07H 7/06* (2013.01); *A61P 31/14* (2018.01); *A61P 31/16* (2018.01); *C07B 2200/05* (2013.01)

(58) Field of Classification Search
None
See application file for complete search history.

(56) References Cited

U.S. PATENT DOCUMENTS

| 9,388,208 B2* | 7/2016 | Clarke ................ C07D 487/04 |
| 9,949,994 B2* | 4/2018 | Chun ...................... A61P 31/14 |
| 2017/0071964 A1 | 3/2017 | Clarke et al. |
| 2018/0346508 A1 | 12/2018 | Brak et al. |

FOREIGN PATENT DOCUMENTS

| CN | 102015714 A | 4/2011 |
| CN | 107073005 A | 8/2017 |
| CN | 108137641 A | 6/2018 |
| CN | 108348526 A | 7/2018 |
| CN | 109748944 A | 5/2019 |
| CN | 110330540 A | 10/2019 |
| CN | 110636884 A | 12/2019 |
| CN | 111135184 A | 5/2020 |
| CN | 111620909 A | 9/2020 |
| CN | 113248508 A | 8/2021 |
| CN | 113387954 A | 9/2021 |
| CN | 114096543 B | 8/2022 |

(Continued)

OTHER PUBLICATIONS

Cho, Aesop et al., "Synthesis and antiviral activity of a series of 1'-substituted 4-aza-7,9-dideazaadenosine C—nucleosides," Bioorganic & Medicinal Chemistry Letters, Mar. 8, 2012, pp. 2705-2707, vol. 23.

Ju, Jingyue, et al., "Nucleotide Analogues as Inhibitors of SARS-CoV Polymerase," BioRxiv, Mar. 14, 2020.

Kocabas, Faith, "Fluorometric RdRp assay with self-priming RNA," Virus Genes, Mar. 7, 2015, 50:498-504, 7 pages.

Li, Qingfeng, et al., "Anti-norovirus activity of C7-modified 4-aminopyrrole[2,1-f][1,2,4] triazine C-nucleosides," European Journal of Medicinal Chemistry, Mar. 7, 2020, vol. 195, 9 pages.

(Continued)

*Primary Examiner* — Patrick T Lewis
(74) *Attorney, Agent, or Firm* — Ice Miller LLP

(57) ABSTRACT

The present invention relates to an antiviral application of nucleoside analogs. Specifically, the present invention relates to uses of nucleoside analogs and a pharmaceutical composition thereof as: (a) inhibitors for inhibiting the replication of coronaviruses, influenza viruses, respiratory syncytial viruses, flaviviridae viruses, filoviridae viruses and/or porcine epidemic diarrhea virus (PEDV); and/or (b) medicines for treating and/or preventing and mitigating diseases caused by coronavirus, influenza virus, respiratory syncytial virus, flaviviridae virus, filoviridae virus and/or porcine epidemic diarrhea virus (PEDV) infections. The nucleoside analogs according to the invention may treat and/or prevent and mitigate respiratory infection, pneumonia (COVID-19) and other related diseases caused by 2019 novel coronavirus infection.

19 Claims, 2 Drawing Sheets

(56) References Cited

FOREIGN PATENT DOCUMENTS

| EP | 4141007 A1 | 1/2023 |
|---|---|---|
| WO | 2009132135 A1 | 10/2009 |
| WO | 2015069939 A1 | 5/2015 |
| WO | 2016069826 A1 | 5/2016 |
| WO | 2017027646 A1 | 2/2017 |
| WO | 2017049060 A1 | 3/2017 |
| WO | 2018204198 A1 | 11/2018 |
| WO | 2019014247 A1 | 1/2019 |
| WO | 2019053696 A1 | 3/2019 |
| WO | 2021022690 A1 | 2/2021 |

OTHER PUBLICATIONS

Li, Qingfeng, et al., "synthesis and biological evaluation of pyrrolo[2,1-f][1,2,4]trazine C-nucleosides with a ribose, 2'-deoxyribose and 2',3'-dideoxyribose sugar moiety," ChemMedChem, Nov. 21, 2017, 10 pages.

Otter, Brian A., et al., "Conformational properties of purine-like c-nucleosides," Nucleosides and Nucleotides, Aug. 21, 2006, vol. 15, No. 1-3, pp. 793-807.

Wang, Manli, et al., "Remdesivir and Chloroquine Effectively Inhibit the Recently Emerged Novel Coronavirus (2019—nCOV) in Vitro," Cell Research, vol. 1, 30, Feb. 4, 2020, ISSN: 1748-7838.

Warren, Travis K., "Therapeutic efficay of the small molecule GS-5734 Against Ebola virus in rhesus monkeys," Nature, Mar. 2, 2016, pp. 381-385, vol. 531, Macmillan Publishers Limited, 19 pages.

International Search Re[prt woth English Translation, of International Application No. PCT/CN2021/087928, mailed Jul. 6, 2021, 11 pages.

Written Opinion International Searching Authority of International Application No. PCT/CN2021/087928, mailed Jul. 1, 2021, 8 pages.

Haodan, Wang, et al., "Five, the study of material metabolism change," Biomedical Marker Tracer Technology, 6 pages, Chinese version and English Translation.

Jiang, Wen-feng, et al., "Application of Deuteration in Drug Research," Sanlugen Pharma Tech, Jinan 250062, Qilu Pharmaceutical Affairs 2010, vol. 29, No. 11, English Abstract.

First Office Action for CN 202180002969.0 mailed May 23, 2022, Chinese version with English translation.

Notification of Grant Patent Rights for Invention for CN202180002969.0 mailed Jul. 22, 2022.

English translation of granted claims for CN202180002969.0.

Baker, David C., et al., "Prodrugs of 9-beta-D-arabinofuranozyladenine. 1. Synthesis and evaluation of some 5'-(O—acyl) derivatives," Journal of Medicinal Chemistry 21.12 (1978): 1218-1221.

Peterson, Larryn, et al., "Prodrug approaches to improving the oral absorption of antiviral nucleotide analogues," Expert opinion on drug delivery 6.4 (2009): 405-420.

Compound Summary, [(2R,3R,4R,5R)-3,4-diacetyloxy-5-(4-aminopyrrolo[2,1-f][1,2,4]triazin7-yl)-5-cyanooxolan-2-yl] methyl acetate, National Library of Medicine, PubChem, C18H19N5O7, CID 145074481, Jul. 30, 2024, 9 pages.

Wang, Zhonglei, et al., "Oral GS-441524 derivatives: Next-generation inhibitors of SARS-CoV-2 RNA-dependent RNA polymerase," Frontiers in Immunology, 10.3389, pp. 1-16, Dec. 6, 2022.

Wei, Daibao, et al., "Potency and Pharmacokinetics of GS-441524 derivatives against SARS-CoV-2," Bioorganic & Medicial Chemistry, vol. 46, (2021) 116364, 12 pages.

\* cited by examiner

ANTIVIRAL APPLICATION OF NUCLEOSIDE ANALOG OR COMBINATION FORMULATION CONTAINING NUCLEOSIDE ANALOG

CROSS-REFERENCE TO RELATED APPLICATION

This application is a continuation of U.S. patent application Ser. No. 17/996,430 filed Oct. 17, 2022, which is a 371 national phase patent application of PCT/CN2021/087928 filed Apr. 16, 2021, which was published in the Chinese language Oct. 28, 2021, under International Publication No. WO 2021/213288 A1, which claims priority to Chinese Patent Application No. 202010313870.X filed Apr. 20, 2020, Chinese Patent Application No. 202010568329.3 filed Jun. 19, 2020, and Chinese Patent Application No. 202011035065.1 filed Sep. 27, 2020, the disclosures of which are incorporated herein by reference in their entireties.

TECHNICAL FIELD

The present invention relates to the field of medicine, and specifically, relates to an antiviral application of nucleoside analog or combination formulation containing nucleoside analog.

BACKGROUND

The vast majority of acute infectious diseases are viral infectious diseases; both morbidity and mortality rate of the viral infectious diseases are high. Viruses are a group of pathogenic microorganisms that are extremely small, lack independent metabolism, and exist in a parasitic manner. There are various types of viruses. At present, many highly infectious and pathogenic viruses have been found. These viruses often cause local or even global outbreaks of infectious diseases and are extremely harmful to human society, such as influenza virus, respiratory syncytial virus (RSV), parainfluenza virus, atypical pneumonia (SARS) virus, Middle East Respiratory Syndrome (MERS) virus, Ebola virus and the like. Some viruses can also infect animals, causing various diseases from mild to severe, while animals also become the source of infection of these viruses, making humans defenseless against them.

Coronaviruses belong to Nidovirale, Coronaviridae, and Coronavirus, and are a large group of single-stranded positive-stranded RNA viruses that are widespread in nature and can cause respiratory, digestive and neurological diseases in humans and animals. According to the phylogenetic tree, coronaviruses can be divided into four genera: α, γ, γ, and δ, wherein coronaviruses of genus β can be further divided into four independent subgroups A, B, C, and D groups.

Up to April 2020, the novel coronavirus (SARS-CoV-2) have caused more than 100,000 deaths, resulting in another very serious global public health event since the Spanish pandemic of 1918. SARS-CoV-2, atypical pneumonia virus (SARS-CoV), and Middle East Respiratory Syndrome coronavirus (MERS-CoV) all belong to β genus coronaviruses, and currently, these three viruses have become the most pathogenic coronaviruses for humans.

At present, there are no specific vaccines and antiviral drugs against severe pneumonia caused by SARS-CoV-2 coronavirus. These infectious diseases have seriously affected people's lives and health, so there is an urgent need to develop antiviral drugs with good effects. It is of great social significance to develop low-toxicity and high-efficiency antiviral drugs for SARS-CoV-2 coronavirus to meet the clinical needs of SARS-CoV-2 coronavirus infected patients at home and abroad.

Coronavirus can also infect many mammals, including bats, pigs, dogs, cats, mice, cattle, horses, camels, etc. Most of these viruses belong to α and β genera. Porcine epidemic diarrhea virus (PEDV) is a kind of coronavirus that can cause acute intestinal infectious diseases in pigs. Pigs of all ages can be infected, especially suckling pigs and newborn piglets are most seriously affected, and the aquaculture industry often suffers heavy losses due to the outbreak of PEDV.

Respiratory virus infection is the most common and most influential viral infectious disease in clinic, which causes a large number of deaths in the world every year. In addition to coronavirus, influenza virus, respiratory syncytial virus and parainfluenza virus and the like can also cause respiratory tract infection and result in pneumonia, which are key killers threatening human life and health.

Summing up, there is an urgent need in this field to develop inhibitors for inhibiting viral replication to be used for treating related diseases caused by viral infection.

SUMMARY OF THE INVENTION

The purpose of the present invention is to provide an active ingredient that can effectively inhibit viral replication and the new use thereof in diseases associated with viral infections.

Specifically, the present invention provides a use of the nucleoside analogs having Formula (I) and compositions thereof in fighting viruses (e.g., coronavirus, influenza virus, respiratory syncytial virus, flaviviridae virus, filoviridae virus, and/or porcine epidemic diarrhea virus), in particular novel coronavirus (SARS-CoV-2).

In the first aspect of the present invention, it provides a compound of formula (I), or the pharmaceutically acceptable salts thereof or the crystalline hydrate thereof or the solvate thereof or the prodrug thereof, (I)

wherein, $R_1$ is selected from hydrogen, deuterium, halogen, cyano, azido, amino, amino substituted with $C_{1-6}$alkyl, $C_{1-6}$acyl, $C_{1-6}$alkyl, $C_{1-6}$alkoxy, amino substituted with $C_{1-6}$alkanoyl, halogenated $C_{1-6}$alkyl, $C_{2-6}$alkenyl, $C_{2-6}$alkenoxy, $C_{2-6}$alkynyloxy, $C_{2-6}$alkynyl, $C_{3-6}$cycloalkyl, halogenated $C_{3-6}$ cycloalkyl, carbamoyl, hydroxymethyl, cyanomethyl (—$CH_2CN$), guanyl, guanidyl, carbamido, thiocyanato (—SCN), cyanato (—OCN);

$R_2$ is selected from hydrogen, halogen, $OR_3$, cyano, $C_{1-6}$alkyl, $C_{1-6}$alkoxy, $C_{2-6}$alkenyl, $C_{2-6}$alkynyl;

$R_3$ is selected from hydrogen, $C_{1-20}$alkanoyl, amino$C_{1-20}$alkanoyl, $C_{1-6}$alkyl amino-$C_{1-6}$ alkanoyl, $C_{1-6}$alkoxy$C_{1-6}$alkyl, α-amino acid, and the carboxyl of the α-amino acid is attached to the hydroxyl on the furan ring via ester bond;

$R_4$ is selected from hydrogen, deuterium, halogen, azido, cyano, $C_{1-6}$alkyl, halogenated $C_{1-6}$ alkyl, azido$C_{1-6}$alkyl, cyano$C_{1-6}$alkyl, hydroxy$C_{1-6}$alkyl, $C_{2-6}$alkenyl, $C_{2-6}$alkynyl, $C_{3-6}$cycloalkyl, $C_{1-6}$alkanoyl, $C_{2-6}$alkenoxy, $C_{2-6}$alkynyloxy, $C_{1-6}$alkoxy$C_{1-6}$alkyl, amino$C_{1-6}$alkyl, $C_{1-6}$alkylamino-$C_{1-6}$alkyl, guanyl, guanidyl, carbamido, thiocyanato, cyanato;

$R_5$ is selected from $R_3$,

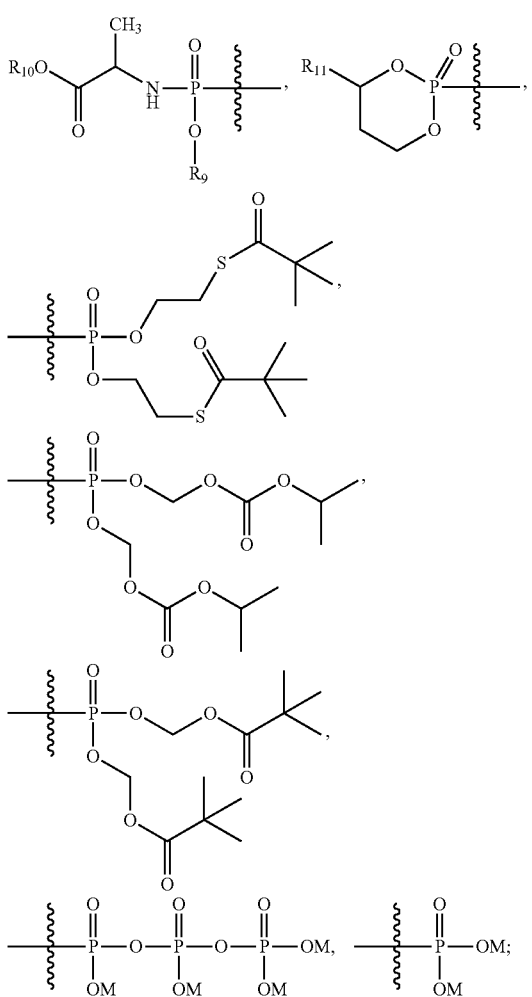

$R_6$ is selected from amino, hydroxy, halogen, cyano, cyanato, thiocyanato, $C_{1-6}$alkoxy, $C_{1-6}$alkylamino, NHOH, NHCOR$_{12}$, NHOCOR$_{12}$, NHCOOR$_{12}$;

$R_7$ is selected from hydrogen, deuterium, halogen, amino, methyl, NHCOR$_{12}$, NHCOOR$_{12}$;

$R_8$ is selected from hydrogen, deuterium, halogen, cyano, carbamoyl, carbamoyl substituted with $C_{1-6}$alkyl, $C_{1-6}$alkoxyamido, $C_{1-6}$alkoxycarbonyl, hydroxy, hydroxy$C_{1-6}$alkyl, amino, amino substituted with $C_{1-6}$alkanoyl, amino substituted with $C_{1-6}$alkyl, $C_{1-6}$alkyl, $C_{1-6}$-alkoxy, $C_{2-6}$alkenyl, $C_{2-6}$alkynyl;

X is selected from —CH$_2$—, —CD$_2$-, —CHD-;

$R_9$ is selected from $C_{1-6}$alkyl, $C_{3-6}$cycloalkyl, $C_{6-20}$aryl, 5-15 membered heteroaryl;

$R_{10}$ is selected from $C_1$isalkyl, methyleneC$_{6-20}$aryl;

$R_{11}$ is selected from $C_{1-6}$alkyl, $C_{3-6}$cycloalkyl, $C_{6-20}$aryl, 5-15 membered heteroaryl;

$R_{12}$ is selected from $C_{1-20}$alkyl;

M is each independently selected from hydrogen, metal, —NH$_4$, or protonated organic amines;

In another preferred embodiment, each position indicated as deuterium (D) has a deuterium enrichment of at least 50%; preferably, each position indicated as deuterium (D) has a deuterium enrichment of at least 80%; more preferably, each position indicated as deuterium (D) has a deuterium enrichment of at least 90%; most preferably, each position indicated as deuterium (D) has a deuterium enrichment of at least 95%.

In another preferred embodiment, the 5-15 membered heteroaryl contains 1, 2, 3 or 4 heteroatoms selected from N, O and S.

In another preferred embodiment, the metal is selected from the group consisting of alkali metal, alkaline earth metal, or the combination thereof.

In another preferred embodiment, in the formula of the compound of formula (I), $R_1$ is selected from hydrogen, deuterium, halogen, cyano, azido, methyl, chloromethyl, fluoromethyl, ethenyl, ethynyl, cyclopropyl, carbamoyl, hydroxymethyl, methoxyl, formyl, guanyl; and/or $R_2$ is selected from halogen, cyano, amino, formyl, OR$_3$; and/or $R_3$ is selected from hydrogen, $C_{1-20}$alkanoyl, α-amino acid, the carboxyl of the α-amino acid is attached to the hydroxyl on the furan ring via ester bond; preferably, the α-amino acid is selected from the group consisting of alanine, valine, isoleucine, tryptophan, phenylalanine; and/or $R_4$ is selected from hydrogen, deuterium, halogen, azido, cyano, methyl, chloromethyl, fluoromethyl, difluoromethyl, ethenyl, ethynyl, cyclopropyl, hydroxymethyl, azidomethyl (—CH$_2$N$_3$), formyl, acetyl, formamido, acetamido; and/or $R_5$ is selected from $R_3$,

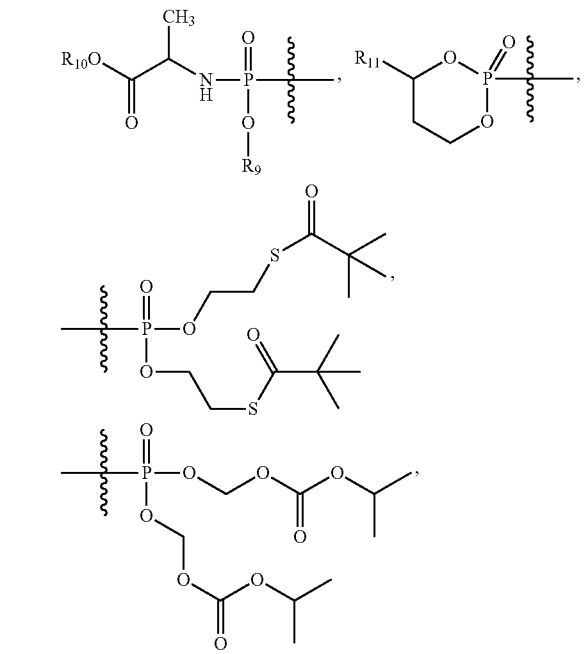

-continued

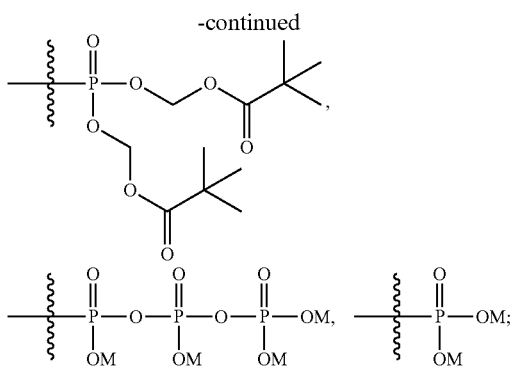

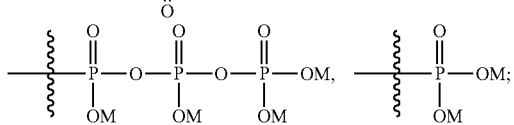

and/or

R$_6$ is selected from amino, hydroxy, halogen, cyano, methylamino (—NH$_2$CH$_3$), NHOH, NHCOR$_{12}$, NHOCOR$_{12}$, NHCOOR$_{12}$; and/or R$_7$ is selected from hydrogen, deuterium, halogen, amino; and/or R$_8$ is selected from hydrogen, deuterium, halogen, cyano, carbamoyl, N-methylcarbamoyl (CH$_3$NHCO—), methyl, ethyl, ethynyl, methoxycarbonyl, ethoxycarbonyl, hydroxy, hydroxymethyl, hydroxyethyl, methoxy, ethoxy, formyl, acetyl, formamido, acetamido, methoxycarbonylamino (CH$_3$OCONH$_2$—), ethoxycarbonylamino (C$_2$H$_5$OCONH$_2$—), methoxycarbonyloxy (CH$_3$OCOO—), ethoxycarbonyloxy (C$_2$H$_5$OCOO—); and/or X is selected from —CH$_2$—, —CD$_2$-, —CHD-; and/or R$_9$ is selected from C$_{6-20}$aryl, 5-15 membered heteroaryl; and/or R$_{10}$ is selected from C$_{1-18}$alkyl, methyleneC$_{6-20}$aryl; and/or R$_{11}$ is selected from C$_{1-6}$alkyl, C$_{3-6}$cycloalkyl, C$_{6-20}$aryl, 5-15 membered heteroaryl; and/or R$_{12}$ is selected from C$_{1-20}$alkyl; and/or M is each independently selected from hydrogen, zinc, magnesium, calcium, sodium, potassium, NH$_4$, protonated trimethylamine, protonated triethylamine, protonated tri-n-butylamine.

In another preferred embodiment, the R$_1$, R$_2$, R$_3$, R$_4$, R$_5$, R$_6$, R$_7$, R$_8$ and X are each independently the specific corresponding groups in each compound of the examples (such as any of the Compounds A1 to A221).

In another preferred embodiment, the compound of formula (I) is any one of Compounds A1 to A221 having the following structure, or the combination thereof:

A1

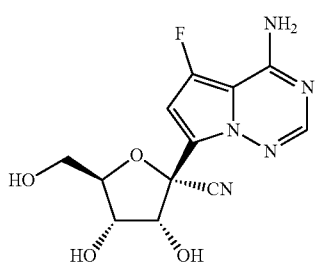

A2

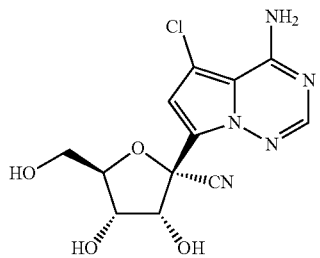

A3

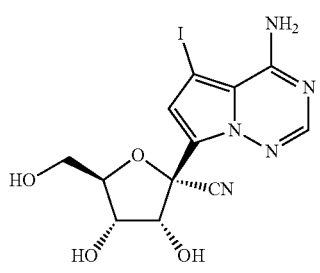

A4

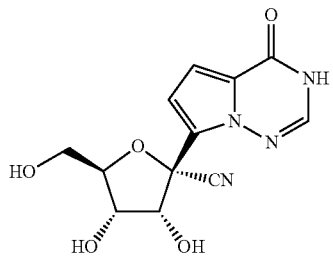 [SMILES: N#C[C@@]1(c2ccc3c(=O)[nH]cnn23)O[C@H](CO)[C@@H](O)[C@H]1O]

A5

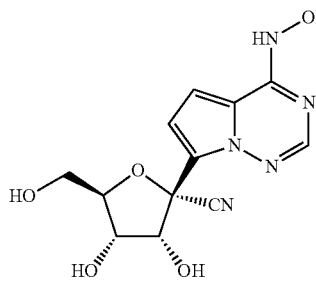

A6

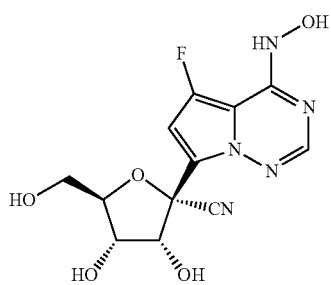

A7

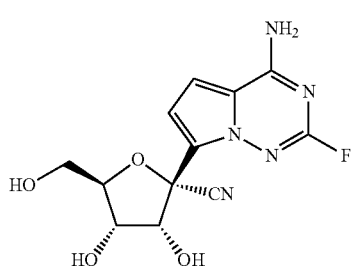

A8
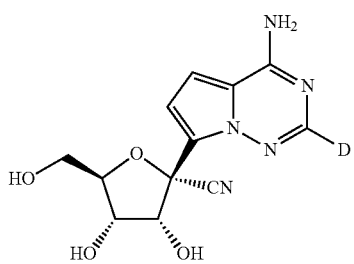
A9
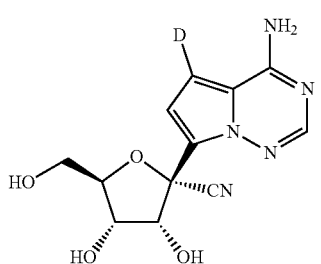
A10
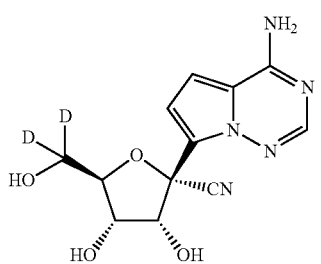
A11
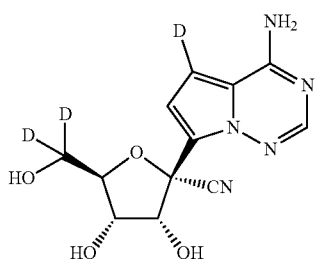
A12
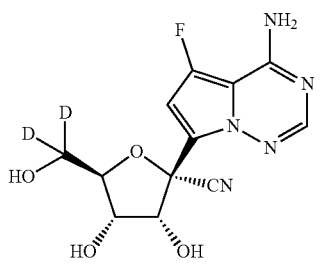
A13
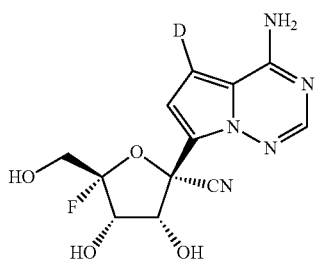
A14
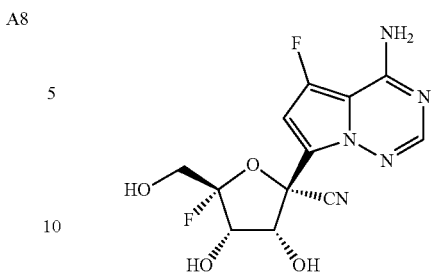
A15
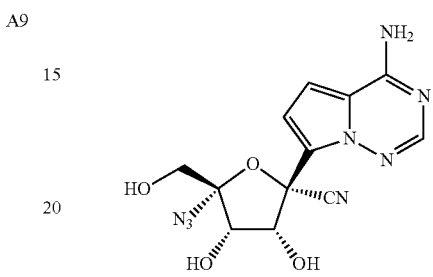
A16
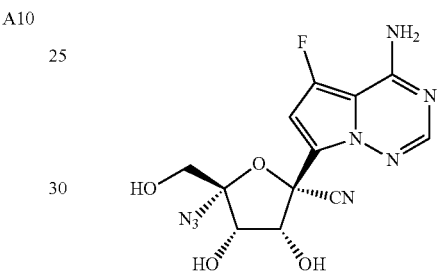
A17
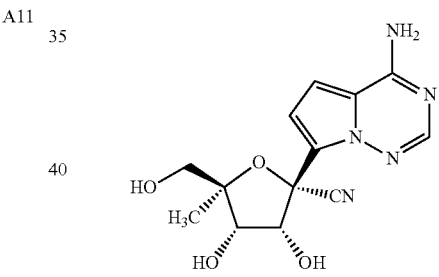
A18
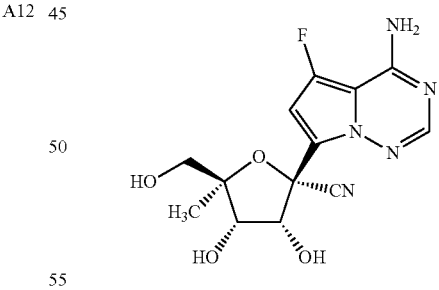
A19
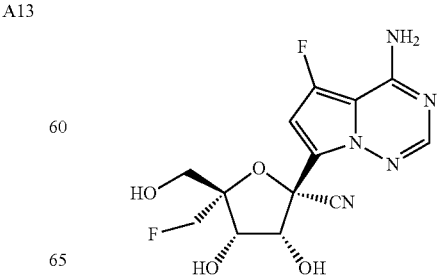

-continued
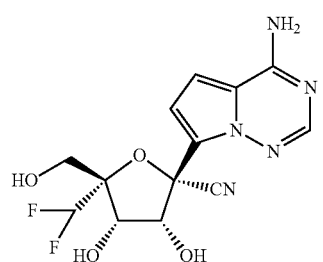
A20
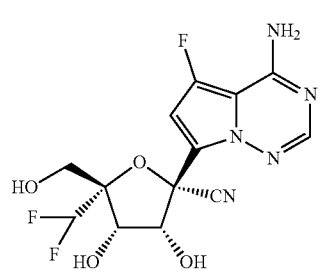
A21
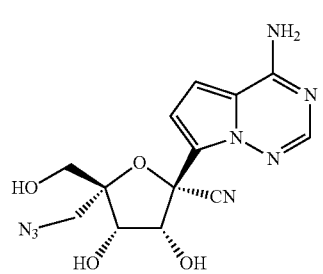
A22
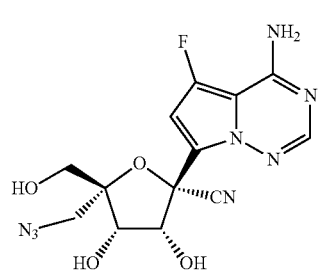
A23
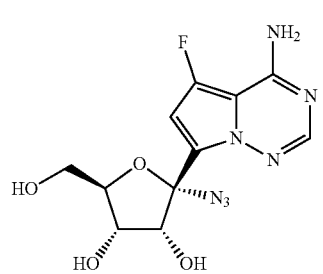
A24
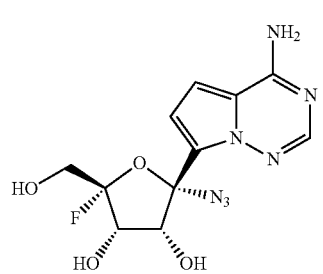
A25
-continued
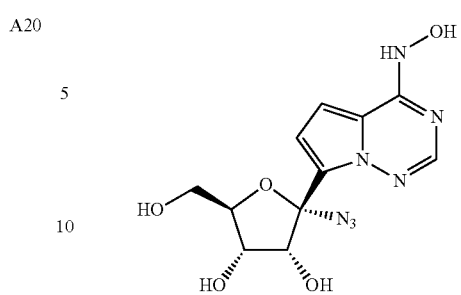
A26
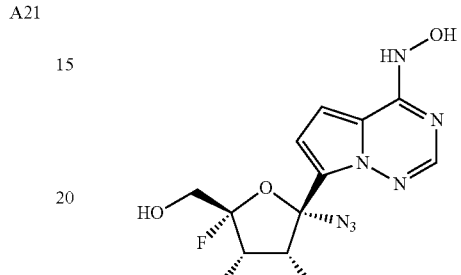
A27
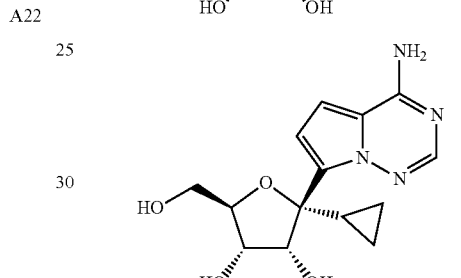
A28
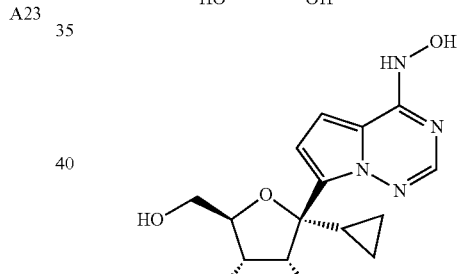
A29
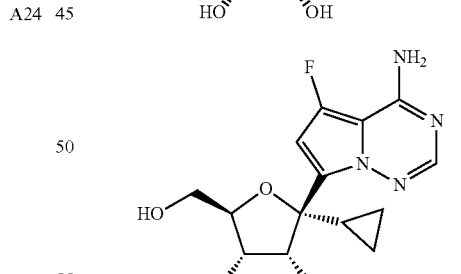
A30
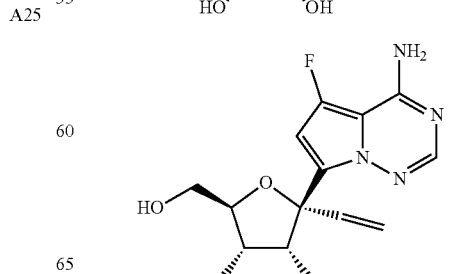
A31

A32
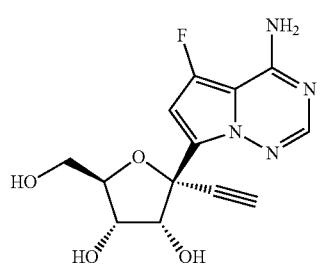
A33
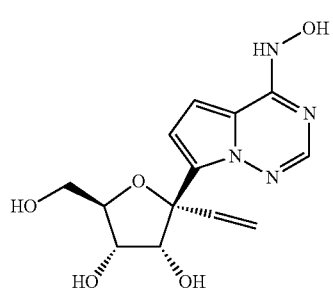
A34
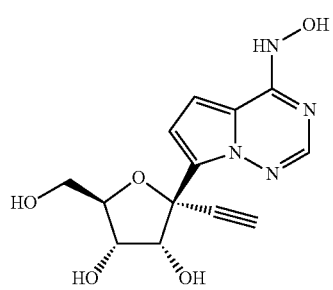
A35
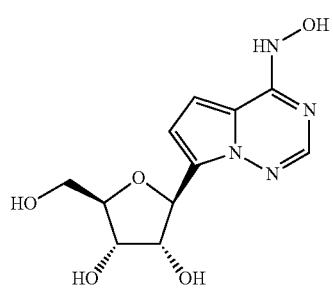 [SMILES: OC[C@H]1O[C@@H](c2ccc3c(NO)ncnn23)[C@H](O)[C@@H]1O]
A36
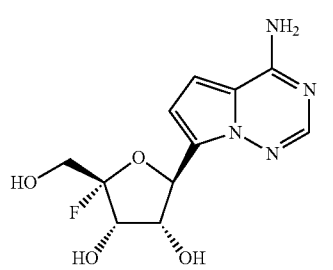
A37
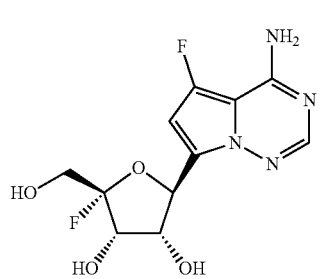
A38
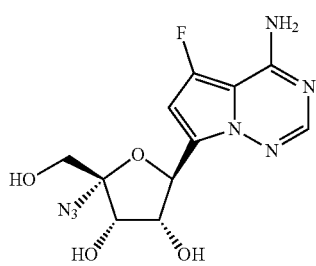
A39
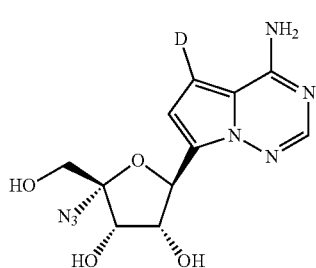
A40
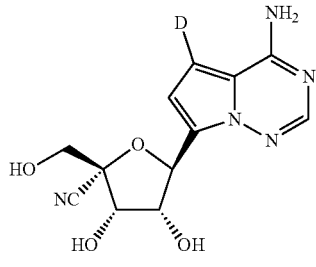
A41
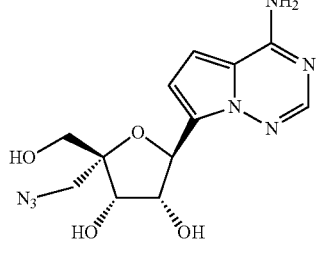
A42
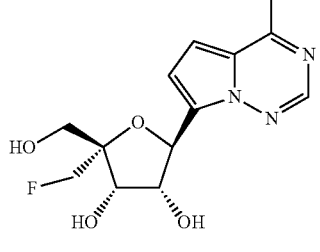
A43
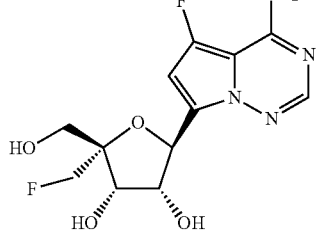

-continued
A44 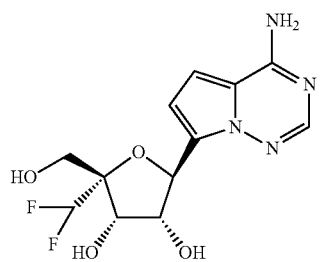
A45 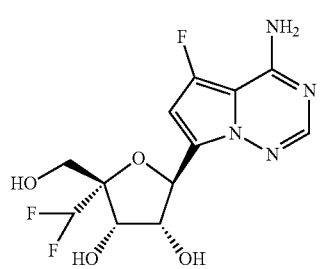
A46 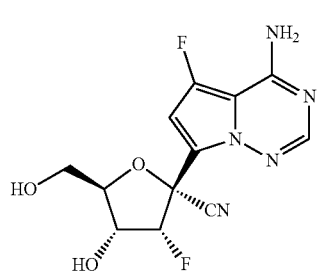
A47 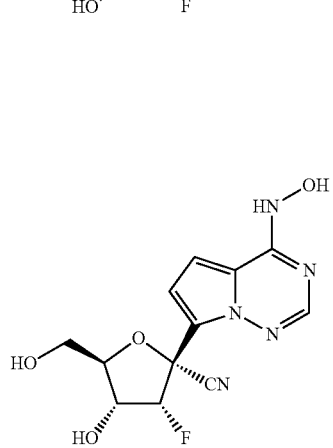
A48 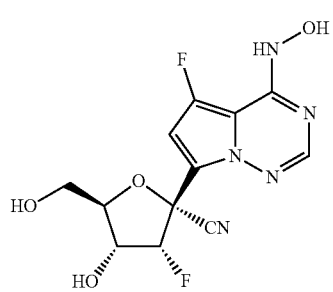
-continued
A49 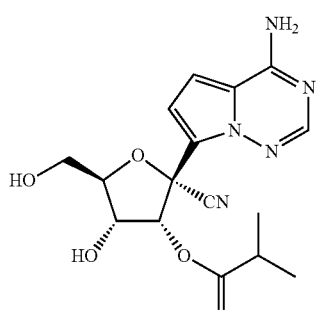
A50 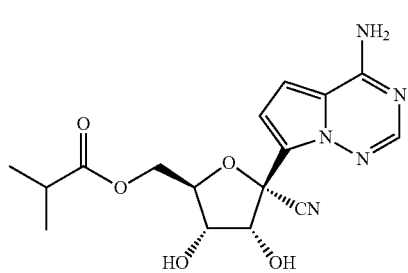 [SMILES: CC(C)C(=O)OC[C@H]1O[C@@](C#N)(c2ccc3c(N)ncnn23)[C@H](O)[C@@H]1O]
A51 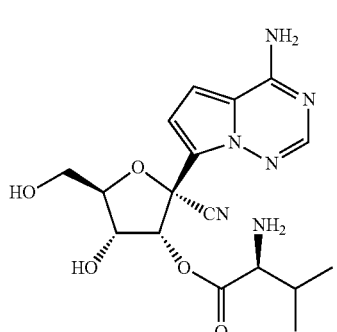
A52 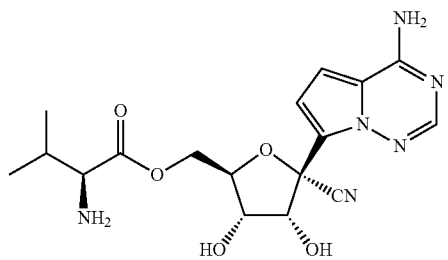 [SMILES: CC(C)[C@H](N)C(=O)OC[C@H]1O[C@@](C#N)(c2ccc3c(N)ncnn23)[C@H](O)[C@@H]1O]
A53 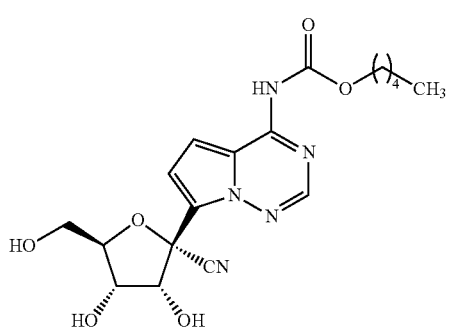

A54 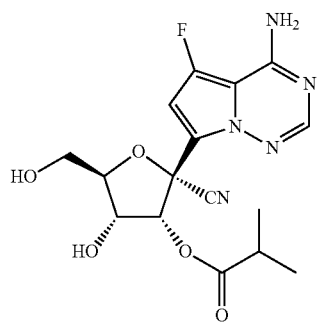
A55 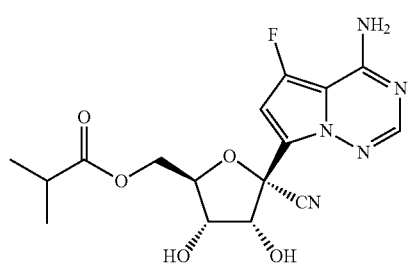
A56 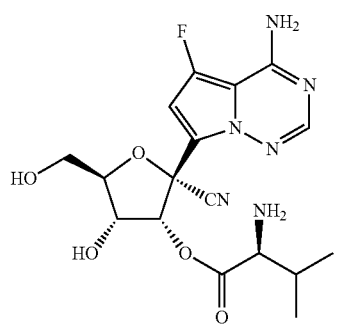
A57 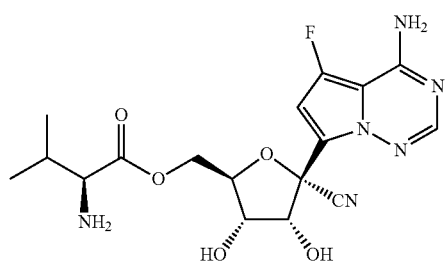
A58 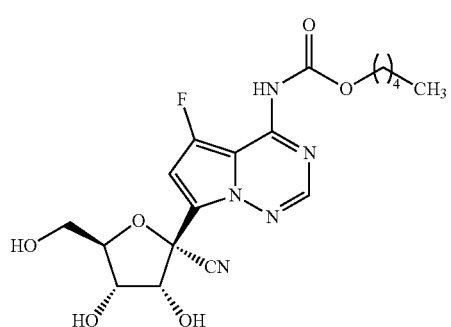
A59 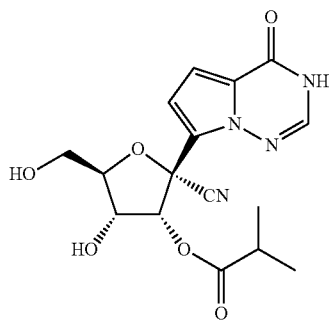
A60 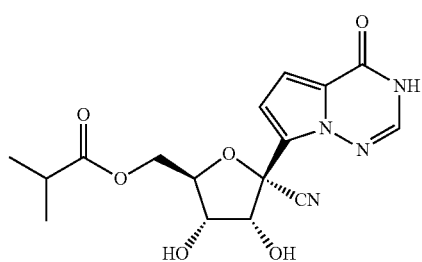
A61 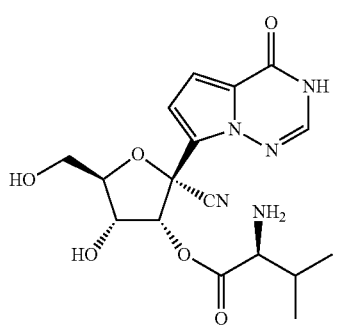
A62 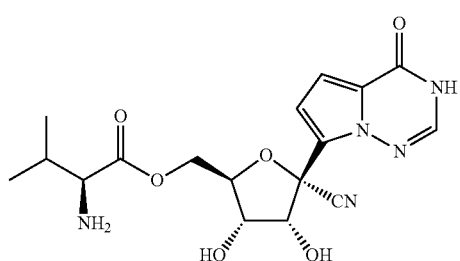
A63 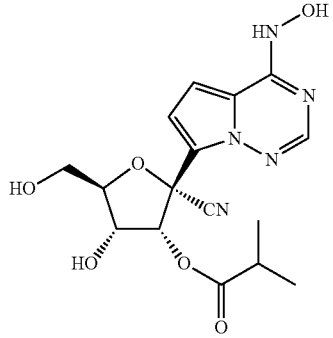

A64 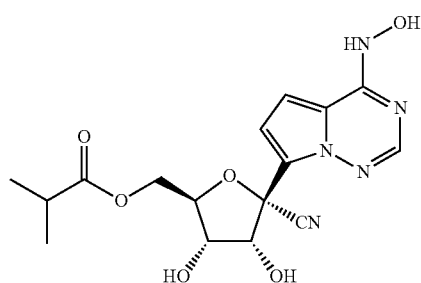
A65 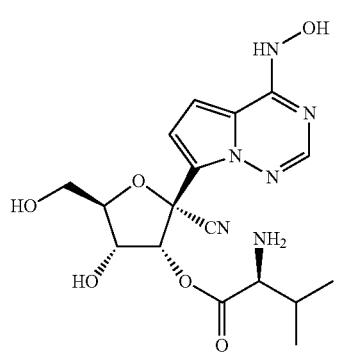
A66 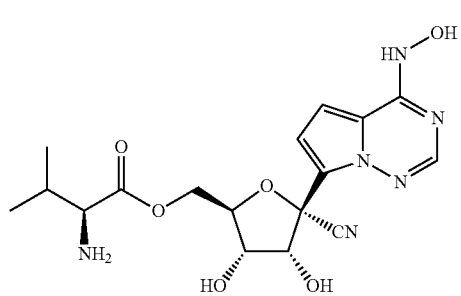
A67 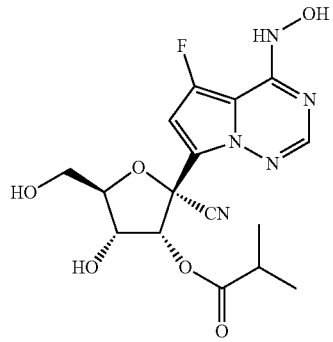
A68 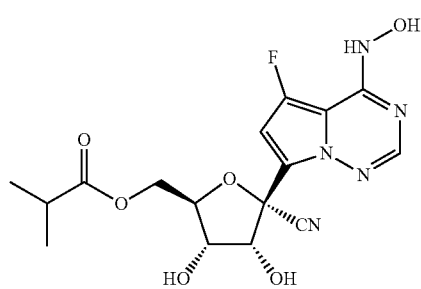
A69 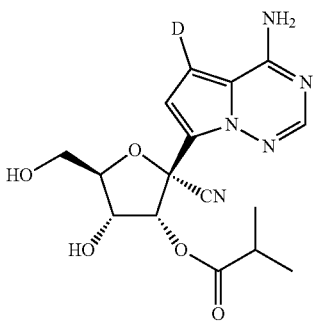
A70 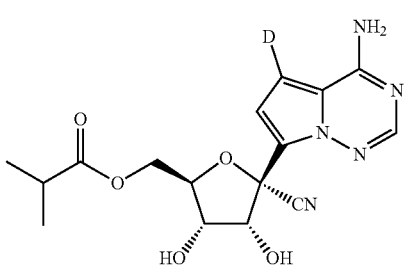
A71 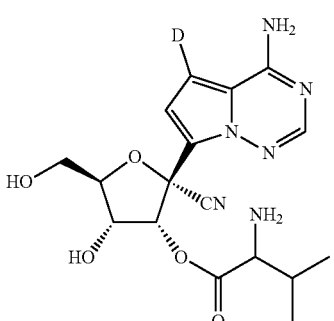
A72 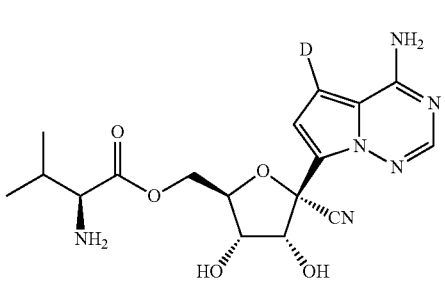 [SMILES: [2H]c1cc([C@]2(C#N)O[C@H](COC(=O)[C@@H](N)C(C)C)[C@@H](O)[C@H]2O)n2ncnc(N)c12]
A73 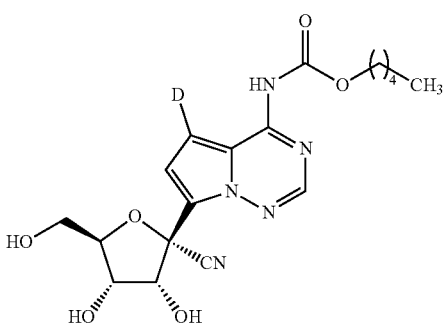

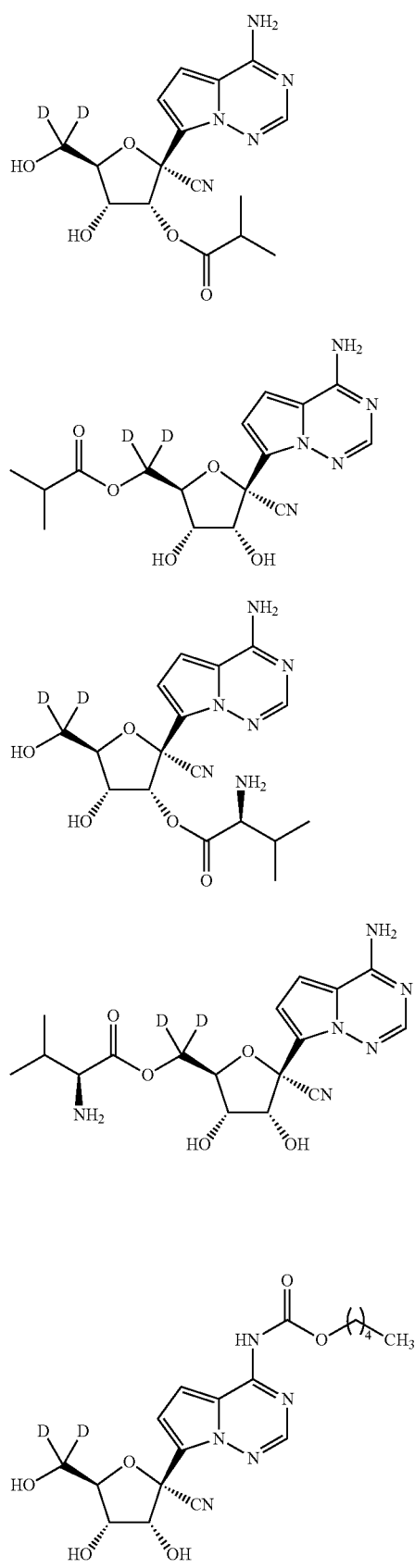
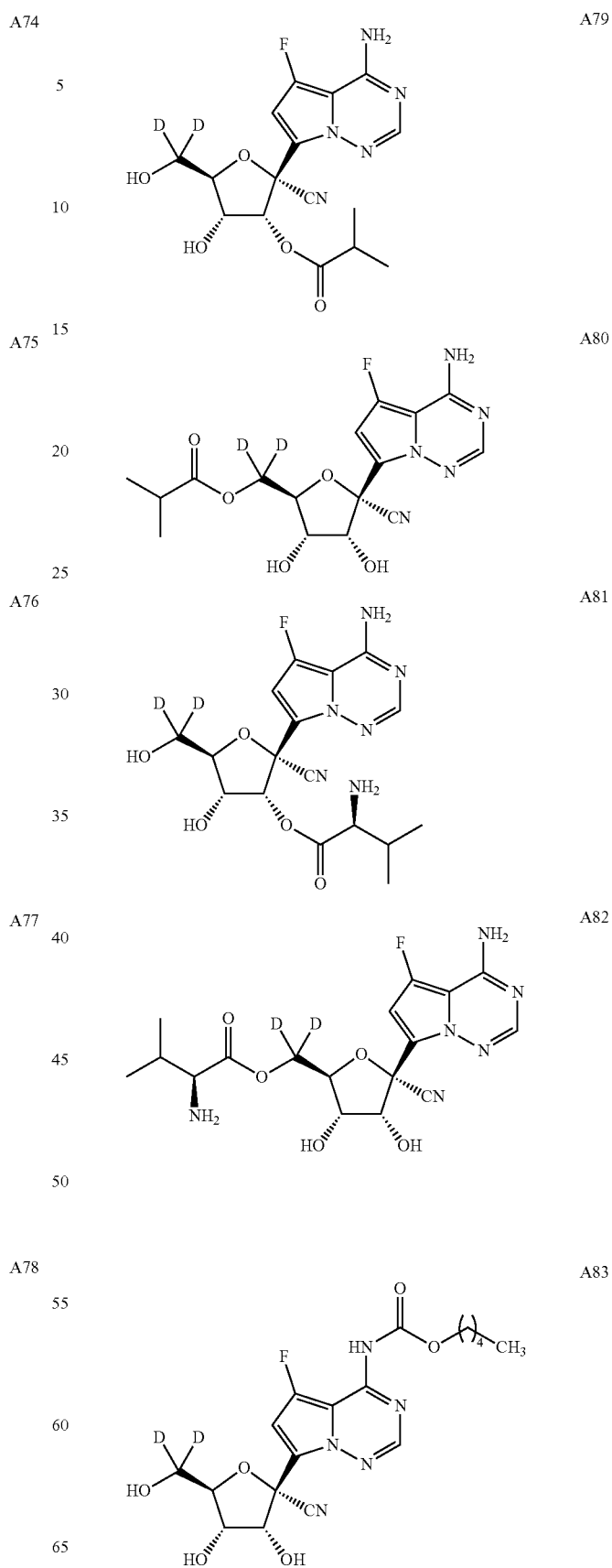

-continued
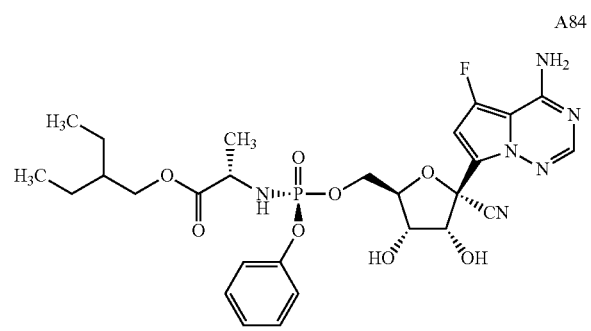
A84
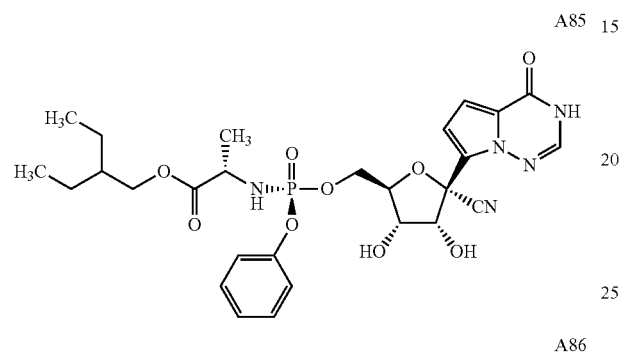
A85
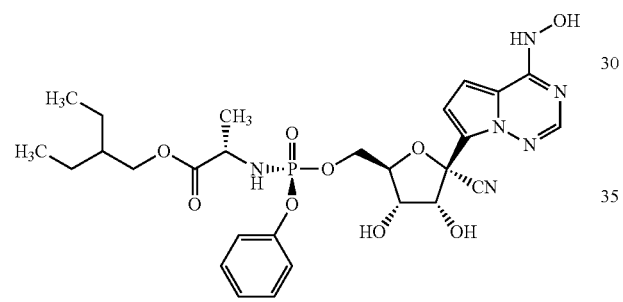
A86
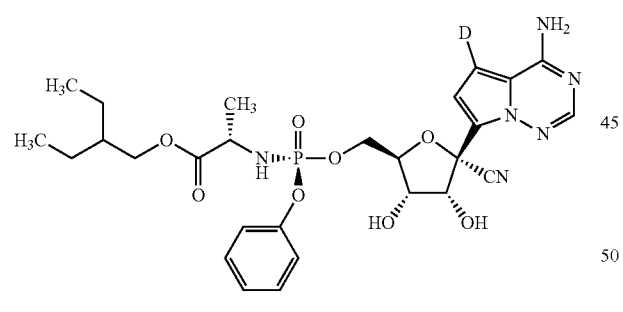
A87
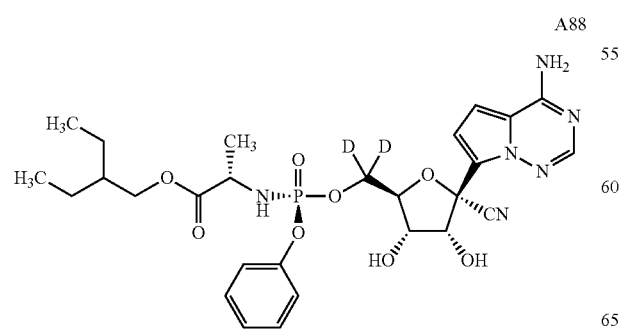
A88
-continued
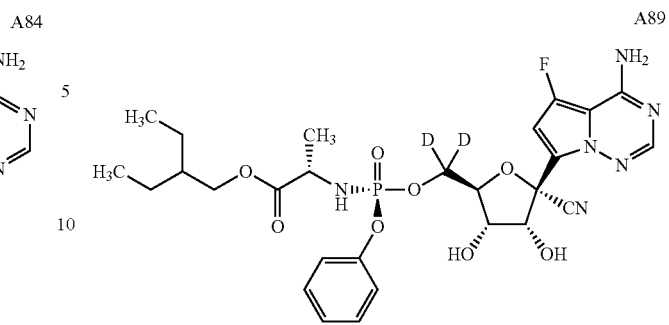
A89
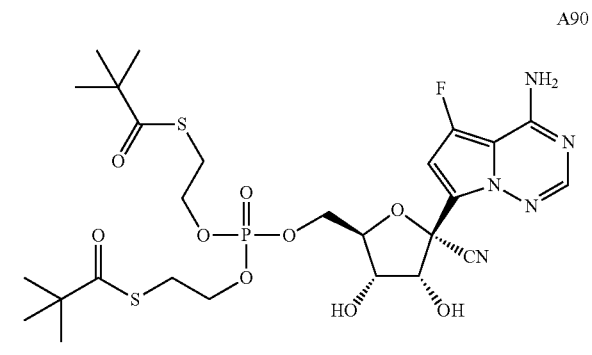
A90
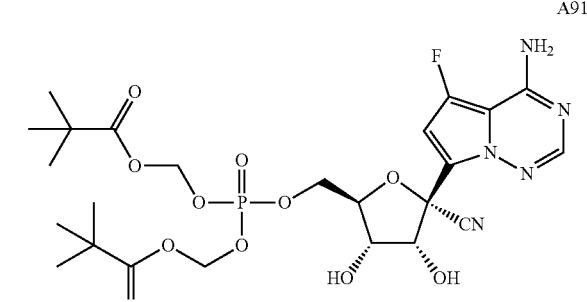
A91
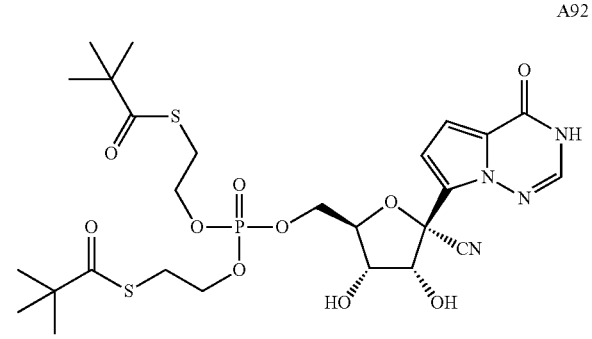
A92
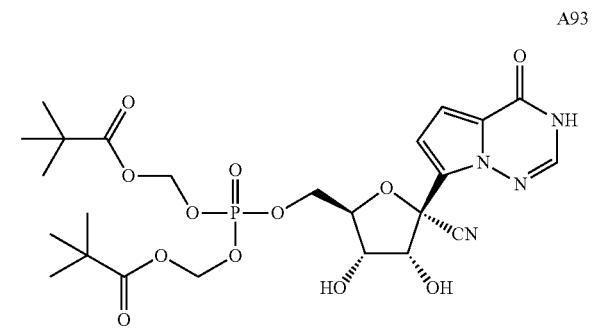
A93

-continued
A94
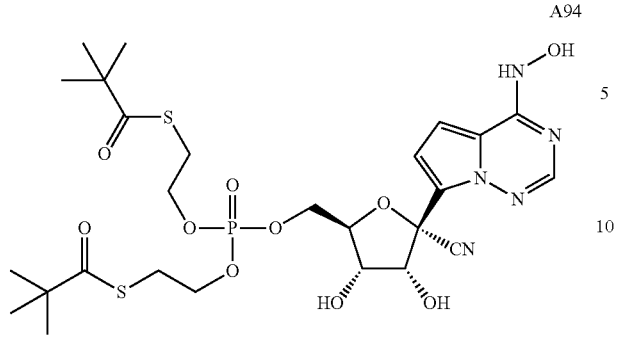
A95
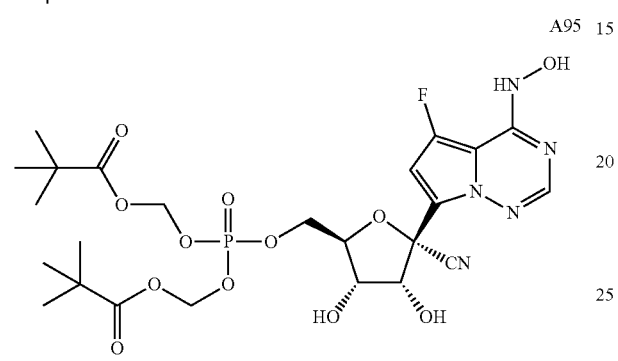
A96
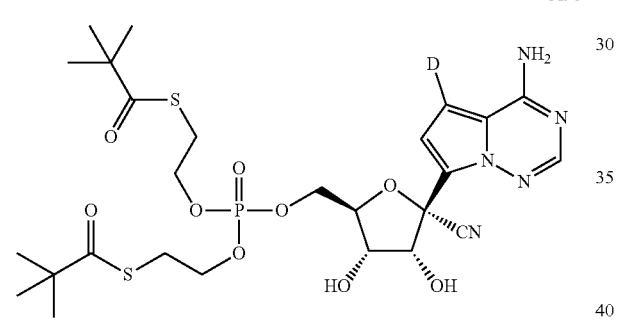
A97
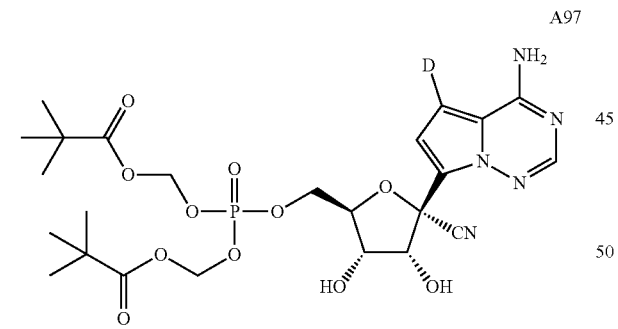
A98
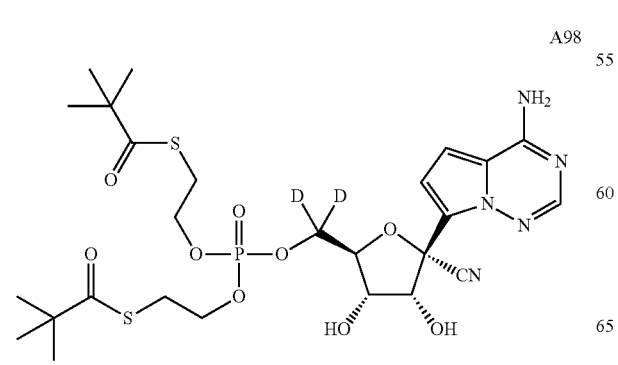
-continued
A99
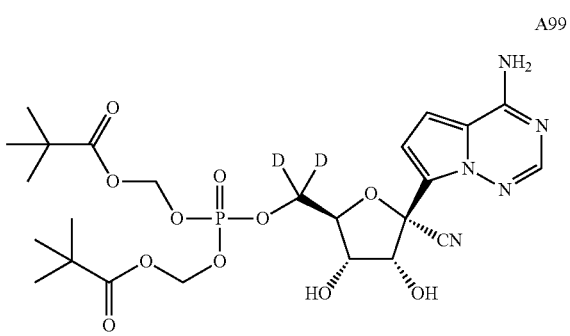
A100
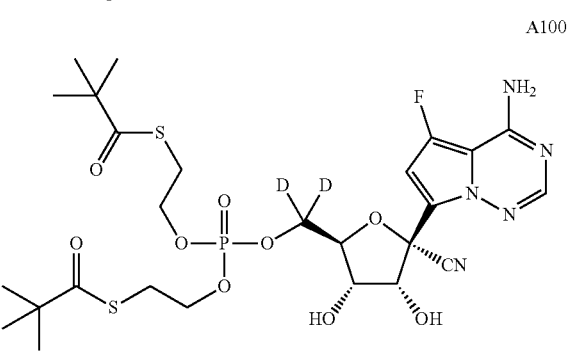
A101
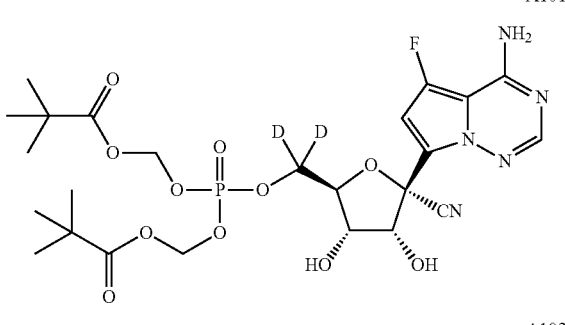
A102
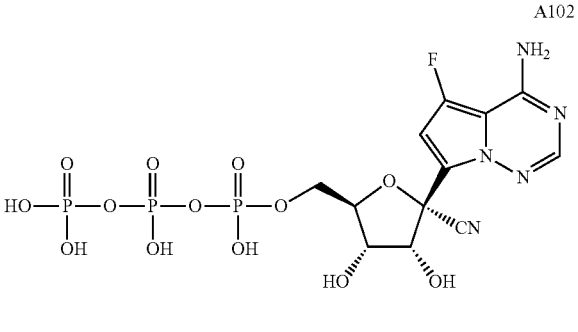
A103
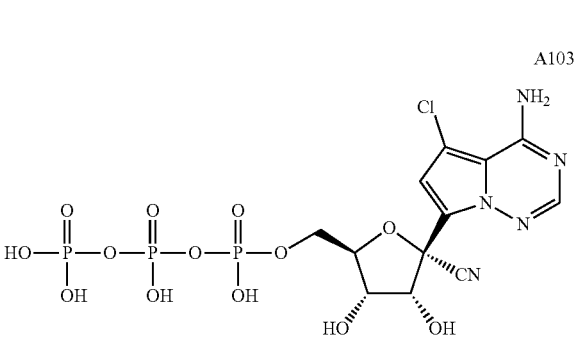

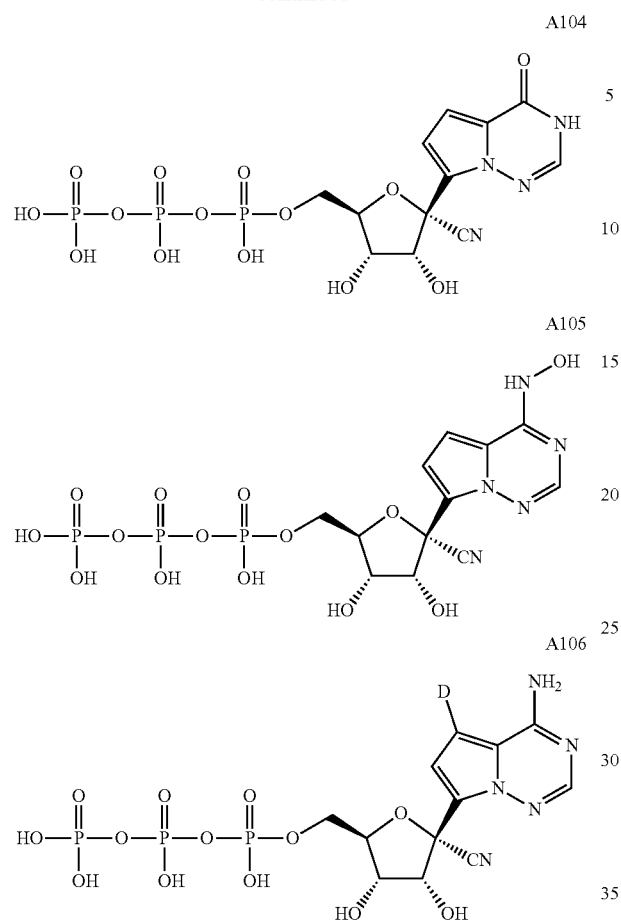
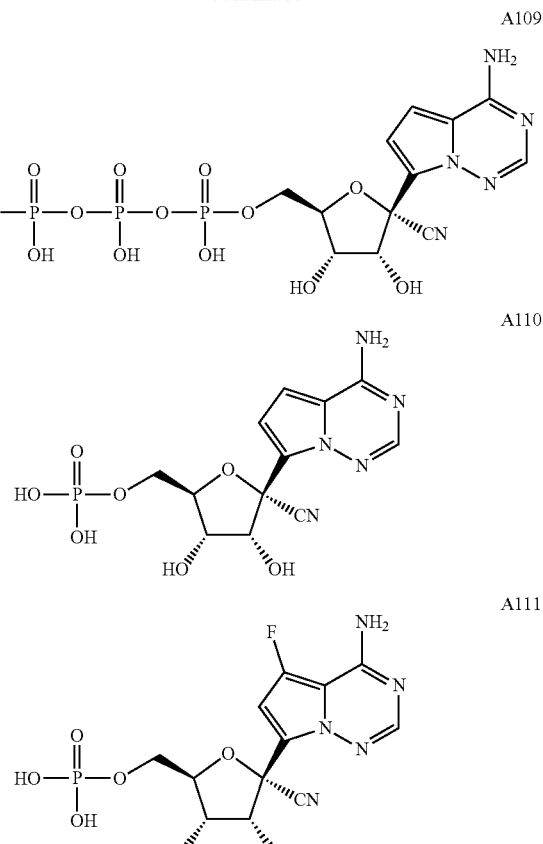
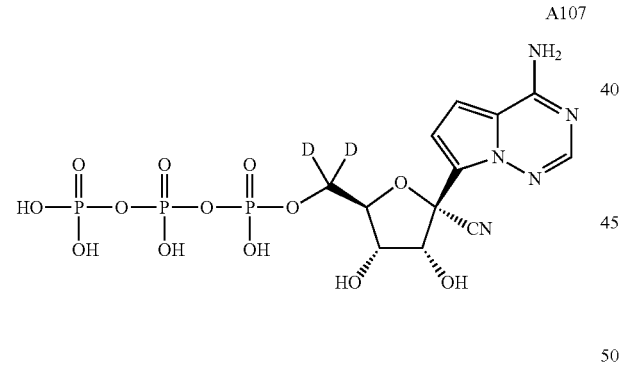
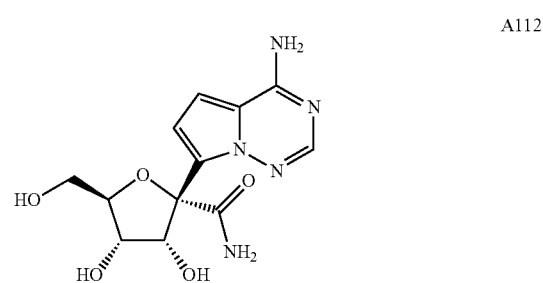
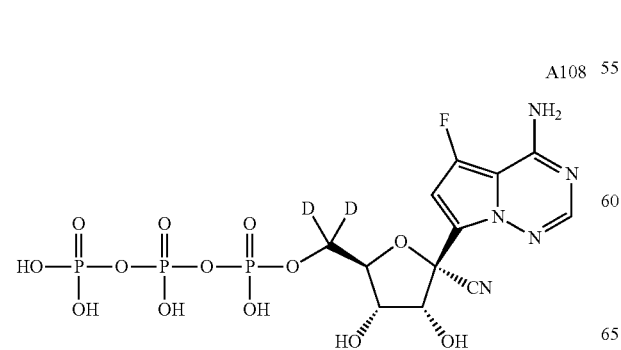
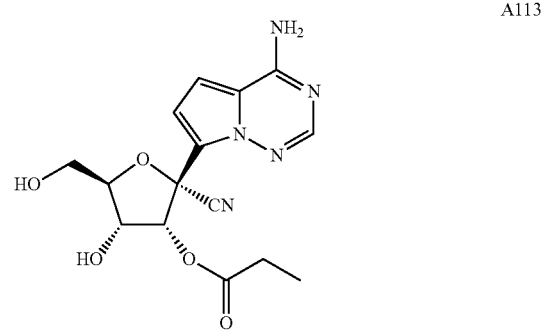

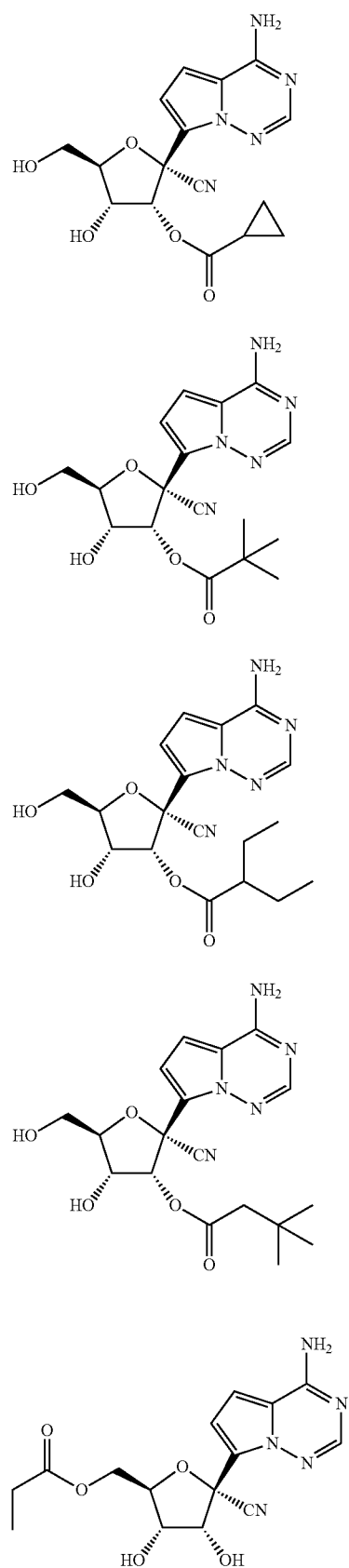
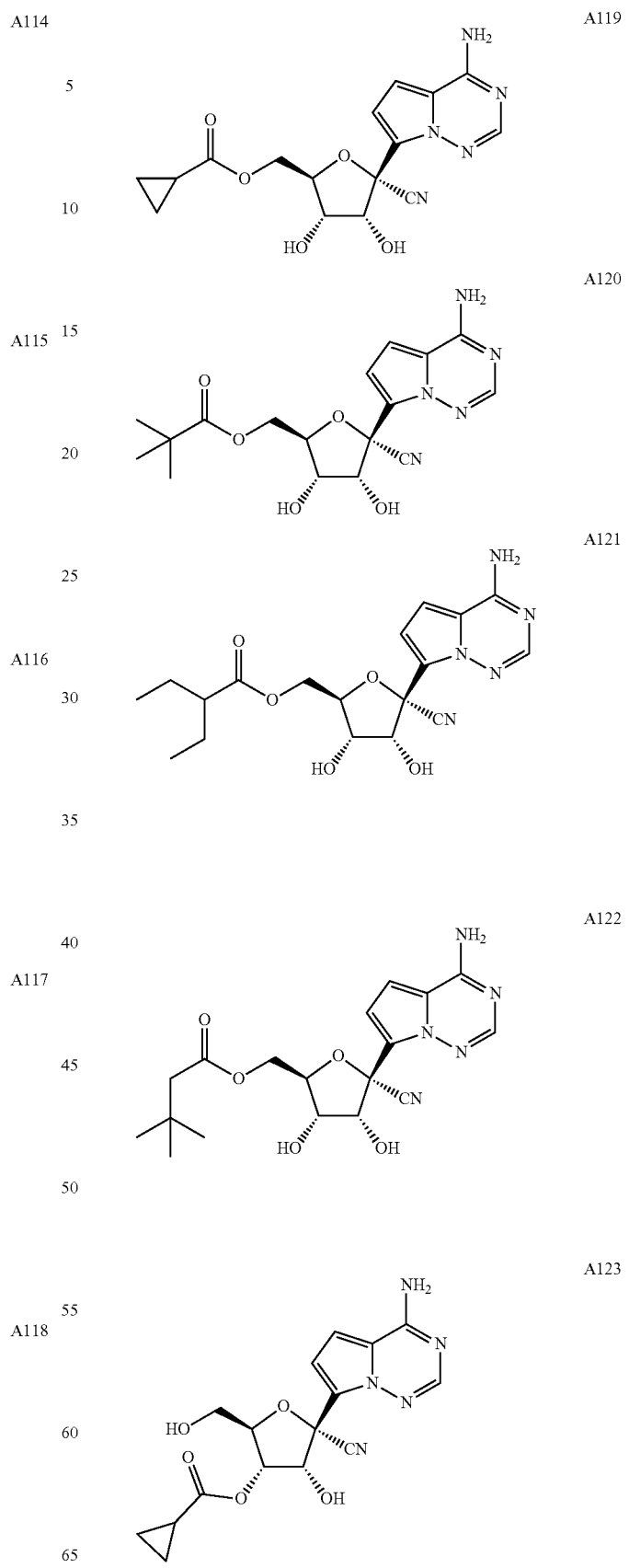

A124 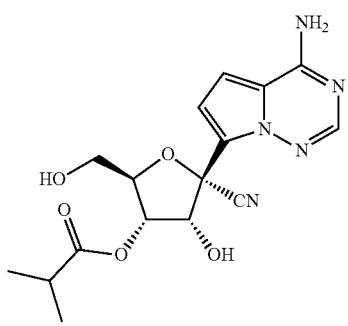
A125 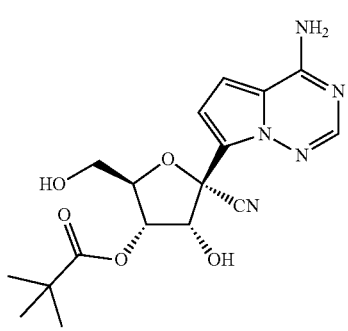
A126 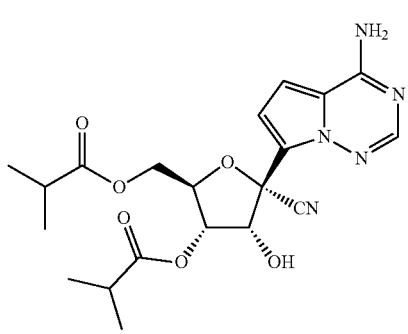
A127 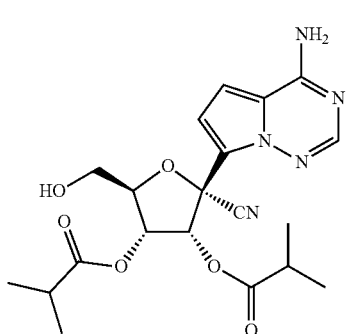
A128 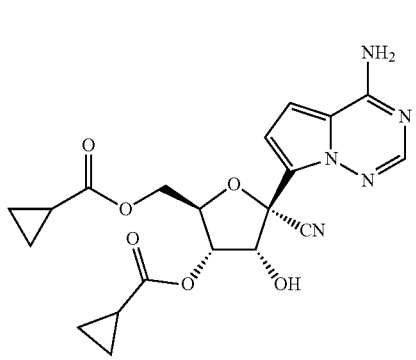
A129 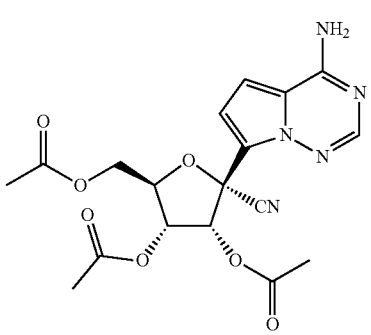
A130 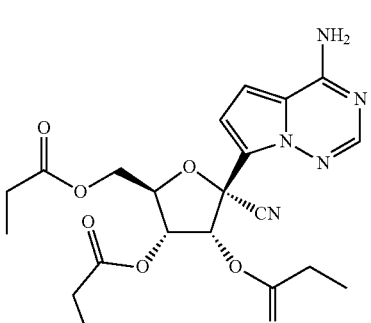
A131 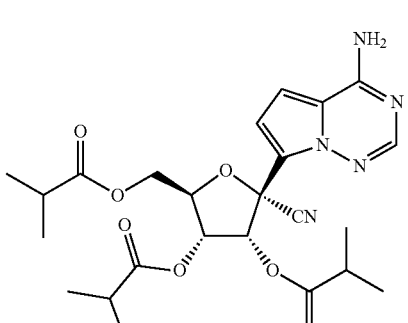
A132 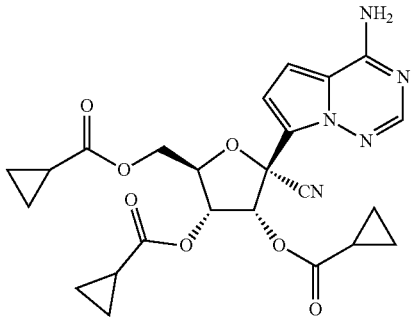
A133 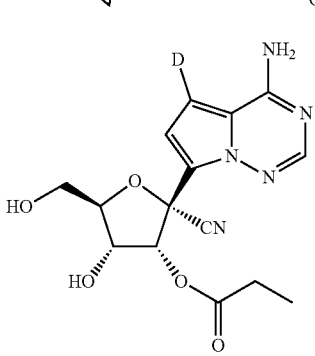

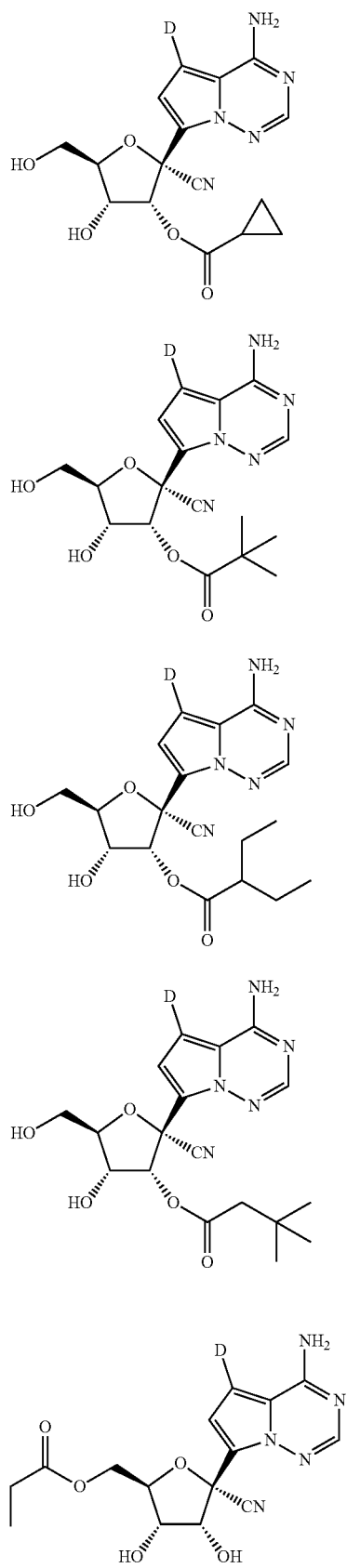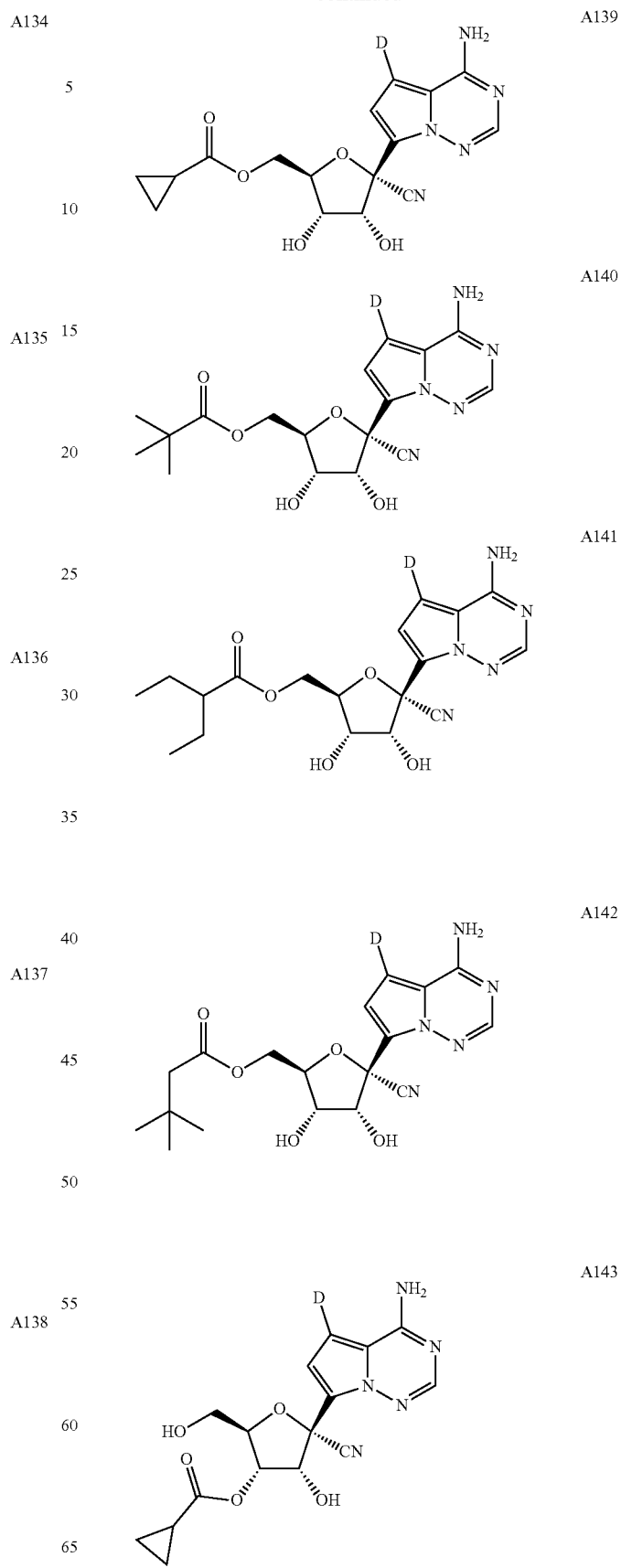

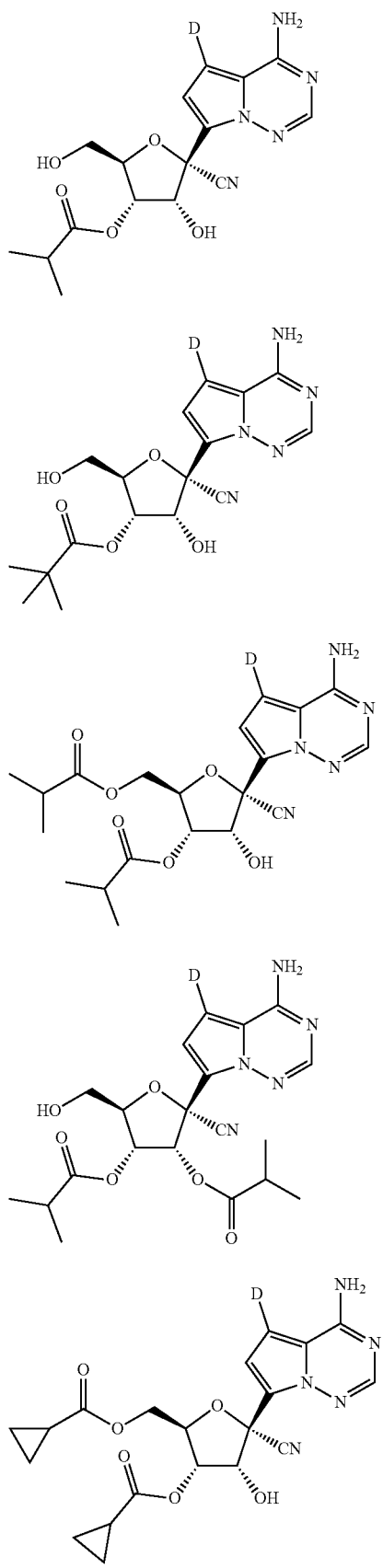

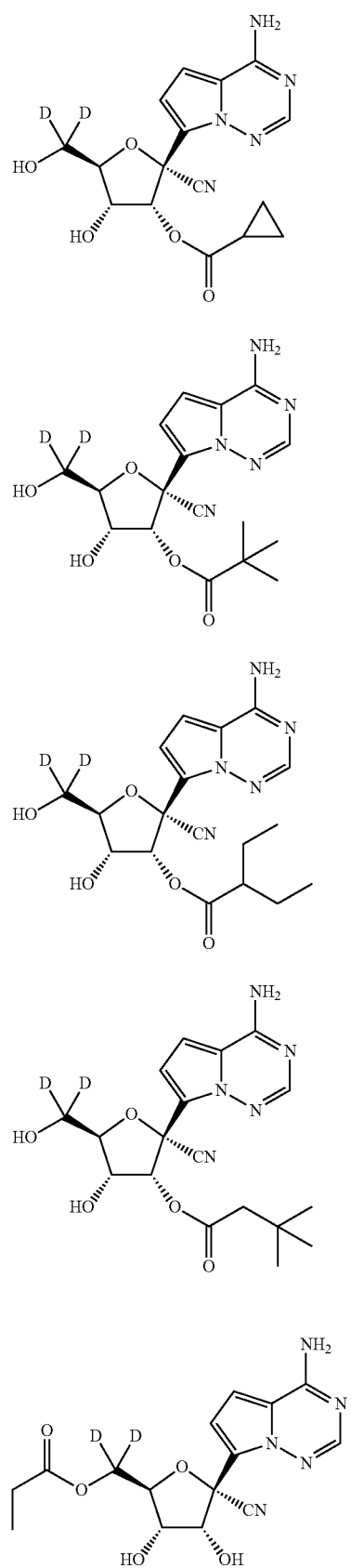
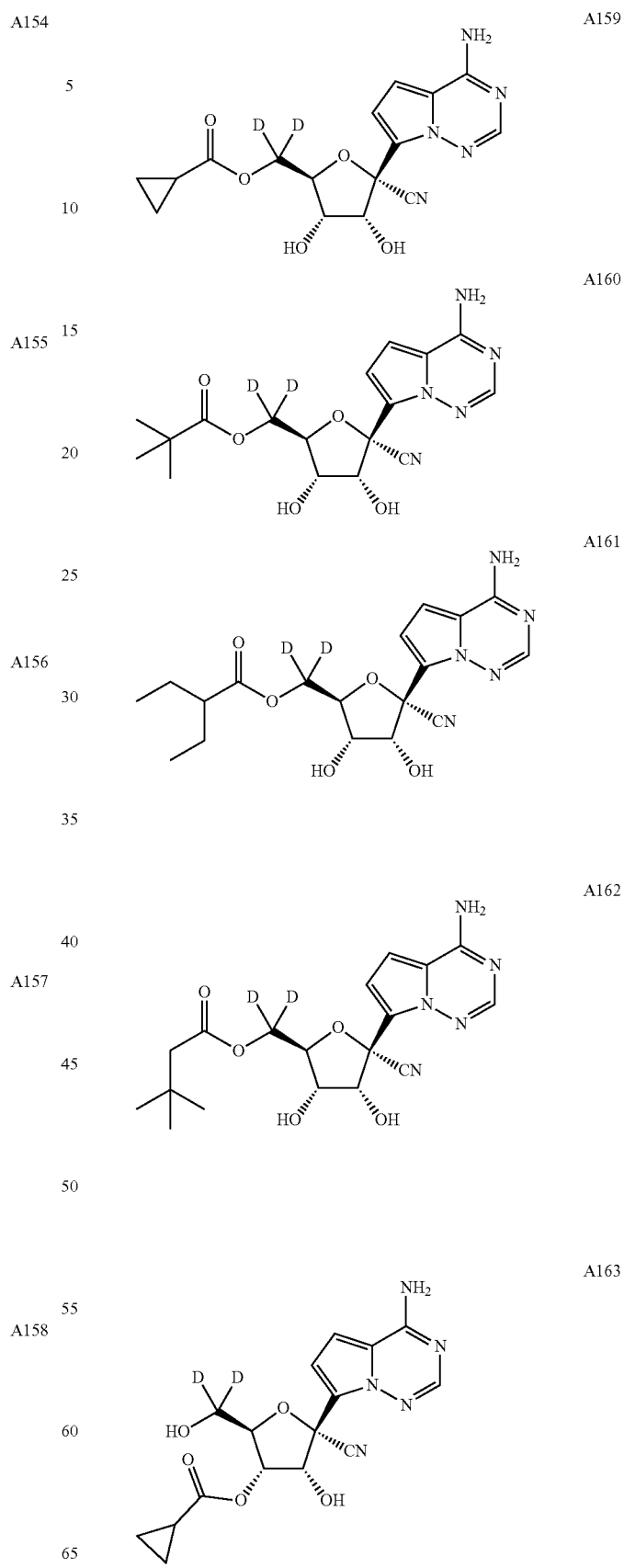

-continued
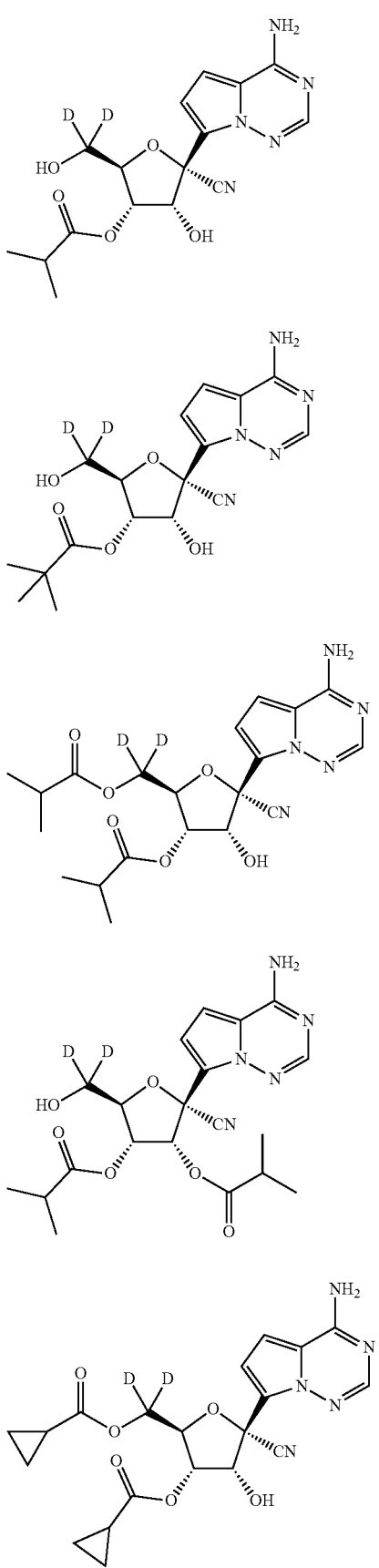
A164
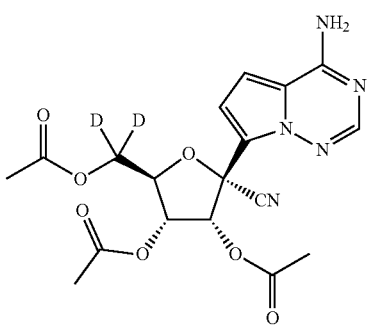
A165
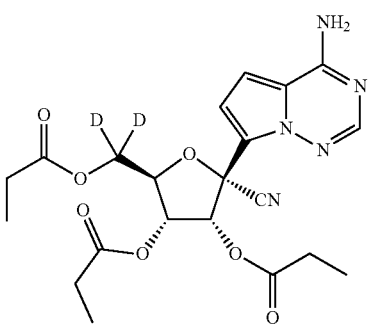
A166
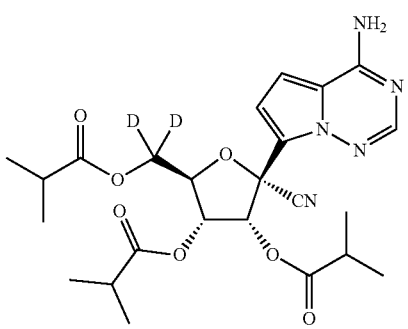 [SMILES: [2H]C([2H])(OC(=O)C(C)C)[C@H]1O[C@@](C#N)(c2ccc3c(N)ncnn23)[C@H](OC(=O)C(C)C)[C@@H]1OC(=O)C(C)C]
A167
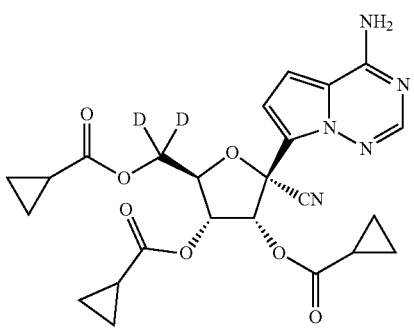
A168
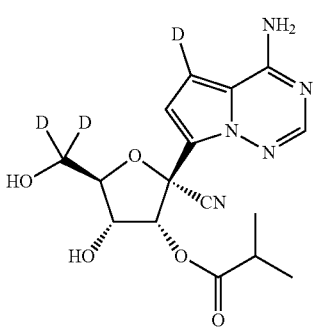
-continued
A169
A170
A171
A172
A173

A174 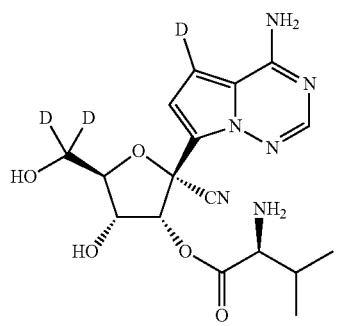
A175 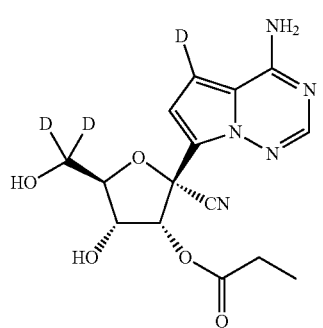
A176 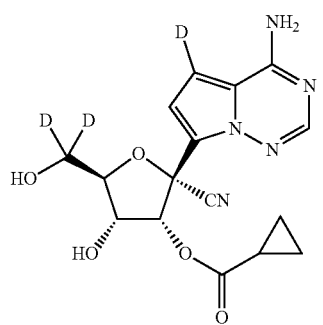
A177 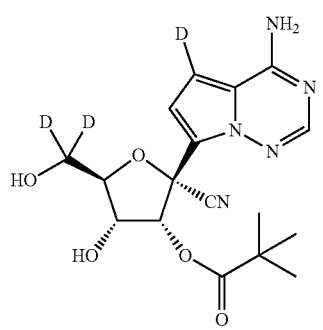
A178 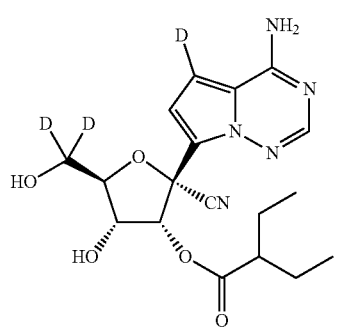
A179 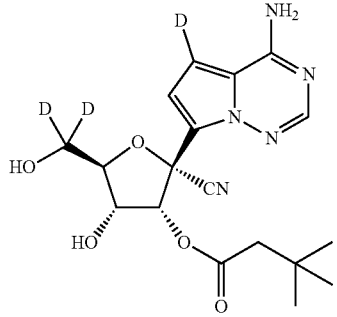
A180 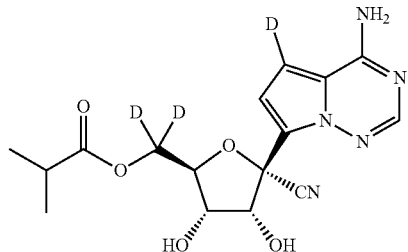 [SMILES: [2H]c1cc([C@]2(C#N)O[C@H](C([2H])([2H])OC(=O)C(C)C)[C@@H](O)[C@H]2O)n2ncnc(N)c12]
A181 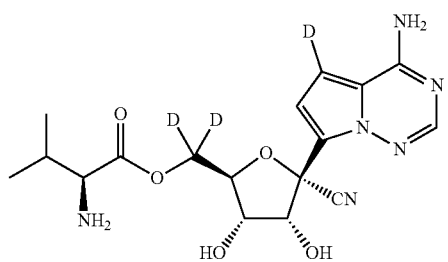 [SMILES: [2H]c1cc([C@]2(C#N)O[C@H](C([2H])([2H])OC(=O)[C@@H](N)C(C)C)[C@@H](O)[C@H]2O)n2ncnc(N)c12]
A182 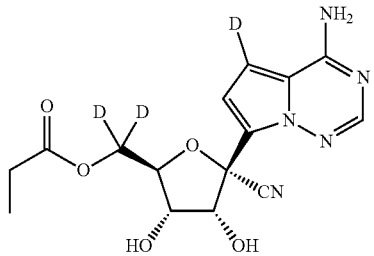
A183 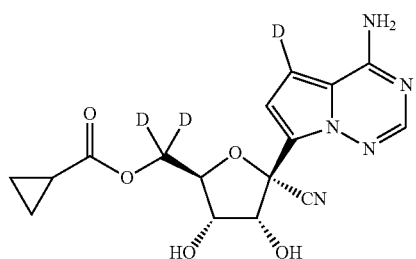
A184 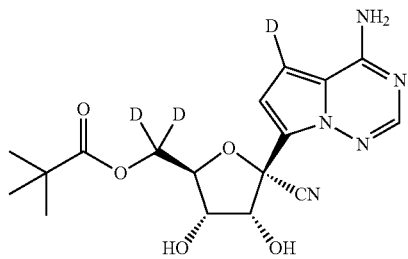

A185
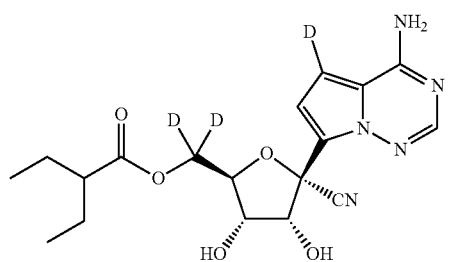
A186
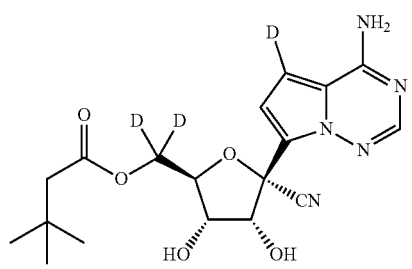
A187
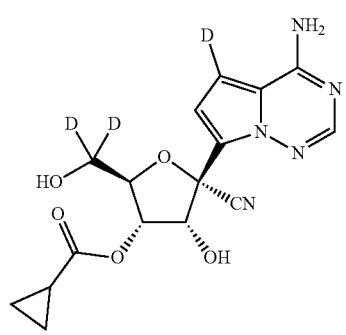
A188
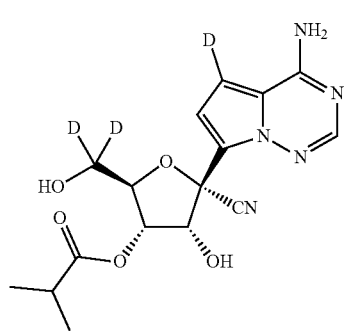
A189
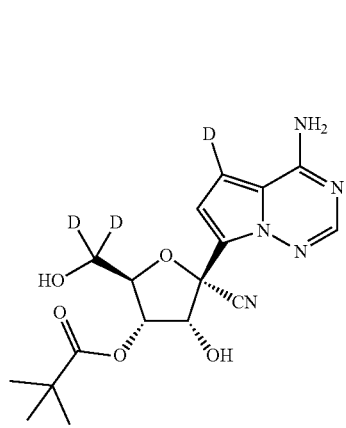
A190
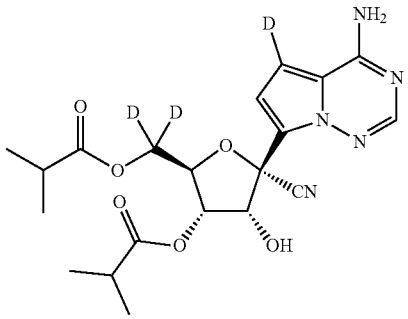
A191
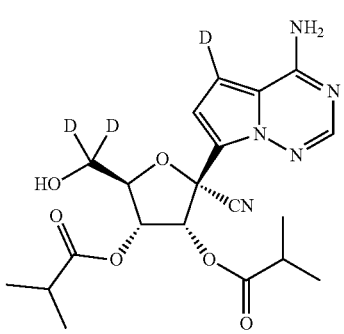
A192
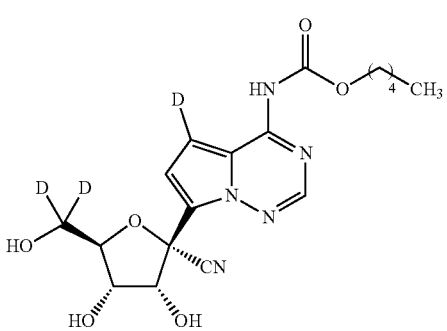
A193
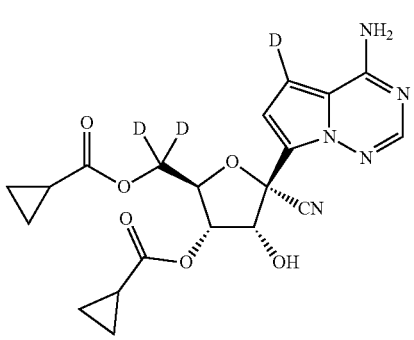
A194
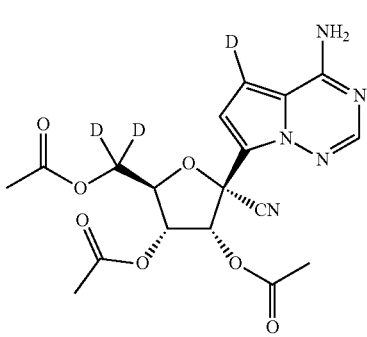

A195
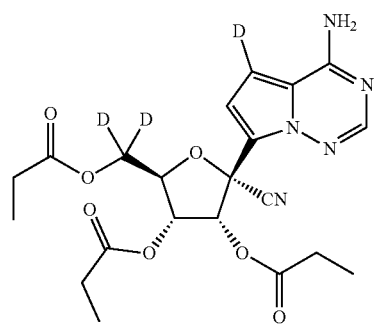
A196
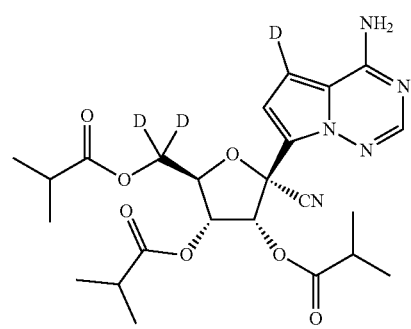 [SMILES: [2H]c1cc([C@]2(C#N)O[C@H](C([2H])([2H])OC(=O)C(C)C)[C@@H](OC(=O)C(C)C)[C@H]2OC(=O)C(C)C)n2ncnc(N)c12]
A197
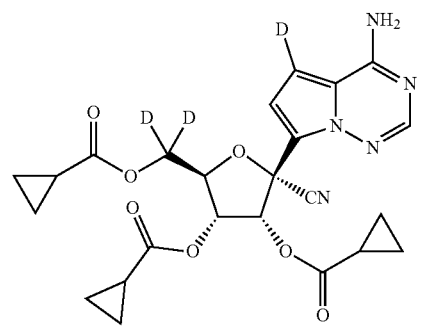
A198
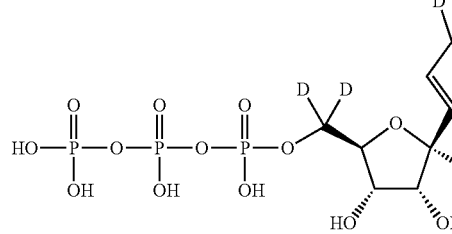
A200
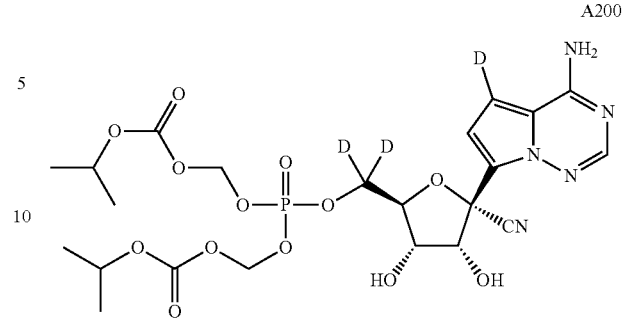
A201
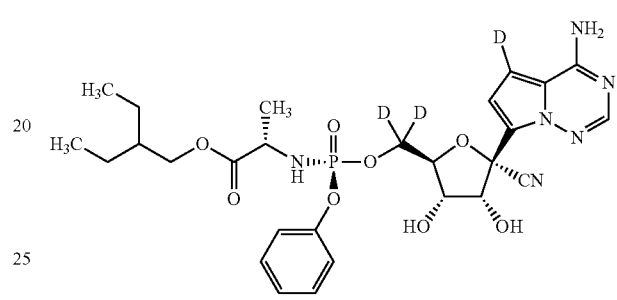
A202
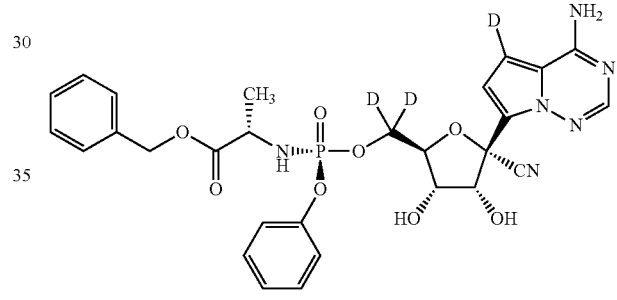
A203
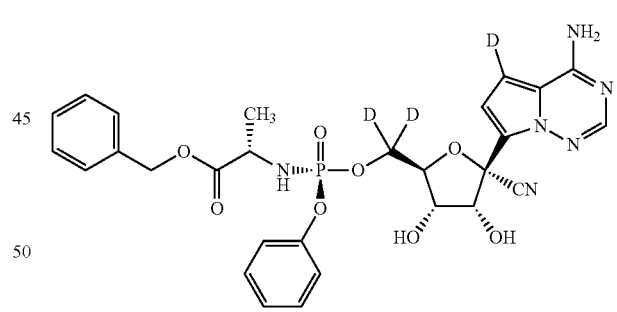
A204
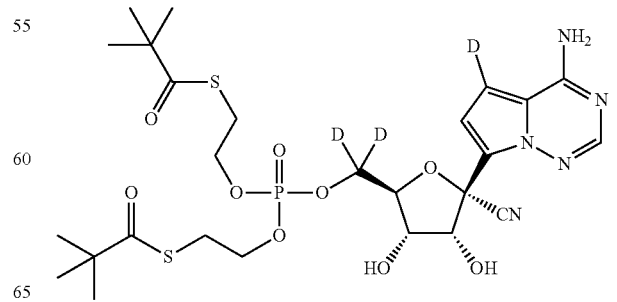

-continued
A205
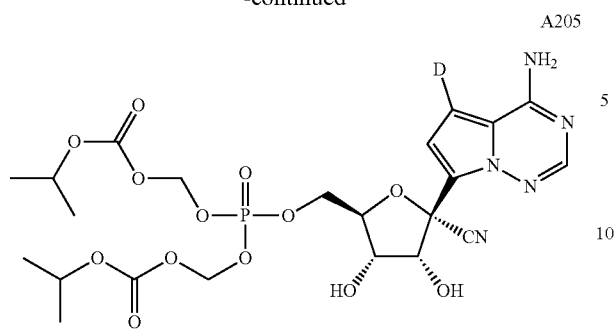
A206
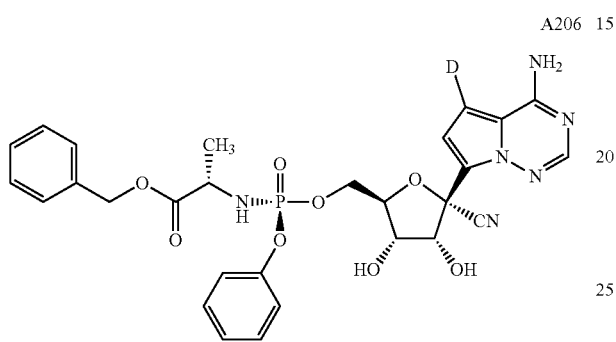
A207
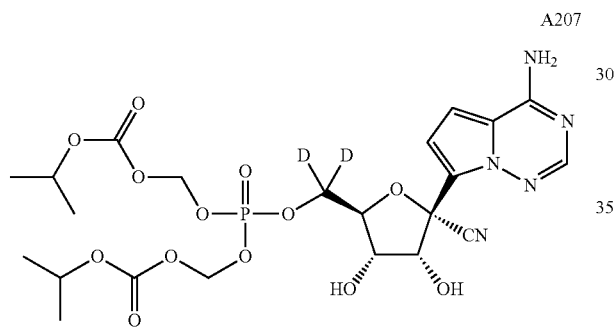
A208
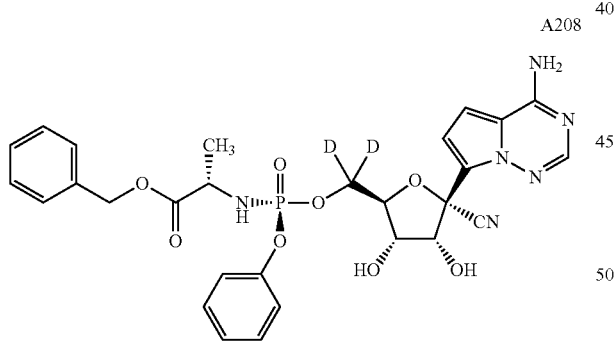
A209
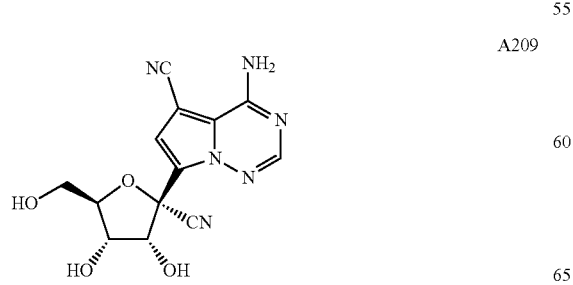
-continued
A210
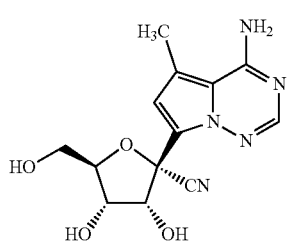 [SMILES: N#Cc1cc([C@]2(C#N)O[C@H](CO)[C@@H](O)[C@H]2O)n2ncnc(N)c12]
A211
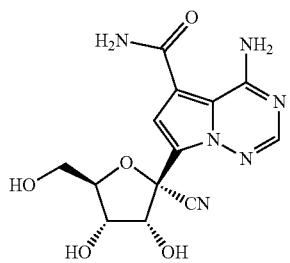
A212
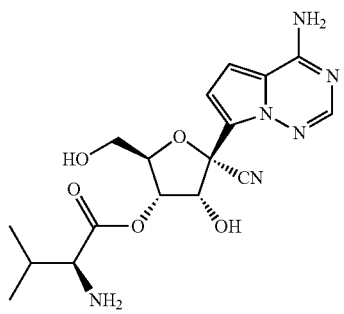
A213
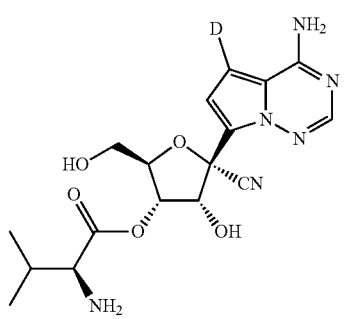
A214

-continued
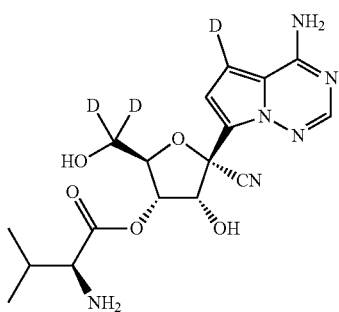
A215
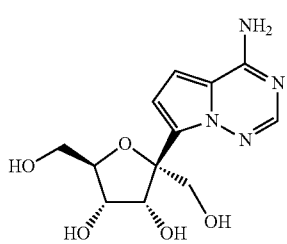
A216
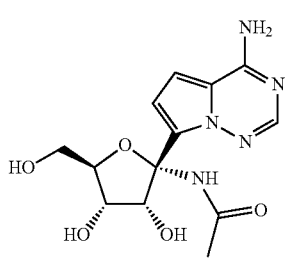
A217
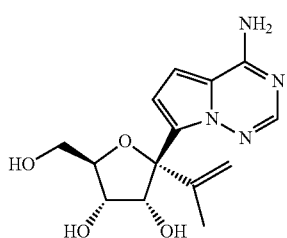
A218
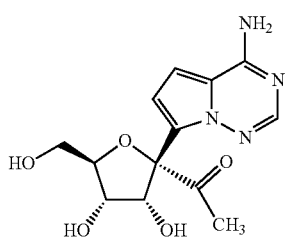
A219
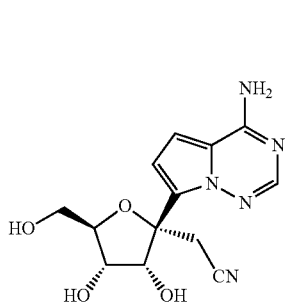
A220
-continued
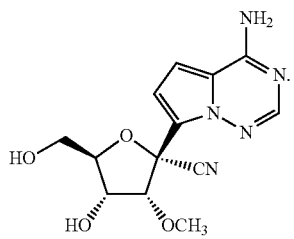
A221
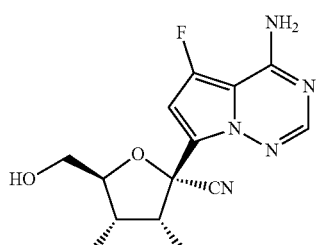
A1
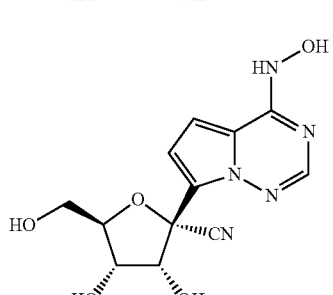
A5
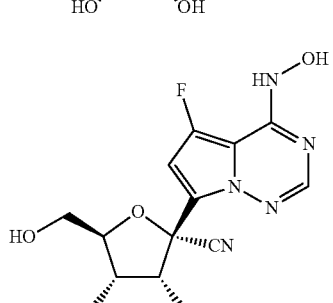
A6
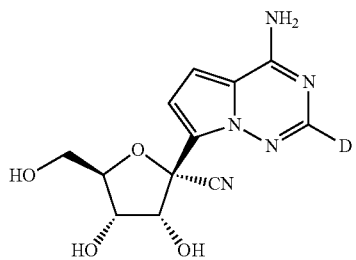
A8

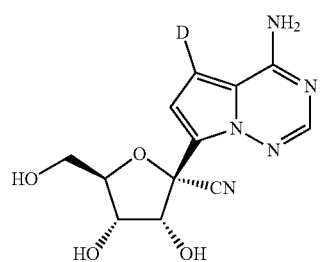
A9
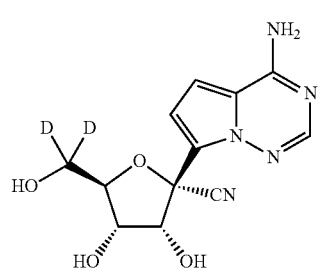
A10
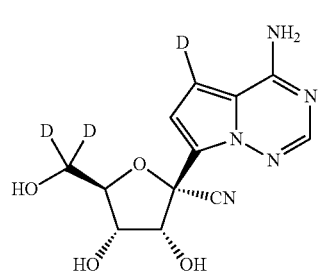
A11
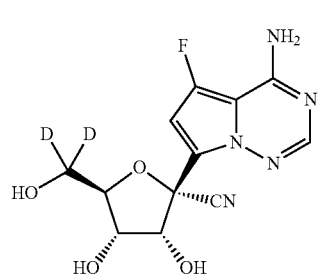
A12
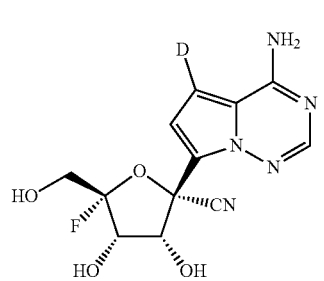
A13
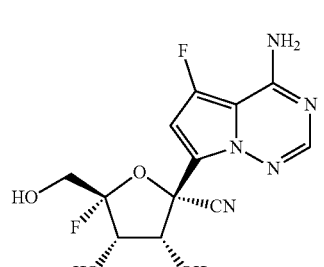
A14
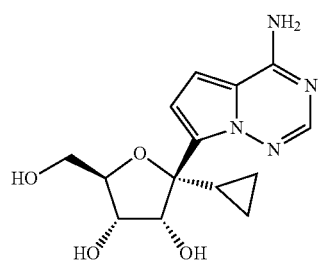
A28
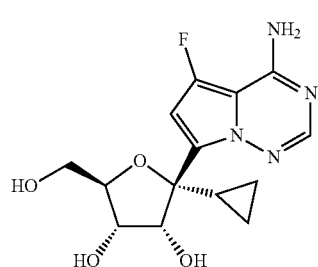
A30
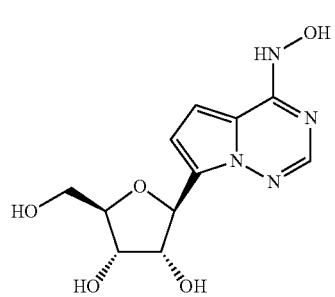
A35
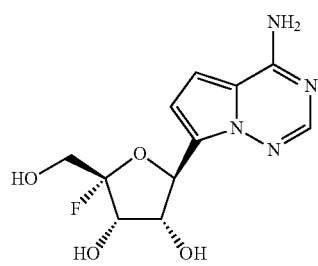
A36
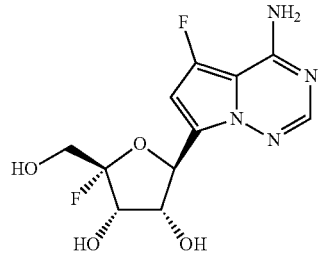
A37
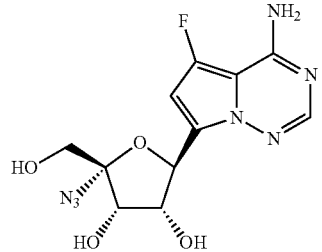
A38

51
-continued
A39
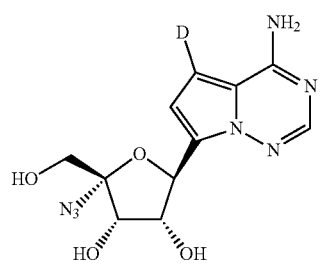
A40
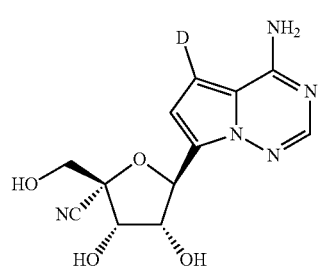
A41
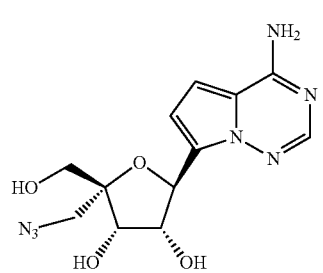
A42
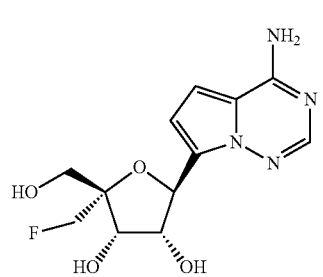
A43
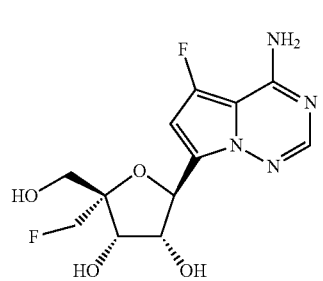
A44
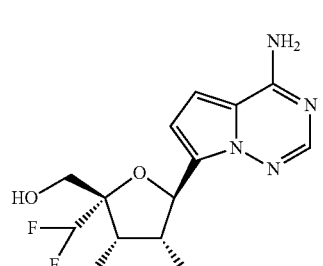
52
-continued
A45
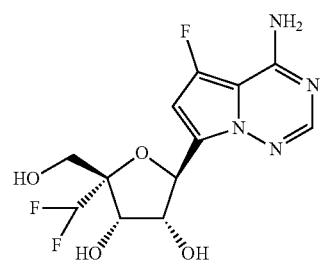
A46
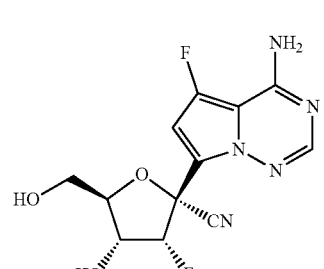
A49
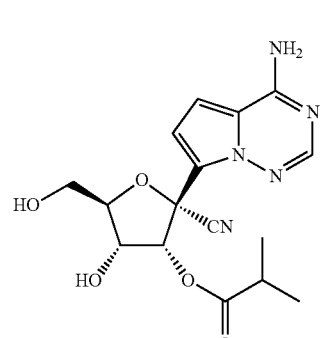
A50
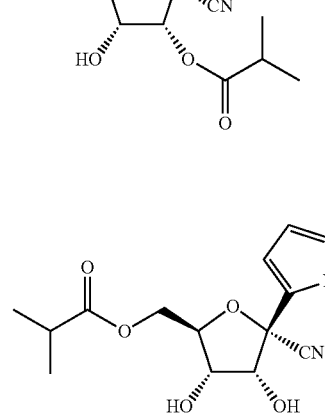
A51
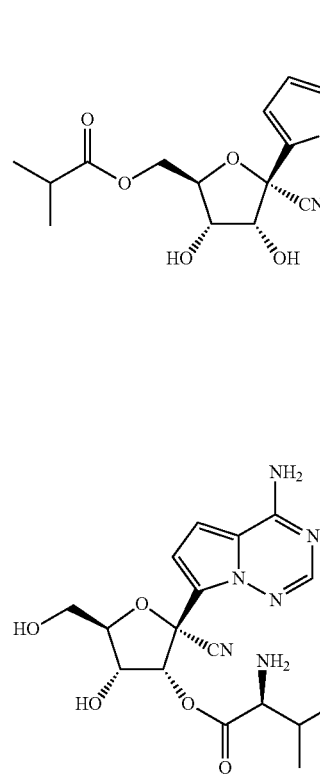

-continued
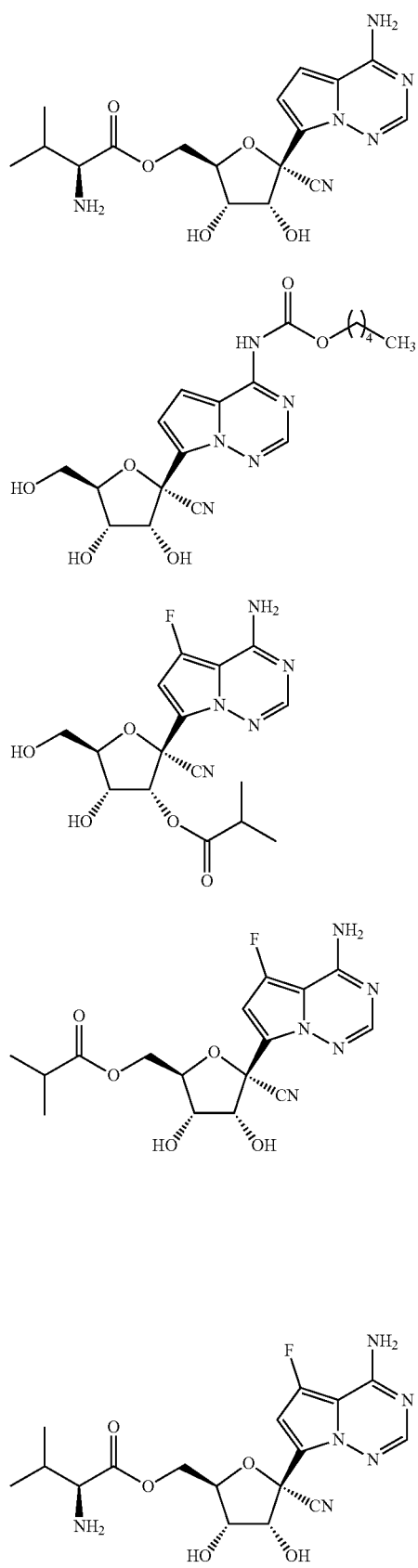
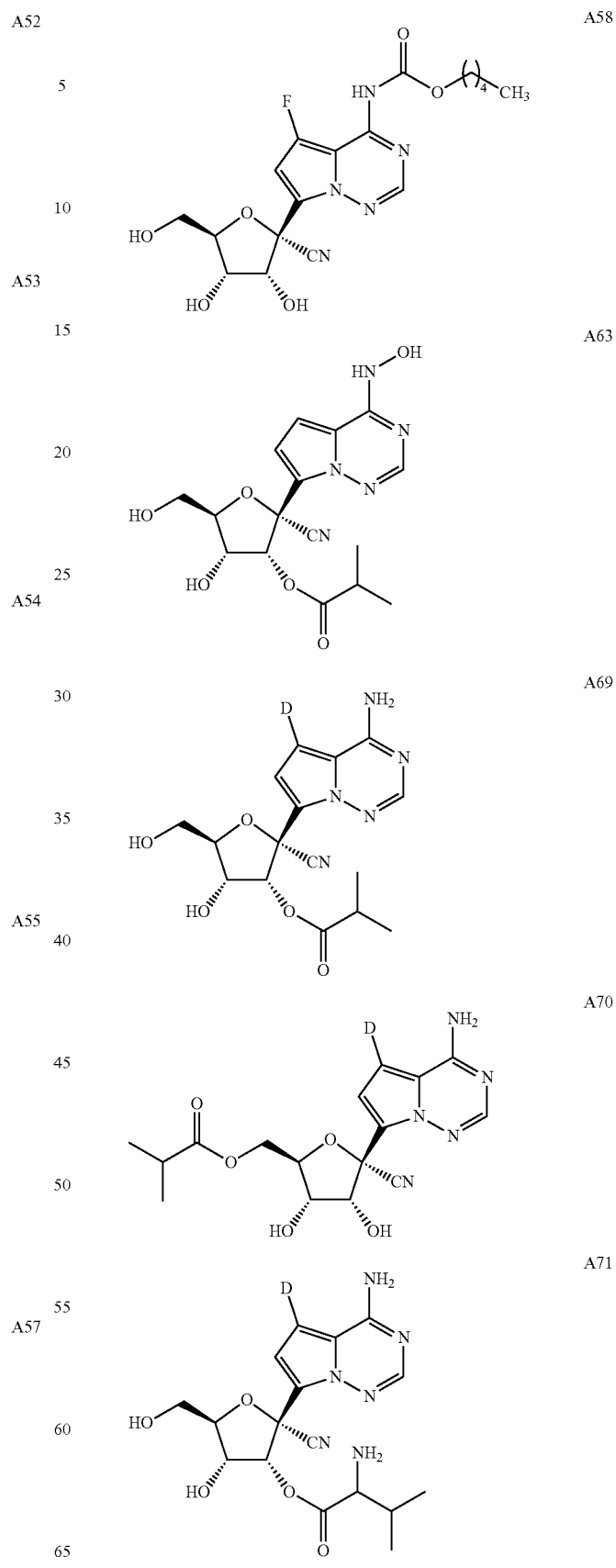

-continued
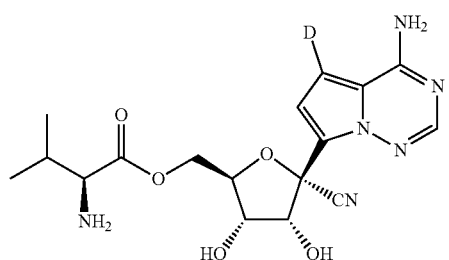 [SMILES: [2H]c1cc([C@]2(C#N)O[C@H](COC(=O)[C@@H](N)C(C)C)[C@@H](O)[C@H]2O)n2ncnc(N)c12]
A72
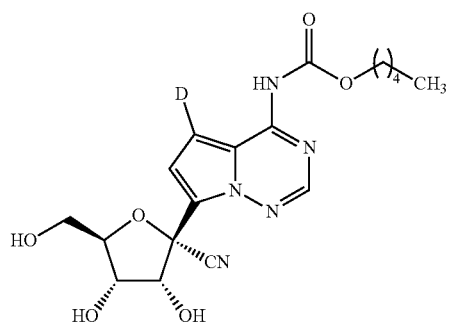
A73
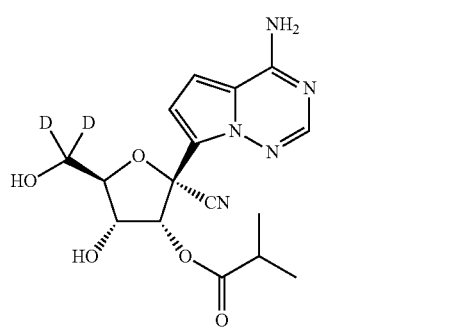
A74
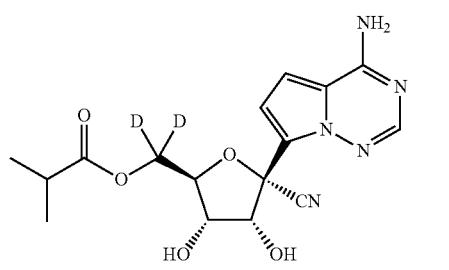 [SMILES: [2H]C([2H])(OC(=O)C(C)C)[C@H]1O[C@@](C#N)(c2ccc3c(N)ncnn23)[C@H](O)[C@@H]1O]
A75
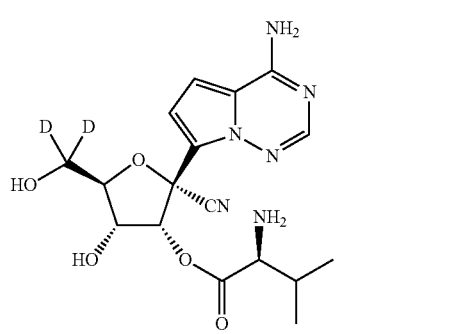
A76
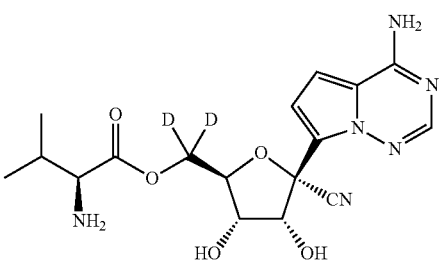 [SMILES: [2H]C([2H])(OC(=O)[C@@H](N)C(C)C)[C@H]1O[C@@](C#N)(c2ccc3c(N)ncnn23)[C@H](O)[C@@H]1O]
A77
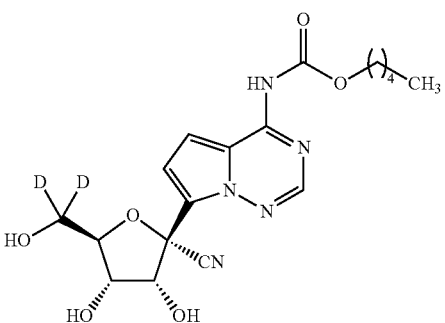
A78
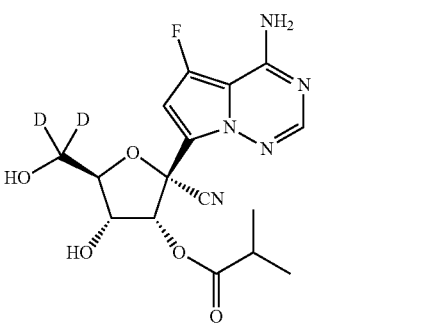
A79
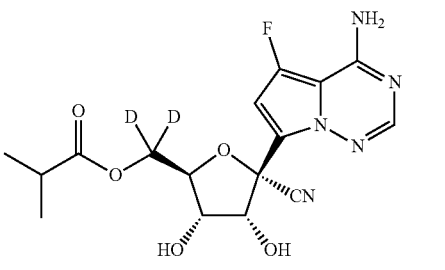
A80
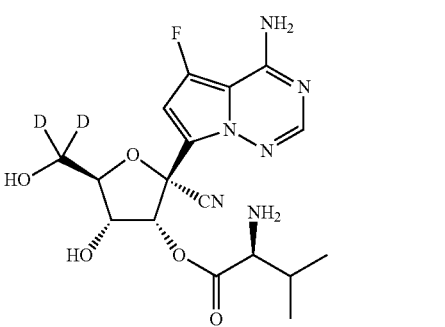
A81

-continued
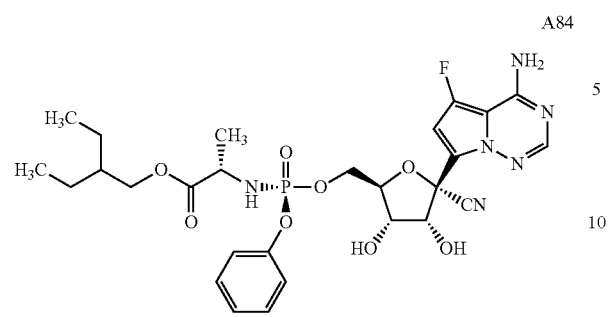
A84
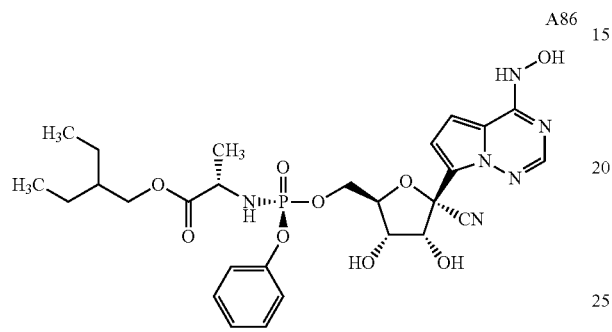
A86
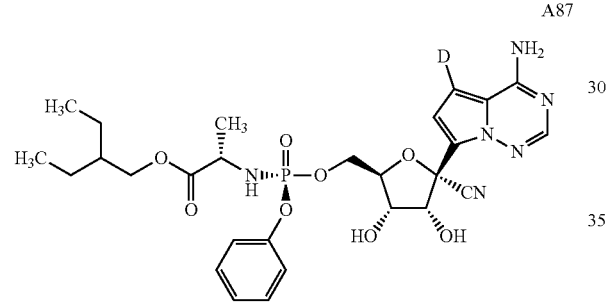
A87
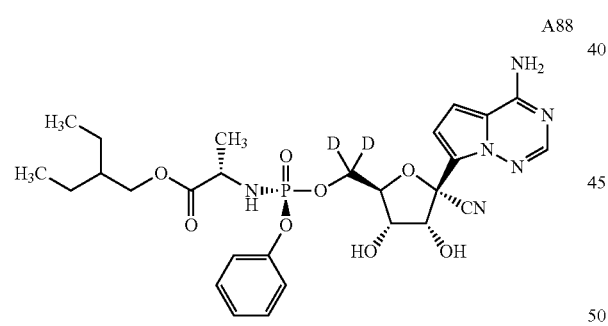
A88
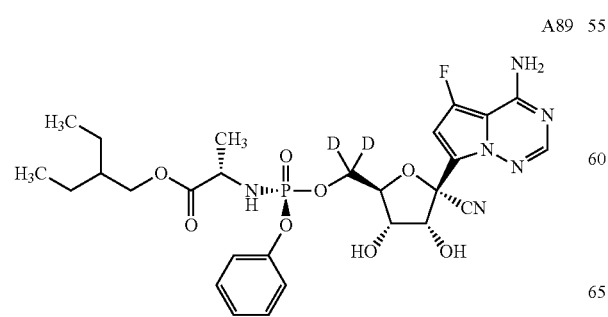
A89
-continued
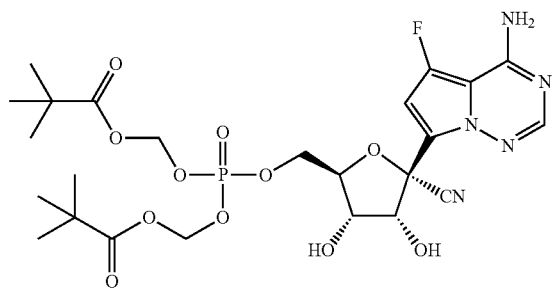
A91
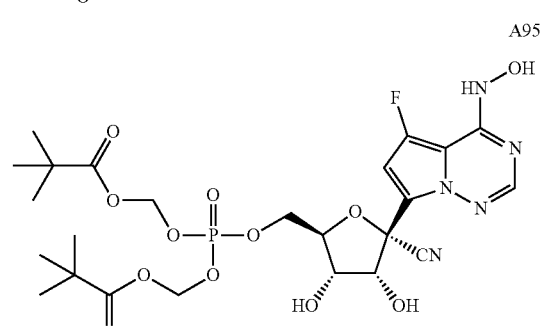
A95
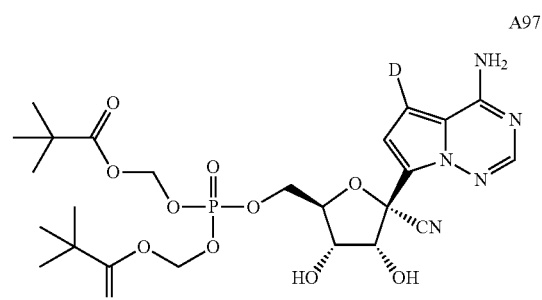
A97
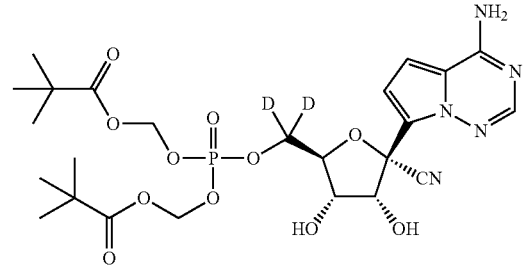
A99
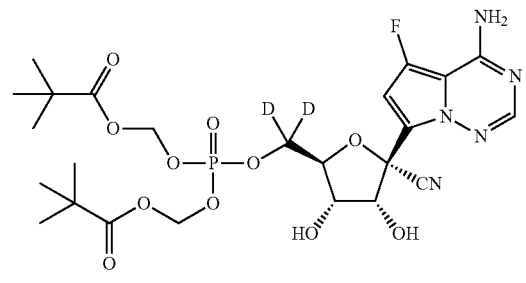
A101

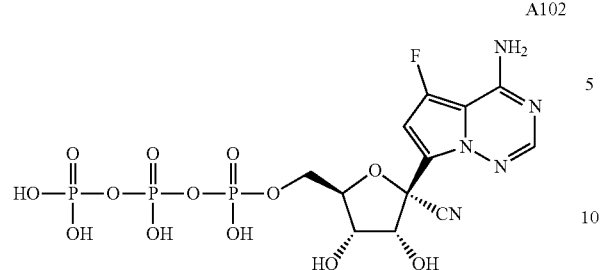
A102
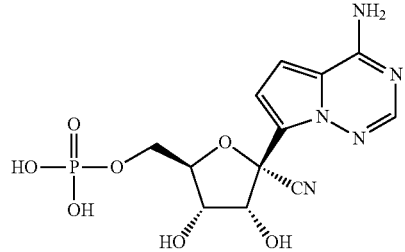
A110
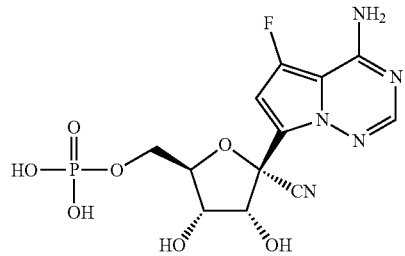
A111
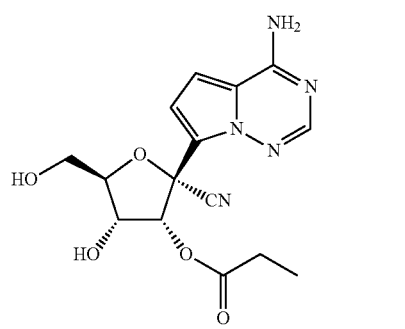
A113
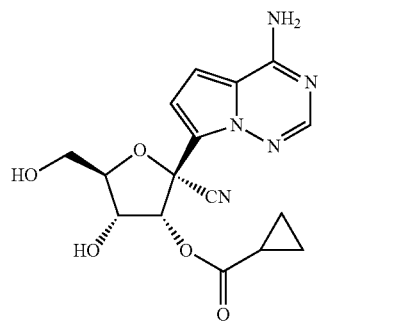
A114
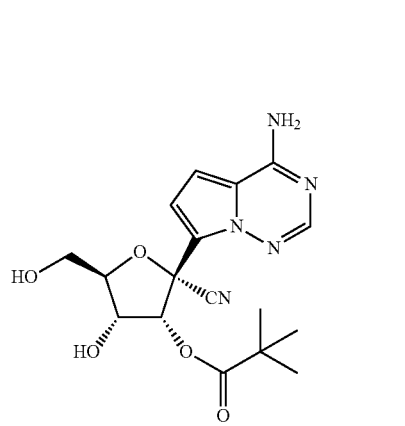
A115

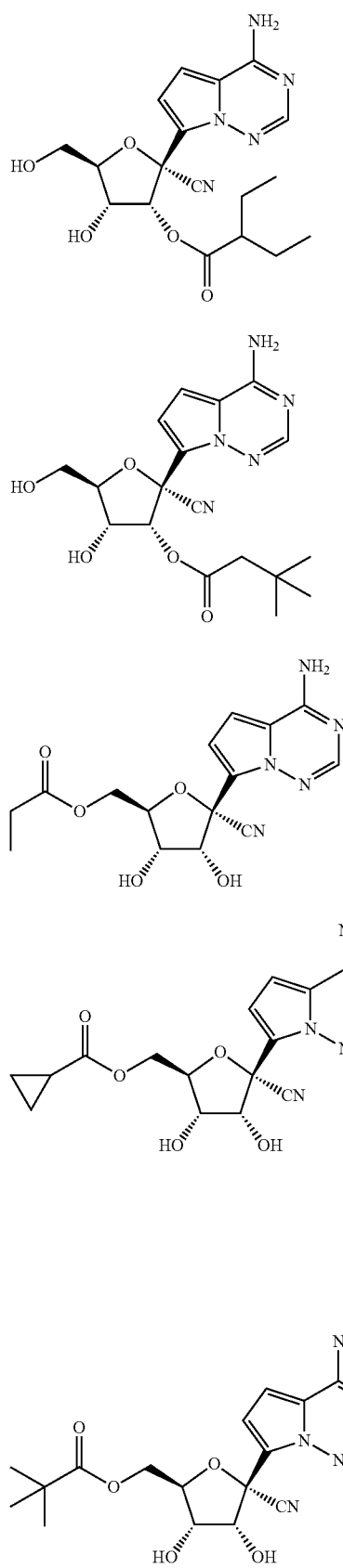
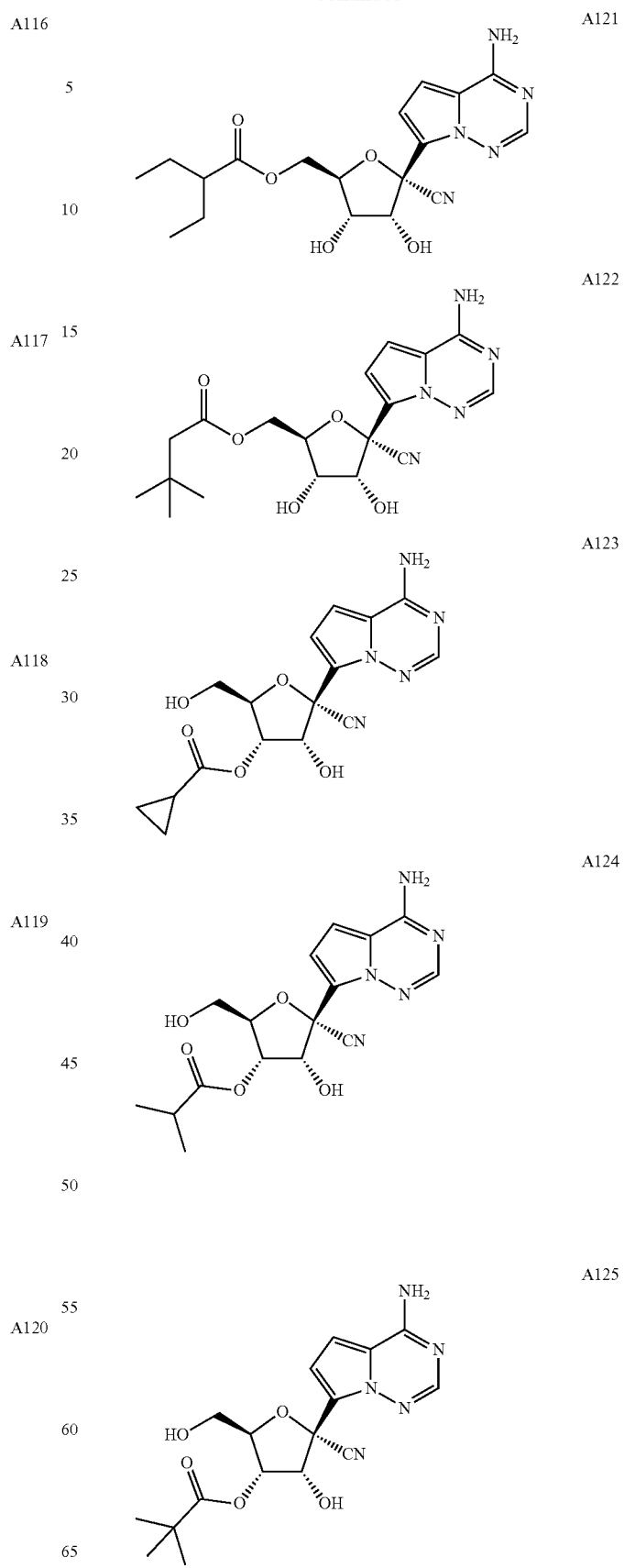

A126 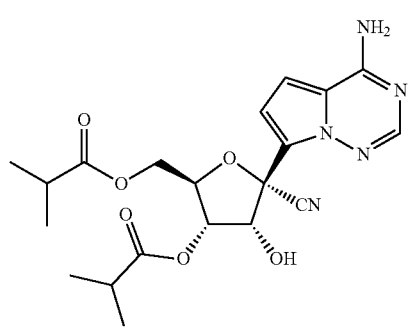
A127 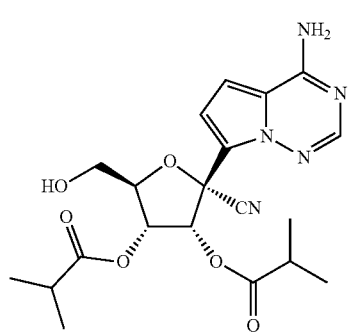
A128 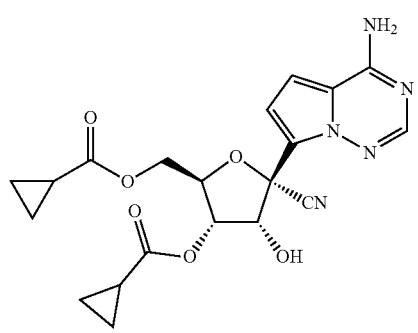
A129 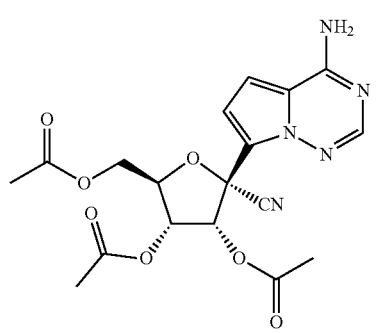
A130 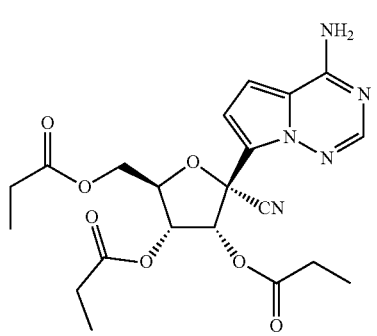
A131 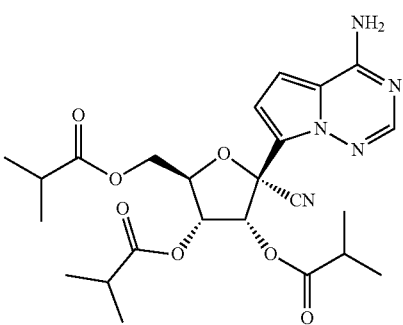 [SMILES: CC(C)C(=O)OC[C@H]1O[C@@](C#N)(c2ccc3c(N)ncnn23)[C@H](OC(=O)C(C)C)[C@@H]1OC(=O)C(C)C]
A132 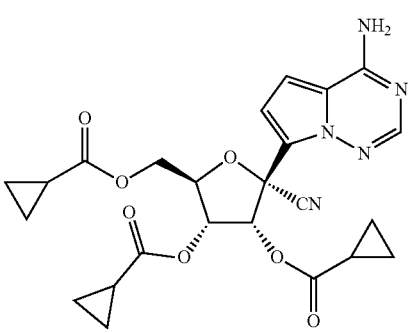
A133 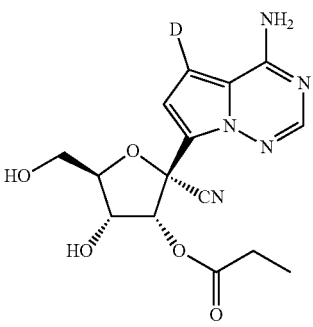
A134 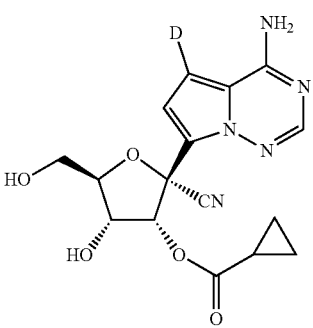
A135 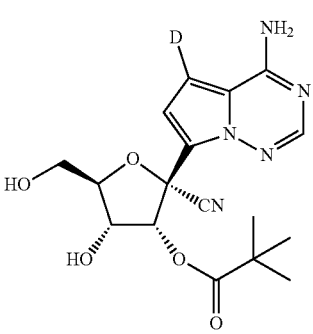

-continued
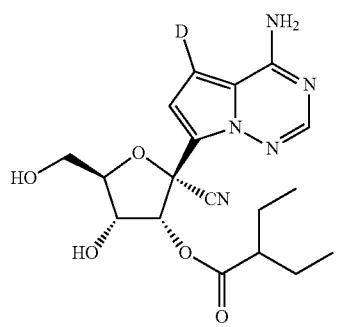
A136
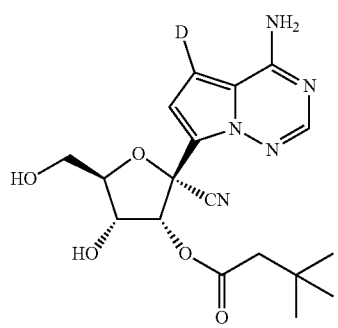
A137
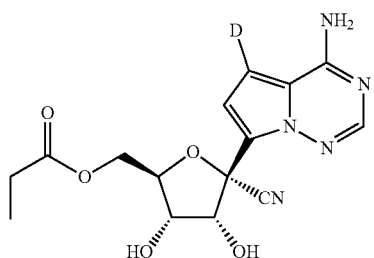
A138
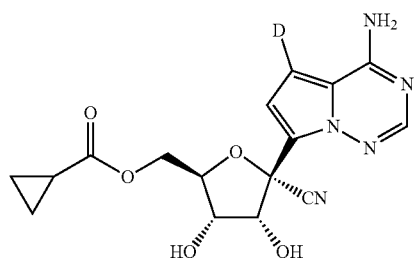
A139
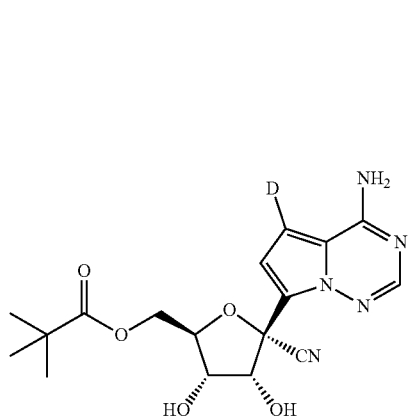
A140
-continued
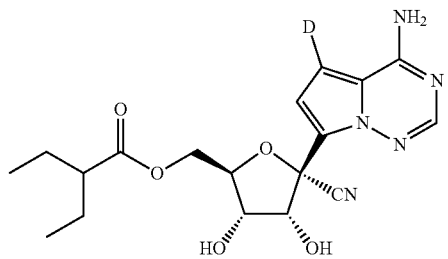
A141
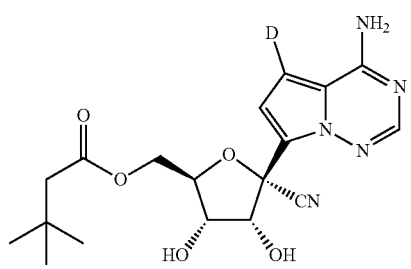
A142
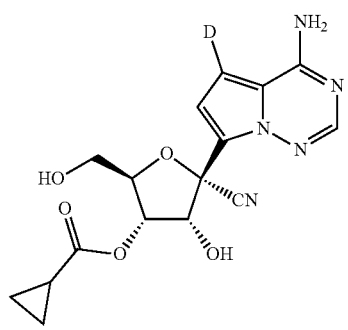
A143
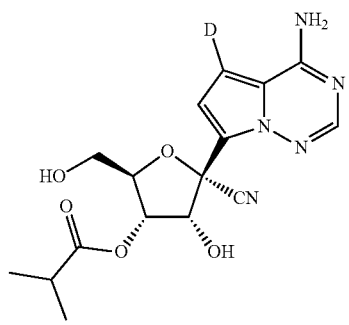
A144
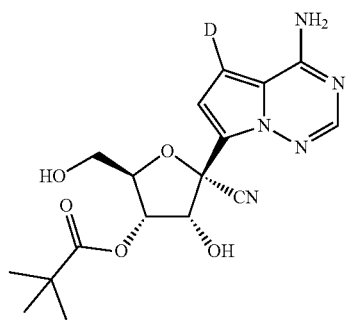
A145

A146 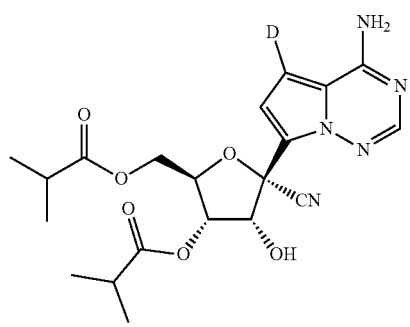
A147 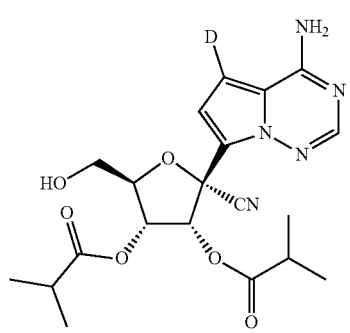
A148 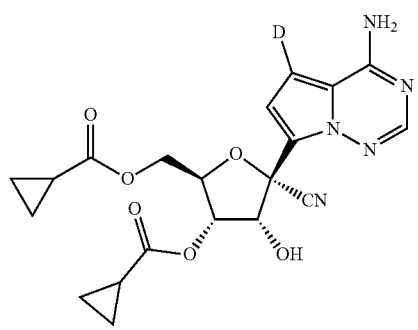
A149 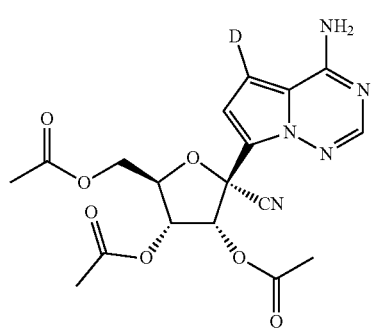
A150 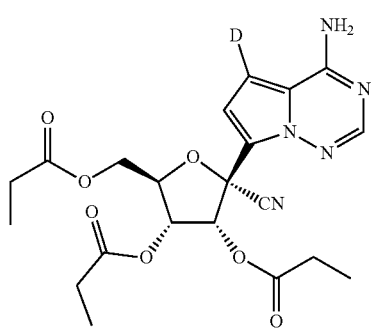
A151 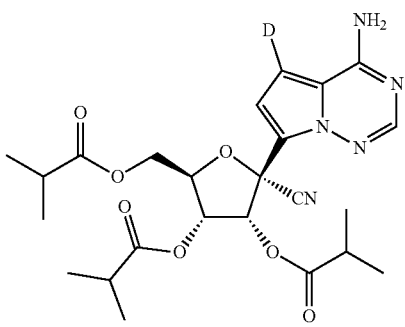 [SMILES: [2H]c1cc([C@]2(C#N)O[C@H](COC(=O)C(C)C)[C@@H](OC(=O)C(C)C)[C@H]2OC(=O)C(C)C)n2ncnc(N)c12]
A152 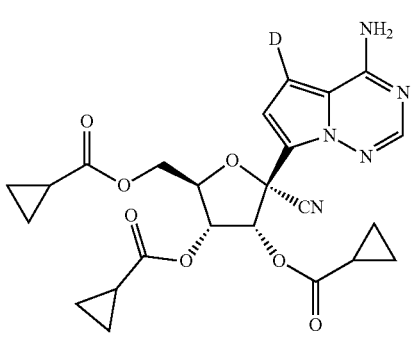
A153 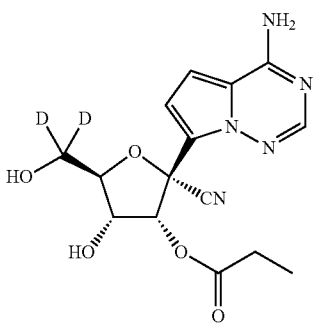
A154 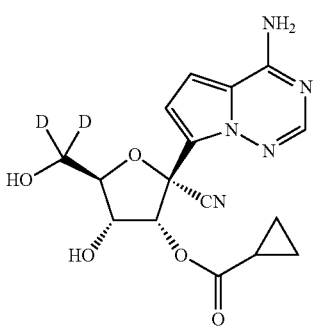

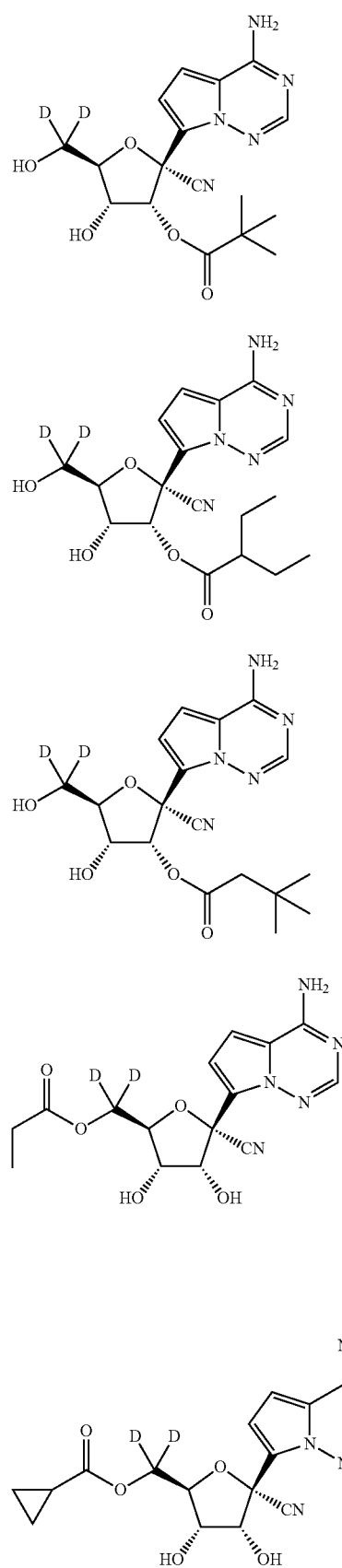
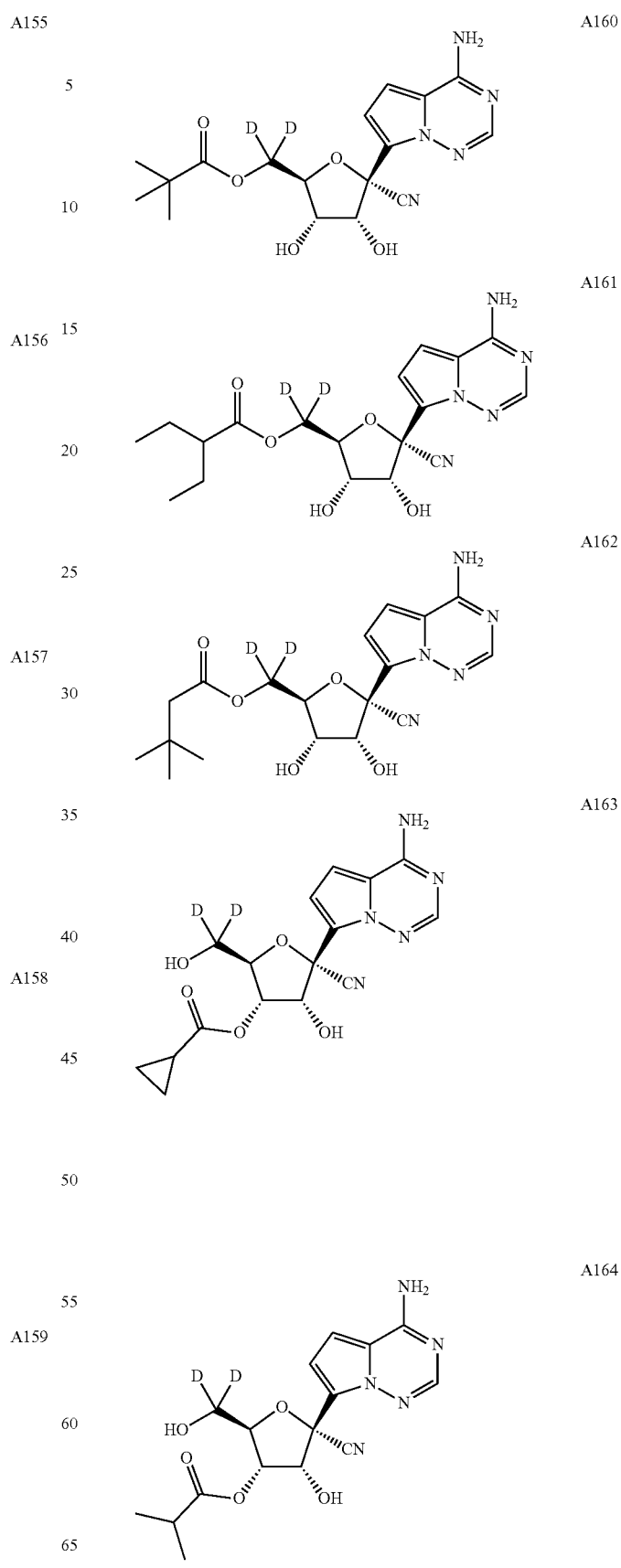

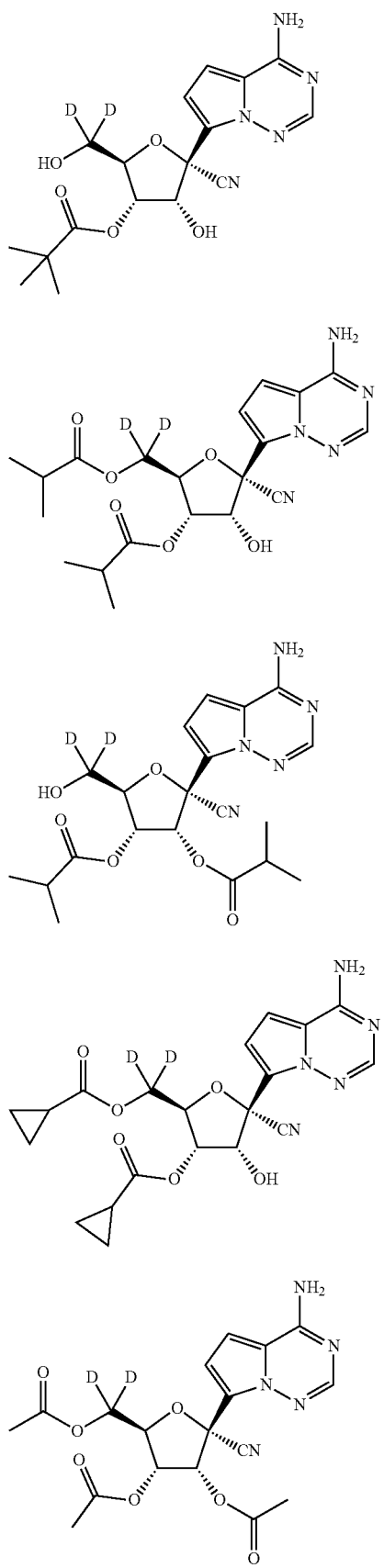
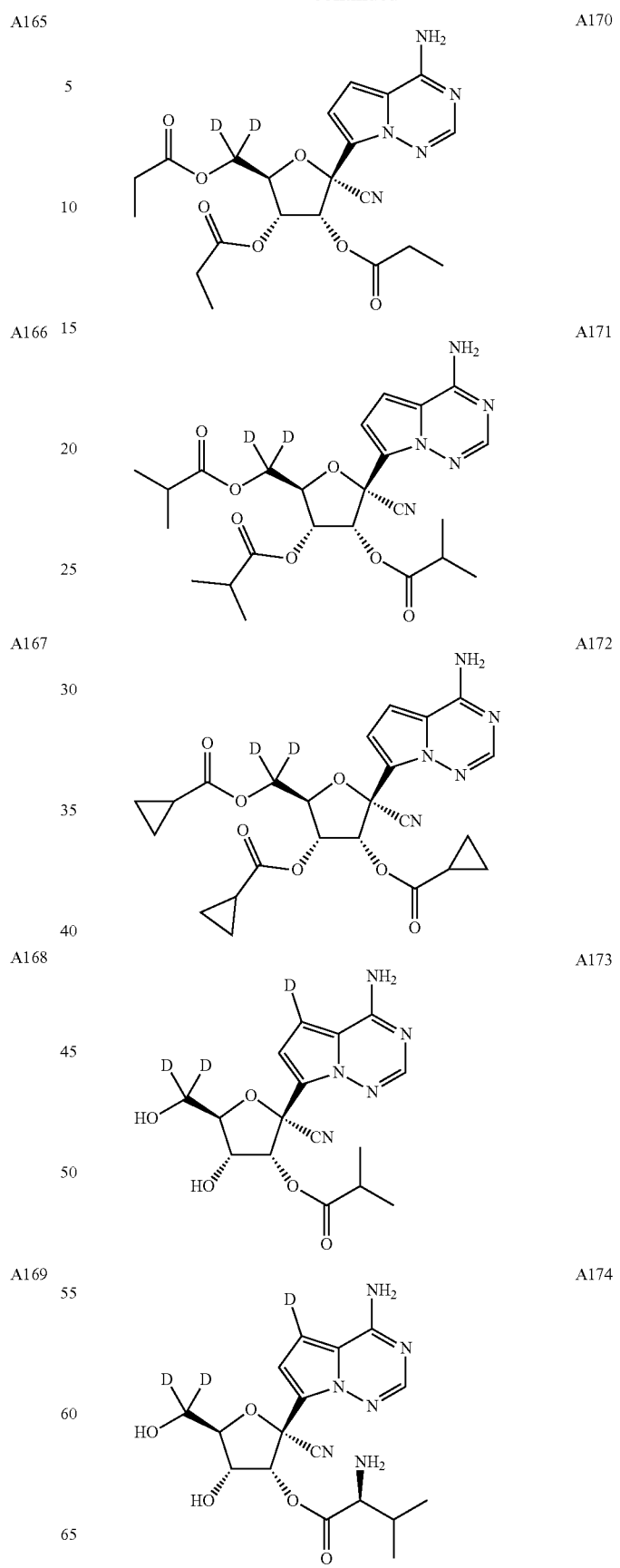

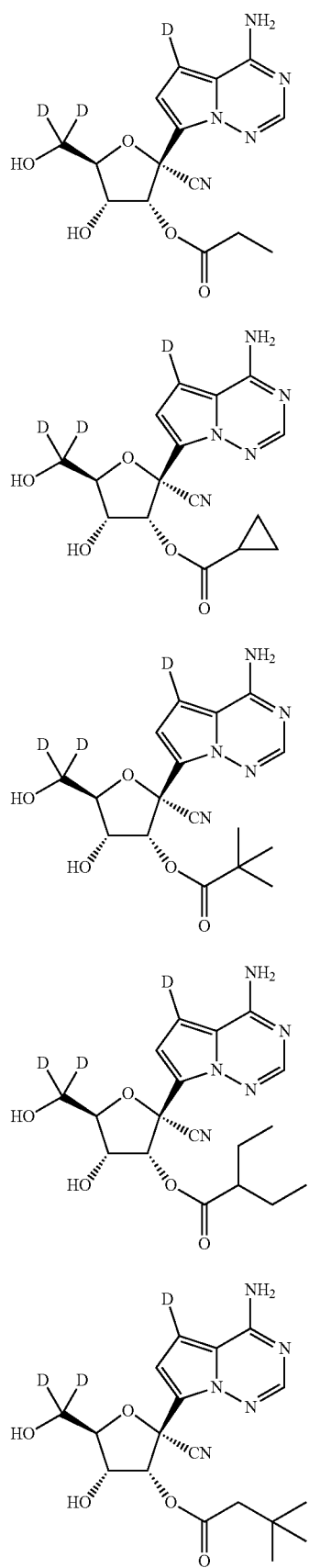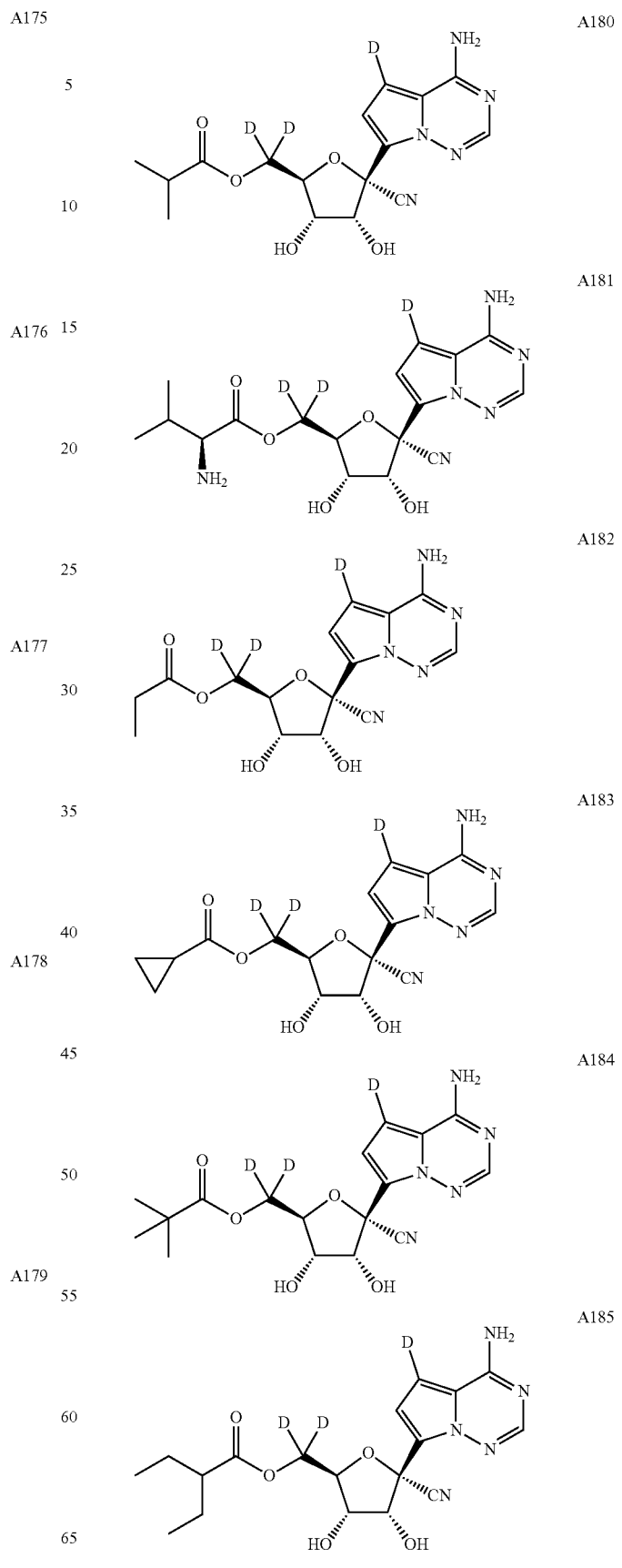

-continued
A186
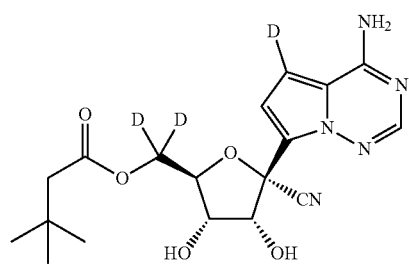
A187
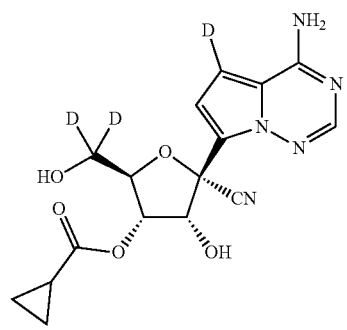
A188
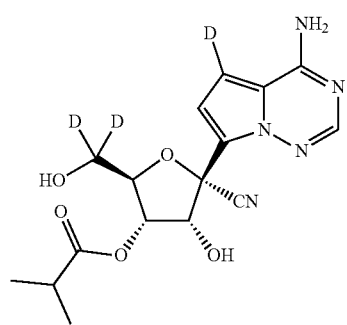
A189
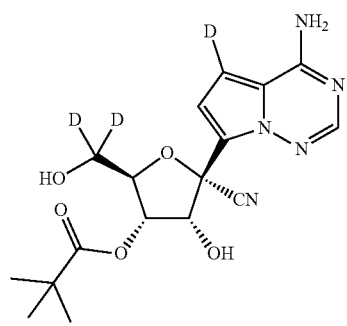
A190
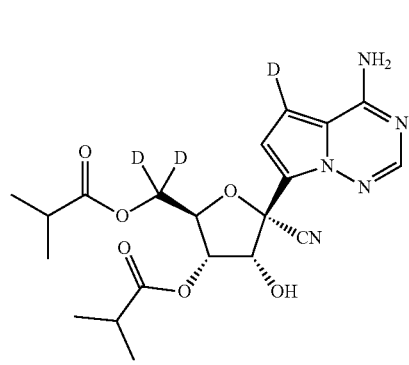
-continued
A191
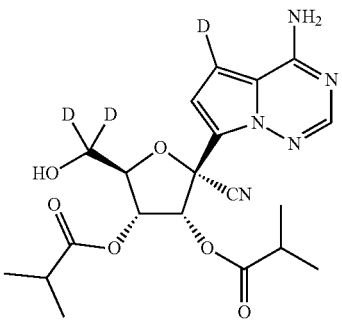
A192
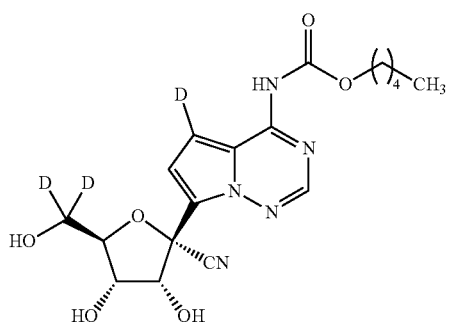
A193
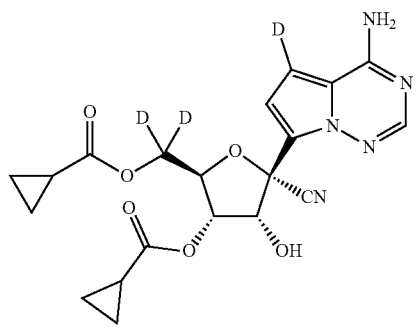
A194
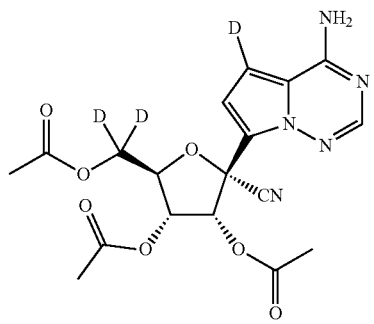
A195
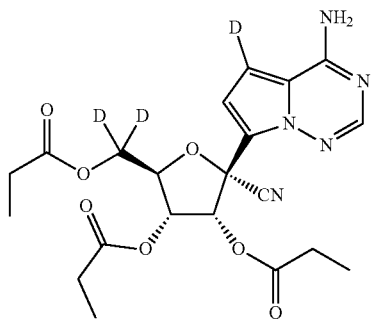

A196
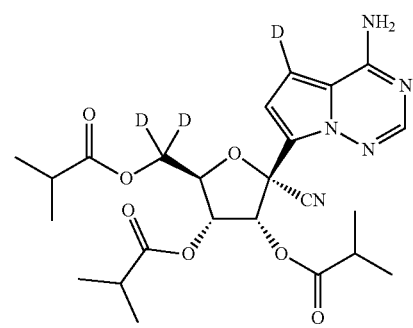
A201
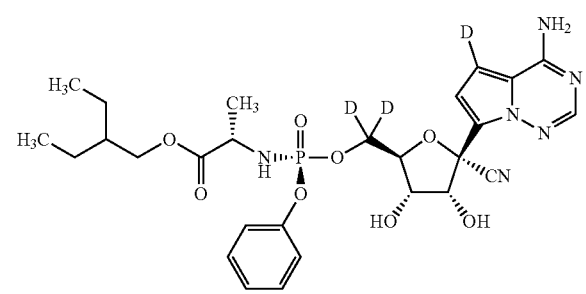
A197
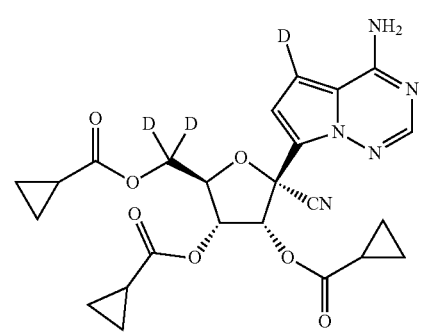
A202
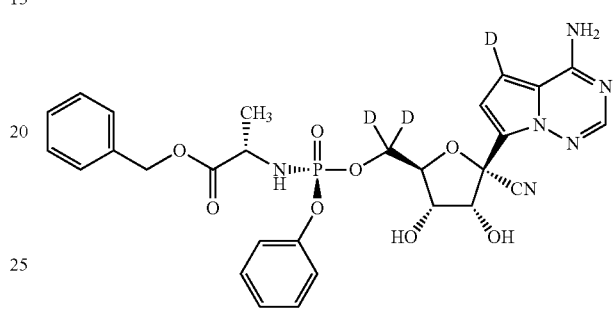
A198
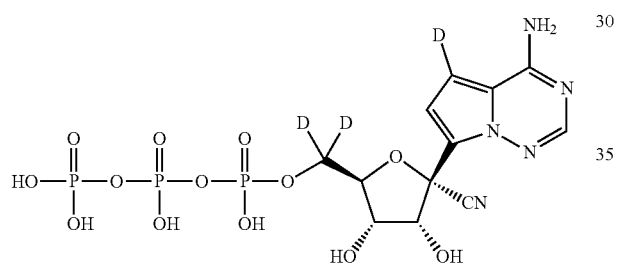
A203
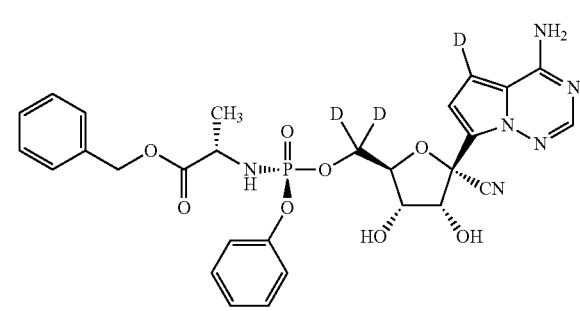
A199
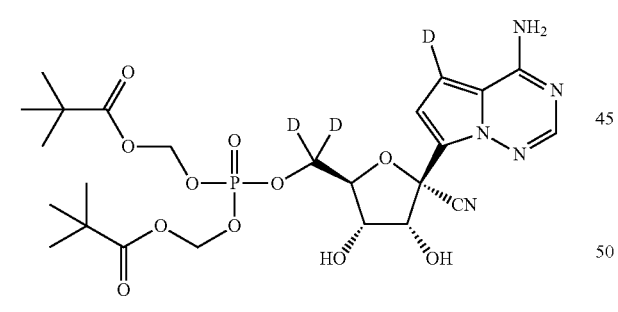
A204
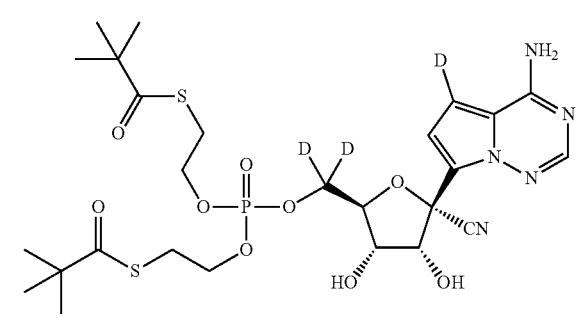
A200
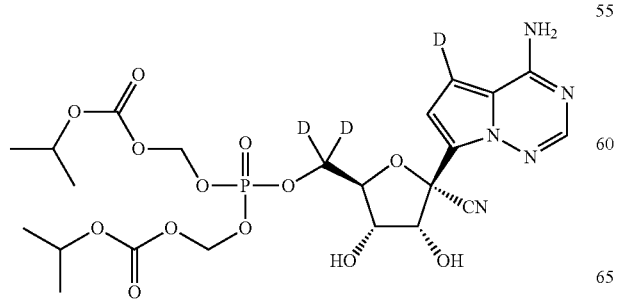
A205
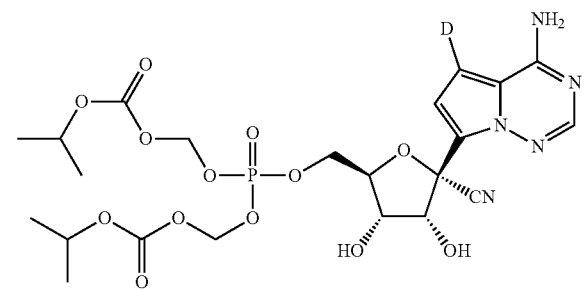

-continued
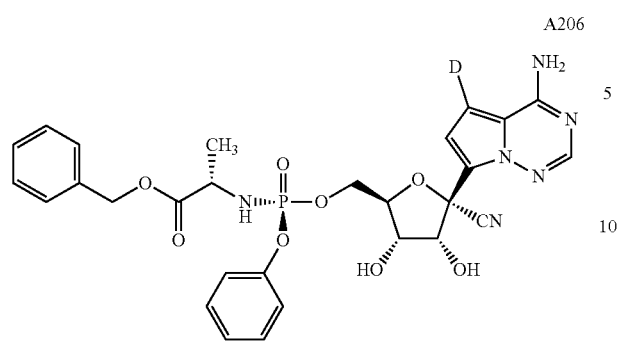
A206
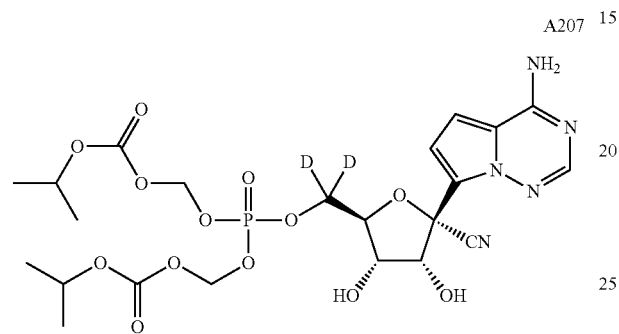
A207
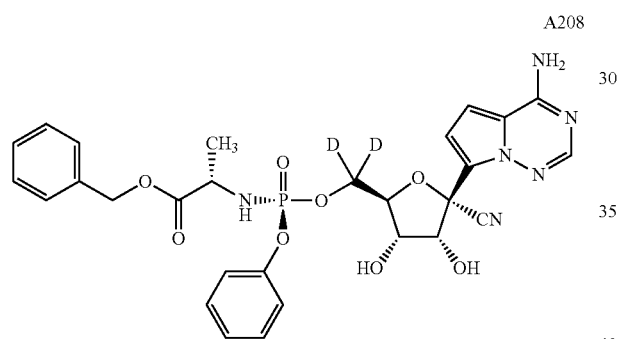
A208
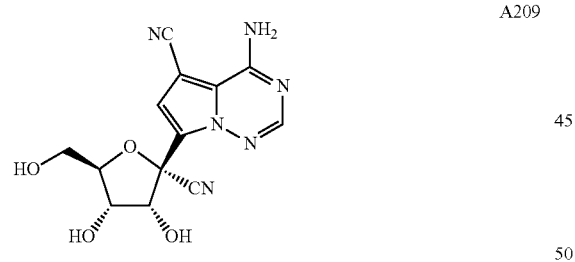
A209
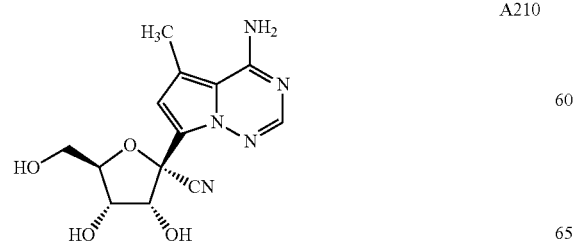
A210
-continued
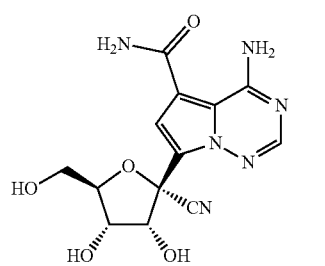
A211
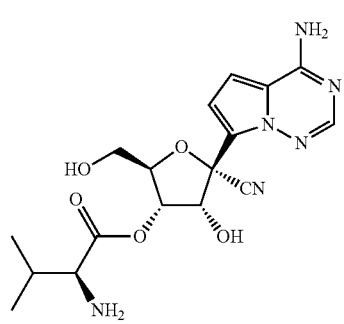
A212
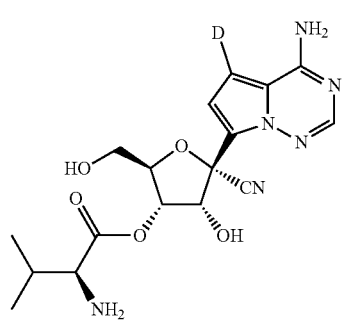
A213
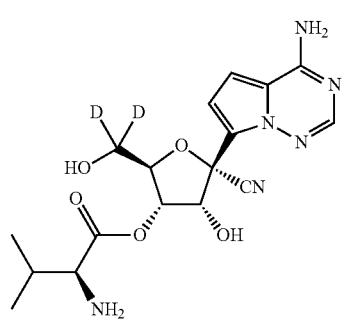
A214
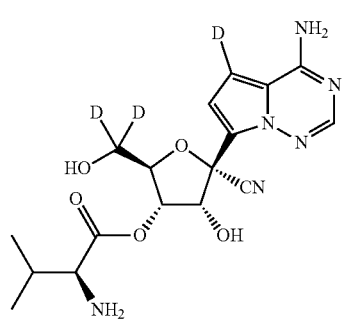
A215

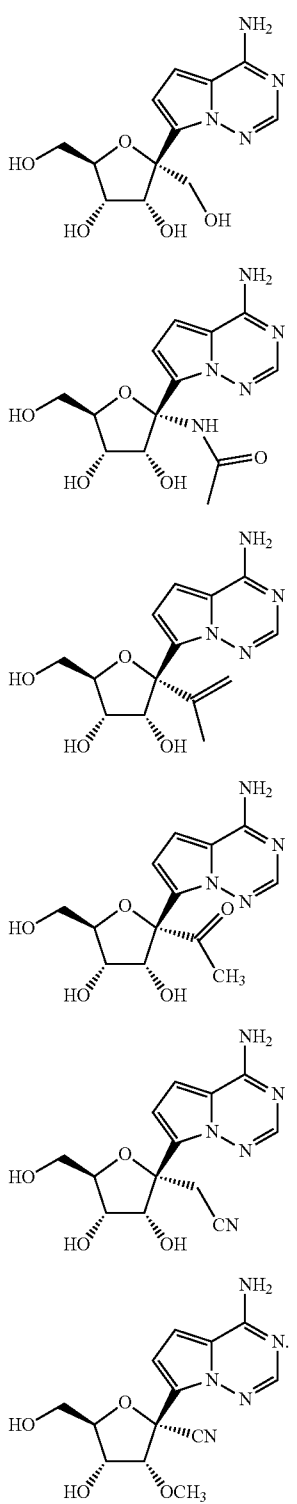

A216

A217

A218

A219

A220

A221

In another preferred embodiment, the compound of formula (I) is selected from the group consisting of: Compound A1, A9, A10, A11, A12, A49, A50, A51, A52, A53, A69, A70, A71, A72, A74, A75, A76, A77, A84, A87, A102, A106, A107, A108, A109, A124, A131, A138, A140, A144, A146, A147, A151, A164, A171, A173, A174, A180, A181, A188, A196, A198, A209, A212, A213, A214, A215, A216, A221, or the combination thereof.

In the second aspect of the present invention, it provides a use of an active ingredient or a formulation containing said active ingredient, the active ingredient is a compound of formula (I) or the pharmaceutically acceptable salts thereof or the crystalline hydrate thereof or the solvate thereof or the prodrug thereof:

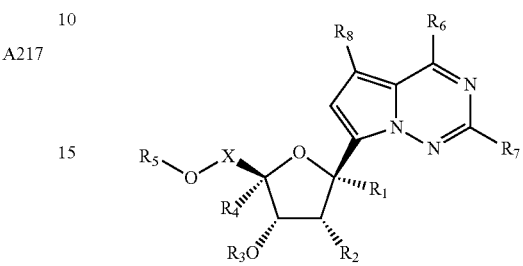

(I)

wherein, $R_1$ is selected from hydrogen, deuterium, halogen, cyano, azido, amino, amino substituted with $C_{1-6}$alkyl, $C_{1-6}$acyl, $C_{1-6}$alkyl, $C_{1-6}$alkoxy, amino substituted with $C_{1-6}$alkanoyl, halogenated $C_{1-6}$alkyl, $C_{2-6}$alkenyl, $C_{2-6}$alkenoxy, $C_{2-6}$alkynyloxy, $C_{2-6}$alkynyl, $C_{3-6}$cycloalkyl, halogenated $C_{3-6}$cycloalkyl, carbamoyl, hydroxymethyl, cyanomethyl (—CH$_2$CN), guanyl, guanidyl, carbamido, thiocyanato (—SCN), cyanato (—OCN);

$R_2$ is selected from hydrogen, halogen, $OR_3$, cyano, $C_{1-6}$alkyl, $C_{1-6}$alkoxy, $C_{2-6}$alkenyl, $C_{2-6}$alkynyl;

$R_3$ is selected from hydrogen, $C_{1-20}$alkanoyl, amino$C_{1-20}$alkanoyl, $C_{1-6}$alkylamino-$C_{1-6}$alkanoyl, $C_{1-6}$alkoxy$C_{1-6}$alkyl, α-amino acid, and the carboxyl of the α-amino acid is attached to the hydroxyl on the furan ring via ester bond;

$R_4$ is selected from hydrogen, deuterium, halogen, azido, cyano, $C_{1-6}$alkyl, halogenated $C_{1-6}$ alkyl, azido$C_{1-6}$alkyl, cyano$C_{1-6}$alkyl, hydroxy$C_{1-6}$alkyl, $C_{2-6}$alkenyl, $C_{2-6}$alkynyl, $C_{3-6}$cycloalkyl, $C_{1-6}$alkanoyl, $C_{2-6}$alkenoxy, $C_{2-6}$alkynyloxy, $C_{1-6}$alkoxy$C_{1-6}$alkyl, amino$C_{1-6}$alkyl, $C_{1-6}$alkylamino-$C_{1-6}$alkyl, guanyl, guanidyl, carbamido, thiocyanato, cyanato;

$R_5$ is selected from $R_3$,

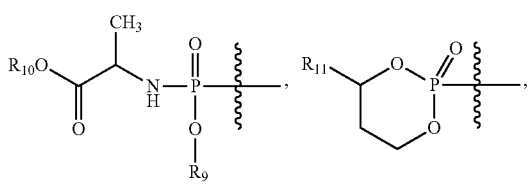

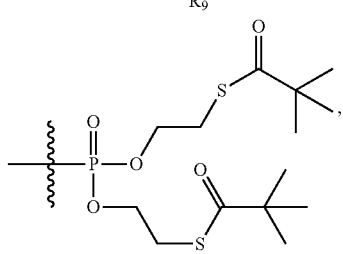

-continued

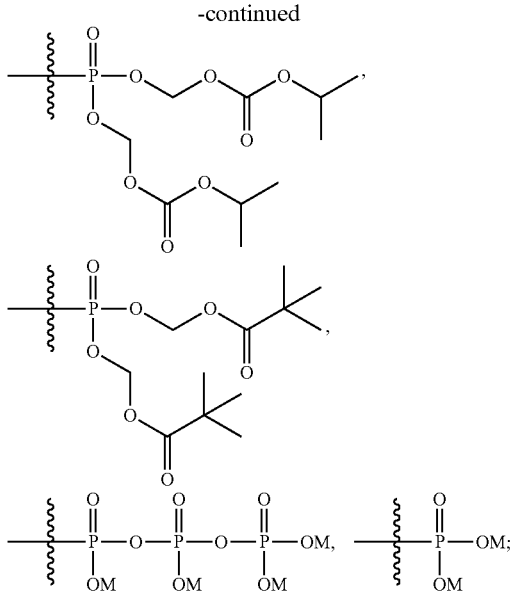

R$_6$ is selected from amino, hydroxy, halogen, cyano, cyanato, thiocyanato, C$_{1-6}$alkoxy, C$_{1-6}$alkylamino, NHOH, NHCOR$_{12}$, NHOCOR$_{12}$, NHCOOR$_{12}$;

R$_7$ is selected from hydrogen, deuterium, halogen, amino, methyl, NHCOR$_{12}$, NHCOOR$_{12}$;

R$_8$ is selected from hydrogen, deuterium, halogen, cyano, carbamoyl, carbamoyl substituted with C$_{1-6}$alkyl, C$_{1-6}$alkoxyamido, C$_{1-6}$alkoxycarbonyl, hydroxy, hydroxyC$_{1-6}$alkyl, amino, amino substituted with C$_{1-6}$alkanoyl, amino substituted with C$_{1-6}$alkyl, C$_{1-6}$alkoxy, C$_{2-6}$alkenyl, C$_{2-6}$alkynyl;

X is selected from —CH$_2$—, —CD$_2$-, —CHD-;

R$_9$ is selected from C$_{1-6}$alkyl, C$_{3-6}$cycloalkyl, C$_{6-20}$aryl, 5-15 membered heteroaryl;

R$_{10}$ is selected from C$_{1-18}$alkyl, methyleneC$_{6-20}$aryl;

R$_{11}$ is selected from C$_{1-6}$alkyl, C$_{3-6}$cycloalkyl, C$_{6-20}$aryl, 5-15 membered heteroaryl;

R$_{12}$ is selected from C$_{1-20}$alkyl;

M is each independently selected from hydrogen, metal, NH$_4$, or protonated organic amines;

and the active ingredient or the formulation containing the said active ingredient is used for preparing (a) inhibitors for inhibiting viral replication; and/or (b) medicaments for treating and/or preventing, alleviating the diseases associated with viral infections.

In another preferred embodiment, each position indicated as deuterium (D) has a deuterium enrichment of at least 50%; preferably, each position indicated as deuterium (D) has a deuterium enrichment of at least 80%; more preferably, each position indicated as deuterium (D) has a deuterium enrichment of at least 90%; most preferably, each position indicated as deuterium (D) has a deuterium enrichment of at least 95%.

In another preferred embodiment, the active ingredient or the formulation containing the said active ingredient is used for preparing (a) inhibitors for inhibiting the replication of coronavirus; and/or (b) medicaments for treating and/or preventing, alleviating the diseases associated with coronavirus infections.

In another preferred embodiment, the active ingredient or the formulation containing the said active ingredient is used for preparing (a) inhibitors for inhibiting the replication of respiratory syncytial virus (RSV); and/or (b) medicaments for treating and/or preventing, alleviating the diseases associated with respiratory syncytial virus (RSV) infections.

In another preferred embodiment, the active ingredient or the formulation containing the said active ingredient is used for preparing (a) inhibitors for inhibiting the replication of influenza virus; and/or (b) medicaments for treating and/or preventing, alleviating the diseases associated with influenza virus infections.

In another preferred embodiment, the active ingredient or the formulation containing the said active ingredient is used for preparing (a) inhibitors for inhibiting the replication of flaviviridae virus; and/or (b) medicaments for treating and/or preventing, alleviating the diseases associated with flaviviridae virus infections.

In another preferred embodiment, the active ingredient or the formulation containing the said active ingredient is used for preparing (a) inhibitors for inhibiting the replication of filoviridae virus; and/or (b) medicaments for treating and/or preventing, alleviating diseases associated with filoviridae virus infections.

In another preferred embodiment, the active ingredient or the formulation containing the said active ingredient is used for preparing (a) inhibitors for inhibiting the replication of porcine epidemic diarrhea virus (PEDV); and/or (b) medicaments for treating and/or preventing, alleviating the diseases associated with porcine epidemic diarrhea virus (PEDV) infections.

In another preferred embodiment, the active ingredient or the formulation containing the said active ingredient is used for preparing (a) inhibitors for inhibiting the replication of novel coronavirus (SARS-CoV-2); and/or (b) medicaments for treating and/or preventing, alleviating the diseases associated with novel coronavirus (SARS-CoV-2) infections.

In another preferred embodiment, the virus is selected from:
  (1) coronavirus infecting human: severe acute respiratory syndrome coronavirus (SARS-CoV), 2019 novel coronavirus (2019-nCoV or SARS-CoV-2), Middle East respiratory syndrome coronavirus (MERS-CoV);
  (2) coronavirus causing the common cold: the coronavirus causing the common cold is preferably selected from the group consisting of Human coronavirus OC43, Human coronvirus 229E, Human coronvirus NL63, Human coronvirus HKUL;
  (3) human respiratory syncytial virus (RSV);
  (4) human influenza virus: influenza A virus, influenza B virus and influenza C virus;
  (5) flaviviridae virus: hepatitis C virus (HCV), dengue virus (DENV), Zika virus (Zika);
  (6) filoviridae virus: Marburg virus (MBV) and Ebola virus (EBV);
  (7) coronavirus infecting other mammals: porcine epidemic diarrhea virus (PEDV).

In another preferred embodiment, the related diseases caused by the viruses are selected from the group consisting of
  (D1) common cold, high-risk symptom infection, respiratory tract infection, pneumonia and the complications thereof caused by human coronavirus infection;
  (D2) common cold, high-risk symptom infection, respiratory tract infection, pneumonia and the complications thereof caused by human respiratory syncytial virus (RSV) infection;
  (D3) common cold, high-risk symptom infection, respiratory tract infection, pneumonia and the complications thereof caused by human influenza virus infection;

(D4) chronic hepatitis C and the complications thereof caused by hepatitis C virus (HCV);
(D5) dengue fever and the complications thereof caused by dengue virus (DENV);
(D6) infection and the complications thereof caused by Zika virus (Zika);
(D7) hemorrhagic fever and the complications thereof caused by Marburg virus (MBV) and Ebola virus (EBV);
(D8) novel coronavirus pneumonia (Corona Virus Disease 2019) caused by SARS-CoV-2 (COVID-19);
(D9) porcine epidemic diarrhea caused by porcine epidemic diarrhea virus (PEDV);
(D10) any combination of the above diseases.

In another preferred embodiment, the related diseases caused by 2019 novel coronavirus infection are selected from the group consisting of respiratory tract infection, pneumonia and the complications thereof, or the combination thereof.

In another preferred embodiment, the compound of formula (I) is any one of Compounds A1 to A221, or the combination thereof.

In another preferred embodiment, the active ingredient is a nucleoside analog selected from the following group, or the pharmaceutically acceptable salts thereof or the crystalline hydrate thereof or the solvate thereof or the prodrug thereof:
Compound A1, A5, A6, A8, A9, A10, A11, A12, A13, A14, A28, A30, A35, A36, A37, A38, A39, A40, A41, A42, A43, A44, A45, A46, A49, A50, A51, A52, A53, A54, A55, A57, A58, A63, A69, A70, A71, A72, A73, A74, A75, A76, A77, A78, A79, A80, A81, A84, A86, A87, A88, A89, A91, A95, A97, A99, A101, A102, A105, A106, A107, A108, A109, A110, A111, A113, A114, A115, A116, A117, A118, A119, A120, A121, A122, A123, A124, A125, A126, A127, A128, A129, A130, A131, A132, A133, A134, A135, A136, A137, A138, A139, A140, A141, A142, A143, A144, A145, A146, A147, A148, A149, A150, A151, A152, A153, A154, A155, A156, A157, A158, A159, A160, A161, A162, A163, A164, A165, A166, A167, A168, A169, A170, A171, A172, A173, A174, A175, A176, A177, A178, A179, A180, A181, A182, A183, A184, A185, A186, A187, A188, A189, A190, A191, A192, A193, A194, A195, A196, A197, A198, A199, A200, A201, A202, A203, A204, A205, A206, A207, A208, A209, A210, A211, A212, A213, A214, A215, A216, A217, A218, A219, A220, A221, or the combination thereof.

In another preferred embodiment, the compound of formula (I) is selected from the group consisting of: Compound A1, A9, A10, A11, A12, A49, A50, A51, A52, A53, A69, A70, A71, A72, A74, A75, A76, A77, A84, A87, A102, A106, A107, A108, A109, A124, A131, A138, A140, A144, A146, A147, A151, A164, A171, A173, A174, A180, A181, A188, A196, A198, A209, A212, A213, A214, A215, A216, A221, or the combination thereof.

In another preferred embodiment, the formulations (or the pharmaceutical compositions containing the compounds) may further contain other antiviral agents.

In another preferred embodiment, the other antiviral agents further comprise additional components selected from the group consisting of:
Remdesivir (GS-5734), favipiravir, Galidesivir, GS-441524, NHC (EIDD-1931), EIDD-2801, GC-376, Lopinavir, Ritonavir, Nelfinavir; Chloroquine, hydroxychloroquine, cyclosporine, Carrimycin, baicalin, baicalein, forsythoside, chlorogenic acid, emodin, mycophenolic acid, Mycophenolate mofetil, Naphthoquine, Ciclesonide, Ribavirin, Penciclovir, Leflunomide, Teriflunomide, nafamostat, nitazoxanide, Darunavir, Arbidol, Camostat, Niclosamide, baricitinib, Ruxolitinib, Dasatinib, Saquinavir, Beclabuvir, Simeprevir, Palivizumab, Motavizumab, RSV-IGIV (RespiGam®), MEDI-557, A-60444 (RSV-604), MDT-637, BMS-433771, or pharmaceutically acceptable salts thereof, or the combination thereof.

In another preferred embodiment, the pharmaceutical composition containing the compound further comprises administering a therapeutically effective amount of at least one other therapeutic agent selected from the group consisting of corticosteroids, anti-inflammatory signal transduction modulators, β2-adrenoceptor agonists bronchodilators, anticholinergic agents, mucolytic agents, hypertonic saline and other drugs for treating viral infections; or the combination thereof.

In another preferred embodiment, the formulation is a pharmaceutical composition.

In another preferred embodiment, the formulation (or pharmaceutical composition) includes oral formulation and non-oral formulation.

In another preferred embodiment, the formulation includes powder, granule, capsule, injection, inhalation, tincture, oral liquid, tablet, buccal tablet, or dropping pill.

In the third aspect of the invention, it provides a pharmaceutical composition comprising:
(a1) first active ingredient, the first active ingredient is a compound of formula (I), and the pharmaceutically acceptable salts thereof or the crystalline hydrate thereof or the solvate thereof or the prodrug thereof:

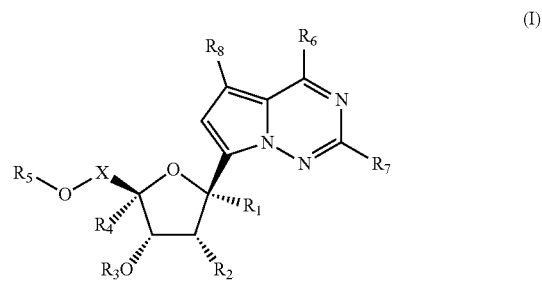

wherein,
R$_1$ is selected from hydrogen, deuterium, halogen, cyano, azido, amino, amino substituted with C$_{1-6}$alkyl, C$_{1-6}$acyl, C$_{1-6}$alkyl, C$_{1-6}$alkoxy, amino substituted with C$_{1-6}$alkanoyl, halogenated C$_{1-6}$alkyl, C$_{2-6}$alkenyl, C$_{2-6}$alkenoxy, C$_{2-6}$alkynyloxy, C$_{2-6}$alkynyl, C$_{3-6}$cycloalkyl, halogenated C$_{3-6}$cycloalkyl, carbamoyl, hydroxymethyl, cyanomethyl (—CH$_2$CN), guanyl, guanidyl, carbamido, thiocyanato (—SCN), cyanato (—OCN);
R$_2$ is selected from hydrogen, halogen, OR$_3$, cyano, C$_{1-6}$alkyl, C$_{1-6}$alkoxy, C$_{2-6}$alkenyl, C$_{2-6}$alkynyl;
R$_3$ is selected from hydrogen, C$_{1-20}$alkanoyl, aminoC$_{1-20}$alkanoyl, C$_{1-6}$alkyl amino-C$_{1-6}$alkanoyl, C$_{1-6}$alkoxyC$_{1-6}$alkyl, α-amino acid, and the carboxyl of the α-amino acid is attached to the hydroxyl on the furan ring via ester bond;
R$_4$ is selected from hydrogen, deuterium, halogen, azido, cyano, C$_{1-6}$alkyl, halogenated C$_{1-6}$ alkyl, azidoC$_{1-6}$alkyl, cyanoC$_{1-6}$alkyl, hydroxyC$_{1-6}$alkyl, C$_{2-6}$alkenyl, C$_{2-6}$alkynyl, C$_{3-6}$cycloalkyl, C$_{1-6}$alkanoyl, C$_{2-6}$alkenoxy, C$_{2-6}$alkynyloxy, C$_{1-6}$alkoxyC$_{1-6}$alkyl, aminoC$_{1-6}$alkyl, C$_{1-6}$alkylamino-C$_{1-6}$alkyl, guanyl, guanidyl, carbamido, thiocyanato, cyanato;

$R_5$ is selected from $R_3$,

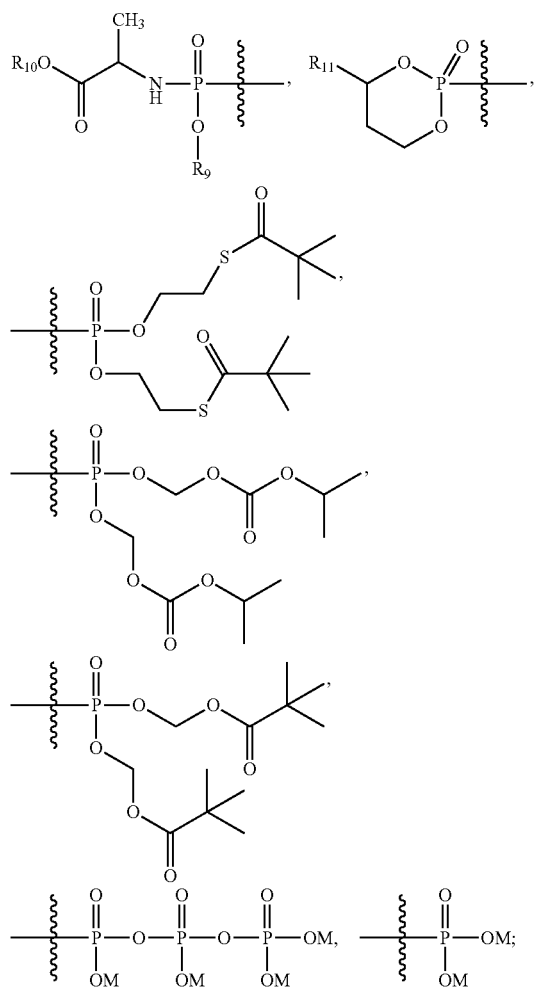

$R_6$ is selected from amino, hydroxy, halogen, cyano, cyanato, thiocyanato, $C_{1-6}$alkoxy, $C_{1-6}$ alkylamino, NHOH, NHCOR$_{12}$, NHOCOR$_{12}$, NHCOOR$_{12}$;

$R_7$ is selected from hydrogen, deuterium, halogen, amino, methyl, NHCOR$_{12}$, NHCOOR$_{12}$;

$R_8$ is selected from hydrogen, deuterium, halogen, cyano, carbamoyl, carbamoyl substituted with $C_{1-6}$alkyl, $C_{1-6}$alkoxyamido, $C_{1-6}$alkoxycarbonyl, hydroxy, hydroxyC$_{1-6}$alkyl, amino, amino substituted with $C_{1-6}$alkanoyl, amino substituted with $C_{1-6}$alkyl, $C_{1-6}$alkoxy, $C_{2-6}$alkenyl, $C_{2-6}$alkynyl;

X is selected from $CH_2$, $CD_2$, —CHD-;

$R_9$ is selected from $C_{1-6}$alkyl, $C_{3-6}$cycloalkyl, $C_{6-20}$aryl, 5-15 membered heteroaryl;

$R_{10}$ is selected from $C_{1-18}$alkyl, methyleneC$_{6-20}$aryl;

$R_{11}$ is selected from $C_{1-6}$alkyl, $C_{3-6}$cycloalkyl, $C_{6-20}$aryl, 5-15 membered heteroaryl;

$R_{12}$ is selected from $C_{1-20}$alkyl;

M is each independently selected from hydrogen, metal, $NH_4$, or protonated organic amines; and (b) pharmaceutically acceptable carriers.

In another preferred embodiment, the composition further comprises (a2) a second active ingredient;
wherein, the second active ingredient is an antiviral drug selected from the group consisting of interferon, RNA-dependent RNA polymerase inhibitors (for example, Remdesivir (GS-5734), favipiravir, Galidesivir, GS-441524, NHC (EIDD-1931), EIDD-2801), 3CL protease inhibitor (for example, GC-376), Lopinavir, Ritonavir, Nelfinavir; Chloroquine, hydroxychloroquine, cyclosporine, Carrimycin, baicalin, baicalein, forsythoside, chlorogenic acid, emodin, mycophenolic acid, Mycophenolate mofetil, Naphthoquine, Ciclesonide, Ribavirin, Penciclovir, Leflunomide, Teriflunomide, nafamostat, nitazoxanide, Darunavir, Arbidol, Camostat, Niclosamide, baricitinib, Ruxolitinib, Dasatinib, Saquinavir, Beclabuvir, Simeprevir, Palivizumab, Motavizumab, RSV-IGIV (RespiGam®), MEDI-557, A-60444 (RSV-604), MDT-637, BMS-433771, or pharmaceutically acceptable salts thereof, or the combination thereof;

and/or the second active ingredient is selected from the group consisting of bronchodilators and corticosteroids for treating respiratory tract infections, wherein the corticosteroid includes dexamethasone, dexamethasone sodium phosphate, fluorometholone, fluorometholone acetate, loteprednol, loteprednol etabonate, hydrocortisone, prednisolone, fludrocortisone, triamcinolone, triamcinolone acetonide, betamethasone, beclomethasone dipropionate, methylprednisolone, fluocinolone, fluocinolone acetonide, flunisolide, fluoctin-21-butylate, flumethasone, flumethasone pivalate, budesonide, halobetasol propionate, mometasone furoate, fluticasone propionate and ciclesonide; or the pharmaceutically acceptable salt thereof.

and/or the second active ingredient is selected from the group consisting of Zinc, Fingolimod, Vitamin C, Olmesartan Medoxomil, valsartan, Losartan, Thalidomide, glycyrrhizic acid, Artemisinin, dihydroartemisinin, Artesunate, Artemisone, Azithromycin, Escin, Naproxen, or the combination thereof.

In another preferred embodiment, in the compound of formula (I), $R_1$ is selected from hydrogen, deuterium, halogen, cyano, azido, methyl, chloromethyl, fluoromethyl, ethenyl, ethynyl, cyclopropyl, carbamoyl, hydroxymethyl, methoxyl, formyl, guanyl;

$R_2$ is selected from halogen, cyano, amino, formyl, OR$_3$;

$R_3$ is selected from hydrogen, $C_{1-20}$alkanoyl, α-amino acid, and the carboxyl of the α-amino acid is attached to the hydroxyl on the furan ring via ester bond; preferably, the α-amino acid is selected from alanine, valine, isoleucine, tryptophan, phenylalanine;

$R_4$ is selected from hydrogen, deuterium, halogen, azido, cyano, methyl, chloromethyl, fluoromethyl, difluoromethyl, ethenyl, ethynyl, cyclopropyl, hydroxymethyl, azidomethyl (—CH$_2$N$_3$), formyl, acetyl, formamido, acetamido;

$R_5$ is selected from $R_3$,

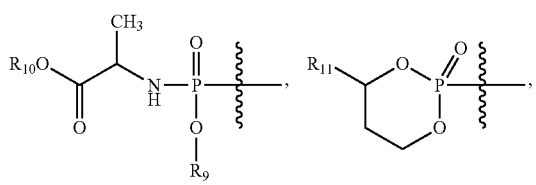

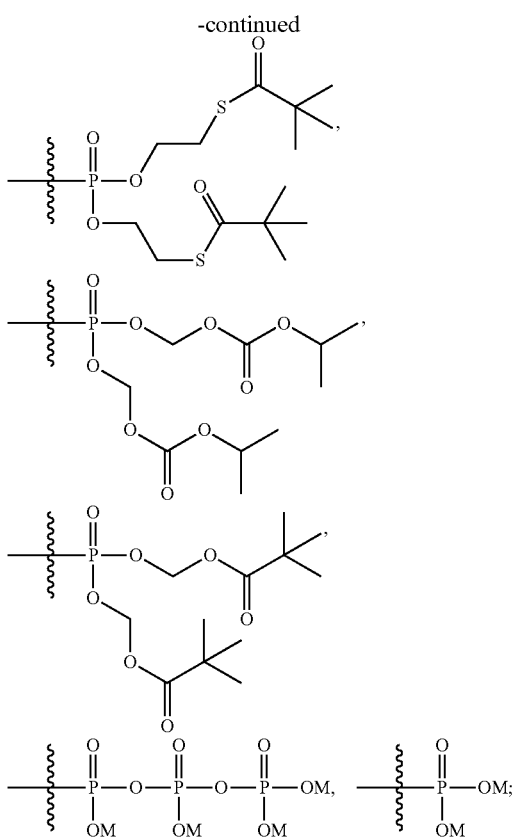

$R_6$ is selected from amino, hydroxy, halogen, cyano, methylamino (—NH$_2$CH$_3$), NHOH, NHCOR$_{12}$, NHOCOR$_{12}$, NHCOOR$_{12}$;

$R_7$ is selected from hydrogen, deuterium, halogen, amino;

$R_8$ is selected from hydrogen, deuterium, halogen, cyano, carbamoyl, N-methylcarbamoyl (CH$_3$NHCO—), methyl, ethyl, ethynyl, methoxycarbonyl, ethoxycarbonyl, hydroxy, hydroxymethyl, hydroxyethyl, methoxy, ethoxy, formyl, acetyl, formamido, acetamido, methoxycarbonylamino (CH$_3$OCONH$_2$—), ethoxycarbonylamino (C$_2$H$_5$OCONH$_2$—), methoxycarbonyloxy (CH$_3$OCOO—), ethoxycarbonyloxy (C$_2$H$_5$OCOO—);

X is selected from CH$_2$, CD$_2$, —CHD-;

$R_9$ is selected from C$_{6-20}$aryl, 5-15 membered heteroaryl;

$R_{10}$ is selected from C$_{1-18}$alkyl, methyleneC$_{6-20}$aryl;

$R_{11}$ is selected from C$_{1-6}$alkyl, C$_{3-6}$cycloalkyl, C$_{6-20}$aryl, 5-15 membered heteroaryl;

$R_{12}$ is selected from C$_{1-20}$alkyl; and/or

M is each independently selected from hydrogen, zinc, magnesium, calcium, sodium, potassium, NH$_4$, protonated trimethylamine, protonated triethylamine, protonated tri-n-butylamine.

In another preferred embodiment, the compound of formula (I) is any one of Compounds A1 to A221, or the combination thereof.

In another preferred embodiment, the compound of formula (I) is selected from the group consisting of Compound A1, A5, A6, A8, A9, A10, A11, A12, A13, A14, A28, A30, A35, A36, A37, A38, A39, A40, A41, A42, A43, A44, A45, A46, A49, A50, A51, A52, A53, A54, A55, A57, A58, A63, A69, A70, A71, A72, A73, A74, A75, A76, A77, A78, A79, A80, A81, A84, A86, A87, A88, A89, A91, A95, A97, A99, A101, A102, A105, A106, A107, A108, A109, A110, A111, A113, A114, A115, A116, A117, A118, A119, A120, A121, A122, A123, A124, A125, A126, A127, A128, A129, A130, A131, A132, A133, A134, A135, A136, A137, A138, A139, A140, A141, A142, A143, A144, A145, A146, A147, A148, A149, A150, A151, A152, A153, A154, A155, A156, A157, A158, A159, A160, A161, A162, A163, A164, A165, A166, A167, A168, A169, A170, A171, A172, A173, A174, A175, A176, A177, A178, A179, A180, A181, A182, A183, A184, A185, A186, A187, A188, A189, A190, A191, A192, A193, A194, A195, A196, A197, A198, A199, A200, A201, A202, A203, A204, A205, A206, A207, A208, A209, A210, A211, A212, A213, A214, A215, A216, A217, A218, A219, A220, A221, or the combination thereof.

In another preferred embodiment, the compound of formula (I) is selected from the group consisting of Compound A1, A9, A10, A11, A12, A49, A50, A51, A52, A53, A69, A70, A71, A72, A74, A75, A76, A77, A84, A87, A102, A106, A107, A108, A109, A124, A131, A138, A140, A144, A146, A147, A151, A164, A171, A173, A174, A180, A181, A188, A196, A198, A209, A212, A213, A214, A215, A216, A221, or the combination thereof.

In another preferred embodiment, the second active ingredient is selected from the group consisting of (Y1) RNA replicase inhibitors (e.g. Remdesivir (GS-5734), favipiravir, Galidesivir, GS-441524, NHC, EIDD-2801); (Y2) Lopinavir; (Y3) Ritonavir; (Y4) favipiravir; (Y5) Chloroquine, hydroxychloroquine, or pharmaceutically acceptable salts thereof (e.g. chloroquine phosphate), (Y6) Nelfinavir; (Y7) any combination of above Y1 to Y6.

In another preferred embodiment, the pharmaceutical composition is used for inhibiting the replication of coronavirus, influenza virus, respiratory syncytial virus, flaviviridae virus, filoviridae virus and/or porcine epidemic diarrhea virus (PEDV).

In another preferred embodiment, the medicament is used for inhibiting the replication of 2019 novel coronavirus (SARS-CoV-2).

In the fourth aspect of the present invention, it provides a use of the pharmaceutical composition according to the third aspect of the present invention in preparing (a) inhibitors that inhibit the replication of coronavirus, influenza virus, respiratory syncytial virus, flaviviridae virus, filoviridae virus and/or porcine epidemic diarrhea virus (PEDV); and/or (b) medicaments for treating and/or preventing, alleviating related diseases caused by coronavirus, influenza virus, respiratory syncytial virus, flaviviridae virus, filoviridae virus and/or porcine epidemic diarrhea virus (PEDV) infection.

In another preferred embodiment, for preparing (a) inhibitors for inhibiting 2019 novel coronavirus (SARS-CoV-2) replication; and/or (b) drugs for treating and/or preventing, alleviating diseases associated with 2019 novel coronavirus (SARS-CoV-2) infections.

In the fifth aspect of the present invention, it provides a method for inhibiting viral replication comprising the steps of:

contacting a first active ingredient or a formulation containing the first active ingredient with a virus, thereby inhibiting the replication of the virus;

wherein the first active ingredient is a compound of formula (I), or the pharmaceutically acceptable salts thereof or the crystalline hydrate thereof or the solvate thereof or the prodrug thereof:

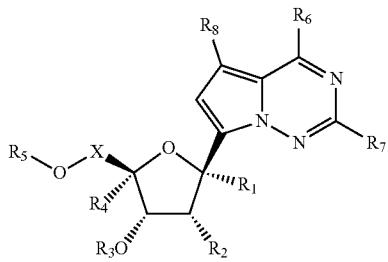

(I)

wherein, $R_1$ is selected from hydrogen, deuterium, halogen, cyano, azido, amino, amino substituted with $C_{1-6}$alkyl, $C_{1-6}$acyl, $C_{1-6}$alkyl, $C_{1-6}$alkoxy, amino substituted with $C_{1-6}$alkanoyl, halogenated $C_{1-6}$alkyl, $C_{2-6}$alkenyl, $C_{2-6}$alkenoxy, $C_{2-6}$alkynyloxy, $C_{2-6}$alkynyl, $C_{3-6}$cycloalkyl, halogenated $C_{3-6}$cycloalkyl, carbamoyl, hydroxymethyl, cyanomethyl (—CH$_2$CN), guanyl, guanidyl, carbamido, thiocyanato (—SCN), cyanato (—OCN);

$R_2$ is selected from hydrogen, halogen, $OR_3$, cyano, $C_{1-6}$alkyl, $C_{1-6}$alkoxy, $C_{2-6}$alkenyl, $C_{2-6}$alkynyl;

$R_3$ is selected from hydrogen, $C_{1-20}$alkanoyl, amino$C_{1-20}$alkanoyl, $C_{1-6}$alkylamino-$C_{1-6}$alkanoyl, $C_{1-6}$alkoxy$C_{1-6}$alkyl, α-amino acid, and the carboxyl of the α-amino acid is attached to the hydroxyl on the furan ring via ester bond; preferably, the α-amino acid is selected from alanine, valine, isoleucine, tryptophan, phenylalanine;

$R_4$ is selected from hydrogen, deuterium, halogen, azido, cyano, $C_{1-6}$alkyl, halogenated $C_{1-6}$ alkyl, azido$C_{1-6}$alkyl, cyano$C_{1-6}$alkyl, hydroxy$C_{1-6}$alkyl, $C_{2-6}$alkenyl, $C_{2-6}$alkynyl, $C_{3-6}$cycloalkyl, $C_{1-6}$alkanoyl, $C_{2-6}$alkenoxy, $C_{2-6}$alkynyloxy, $C_{1-6}$alkoxy$C_{1-6}$alkyl, amino$C_{1-6}$alkyl, $C_{1-6}$alkylamino-$C_{1-6}$alkyl, guanyl, guanidyl, carbamido, thiocyanato, cyanato;

$R_5$ is selected from $R_3$,

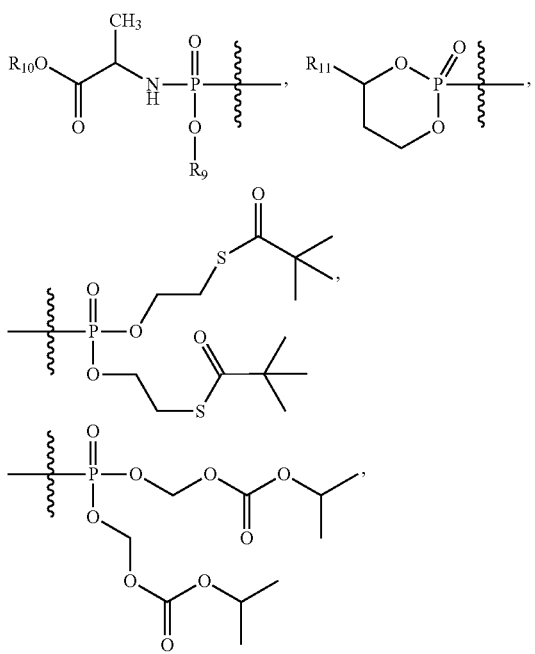

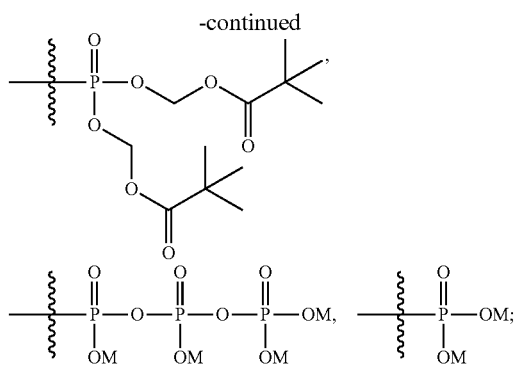

$R_6$ is selected from amino, hydroxy, halogen, cyano, cyanato, thiocyanato, $C_{1-6}$alkoxy, $C_{1-6}$ alkylamino, NHOH, NHCOR$_{12}$, NHOCOR$_{12}$, NHCOOR$_{12}$;

$R_7$ is selected from hydrogen, deuterium, halogen, amino, methyl, NHCOR$_{12}$, NHCOOR$_{12}$;

$R_8$ is selected from hydrogen, deuterium, halogen, cyano, carbamoyl, carbamoyl substituted with $C_{1-6}$alkyl, $C_{1-6}$alkoxyamido, $C_{1-6}$alkoxycarbonyl, hydroxy, hydroxy$C_{1-6}$alkyl, amino, amino substituted with $C_{1-6}$alkanoyl, amino substituted with $C_{1-6}$alkyl, $C_{1-6}$alkyl, $C_{2-6}C_{1-6}$alkoxy, alkenyl, $C_{2-6}$alkynyl;

X is selected from CH$_2$, CD$_2$, —CHD-;

$R_9$ is selected from $C_{1-6}$alkyl, $C_{3-6}$cycloalkyl, $C_{6-20}$aryl, 5-15 membered heteroaryl;

$R_{10}$ is selected from $C_{1-18}$alkyl, methylene$C_{6-20}$aryl;

$R_{11}$ is selected from $C_{1-6}$alkyl, $C_{3-6}$cycloalkyl, $C_{6-20}$aryl, 5-15 membered heteroaryl;

$R_{12}$ is selected from $C_{1-20}$alkyl;

M is each independently selected from hydrogen, metal, NH$_4$, or protonated organic amines;

In another preferred embodiment, the virus is selected from the group consisting of coronavirus, influenza virus, respiratory syncytial virus, flaviviridae virus, filoviridae virus, porcine epidemic diarrhea virus, and the combination thereof.

In another preferred embodiment, the virus is 2019 novel coronavirus (SARS-CoV-2).

In another preferred embodiment, the compound of formula (I) is any one of Compounds A1 to A221, or the combination thereof.

In another preferred embodiment, the compound of formula (I) is selected from the group consisting of Compound A1, A5, A6, A8, A9, A10, A11, A12, A13, A14, A28, A30, A35, A36, A37, A38, A39, A40, A41, A42, A43, A44, A45, A46, A49, A50, A51, A52, A53, A54, A55, A57, A58, A63, A69, A70, A71, A72, A73, A74, A75, A76, A77, A78, A79, A80, A81, A84, A86, A87, A88, A89, A91, A95, A97, A99, A101, A102, A105, A106, A107, A108, A109, A110, A111, A113, A114, A115, A116, A117, A118, A119, A120, A121, A122, A123, A124, A125, A126, A127, A128, A129, A130, A131, A132, A133, A134, A135, A136, A137, A138, A139, A140, A141, A142, A143, A144, A145, A146, A147, A148, A149, A150, A151, A152, A153, A154, A155, A156, A157, A158, A159, A160, A161, A162, A163, A164, A165, A166, A167, A168, A169, A170, A171, A172, A173, A174, A175, A176, A177, A178, A179, A180, A181, A182, A183, A184, A185, A186, A187, A188, A189, A190, A191, A192, A193, A194, A195, A196, A197, A198, A199, A200, A201, A202, A203, A204, A205, A206, A207, A208, A209, A210, A211, A212, A213, A214, A215, A216, A217, A218, A219, A220, A221, or the combination thereof.

In another preferred embodiment, the compound of formula (I) is selected from the group consisting of Compound A1, A9, A10, A11, A12, A49, A50, A51, A52, A53, A69, A70, A71, A72, A74, A75, A76, A77, A84, A87, A102, A106, A107, A108, A109, A124, A131, A138, A140, A144, A146, A147, A151, A164, A171, A173, A174, A180, A181, A188, A196, A198, A209, A212, A213, A214, A215, A216, A221, or the combination thereof.

In another preferred embodiment, the method is a method in vitro.

In another preferred embodiment, the method is non-therapeutic and non-diagnostic.

In the sixth aspect of the present invention, it provides a method for (a) inhibiting viral replication and/or (b) treating and/or preventing, alleviating related diseases caused by viral infection, comprising the steps of administrating safe and effective amount of a compound of formula (I), or the pharmaceutically acceptable salts thereof or the crystalline hydrate thereof or the solvate thereof or the prodrug thereof to the subject in need thereof:

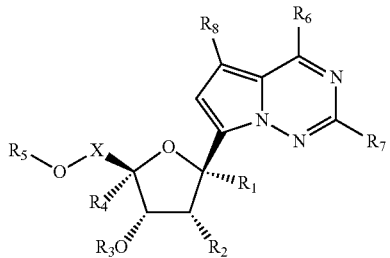

(I)

wherein $R_1$, $R_2$, $R_3$, $R_4$, $R_5$, $R_6$, $R_7$, $R_8$ and X are defined as in the first aspect of the invention.

In another preferred embodiment, the subject is mammal (such as human).

It should be understood that within the scope of the present invention, the above technical features of the present invention and the technical features specifically described in the following (e.g., examples) can be combined with each other, thereby forming a new or preferred technical solution. Due to space limitations, it will not be repeated herein.

DETAILED DESCRIPTION OF THE INVENTION

Figure 1:
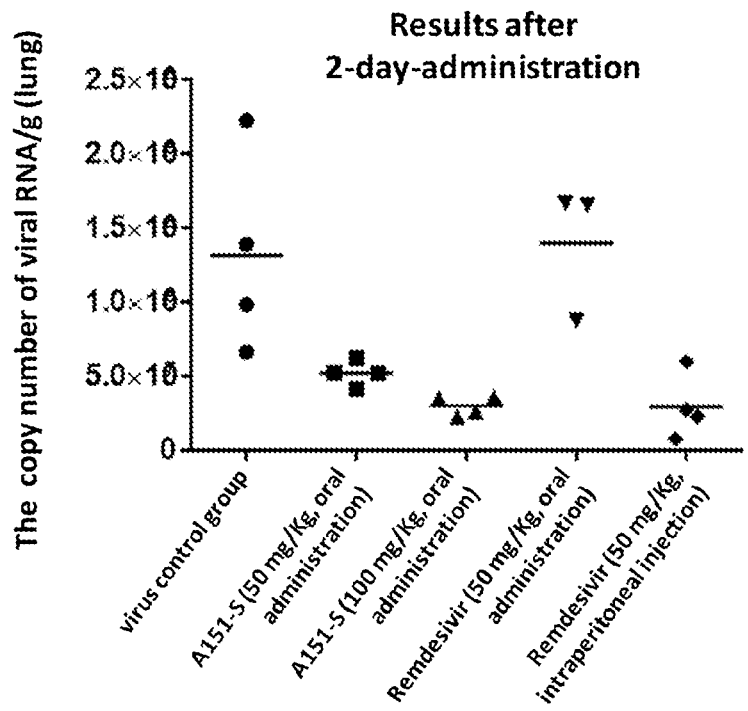
FIG. 1 shows the status of viral RNA replication after administration for 2 days in the examples of the present invention, wherein virus control group, 50 mg/kg oral A151-S group, 100 mg/kg oral A151-S group, 50 mg/kg oral Remdesivir group, and 50 mg/kg intraperitoneal injection Remdesivir group are set.

After extensive and in-depth research, and through a large number of screenings, the inventors unexpectedly developed a class of active ingredients which can effectively inhibit virus replication for the first time. Experimental result demonstrates that the active ingredient of the present invention can efficiently inhibit the replication and viability of 2019 novel coronavirus (SARS-CoV-2) and other viruses, thus can be used for inhibiting the replication of coronavirus, influenza virus, respiratory syncytial virus, flaviviridae virus, filoviridae virus and/or porcine epidemic diarrhea virus. The present invention is completed on this basis.

Specifically, the present invention disclosed a use of the nucleoside analogs of formula (I) and the compositions thereof in fighting viruses, for example, coronavirus, influenza virus, respiratory syncytial virus, flaviviridae virus, filoviridae virus and/or porcine epidemic diarrhea virus. The nucleoside analogs of formula (I) have excellent inhibitory effect on the replication of SARS-CoV-2 and other viruses, and have a good clinical application prospect.

Terms

As used herein, "active compound of the present invention", "active ingredient of the present invention", "nucleoside analog of the present invention" and "active compound inhibiting the replication of coronavirus of the present invention" are used interchangeably and refer to nucleoside analogs having excellent inhibitory activity on the replication of coronavirus, including compound of formula (I), or pharmaceutically acceptable salts thereof, or solvates thereof, or prodrugs thereof, or the combinations thereof.

As used herein, "formulation of the present invention" refers to formulation containing the active compound of the invention.

As used herein, the term "comprise" or variations thereof such as "comprises" or "comprising", etc. are understood to comprise the said elements or components without excluding other elements or other components.

As use herein, the term "novel coronavirus", "2019-nCoV" or "SARS-CoV-2" can be used interchangeably. The 2019-nCoV is the seventh coronavirus known to infect people and causes novel coronavirus pneumonia (COVID-19), which is one of the serious infectious diseases threatening human health all over the world.

As used herein, "halogen" generally refers to fluorine, chlorine, bromine and iodine; preferably fluorine, chlorine or bromine; more preferably fluorine or chlorine.

As use herein, the terms "$C_n$-$C_m$" and "$C_{n-m}$" can be used interchangeably, and means having n to m carbon atoms.

As use herein, the term "$C_1$-$C_6$alkyl" refers to straight or branched saturated hydrocarbon group containing 1-6 carbon atoms, for example, methyl, ethyl, n-propyl, isopropyl, n-butyl, isobutyl, tert-butyl, sec-butyl, n-pentyl, 1-ethylpropyl, isopentyl, neopentyl, isohexyl, 3-methylpentyl or n-hexyl, preferably, methyl, ethyl, n-propyl, isopropyl, butyl, isobutyl or tert-butyl.

Halogenated $C_1$-$C_6$alkyl refers to straight or branched saturated hydrocarbon group containing 1-6 carbon atoms substituted with one or more identical or different halogen atoms; for example, trifluoromethyl, fluoromethyl, difluoromethyl, chloromethyl, bromomethyl, dichlorofluoromethyl, chloroethyl, bromopropyl, 2-chlorobutyl or pentafluoroethyl, and the like.

$C_1$-$C_6$alkoxy refers to straight or branched alkoxy containing 1-6 carbon atoms; for example, methoxy, ethoxy, n-propoxy, isopropoxy, n-butoxy, isobutoxy, tert-butoxy, sec-butoxy, n-pentyloxy, isopentyloxy, neopentyloxy, isohexyloxy, 3-methylpentyloxy or n-hexyloxy and the like; preferably methoxy, ethoxy, n-propoxy, isopropoxy, n-butoxy, isobutoxy or tert-butoxy; $C_1$-$C_6$alkanoyl refers to straight or branched alkanoyl containing 1-6 carbon atoms, for example, formyl, acetyl, propionyl, butyryl, isobutyryl, valeroyl, tert-butyryl or hexanoyl and the like.

Amino substituted with $C_{1-6}$alkyl means that the hydrogen atoms in amino are substituted with one or more $C_1$-$C_6$alkyl, for example, —NHCH$_3$, —N(CH$_3$)$_2$ and the like.

Amino substituted with $C_{1-6}$alkanoyl means that the hydrogen atoms in amino are substituted with one or more $C_1$-$C_6$ alkyl, such as —NHCOCH$_3$, —NHCOCH$_2$CH$_3$ and the like.

$C_2$-$C_6$alkenyl refers to straight or branched unsaturated hydrocarbon group containing 1-3 double bonds and 2-6 carbon atoms, including both cis and trans configurations; for example, vinyl, 1-propenyl, 2-propenyl, 1-methyl-1-propenyl, 2-methyl-1-propenyl, 2-methyl-2-propenyl, 1-butenyl, 2-butenyl, 3-butenyl, 1-pentenyl, 2-pentenyl, 3-pentenyl, 4-pentenyl, 1,3-butadienyl, 1,3-pentadienyl, 1-hexenyl, 2-hexenyl, 3-hexenyl, 4-hexenyl, 5-hexenyl, 3,3-dimethyl-1-propenyl or 2-ethyl-1-propenyl, and the like.

$C_2$-$C_6$alkynyl refers to straight or branched alkynyl containing 2-6 carbon atoms, for example, ethynyl, 2-propynyl, 2-butynyl, 3-butynyl, 1-methyl-2-propynyl, 2-pentynyl, 2-pentynyl or 2-hexynyl and the like.

$C_2$-$C_6$alkenoxy refers to straight or branched alkenoxy containing 1-3 double bonds and 2-6 carbon atoms, for example, vinyloxy, 1-propenyloxy, 1-methyl-1-propenyloxy, 2-methyl-1-propenyloxy, 1-pentenyloxy, 1,3-pentadienyloxy or 2-pentenyloxy, and the like.

$C_2$-$C_6$alkynyloxy refers to straight or branched alkynyloxy containing 2-6 carbon atoms, for example, ethynyloxy, 2-propynyloxy, 2-butynyloxy, 3-butynyloxy, 1-methyl-2-propynyloxy, 2-pentynyloxy, 2-pentynyloxy or 2-hexynyloxy, and the like.

Amino$C_{1-20}$alkanoyl means that a carbon atom of a straight or branched alkanoyl containing 1-20 carbon atoms is attached to an amino; for example, —COCH$_2$NH$_2$, —COCH$_2$CH$_2$NH$_2$ and the like.

$C_{1-6}$alkylamino-$C_{1-6}$alkanoyl means that the nitrogen atom of amino substituted with $C_{1-6}$alkyl is attached to a non-carbonyl carbon atom of a straight or branched alkanoyl containing $C_{1-6}$ carbon atoms, for example, —COCH$_2$NHCH$_3$, —COCH$_2$CH$_2$NHCH$_2$CH$_3$ and the like.

$C_{1-6}$alkoxy$C_{1-6}$alkyl means that the oxygen atom of a straight or branched alkoxy-containing 1-6 carbon atoms is attached to the carbon atom of $C_{1-6}$alkyl, for example, —CH$_2$OCH$_3$, —CH$_2$CH$_2$OCH$_2$CH$_3$ and the like.

Amino$C_{1-6}$alkyl means that a carbon atom of a straight or branched alkyl containing 1-6 carbon atoms is attached to an amino; for example, —CH$_2$NH$_2$, —CH$_2$CH$_2$NH$_2$, —CH(NH$_2$)CH$_3$, —CH$_2$CH$_2$CH$_2$NH$_2$, or —CH$_2$CH$_2$CH$_2$CH$_2$NH$_2$, and the like.

Carbamoyl substituted with $C_{1-6}$alkyl means that the hydrogen atom on carbamoyl is substituted with one or two identical or different $C_1$-$C_6$alkyl; e.g. —CONHMe, —CONHEt, —CON(Me)Et, —CONEt$_2$, or —CONMe$_2$, and the like.

Hydroxy$C_{1-6}$alkyl means that a carbon atom of a straight or branched alkyl containing 1-6 carbon atoms is attached to a hydroxy; for example, —CH$_2$OH, —CH$_2$CH$_2$OH, —CH(OH)CH$_3$, —CH$_2$CH$_2$CH$_2$OH, —CH$_2$CH$_2$CH$_2$CH$_2$OH, or —CH$_2$CH(CH$_3$)CH$_2$OH, and the like.

$C_{1-6}$alkoxyamido means that the oxygen atom of a straight or branched alkoxy containing 1-6 carbon atoms is attached to the carbonyl of an amido, for example, —NHCOOCH$_3$, —NHCOOCH$_2$CH$_3$, and the like.

$C_{1-6}$alkoxycarbonyl means that the oxygen atom of a straight or branched alkoxy containing 1-6 carbon atoms is attached to a carbonyl, such as —COOCH$_3$, —COOCH$_2$CH$_3$, and the like.

Coronavirus

Coronavirus (CoV) belongs to Coronaviridae of Nidovirales, which is an enveloped positive-stranded RNA virus, and its subfamily includes four genera α, β, δ and γ.

Among currently known coronavirus infecting people, HCoV-229E and HCoV-NL63 belong to genus alpha coronavirus, and HCoV—OC43, SARS-CoV, HCoV—HKU1, MERS-CoV and SARS-CoV-2 are genus beta coronavirus. SARS-CoV-2 is also known as 2019-nCoV.

Highly pathogenic coronavirus, "severe acute respiratory syndrome" (SARS-CoV) and "Middle East respiratory syndrome" (MERS-CoV), which broke out in 2003 and 2012 respectively, belong to genus beta coronavirus. Novel coronavirus (SARS-CoV-2) breaking out at the end of 2019 has about 80% similarity with SARS-CoV and 40% similarity with MERS-CoV, and also belongs to genus beta coronavirus.

The genome of this kind of virus is a positive-sense single-stranded RNA, one of RNA viruses having largest genome; encoding replicase, spike protein, envelope protein, enveloped protein and nucleocapsid protein and the like. In the initial stage of virus replication, the genome is translated into two peptide chains with thousands of amino acids, namely precursor polyprotein, and then the precursor protein is cut by protease to produce non-structural proteins (such as RNA polymerase and helicase) and structural proteins (such as spike protein) and accessory protein.

Influenza Virus

Influenza virus is referred to as flu virus for short. Common influenza viruses are divided into type A, B, C and D. Influenza virus can cause infection and morbidity of many kinds of animals such as human, poultry, pigs, horses, bats and the like, and is the pathogen of human and animal diseases such as human influenza, avian influenza, swine influenza and horse influenza.

Clinical symptoms caused by influenza virus include acute high fever, general pain, significant fatigue and respiratory symptoms. Human influenza is mainly caused by influenza A virus and influenza B virus. Influenza A virus often undergoes antigenic variation, which can be further divided into H1N1, H3N2, H5N1, H7N9 and other subtypes.

Respiratory Syncytial Virus

Respiratory syncytial virus (RSV, syncytial virus for short, also belongs to Paramyxoviridae) is the most common pathogen causing children's virus pneumonia, and can cause interstitial pneumonia.

RSV is similar to parainfluenza virus and its virus particle size is about 150 nm slightly smaller than parainfluenza virus, and is RNA virus.

Flaviviridae Virus

Flaviviridae viruses are a kind of RNA virus mainly infecting mammal, including three virus genera, namely, flavivirus, pestivirus and hepatitis C. Dengue fever virus (DENV) and Zika virus (Zika) belong to flavivirus and are transmitted by mosquitoes. Dengue virus infection can cause obvious fever and pain symptoms, and severe dengue fever symptoms are headache, nausea, vomiting, unconsciousness and even shock. The symptoms of Zika virus (Zika) infection are similar to dengue fever and generally mild. Hepatitis C virus (HCV) belongs to Hepacivirus, which is the pathogen of chronic hepatitis C and can lead to liver cirrhosis and liver cancer.

Filoviridae Virus

Filoviridae currently includes three genera, namely Ebola virus, Marburg virus and Quiva virus. Both Marburg virus and Ebola virus can cause severe hemorrhagic fever. After infection, people will show high fever and bleeding symptoms, which will further lead to shock, organ failure and even death.

Porcine Epidemic Diarrhea Virus (PEDV)

Porcine epidemic diarrhea virus (PEDV) belongs to Coronaviruses of Coronaviridae.

Porcine epidemic diarrhea is an acute intestinal infectious disease in piglets and fattening pigs caused by PEDV virus.

PEDV virus directly enters the small intestine after oral and nasal infection. The replication of PEDV virus can be carried out in the cytoplasm of villous epithelium of small intestine and colon. PEDV can cause diarrhea belonging to osmotic diarrhea. Dehydration caused by severe diarrhea is the main cause of death of sick pigs.

Active Compounds and Active Ingredients of the Present Invention

In the present invention, it provides active ingredients capable of the effectively inhibiting the replication of coronavirus, influenza virus, respiratory syncytial virus and/or porcine epidemic diarrhea virus (PEDV), especially 2019 novel coronavirus (SARS-CoV-2).

In the present invention, the active ingredients are selected from nucleoside analogs of formula (I) according to the first aspect of the present invention, or the pharmaceutically acceptable salts thereof or the prodrug thereof, or the combination thereof, or the crystal thereof or the solvate thereof.

Preferred nucleoside analogs have the structure of the compounds prepared in examples, or pharmaceutically acceptable salts thereof, or prodrugs thereof, or the combinations thereof, or crystals thereof, or solvates thereof, in particular any one of compounds A1 to A221, or the combination thereof.

In another preferred embodiment, the compound of formula (I) is selected from the group consisting of Compound A1, A5, A6, A8, A9, A10, A11, A12, A13, A14, A28, A30, A35, A36, A37, A38, A39, A40, A41, A42, A43, A44, A45, A46, A49, A50, A51, A52, A53, A54, A55, A57, A58, A63, A69, A70, A71, A72, A73, A74, A75, A76, A77, A78, A79, A80, A81, A84, A86, A87, A88, A89, A91, A95, A97, A99, A101, A102, A105, A106, A107, A108, A109, A110, A111, A113, A114, A115, A116, A117, A118, A119, A120, A121, A122, A123, A124, A125, A126, A127, A128, A129, A130, A131, A132, A133, A134, A135, A136, A137, A138, A139, A140, A141, A142, A143, A144, A145, A146, A147, A148, A149, A150, A151, A152, A153, A154, A155, A156, A157, A158, A159, A160, A161, A162, A163, A164, A165, A166, A167, A168, A169, A170, A171, A172, A173, A174, A175, A176, A177, A178, A179, A180, A181, A182, A183, A184, A185, A186, A187, A188, A189, A190, A191, A192, A193, A194, A195, A196, A197, A198, A199, A200, A201, A202, A203, A204, A205, A206, A207, A208, A209, A210, A211, A212, A213, A214, A215, A216, A217, A218, A219, A220, A221, or the combination thereof.

Experiments show that the active ingredients of the present invention can effectively inhibit the replication of 2019 novel coronavirus (SARS-CoV-2), thereby preventing, treating and/or alleviating SARS-CoV-2 related diseases.

As used herein, "active compounds of the present invention" and "active compounds inhibiting the replication of virus of the present invention" are used interchangeably and refer to compounds having excellent inhibitory activity on the replication of virus, including nucleoside analogs of formula (I), or pharmaceutically acceptable salts thereof, or the crystal thereof, or solvates thereof.

It should be understood that the active ingredients of the present invention include compounds of formula (I), or pharmaceutically acceptable salts, enantiomers, diastereomers or racemes thereof, or prodrugs thereof. It should be understood that the active ingredients of the present invention also include crystalline forms, amorphous compounds, deuterated compounds and the like of the active compounds of the present invention.

The "pharmaceutically acceptable salt" is a conventional non-toxic salt formed by the reaction of the active compound of the present invention with inorganic acid or organic acid. For example, conventional non-toxic salts can be prepared by reacting the active compound of the present invention with inorganic acids or organic acids. The inorganic acid includes hydrochloric acid, hydrobromic acid, sulfuric acid, nitric acid, aminosulfonic acid, and phosphoric acid and the like, and the organic acid includes citric acid, tartaric acid, lactic acid, pyruvic acid, acetic acid, benzenesulfonic acid, p-toluenesulfonic acid, methanesulfonic acid, naphthalenesulfonic acid, ethane sulfonic acid, naphthalene disulfonic acid, maleic acid, malic acid, malonic acid, fumaric acid, succinic acid, propionic acid, oxalic acid, trifluoroacetic acid, stearic acid, pamoic acid, hydroxymaleic acid, phenylacetic acid, benzoic acid, salicylic acid, glutamic acid, ascorbic acid, p-aminobenzenesulfonic acid, 2-acetoxybenzoic acid and isethionic acid, and the like; or the esters formed by the active compound of the present invention with propionic acid, oxalic acid, malonic acid, succinic acid, fumaric acid, maleic acid, lactic acid, malic acid, tartaric acid, citric acid, aspartic acid or glutamic acid, and the esters further form sodium salt, zinc salt, potassium salt, calcium salt, aluminum salt or ammonium salt with inorganic base; or the esters formed by the active compound of the present invention with lysine, arginine, ornithine, and the esters further form corresponding inorganic acid salt with hydrochloric acid, hydrobromic acid, hydrofluoric acid, sulfuric acid, nitric acid or phosphoric acid or further form corresponding organic acid salts with formic acid, acetic acid, picric acid, methanesulfonic acid or ethanesulfonic acid; or 1-4 phosphate groups in the molecule of the active compound of the present invention form salts with 1-4 molecules of organic amines, including but not limited to monophosphate trimethylamine salt, monophosphate triethylamine salt, monophosphate tri-n-butylamine salt, triphosphate trimethylamine salt, triphosphate triethylamine salt, triphosphate tri-n-butylamine salt.

In addition, the active ingredient of the present invention is particularly suitable for use with other antiviral drugs or anti-coronavirus drugs. Representative other antiviral drugs or anti-coronavirus drugs include (but not limited to): Interferon, RNA-dependent RNA polymerase inhibitor (for example, Remdesivir (GS-5734), favipiravir, Galidesivir, GS-441524, NHC, EIDD-2801), 3CL protease inhibitor (for example, GC-376), Lopinavir, Ritonavir, Nelfinavir; Chloroquine (Sigma-C6628), hydroxychloroquine, cyclosporine, Carrimycin, baicalin, baicalein, forsythoside, chlorogenic acid, emodin, mycophenolic acid, Mycophenolate mofetil, Naphthoquine, Ciclesonide, Ribavirin, Penciclovir, Leflunomide, Teriflunomide, nafamostat, nitazoxanide, Darunavir, Arbidol, Camostat, Niclosamide, baricitinib, Ruxolitinib, Dasatinib, Saquinavir, Beclabuvir, Simeprevir, Palivizumab, Motavizumab, RSV-IGIV (RespiGam®), MEDI-557, A-60444 (RSV-604), MDT-637, BMS-433771, or pharmaceutically acceptable salts thereof, or the combination thereof. The interferon comprises one or more of the following: interferon α-2a, interferon α-2b, interferon α-n1, interferon α-n3, interferon β-1a and interferon β-1b.

Additional active therapeutic agents for treating respiratory symptoms and infection sequelae may also be used in combination with compounds of formula (I). Other agents are preferably administered orally or by direct inhalation. For example, other preferred additional therapeutic agents used in combination with compounds of formula (I) for the treatment of respiratory tract infections include but are not limited to bronchodilators and corticosteroids.

Glucocorticoids, first introduced as asthma therapies in 1950 (Carryer, Journal of Allergy, 21, 282-287, 1950), remain the most effective and consistently effective therapies for the disease, but their mechanisms of action are not fully understood (Morris, J. Allergy Clin. Immunol., 75(1Pt) 1-13, 1985). Unfortunately, oral glucocorticoid therapy is associated with far-reaching undesirable side effects such as concentric obesity, hypertension, glaucoma, glucose intolerance, accelerated cataract formation, bone mineral loss, and psychological effects, all of which limit their use as long-term therapeutic agents (Goodman and Gilman, 10th edition, 2001). The solution against systemic side effects is to deliver steroid drugs directly to inflammatory sites. Inhaled corticosteroids (ICS) have been developed to alleviate the severe side effects of oral steroids. Non-limiting examples of corticosteroids that may be used in combination with compounds of formula (I) are dexamethasone, dexamethasone sodium phosphate, fluorometholone, fluorometholone acetate, loteprednol, loteprednol etabonate, hydrocortisone, prednisolone, fludrocortisone, triamcinolone, triamcinolone acetonide, betamethasone, beclomethasone dipropionate, methylprednisolone, fluocinolone, fluocinolone acetonide, flunisolide, fluoctin-21-butylate, flumethasone, flumethasone pivalate, budesonide, halobetasol propionate, mometasone furoate, fluticasone propionate and ciclesonide; or the pharmaceutically acceptable salt thereof.

Other anti-inflammatory agents acting through an anti-inflammatory cascade mechanism may also be used as additional therapeutic agents in combination with compounds of formula (I) for the treatment of viral respiratory infections. The use of "anti-inflammatory signal transduction modulators" (referred as AISTM herein), such as phosphodiesterase inhibitors (e.g. PDE-4, PDE-5 or PDE-7 specific), transcription factor inhibitors (e.g. blocking NF KB via IKK inhibition) or kinase inhibitors (e.g. blocking P38MAP, JNK, PI3K, EGFR or Syk), is a logical way to cut off inflammation, because the targets of these small molecules are the limited number of common intracellular pathways-those signal transduction pathways which are key points of anti-inflammatory therapeutic interventions (see, reviewed by P. J. Barnes, 2006). These non-limiting additional therapeutic agents include 5-(2,4-difluorophenoxy)-1-isobutyl-1H-indazole-6-carboxylic acid (2-dimethyl-amino-ethyl)-amide (P38 Map kinase inhibitor ARRY-797); 3-cyclopropylmethoxy-N-(3,5-dichloro-pyridin-4-yl)-4-difluoromethoxy-benzamide (PDE-4 inhibitor, Roflumilast); 4-[2-(3-cyclopentyloxy-4-methoxyphenyl)-2-phenyl-ethyl]-pyridine (PDE-4 inhibitor, CDP-840); N-(3,5-dichloro-4-pyridyl)-4-(difluoromethoxy)-8-[(methylsulfonyl)amino]-1-dibenzofuranamide (PDE-4 inhibitor, Omester); N-(3,5-dichloro-pyridin-4-yl)-2-[1-(4-fluorobenzyl)-5-hydroxy-1H-indol-3-yl]-2-oxo-acetamide (PDE-4 inhibitor, AWD12-281); 8-methoxy-2-trifluoromethyl-quinolin-5-carboxylic acid (3,5-dichloro-1-oxy-pyridin-4-yl)-amide (PDE-4 inhibitor, Sch351591); 4-[5-(4-fluorophenyl)-2-(4-methyl-sulfinyl-phenyl)-1H-imidazol-4-yl]-pyridine (P38 inhibitor, SB-203850); 4-[4-(4-fluorophenyl)-1-(3-phenyl-propyl)-5-pyridin-4-yl-1H-imidazol-2-yl]-butan-3-yn-1-ol (P38 inhibitor, RWJ-67657); 2-diethylamino-ethyl 4-cyano-4-(3-cyclopentyloxy-4-methoxy-phenyl)-cyclohexanecarboxylate (a prodrug of 2-diethyl-ethyl carboxylate of Cilomilast, PDE-4 inhibitor); (3-chloro-4-fluorophenyl)-[7-methoxy-6-(3-morpholin-4-yl-propoxy)-quinazolin-4-yl]-amine (Gefitinib, EGFR inhibitor); and 4-(4-methyl-piperazin-1-ylmethyl)-N-[4-methyl-3-(4-pyridin-3-yl-pyrimidin-2-ylamino)-phenyl]-benzamide (Imatinib, EGFR inhibitor).

The combinations of bronchodilators including inhaled β2-adrenergic agonists, such as Formoterol, salbutamol or salmeterol, and compounds of formula (I) are further suitable but non-limiting combination for use in the treatment of respiratory viral infections.

The combinations of inhaled β2-adrenergic agonists bronchodilators, such as Formoterol or salmeterol, and ICS are further used for treating both bronchial stenosis and inflammation. The combinations of these ICS and β2-adrenergic agonists together with compounds of formula (I) are further suitable but non-limiting combination for use in the treatment of respiratory viral infections.

Anticholinergic agents have potential use for treating or preventing pulmonary bronchial stenosis, thereby they can used as additional therapeutic agents in combination with compounds of formula (I) for the treatment of viral respiratory infections. These anticholinergic agents include, but are not limited to, muscarinic receptor (particularly M3 subtype) antagonists that have shown therapeutic efficacy in humans for the control of cholinergic properties in COPD (Witek, 1999); 1-{4-hydroxy-1-[3,3,3-tris-(4-fluorophenyl)-propionyl]-pyrrolidine-2-carbonyl}-pyrrolidine-2-carboxylic acid (1-methyl-piperidin-4-ylmethyl)-amide; 3-[3-(2-diethylamino-acetoxy)-2-phenyl-propionyloxy]-8-isopropyl-8-methyl-8-azonia-bicyclo[3.2.1]octane(N, N-diethylglycine ester or salt of ipratropium); 1-cyclohexyl-3,4-dihydro-TH-isoquinolin-2-carboxylic acid 1-aza-bicyclo[2.2.2]oct-3-yl ester (Solifenacin); 2-hydroxymethyl-4-methylsulfinyl-2-phenylbutyric acid 1-aza-bicyclo[2.2.2]oct-3-yl ester (Revatropate); 2-{1-[2-(2,3-dihydro-benzofuran-5-yl)-ethyl]-pyrrolidin-3-yl}-2,2-diphenyl-acetamide (Darifenacin); 4-azacycloheptane-1-yl-2,2-diphenyl-butyramide (Buzepide); 7-[3-(2-diethylamino-acetoxy)-2-phenyl-propionyloxy]-9-ethyl-9-methyl-3-oxa-9-azcation-tricyclo[3.3.1.02,4]nonane (N,N-diethylglycine ester or salt of Oxitropium); 7-[2-(2-diethylamino-acetoxy)-2,2-dithiophen-2-yl-acetoxy]-9,9-dimethyl-3-oxa-9-azcation-tricyclo[3.3.1.02,4]nonane (N,N-diethylglycine ester or salt of Tiotropium Bromide); 2-(3-diisopropylamino-1-phenyl-propyl)-4-methyl-phenyl dimethylaminoacetate (N, N-dimethylglycine ester or salt of tolterodine); 3-[4,4-bis-(4-fluorophenyl)-2-oxo-imidazolin-1-yl]-1-methyl-1-(2-oxo-2-pyridin-2-yl-ethyl)-pyrrolidinium; 1-[1-(3-fluoro-benzyl)-piperidin-4-yl]-4,4-bis-(4-fluoro-phenyl)-imidazolidin-2-one; 1-cyclooctyl-3-(3-methoxy-1-aza-bicyclo[2.2.2]oct-3-yl)-1-phenyl-propan-2-yn-1-ol; 3-[2-(2-diethylamino-acetoxy)-2,2-dithiophen-2-yl-acetoxy]-1-(3-phenoxy-propyl)-1-azcation-bicyclo[2.2.2]octane (N, N-diethylglycine ester or salt of aclidinium bromide); or (2-diethylamino-acetoxy)-di-thiophen-2-yl-acetic acid 1-methyl-1-(2-phenoxy-ethyl)-piperidin-4-yl ester.

In addition, due to SARS-CoV-2 infection can cause acute lung injury, and the active ingredient of the present invention is particularly suitable for use in combination with drugs having the effect of improving acute lung injury. Representative drugs include but are not limited to Zinc, Fingolimod, Vitamin C, Olmesartan Medoxomil, valsartan, Losartan, Thalidomide, glycyrrhizic acid, Artemisinin, dihydroartemisinin, Artesunate, Artemisone, Azithromycin, Escin, Naproxen, or the combination thereof. The Zinc includes but is not limited to zinc sulfate, zinc glycyrrhetate, and zinc gluconate.

The active ingredient of the present invention can inhibit the infection activity of novel coronavirus such as SARS-CoV-2. Therefore, when the active ingredient of the present invention is administered or dosed, the infection of 2019 novel coronavirus (SARS-CoV-2) can be inhibited, and then achieve antiviral effect.

Compounds of formula (I) can also be in combination with mucolytic agents to treat both infection and respiratory tract infection symptoms. Non-limiting example of a mucolytic drug is ambroxol. Similarly, compounds of formula (I) can also be in combination with expectorant to treat both infection and respiratory tract infection symptoms. Non-limiting example of an expectorant is guaifenesin.

Atomized hypertonic saline is used to improve immediate and long-term clearance of small airways in patients with lung disease (Kuzik, J. Pediatrics 2007, 266). Compounds of formula (I) can also be combined with atomized hypertonic saline, especially when paramyxoviridae virus infection complicated with bronchiolitis. The combination of compounds of formula (I) and hypertonic saline may also include any of the additional agents discussed above. In a preferred aspect, about 3% atomized hypertonic saline is used.

It is also possible to combine any of the compounds of the present invention with one or more additional active therapeutic agents in a unit dosage form for simultaneous or sequential administration to a patient. Combination therapy can be administered as a simultaneous or sequential regimen. When administered sequentially, the combination can be administered in two or more administration.

Co-administration of a compound of the present invention with one or more additional active therapeutic agents generally means simultaneous or sequential administration of the compound of the present invention with one or more additional active therapeutic agents thereby therapeutically effective amounts of the compound of the present invention and one or more additional active therapeutic agents are present in the patient.

Co-administration includes administering a unit dose of a compound of the present invention before or after administering a unit dose of one or more additional active therapeutic agents, e.g. administering the compound of the present invention within several seconds, minutes, or hours of administration of one or more additional active therapeutic agents. For example, a unit dose of the compounds of the present invention may be administered first, followed by a unit dose of one or more additional active therapeutic agents within seconds or minutes. Alternatively, a unit dose of one or more other therapeutic agents may be administered first, followed by a unit dose of the compound of the present invention within seconds or minutes. In some cases, it may be required that a unit dose of the compound of the present invention may be administered first, followed by a unit dose of one or more additional active therapeutic agents after a period of several hours (e.g. 1-12 hours). In other cases, it may be required that a unit dose of one or more additional active therapeutic agents may be administered first, followed by a unit dose of the compound of the present invention after a period of several hours (e.g. 1-12 hours).

Combination therapy can provide "synergism" and "synergistic effect", i.e., the effect when active ingredients are used together is greater than the summation of effects when the compounds are used separately. Synergistic effect can be achieved when the active ingredients: (1) are co-formulated and simultaneously administered or delivered in the form of combined formulations; (2) alternately administrated or parallelly delivered as separate formulations; or (3) delivered via some other administration regimens. Synergistic effects may be achieved when delivered in alternative therapy, when the compounds are administered or delivered in turn, such as in separate tablets, pills or capsules, or by different injections using separate syringes. Typically, during alternative therapy, effective amount of each active ingredient is administered sequentially, i.e. continuously, while in combination treatments, two or more active ingredients of an effective dose are administered together. Synergistic antiviral effect means an antiviral effect greater than the predicted pure cumulative effect of individual compounds in the combination.

In yet another embodiment, it provides a method for inhibiting viral RNA polymerase in a cell, comprising exposing a virus-infected cell to an effective amount of a compound of formula (I) or a pharmaceutically acceptable salt, solvate and/or prodrug (e.g., ester) thereof, thereby inhibiting viral RNA polymerase.

In yet another embodiment, it provides a method for inhibiting viral RNA polymerase in a cell, comprising exposing a virus-infected cell to an effective amount of a compound of formula (I) or a pharmaceutically acceptable salt, solvate and/or prodrug (e.g., ester) thereof, and at least one additional active therapeutic agent, thereby inhibiting viral RNA polymerase.

In yet another embodiment, it provides a method for inhibiting viral RNA polymerase in a cell, comprising exposing a virus-infected cell to an effective amount of a compound of formula (I) or a pharmaceutically acceptable salt, solvate and/or prodrug (e.g., ester) thereof, and at least one selected additional active therapeutic agent.

In yet another embodiment, it provides a method for treating respiratory viral infections in human or other mammals, comprising administering an effective amount of the compound of formula (I) or a pharmaceutically acceptable salt, solvate and/or prodrug (e.g., ester) thereof to human or other mammals.

In yet another embodiment, it provides a method for treating respiratory viral infections in human or other mammals, comprising administering an effective amount of the compound of formula (I) or a pharmaceutically acceptable salt, solvate and/or prodrug (e.g., ester) thereof, and at least one additional active therapeutic agent, thereby inhibiting viral RNA polymerase.

In yet another embodiment, it provides a method for treating respiratory viral infections in human or other mammals, comprising administering an effective amount of the compound of formula (I) or a pharmaceutically acceptable salt, solvate and/or prodrug (e.g., ester) thereof, and at least one additional active therapeutic agent.

Pharmaceutical Compositions and Applications

The present invention also provides a use of a mixture of one or more active compounds of the present invention for inhibiting the replication of virus, or a pharmaceutically acceptable salt thereof, or prodrugs thereof as active ingredient in preparing treating and/or preventing, alleviating respiratory infections, pneumonia and other related diseases caused by infection of viruses such as coronavirus, influenza virus, respiratory syncytial virus and/or porcine epidemic diarrhea virus (PEDV) (especially 2019-nCoV).

The pharmaceutical compositions provided by the invention preferably contain the active ingredient in a weight ratio of 0.001-99 wt %. Its preferred ratio was that the active compounds of the present invention as active ingredient account for 0.1 wt % to 90 wt % or 1 wt % to 50 wt % of the total weight, and the remainder are pharmaceutically acceptable carriers, diluents or solutions or saline solutions.

When necessary, one or more pharmaceutically acceptable carriers can be added to the medicine of the invention. The carriers comprise conventional diluents, excipients, fillers, binders, wetting agents, disintegrants, absorption enhancers, surfactants, adsorption carriers, lubricants and the like in the pharmaceutical field.

The compounds and pharmaceutical compositions provided by the invention can be in various forms, such as tablets, capsules, powders, syrups, solutions, suspensions, and aerosols, etc, and can be stocked in a suitable solid or liquid carriers or diluents and in suitable disinfection device for injection or drip infusion.

Various dosage forms of the pharmaceutical compositions of the invention can be prepared according to the conventional preparation methods in the pharmaceutical field. The unit dose of the formulation generally contains 0.05-1000 mg of the active compounds of the present invention. Preferably, the unit dose of the formulation contains 1-500 mg of the active compounds of the present invention.

The compounds and pharmaceutical compositions of the invention can be used clinically in mammals, including humans and animals and can be administered through mouth, nose, skin, lung, or gastrointestinal tract. Most preferred is through mouth. Most preferred daily dose is of 0.01-400 mg/kg body weight, one-time administration, or 0.01-200 mg/kg body weight in divided doses. Regardless of any method of administration, the optimal dosage for an individual should be determined based on the specific treatment. Normally, start with a small dose and gradually increase the dose until the most suitable dose is found.

The drugs or inhibitors of the present invention can be administered in various different ways, such as being introduced into the body such as muscle, intradermal, subcutaneous, venous, or mucosal tissues by injection, spray, nasal, eye drops, osmosis, absorption, physical or chemically mediated methods; or be mixed or enveloped by other substances and introduced into the body.

Typically, the active ingredient of the present invention or pharmaceutical compositions containing the same may be administered in the form of unit dose. Administration routes can be intestinal or parenteral administration, such as oral, intravenous, intramuscular, subcutaneous, nasal, oral mucosa, eye, lung and respiratory tract, skin, vagina, rectum and the like.

The dosage form of administration can be a liquid dosage form, solid dosage form or semi-solid dosage form. The liquid dosage form can be solutions (including true solutions and colloidal solutions), emulsions (including type O/W, type W/O and multiple emulsion), suspensions, injections (including water injection, powder injection and infusions), eye drops, nasal drops, lotions and liniments, and the like; solid dosage form can be tablets (including ordinary tablets, enteric-coated tablets, buccal tablets, dispersible tablets, chewable tablets, effervescent tablets and orally disintegrating tablets), capsules (including hard capsules, soft capsules and enteric-coated capsules), granules, powders, pellets, dropping pills, suppositories, films, patches, aerosol (powder inhalations), sprays, and the like; semi-solid dosage form can be ointments, gels, cataplasm, and the like.

The active ingredient of the invention can be made into common preparation, also can be made into sustained release preparation, controlled-release preparation, targeted preparation and various microparticle drug delivery systems.

In order to make the active ingredient of the invention into tablets, various excipients known in the art can be generally used, including diluents, binders, wetting agents, disintegrants, lubricants and glidants. Diluents can be starch, dextrin, sucrose, glucose, lactose, mannitol, sorbitol, xylitol, microcrystalline cellulose, calcium sulfate, calcium hydrogen phosphate, calcium carbonate, and the like; wetting agents can be water, ethanol, isopropanol, and the like; binders can be starch slurry, dextrin, syrup, honey, glucose solution, microcrystalline cellulose, arabic mucilage slurry, gelatin slurry, sodium carboxymethyl cellulose, methyl cellulose, hydroxypropyl methyl cellulose, ethyl cellulose, acrylic resin, carbomer, polyvinylpyrrolidone, polyethylene glycol, and the like; disintegrants can be dry starch, microcrystalline cellulose, low substituted hydroxypropyl cellulose, cross-linked polyvinylpyrrolidone, cross-linked sodium carboxymethyl cellulose, sodium carboxymethyl starch, sodium bicarbonate and citric acid, polyoxyethylene sorbitol fatty acid ester, sodium dodecyl sulfonate and the like; lubricants and glidants can be talc powder, silica, stearate, tartaric acid, liquid paraffin, polyethylene glycol, and the like.

Tablets can also be further made into coating tablets, such as sugar coated tablets, film coated tablets, enteric coated tablets, or double-layer tablets and multi-layer tablets.

In order to make the administration unit into a capsule, the active ingredient of the present invention can be mixed with diluent, glidants; and the mixture is directly placed in a hard capsule or a soft capsule. The active ingredients can also be prepared into granules or pellets with diluents, binders and disintegrants first, and then placed in hard capsules or soft capsules. The kind of each of diluents, binders, wetting agents, disintegrants and glidants used for preparing the tablets of the invention can also be used for preparing the capsules of the invention.

In order to prepare the active ingredient of the invention into an injection, water, ethanol, isopropanol, propylene glycol or their mixture can be used as a solvent, and an appropriate amount of solubilizer, cosolvent, pH modulator, and osmotic pressure modulator that are common in the art can be added. Solubilizers or cosolvents can be poloxamer, lecithin, hydroxypropyl-β-cyclodextrin; pH modulator can be phosphate, acetate, hydrochloric acid, sodium hydroxide, and the like; osmotic pressure modulator can be sodium chloride, mannitol, glucose, phosphate, acetate, and the like. For example, mannitol and glucose and the like can be further added as proppants to prepare freeze-dried powder injection.

In addition, colorants, preservatives, spices, flavorants or other additives can be added to pharmaceutical formulations if necessary.

The active ingredient or composition of the present invention can be taken alone or in combination with other therapeutic drugs or symptomatic drugs.

When the active ingredient of the present invention has synergistic effect with other therapeutic drugs, the dosage should be adjusted according to the actual situation.

the Main Advantages of the Present Invention Include:
(a) The active compounds of the present invention can efficiently inhibit the replication of SARS-CoV-2, human respiratory syncytial virus (RSV), human coronavirus OC43 (HCoV OC43), porcine epidemic diarrhea virus (PEDV), Zika virus (Zika), dengue fever virus (DENV) and other viruses with low $EC_{50}$ value, and broad-spectrum antiviral characteristics.
(b) The active compounds of the present invention have low toxic side effects (cytotoxicity $CC_{50}>10$ μM), and have good medicinal properties which suggest that the nucleoside analogs of the present invention have a good medicinal prospect in the field of treatment of viral infectious diseases, especially fighting against novel coronavirus pneumonia.

The present invention was further described hereafter in combination with specific embodiments. It should be understood that these examples are only used to illustrate the and not to limit the scope of the invention. The experimental methods without specific conditions in the following examples generally follow the conventional conditions or the conditions suggested by the manufacturer. Unless otherwise stated, percentages and parts are by weight.

Preparation Example 1: Synthesis of Compound A1

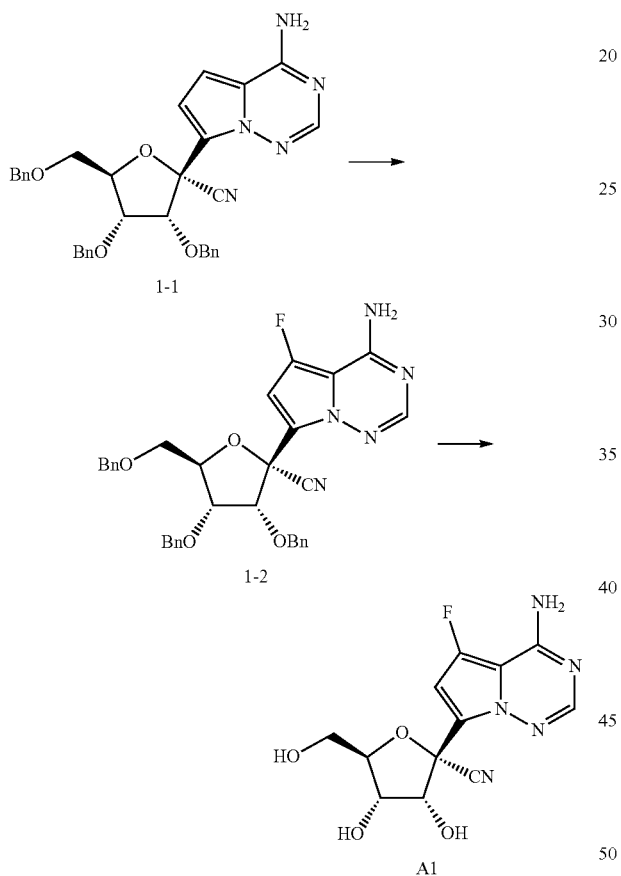

Compound 1-1 was synthesized by the method described in the literature (Nature. 2016, 531, 381-385). Compound 1-1 (1.5 g, 2.67 mmol) was added to acetonitrile (30 mL), followed by the addition of 1-chloromethyl-4-fluoro-1,4-diazoniabicyclo[2.2.2]octane bis(tetrafluoroborate) (Selectfluor, 1.13 g, 3.2 mmol, 1.2 eq) and sodium bicarbonate (0.67 g, 8.0 mmol, 3 eq). Upon complete addition, the reaction was carried at room temperature for 3-4 hours. TLC showed the reaction was complete. The reaction solution was added into water (120 mL), and extracted with ethyl acetate. The organic layer was separated, dried, concentrated and separated by silica gel column chromatography to give Compound 1-2 as an off-white solid (0.43 g, 28% yield). $^1$H NMR (500 MHz, DMSO-d$_6$) δ 8.12 (brs, 1H), 7.87 (s, 1H), 7.50-7.20 (m, 16H), 6.59 (s, 1H), 4.92 (d, J=11.7 Hz, 1H), 4.85-4.78 (m, 2H), 4.57-4.46 (m, 4H), 4.42-4.35 (m, 1H), 4.12 (t, J=5.7 Hz, 1H), 3.73 (dd, J=11.2, 3.2 Hz, 1H), 3.60 (dd, J=11.2, 4.3 Hz, 1H).

Compound 1-2 (0.25 g, 0.43 mmol) was added to dichloromethane (10 mL), cooled to −60° C., and 1M boron tribromide in dichloromethane (1.72 mL, 1.72 mmol, 4.0 eq) was added dropwise. After addition, the mixture was warmed naturally to −40° C., and further stirred for 2 hours at the same temperature. The reaction was monitored by TLC until it was complete. After cooling to −60° C., methanol (0.2 mL) and triethylamine (0.52 g, 5.16 mmol, 12 eq) were dropwise added successively. After addition, the solvent was removed by evaporation to obtain a yellow solid. The solid was added to methanol (2 mL) and ethyl acetate (10 mL), stirred and then filtered to remove white insoluble substances. The filtrate was concentrated and separated on preparative TLC plates to give Compound A1 as an off-white solid (49 mg, 37% yield). $^1$H NMR (500 MHz, DMSO-d$_6$) δ 8.11 (brs, 1H), 7.88 (s, 1H), 7.41 (brs, 1H), 6.80 (s, 1H), 6.23 (d, J=6.1 Hz, 1H), 5.20 (d, J=5.7 Hz, 1H), 4.93 (t, J=5.7 Hz, 1H), 4.54 (t, J=5.5 Hz, 1H), 4.08-4.01 (m, 1H), 3.96-3.90 (m, 1H), 3.71-3.64 (m, 1H), 3.55-3.48 (m, 1H). MS m/z=310.1 [M+1]$^+$.

Preparation Example 2: Synthesis of Compound A2

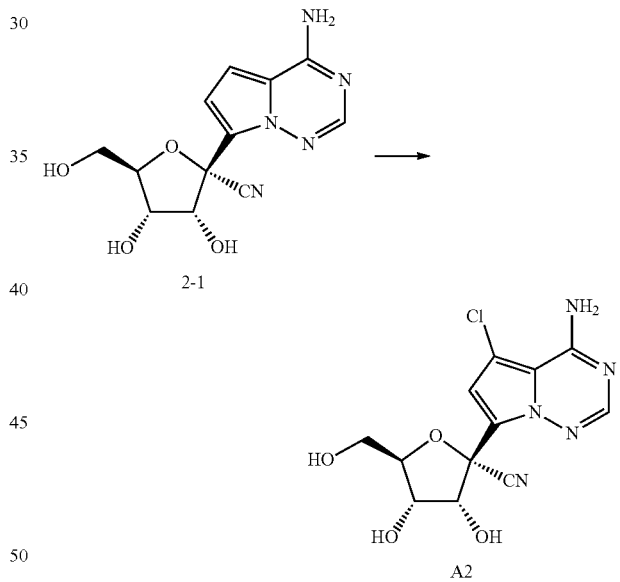

Compound 2-1 was synthesized according to the method described in the literature (Nature. 2016, 531, 381-385). Compound 2-1 (291 mg, 1.0 mmol) was added to N,N-dimethylformamide (5 mL), then N-chlorosuccinimide (245 mg, 1.1 mmol, 1.1 eq) and trifluoroacetic acid (24 mg, 0.2 mmol, 0.2 eq) were added, and reacted at 50° C. for 1 hour. TLC showed the reaction was complete. The reaction solution was added into the mixed solution of sodium sulfite and sodium carbonate, and filtered to obtain Compound A2 as a white solid (185 mg, 57% yield). $^1$H NMR (500 MHz, DMSO-d$_6$) δ 8.26 (brs, 1H), 7.95 (s, 1H), 7.09 (brs, 1H), 6.98 (s, 1H), 6.23 (d, J=5.7 Hz, 1H), 5.18 (d, J=5.6 Hz, 1H), 4.92 (t, J=5.6 Hz, 1H), 4.52 (t, J=5.0 Hz, 1H), 4.06-4.00 (m, 1H), 3.96-3.88 (m, 1H), 3.69-3.61 (m, 1H), 3.54-3.45 (m, 1H). MS m/z=326.0 [M+1]$^+$.

Preparation Example 3: Synthesis of Compound A3

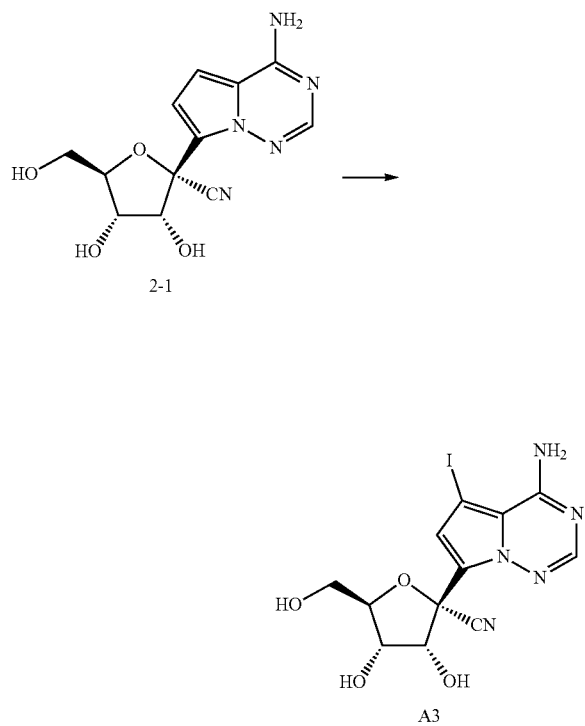

Compound 2-1 (291 mg, 1.0 mmol) was added to N,N-dimethylformamide (5 mL), then N-iodosuccinimide (245 mg, 1.1 mmol, 1.1 eq) and trifluoroacetic acid (24 mg, 0.2 mmol) were added, and reacted at 50° C. for 1 hour. TLC showed the reaction was complete. The reaction solution was added into the mixed solution of sodium sulfite and sodium carbonate, and filtered to obtain Compound A3 as a white solid (200 mg, 48% yield). $^1$H NMR (500 MHz, DMSO-$d_6$) δ 7.98 (s, 1H), 7.12 (s, 1H), 6.21 (brs, 1H), 5.20 (brs, 1H), 4.91 (s, 1H), 4.52 (d, J=4.6 Hz, 1H), 4.11-3.99 (m, 1H), 3.97-3.85 (m, 1H), 3.64 (d, J=11.3 Hz, 1H), 3.49 (d, J=10.9 Hz, 1H). MS m/z=418.0 [M+1]$^+$.

Preparation Example 4: Synthesis of Compound A4

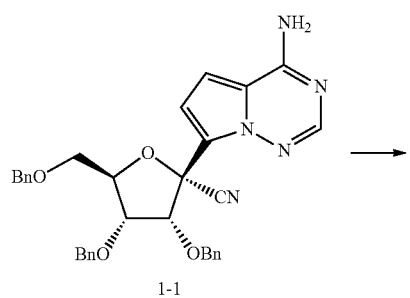

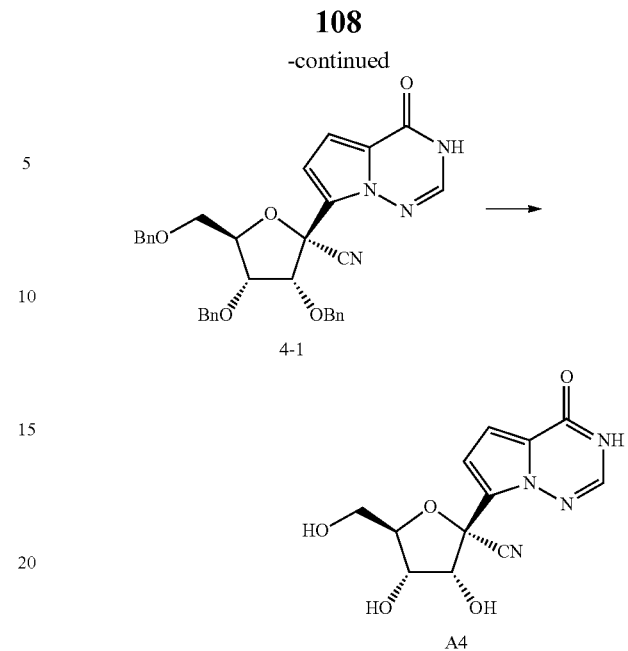

Compound 1-1 (350 mg, 0.62 mmol) was added to 80% aqueous acetic acid solution (10 mL) and cooled to 0° C. Sodium nitrite (856 mg, 12.4 mmol, 20 eq) was added portionwise. After addition, the temperature was maintained for 5 minutes. The mixture was stirred at room temperature for 30 minutes, then gradually warmed to 90° C., and stirred for 4 hours at the same temperature. TLC showed that the conversion of the raw materials was completed. Water (5 mL) and toluene (15 mL) were added, and the organic layer was separated. The aqueous layer was extracted with toluene again. The organic phases were combined. The organic phase was washed with water, aqueous sodium bicarbonate solution and brine successively, then dried, concentrated, and separated by silica gel column chromatography to give Compound 4-1 as a light-yellow foam solid (345 mg).

Under nitrogen protection, the product 4-1 obtained from the previous step was dissolved in dichloromethane (3 mL), cooled to −35° C., and 1M boron trichloride in dichloromethane (2.1 mL, 2.1 mmol) was added dropwise. The addition was completed in about 10 minutes. The mixture was stirred at the same temperature for 15 minutes, and methanol (0.3 mL) was slowly added. After addition, the temperature was maintained for 20 minutes, then the reaction solution was concentrated, followed by the addition of n-heptane (5 mL), and stirred at room temperature for 1 hour. The mixture was filtered, and the filter cake was washed with a small amount of n-heptane to give a yellow solid (255 mg). The solid was refluxed in methanol (0.75 mL) and water (0.1 mL) for 30 minutes. Active carbon (12 mg) was added, the mixture was filtered, and the filter residue was washed with a small amount of methanol. The filtrate was evaporated to dryness. A small amount of ethyl acetate was added, the resulting solid was slurried and filtered to obtain Compound A4 as a light-yellow solid (85 mg, 44% yield). $^1$H NMR (500 MHz, DMSO-$d_6$) δ 11.91 (d, J=4.1 Hz, 1H), 7.98 (d, J=4.1 Hz, 1H), 6.91 (d, J=4.4 Hz, 1H), 6.81 (d, J=4.4 Hz, 1H), 6.14 (brs, 1H), 5.22 (brs, 1H), 4.55 (d, J=5.1 Hz, 1H), 4.06-4.03 (m, 1H), 3.95 (t, J=5.4 Hz, 1H), 3.62 (dd, J=12.2, 3.4 Hz, 1H), 3.49 (dd, J=12.2, 4.6 Hz, 1H). MS m/z=293.0 [M+1]$^+$, m/z=291.0 [M−1]$^-$.

Preparation Example 5: Synthesis of Compound A9

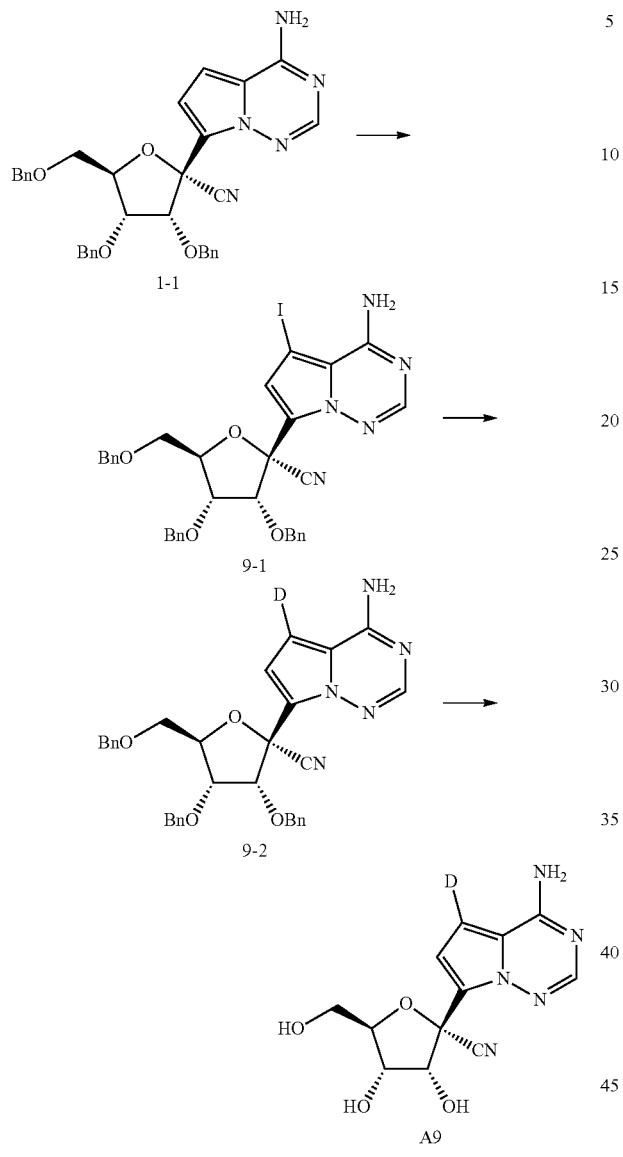

Compound 1-1 (561 mg, 1.0 mmol) was dissolved in N,N-dimethylformamide (5 mL), iodine (508 mg, 2 mmol, 2 eq) was added portionwise, and reacted at room temperature overnight. TLC showed that the starting material was remained. The reaction solution was added to the mixed solution of sodium sulfite and sodium carbonate, and extracted with ethyl acetate. The organic phase was separated, and washed with water and saturated brine successively, dried over anhydrous sodium sulfate, and separated by silica gel column chromatography to give Compound 9-1 as a white solid (400 mg, 58% yield). $^1$H NMR (500 MHz, DMSO-$d_6$) δ 7.98 (s, 1H), 7.40-7.22 (m, 15H), 6.86 (s, 1H), 4.91 (d, J=11.7 Hz, 1H), 4.84-4.78 (m, 2H), 4.50 (q, J=12.0 Hz, 4H), 4.41-4.35 (m, 1H), 4.12-4.08 (m, 1H), 3.72 (dd, J=11.2, 2.8 Hz, 1H), 3.59 (dd, J=11.2, 4.1 Hz, 1H).

Compound 9-1 (69 mg, 0.1 mmol) was dissolved in anhydrous tetrahydrofuran (5 mL), followed by the addition of trimethylchlorosilane (24 mg, 0.22 mmol, 2.2 eq) in an ice bath. The mixture was stirred for 10 minutes, then cooled to −10° C., and 3.0M methylmagnesium bromide in 2-methyltetrahydrofuran (74 μL, 0.22 mmol, 2.2 eq) was added. After the addition, the mixture was stirred for 30 minutes. The mixture was cooled to −20° C., 1.3M isopropylmagnesium chloride lithium chloride in tetrahydrofuran (0.1 mL, 0.13 mmol, 1.3 eq) was added, and further stirred for 1 hour. Deuteroxide (0.2 mL) was added to the reaction solution. After stirring for 15 minutes, the reaction solution was added into saturated ammonium chloride solution, and extracted with ethyl acetate. The organic phase was separated, washed with water and saturated brine successively, dried over anhydrous sodium sulfate, and separated by silica gel column chromatography to obtain Compound 9-2 as a white solid (28 mg, 50% yield). $^1$H NMR (500 MHz, Methanol-$d_4$) δ 7.65 (s, 1H), 7.34-7.16 (m, 15H), 6.84 (s, 1H), 4.95 (d, J=5.1 Hz, 1H), 4.74 (q, J=11.9 Hz, 2H), 4.57 (d, J=11.9 Hz, 1H), 4.53-4.43 (m, 4H), 4.11 (t, J=5.2 Hz, 1H), 3.73 (dd, J=10.9, 4.1 Hz, 1H), 3.62 (dd, J=10.9, 4.5 Hz, 1H).

Compound 9-2 (90 mg, 0.16 mmol) was dissolved in dichloromethane (10 mL), and 1.0M boron trichloride in dichloromethane (0.56 mL, 0.56 mmol) was added dropwise at −60° C. After the addition, the mixture was stirred at −40° C. for 1 hour. TLC showed the reaction was complete. Methanol (0.1 mL) was added to the reaction solution, followed by the addition of triethylamine to adjust the pH to 7-8. The reaction solution was concentrated and separated by silica gel column chromatography to give Compound A9 as an off-white solid (15 mg, 50% yield). $^1$H NMR (500 MHz, DMSO-$d_6$) δ 8.03-7.78 (m, 3H), 6.87 (s, 1H), 6.09 (d, J=6.3 Hz, 1H), 5.19 (d, J=5.2 Hz, 1H), 4.91 (t, J=5.7 Hz, 1H), 4.64 (t, J=5.7 Hz, 1H), 4.09-4.02 (m, 1H), 3.99-3.92 (m, 1H), 3.68-3.59 (m, 1H), 3.55-3.47 (m, 1H). MS m/z=293.0 [M+1]$^+$.

Preparation Example 6: Synthesis of Compound A9

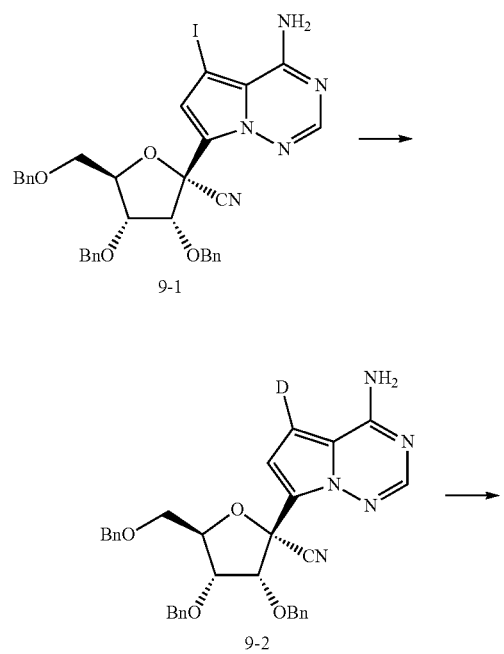

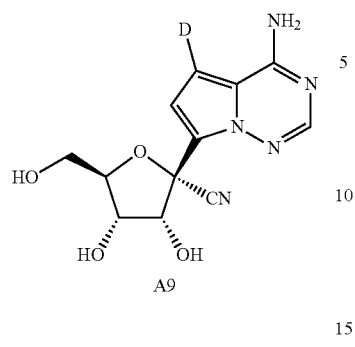

A9

Compound 9-1 (69 mg, 0.1 mmol) was added to a mixed solution of dry tetrahydrofuran (5 mL) and deuteroxide (1 mL). After the solution was concentrated to dryness, dry tetrahydrofuran (5 mL) and deuteroxide (1 mL) were added again, followed by the addition of [1,1'-bis(diphenylphosphino)ferrocene]palladium(II)dichloride dichloromethane complex (8 mg, 0.01 mmol) and tetramethylethylenediamine (3 mg, 0.02 mmol). After the addition, the mixture was stirred for 10 minutes, and sodium borodeuteride (21 mg, 0.5 mmol) was added portionwise. 2 hours later, TLC showed that the raw materials were entirely reacted. The reaction solution was added into water, and extracted with ethyl acetate. The organic phase was separated. The organic phase was washed with saturated brine, dried over anhydrous sodium sulfate, and separated by silica gel column chromatography to give Compound 9-2 as a white solid (30 mg, 53% yield) with a deuteration rate of no less than 97%.

According to the synthetic method of Example 5, Compound 9-2 (90 mg, 0.16 mmol) was deprotected to give Compound A9 as an off-white solid (15 mg, 50% yield). $^1$H NMR (500 MHz, DMSO-d$_6$) δ 8.01-7.79 (m, 3H), 6.88 (s, 1H), 6.09 (d, J=6.4 Hz, 1H), 5.19 (d, J=5.3 Hz, 1H), 4.91 (t, J=5.8 Hz, 1H), 4.65 (t, J=5.7 Hz, 1H), 4.08-4.04 (m, 1H), 3.98-3.93 (m, 1H), 3.67-3.61 (m, 1H), 3.54-3.48 (m, 1H). $^{13}$C NMR (126 MHz, DMSO-d$_6$) δ 156.08, 148.32, 124.35, 117.82, 116.94, 111.16, 85.92, 79.04, 74.72, 70.56, 61.43. The deuteration rate was no less than 97%, MS m/z=293.0 [M+1]$^+$.

Preparation Example 7: Synthesis of Compound A10

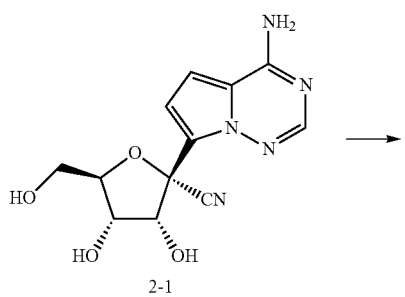

2-1

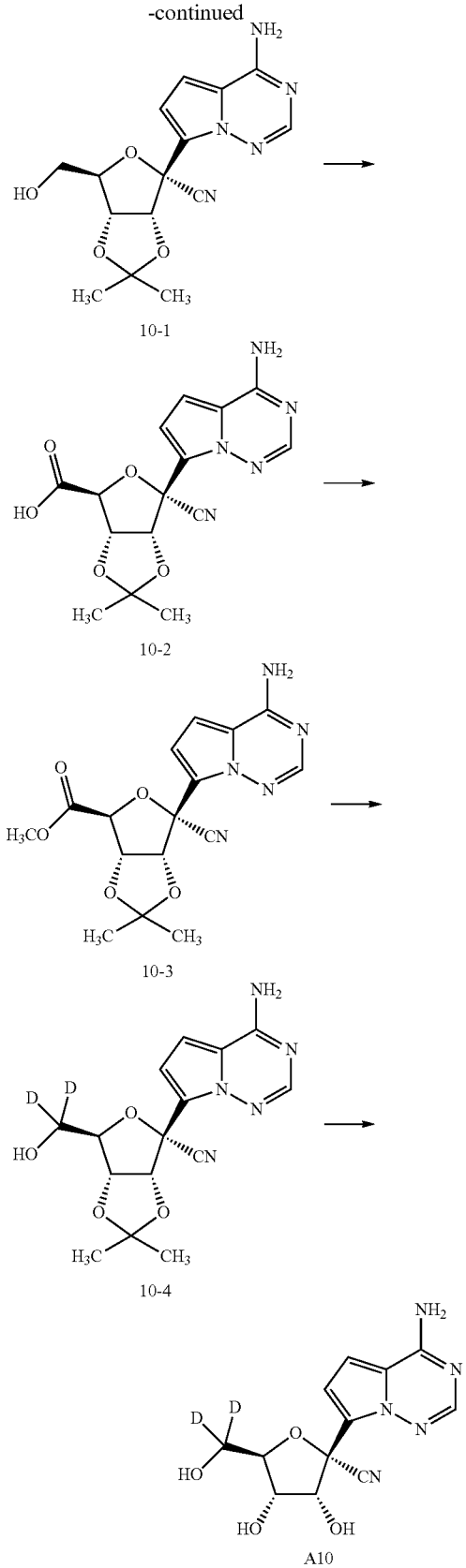

Compound 2-1 (0.5 g, 1.72 mmol) was added to acetone (10 mL), followed by the successive addition of 2,2-dimethoxypropane (0.89 g, 8.6 mmol, 5 eq) and p-toluenesulfonic acid monohydrate (0.59 g, 3.1 mmol, 1.8 eq). After the addition, the reaction was stirred at 45° C. for 2 hours, and TLC showed that the reaction was complete. The reaction solution was added to saturated aqueous sodium bicarbonate (20 mL), and extracted with ethyl acetate. The organic layer was separated, dried, and evaporated to give Compound 10-1 as a white solid (0.33 g, 58% yield).

Compound 10-1 (0.25 g, 0.75 mmol) was added to acetonitrile/water (V/V=1/1, 15 mL), followed by the successive addition of TEMPO (0.047 g, 0.3 mmol, 0.4 eq), iodobenzene diacetate (1.06 g, 3.3 mmol, 4.4 eq) and sodium bicarbonate (0.25 g, 3 mmol, 4.0 eq). After the addition, the mixture was stirred at room temperature for about 5 hours. TLC showed that the reaction was complete. The reaction solution was added into 0.5M sodium hydroxide solution (20 mL), and extracted twice with ethyl acetate (20 ml×2). The organic phase was discarded, and the pH of the aqueous layer was adjusted to 4-5 with diluted hydrochloric acid (2M). The solution was extracted with ethyl acetate (50 mL×2). The organic layers were combined, dried and concentrated to give Compound 10-2 as a white solid (0.23 g, 89% yield).

The product 10-2 (0.18 g, 0.52 mmol) obtained from the previous step was added into tetrahydrofuran and methanol (8 mL, 1:1), and 2M trimethylsilyldiazomethane in n-hexane (1.2 mL, 2.4 mmol, 4.5 eq) was added dropwise at room temperature. After the addition, the reaction was carried out at room temperature, and 1 hour later, the reaction was complete. Acetic acid was added to the reaction solution dropwise until no bubbles were generated. The solvent was removed by evaporation, and the residue was separated on preparative TLC plates to obtain Compound 10-3 as a white solid (0.11 g, 59% yield). $^1$H NMR (500 MHz, DMSO-d$_6$) δ 8.06-7.88 (m, 3H), 6.92 (d, J=4.6 Hz, 1H), 6.89 (d, J=4.6 Hz, 1H), 5.52 (d, J=6.1 Hz, 1H), 5.37 (dd, J=6.1, 2.2 Hz, 1H), 4.92 (d, J=2.2 Hz, 1H), 3.40 (s, 3H), 1.62 (s, 3H), 1.42 (s, 3H).

Compound 10-3 (0.10 g, 0.28 mmol) was added to anhydrous tetrahydrofuran (4 mL) and deuterated methanol (1 mL). Then, sodium borodeuteride (0.047 g, 1.12 mmol, 4 eq) was added in an ice bath. After the addition, the reaction was carried at room temperature, and 1 hour later, TLC showed the reaction was complete. Diluted hydrochloric acid was added to the reaction solution dropwise until no bubbles were generated. The reaction solution was concentrated, and separated on preparative TLC plates to obtain Compound 10-4 as a white solid (0.06 g, 64% yield).

The product 10-4 obtained from the previous step (60 mg, 0.18 mmol) was added to tetrahydrofuran (2 mL), followed by the dropwise addition of concentrated hydrochloric acid (0.4 mL), and the reaction was carried at 40° C. until the reaction was complete. To the reaction solution was added sodium bicarbonate solution until the pH was neutral. The mixture was extracted with tetrahydrofuran. The organic phase was separated, dried and evaporated to dryness to obtain an off-white solid. The resulting solid was added to ethyl acetate, stirred for 0.5 hours, filtered and dried to give Compound A10 as a white solid (34 mg, 64% yield). $^1$H NMR (500 MHz, DMSO-d$_6$) δ 8.03-7.82 (m, 3H), 6.92 (d, J=4.5 Hz, 1H), 6.89 (d, J=4.6 Hz, 1H), 6.10 (d, J=6.3 Hz, 1H), 5.20 (d, J=5.2 Hz, 1H), 4.89 (s, 1H), 4.66 (t, J=5.7 Hz, 1H), 4.06 (d, J=5.4 Hz, 1H), 4.00-3.93 (m, 1H). $^{13}$C NMR (126 MHz, DMSO-d$_6$) δ 156.10, 148.35, 124.35, 117.81, 117.01, 111.26, 101.27, 85.80, 79.04, 74.70, 70.54. The deuteration rate was 99%, MS m/z=294.0 [M+1]$^+$.

Preparation Example 8: Synthesis of Compound A11

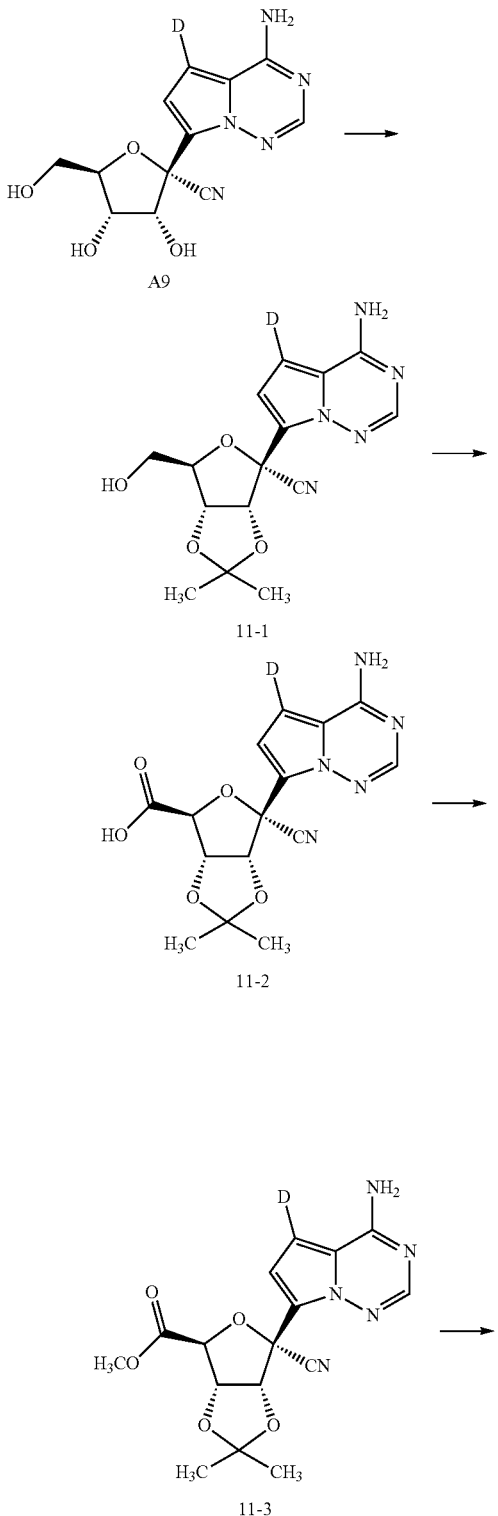

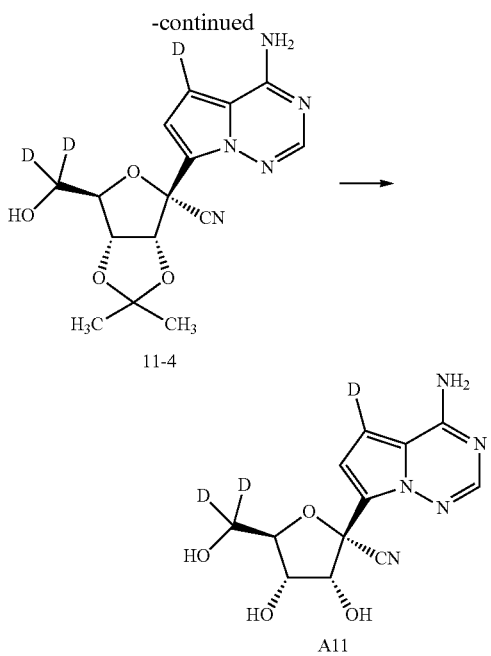

11-4

A11

Compound A9 (1.17 g, 4.0 mmol, with a deuteration rate of no less than 97%) was added to acetone (20 mL), followed by the successive addition of 2,2-dimethoxypropane (2.08 g, 20.0 mmol, 5 eq) and p-toluenesulfonic acid monohydrate (1.37 g, 7.2 mmol, 1.8 eq). After the addition, the reaction mixture was stirred at 45° C. for 2 hours. A lot of precipitates appeared and TLC showed that the reaction was complete. The reaction solution was added into saturate aqueous sodium bicarbonate, and extracted with ethyl acetate. The organic layer was separated, dried, and the solvent was removed by evaporation to give Compound 11-1 as a white solid (0.86 g, 65% yield).

Compound 11-1 (0.225 g, 0.68 mmol) was added to acetonitrile/water (V/V=1/1, 10 mL), followed by the successive addition of TEMPO (0.02 g, 0.14 mmol, 0.2 eq), iodobenzene diacetate (0.66 g, 2.04 mmol, 3.0 eq) and sodium bicarbonate (0.17 g, 2.04 mmol, 3.0 eq). After the addition, the mixture was stirred at room temperature for 4-5 hours. TLC showed that the reaction was complete. The reaction solution was added into KOH aqueous solution (0.5M, 20 mL), and extracted with ethyl acetate (20 mL×3). The aqueous layer was separated, then adjusted to pH 4-5 with diluted hydrochloric acid (2M), and extracted with ethyl acetate (20 mL×3). The organic layers were combined, dried and concentrated to obtain crude Compound 11-2, which was directly used in the next step.

Crude Compound 11-2 (0.68 mmol, based on 100% yield) was added to tetrahydrofuran/methanol (V/V=1/1, 8 mL), and trimethylsilyldiazomethane in n-hexane (2M, 1.36 mL, 4.0 eq) was added dropwise at room temperature. After the addition, the reaction was carried out at room temperature, and 30 mins later, the reaction was complete. Acetic acid was added dropwise to the reaction solution until no bubbles were generated. The reaction solution was evaporated to dryness, and ethyl acetate (20 mL) was added. After washed with saturated sodium bicarbonate (10 mL×2), the organic layer was separated, dried, concentrated and purified by silica gel column chromatography to give Compound 11-3 as a white solid (0.06 g, 24% yield for two steps).

Compound 11-3 (0.06 g, 0.17 mmol) was added to deuterated methanol/tetrahydrofuran (V/V=1/5, 6 mL) and NaBD$_4$ (0.028 g, 0.68 mmol, 4 eq) was added in an ice bath. After the addition, the mixture was reacted at room temperature, and 1-2 hours later, the reaction was complete. The reaction solution was added to a mixed liquid of ethyl acetate/water (20 mL/20 mL). The organic layer was separated, and the aqueous layer was extracted once with ethyl acetate (20 mL) again. The ethyl acetate layers were combined and evaporated to dryness. The obtained product was added to methanol (10 mL), and dilute hydrochloric acid (1M) was added dropwise to adjust the pH of the solution to 2-3. The mixture was stirred at room temperature for 1-2 hours, and the pH was adjusted to neutral using saturated sodium bicarbonate aqueous solution. A mixed solution of ethyl acetate/water (20 mL/20 mL) was added. The organic phase was separated. The aqueous layer was extracted once with ethyl acetate (20 mL) again. The organic layers were combined, dried, concentrated and separated on silica gel preparative TLC plates to obtain Compound 11-4 as a white solid (0.05 g, 89% yield).

11-4 (0.05 g, 0.15 mmol) was added to tetrahydrofuran (1.5 mL), and then concentrated hydrochloric acid (0.3 mL) was added dropwise in an ice bath. After the addition, the reaction mixture was stirred at room temperature for 2-3 hours. TLC showed that the reaction was complete. The pH of the reaction solution was adjusted to neutral with 1M NaOH aqueous solution in an ice bath. Tetrahydrofuran was removed by evaporation, and the mixture was filtered. The filter cake was slurried with distilled water (10 mL) and ethyl acetate (10 mL) successively, then filtered and dried to obtain Compound A11 as a white solid (0.03 g, 68% yield). $^1$H NMR (500 MHz, DMSO-d$_6$) δ 8.04-7.76 (m, 3H), 6.89 (s, 1H), 6.07 (d, J=6.3 Hz, 1H), 5.18 (d, J=5.2 Hz, 1H), 4.87 (s, 1H), 4.67 (t, J=5.8 Hz, 1H), 4.07 (d, J=5.3 Hz, 1H), 4.01-3.93 (m, 1H). m/z=295.0 [M+1]$^+$. The deuteration rates for the two positions were no less than 97%, respectively.

Preparation Example 9: Synthesis of Compound A12

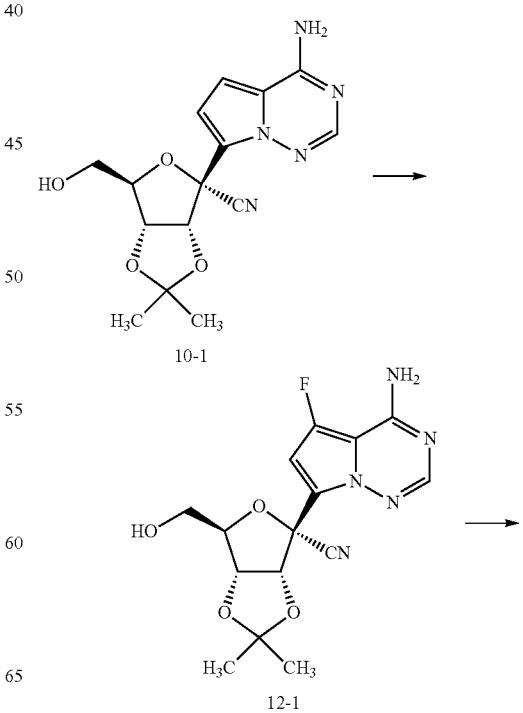

10-1

12-1

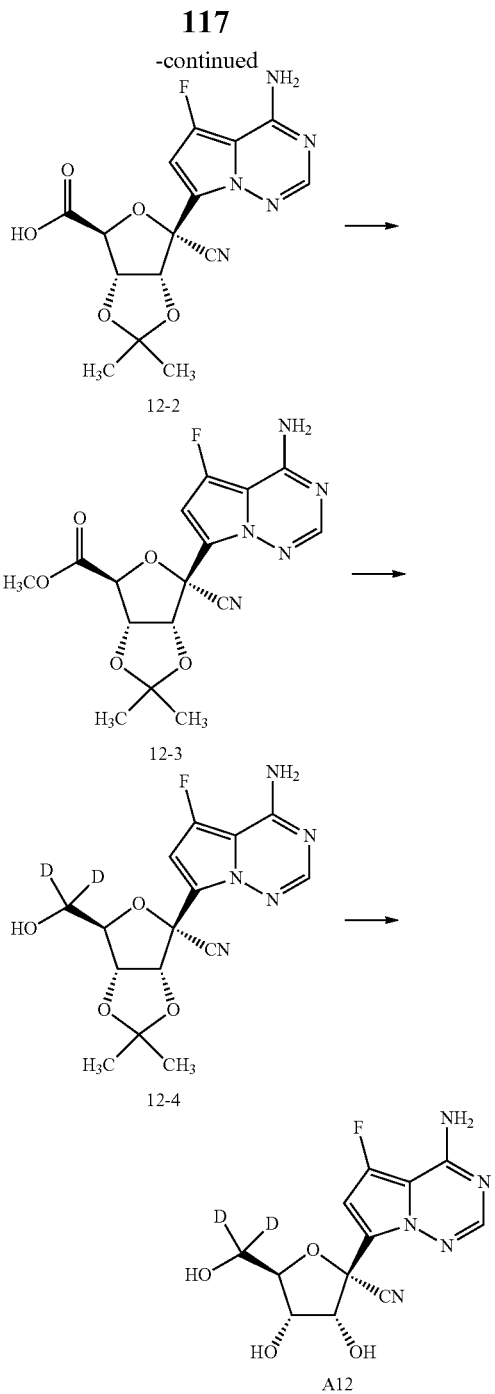

12-2

12-3

12-4

A12

Compound 10-1 (662 mg, 2.0 mmol) was added to acetonitrile (15 mL), followed by the addition of sodium bicarbonate (336 mg, 4 mmol, 2 eq) and 1-chloromethyl-4-fluoro-1,4-diazoniabicyclo[2.2.2]octane bis(tetrafluoroborate) (850 mg, 2.4 mmol, 1.2 eq). The mixture was stirred at room temperature for 24 hours, and TLC showed that some starting material remained. Ethyl acetate (50 mL) and water (20 mL) were added to the reaction solution. The organic layer was separated, dried, concentrated and purified by silica gel column chromatography to give Compound 12-1 as an off-white solid (140 mg, 20% yield).

Compound 12-1 (140 mg, 0.4 mmol) was added to a mixed solution of acetonitrile and water (6 mL, 1:1), followed by the successive addition of iodobenzene diacetate (515 mg, 1.6 mmol, 4 eq), sodium bicarbonate (135 mg, 1.6 mmol, 4 eq) and TEMPO (25 mg, 0.16 mmol, 0.4 eq) at room temperature. The reaction was complete in about 3 hours. Sodium hydroxide aqueous solution (10 mL, 224 mg, 10 eq) was added to the reaction solution. The mixture was extracted with ethyl acetate twice, and the organic phase was discarded. 2M dilute hydrochloric acid was added into the aqueous phase, adjusting the pH to 4-5, and extracted with ethyl acetate for three times. The organic phases were combined, dried, and evaporated to obtain Compound 12-2 as an off-white solid (116 mg, 80% yield).

Compound 12-2 (116 mg, 0.32 mmol) was added to the mixed solution of tetrahydrofuran and methanol (4 mL, 1:1), followed by the addition of 2M trimethylsilyldiazomethane in n-hexane (0.48 mL, 0.96 mmol, 3 eq) slowly. The reaction was monitored by TLC, and if the raw materials were remained, an appropriate amount of trimethylsilyldiazomethane could be added until the reaction was complete. Acetic acid was added to the reaction solution dropwise until no bubbles were generated. The solvent was removed by evaporation, and the residue was purified by silica gel column chromatography to obtain Compound 12-3 as a white solid (105 mg, 87% yield).

The product 12-3 (105 mg, 0.28 mmol) obtained from the previous step was added to anhydrous tetrahydrofuran (2 mL), followed by the addition of deuterated methanol (0.5 mL), and sodium borodeuteride (35 mg, 0.84 mmol, 3 eq) was added portionwise in 1 hour at room temperature. The mixture continued to be stirred for 5 hours, and TLC showed the reaction was complete. Ethyl acetate (0.5 mL) was added to the reaction solution. The reaction solution was concentrated, and the residue was purified by preparative TLC to give Compound 12-4 as a white foam solid (80 mg, 82% yield).

The product 12-4 obtained from the previous step (80 mg, 0.23 mmol) was added to tetrahydrofuran (3 mL), followed by the dropwise addition of concentrated hydrochloric acid (0.5 mL). The reaction was carried out at 40° C. until the reaction was complete. Insoluble substances were precipitated from the reaction solution, and filtered to give 55 mg white solid. The solid was added to water (1.5 mL), followed by the addition of sodium carbonate (16 mg). The mixture was stirred for 0.5 h, filtered and dried to give Compound A12 as a white solid (44 mg, 62% yield). $^1$H NMR (500 MHz, DMSO-$d_6$) δ 8.10 (brs, 1H), 7.88 (s, 1H), 7.41 (brs, 1H), 6.80 (s, 1H), 6.23 (brs, 1H), 5.20 (brs, 1H), 4.89 (s, 1H), 4.54 (d, J=4.9 Hz, 1H), 4.04 (d, J=6.3 Hz, 1H), 3.94 (t, J=5.5 Hz, 1H). The deuteration rate was 98%, MS m/z=312.0 [M+1]$^+$.

Preparation Example 10: Synthesis of Compound A35

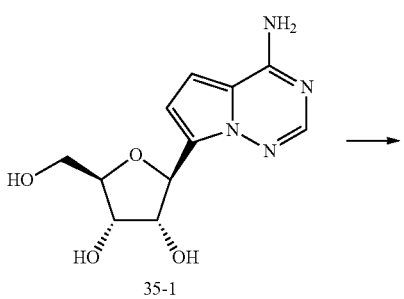

35-1

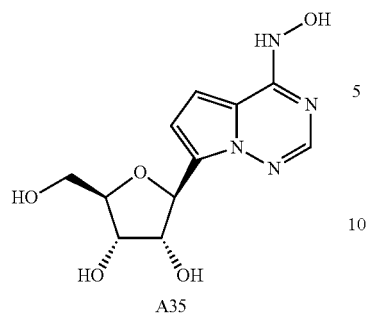

A35

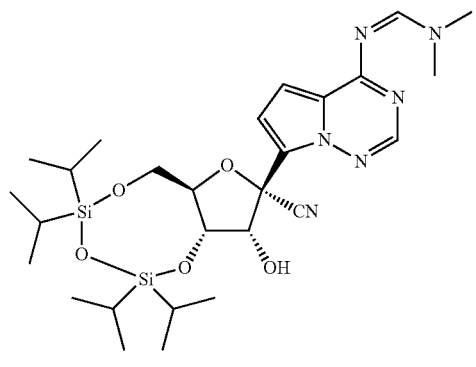

49-2

Compound 35-1 was synthesized according to the method reported in the literature (WO2015069939). Hydroxylamine hydrochloride (547 mg, 7.87 mmol, 30 eq) was added to water (3.2 mL), followed by the slow addition of 10% sodium hydroxide solution to adjust the pH of the solution to 6.0, then compound 35-1 (69 mg, 0.26 mmol, 1 eq) was added, and stirred overnight at 40° C. under nitrogen protection. TLC showed the reaction was complete.

The reaction solution was separated by reversed-phase column chromatography to give A35 as an off-white solid (52 mg, 71% yield). $^1$H NMR (500 MHz, DMSO-$d_6$) δ 10.61 (d, J=4.0 Hz, 1H), 10.06 (s, 1H), 7.39 (d, J=4.0 Hz, 1H), 6.38-6.33 (m, 2H), 4.96 (d, J=6.6 Hz, 1H), 4.93 (d, J=6.3 Hz, 1H), 4.86 (d, J=5.1 Hz, 1H), 4.74-4.68 (m, 1H), 4.15 (q, J=6.1 Hz, 1H), 3.91 (q, J=4.9 Hz, 1H), 3.74 (q, J=4.5 Hz, 1H), 3.55-3.49 (m, 1H), 3.47-3.43 (m, 1H). MS m/z=283.0 [M+1]$^+$.

Preparation Example 11: Synthesis of Compounds A49 and A124

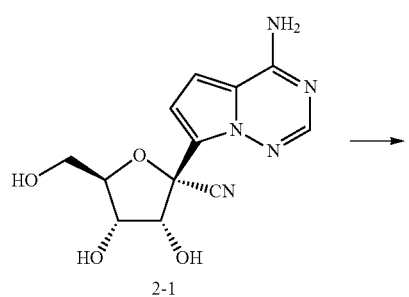

2-1

Compound 2-1 (2.2 g, 7.6 mmol) was added to N,N-dimethylformamide (20 mL), followed by the addition of imidazole (3.1 g, 45.6 mmol, 6 eq), and 1,3-dichloro-1,1,3,3-tetraisopropyldisiloxane (2.9 g, 9.5 mmol, 1.2 eq) was added dropwise in an ice bath. After the addition, the reaction was carried out at room temperature, and 4 hours later, the reaction was complete. The reaction solution was added into water (120 mL), and extracted with ethyl acetate. The organic layer was separated, dried, concentrated and separated by silica gel column chromatography to give Compound 49-1 as a white solid (3.2 g, 80% yield). $^1$H NMR (500 MHz, DMSO-$d_6$) δ 7.99-7.82 (m, 3H), 6.88 (d, J=4.5 Hz, 1H), 6.79 (d, J=4.4 Hz, 1H), 6.45 (d, J=5.7 Hz, 1H), 4.56 (t, J=5.0 Hz, 1H), 4.22-4.09 (m, 3H), 3.95-3.86 (m, 1H), 1.09-0.76 (m, 28H).

Compound 49-1 (1.2 g, 2.2 mmol) was added to toluene (20 mL), followed by the addition of N,N-dimethylformamide dimethyl acetal (0.52 g, 4.4 mmol, 2 eq), and the reaction was carried at 50° C. The reaction was complete in about 3 hours. The solvent was evaporated under reduced pressure, and ethyl acetate (60 mL) and water (20 mL) were added. The organic phase was separated, washed with saturated brine, dried, and evaporated to give Compound 49-2 as a white solid (1.2 g, 92% yield). $^1$H NMR (500 MHz, DMSO-$d_6$) δ 8.96 (s, 1H), 8.16 (s, 1H), 6.91 (d, J=4.5 Hz, 1H), 6.81 (d, J=4.4 Hz, 1H), 6.49 (d, J=5.8 Hz, 1H), 4.59 (t, J=5.1 Hz, 1H), 4.26-4.11 (m, 3H), 3.93 (dd, J=13.3, 2.4 Hz, 1H), 3.26 (s, 3H), 3.20 (s, 3H), 1.09-0.87 (m, 28H).

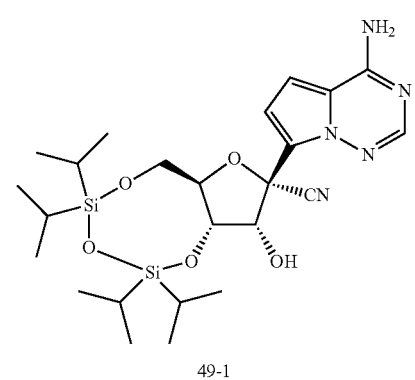

49-1

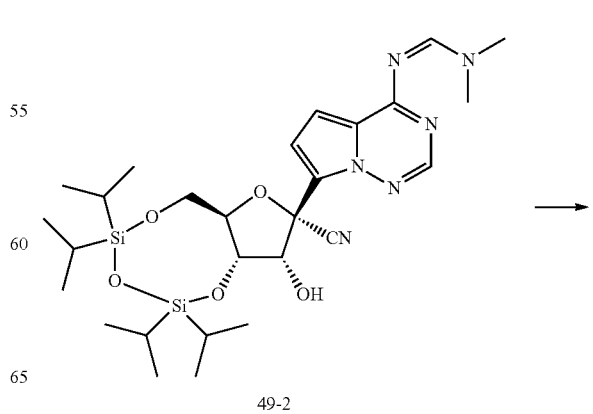

49-2

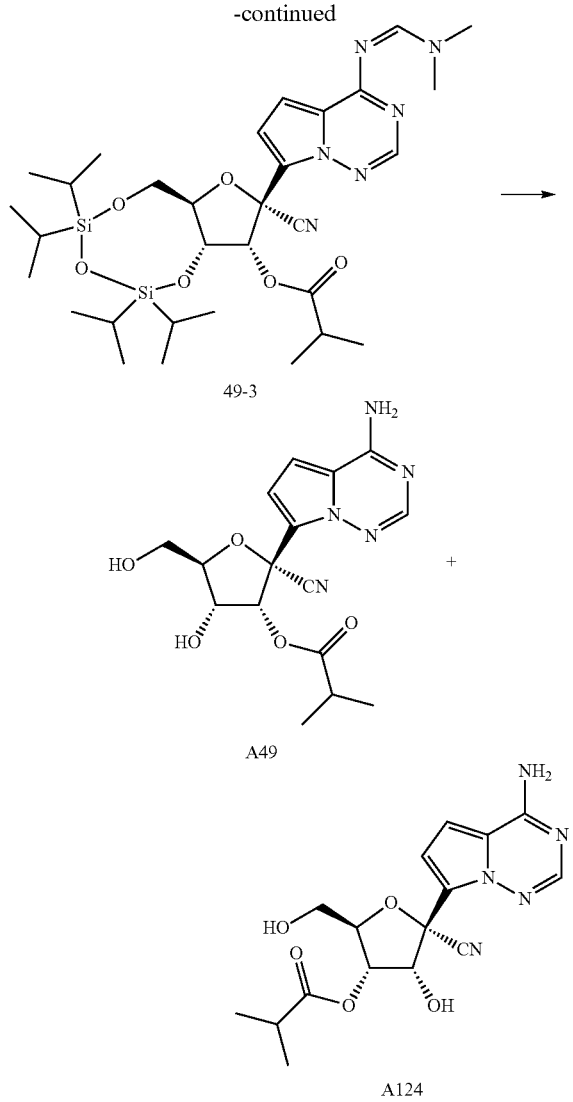

was separated, dried, concentrated and separated using silica gel column chromatography to obtain Compounds A49 and A124. The proportion of A124 was more than 95%, and recrystallization in isopropyl acetate afforded A124 as a white solid (80 mg, 61% yield for two steps). For the obtained Compound A124: $^1$H NMR (500 MHz, DMSO-$d_6$) δ 8.09-7.84 (m, 3H), 6.94 (d, J=4.6 Hz, 1H), 6.90 (d, J=4.6 Hz, 1H), 6.43 (d, J=6.5 Hz, 1H), 5.22 (dd, J=5.7, 3.3 Hz, 1H), 5.07 (t, J=5.8 Hz, 1H), 5.01 (t, J=6.1 Hz, 1H), 4.31-4.25 (m, 1H), 3.66-3.52 (m, 2H), 2.68-2.58 (m, 1H), 1.19 (d, J=7.0 Hz, 3H), 1.17 (d, J=7.0 Hz, 3H). MS m/z=362.0 [M+1]$^+$.

Preparation Example 12: Synthesis of Compound A50

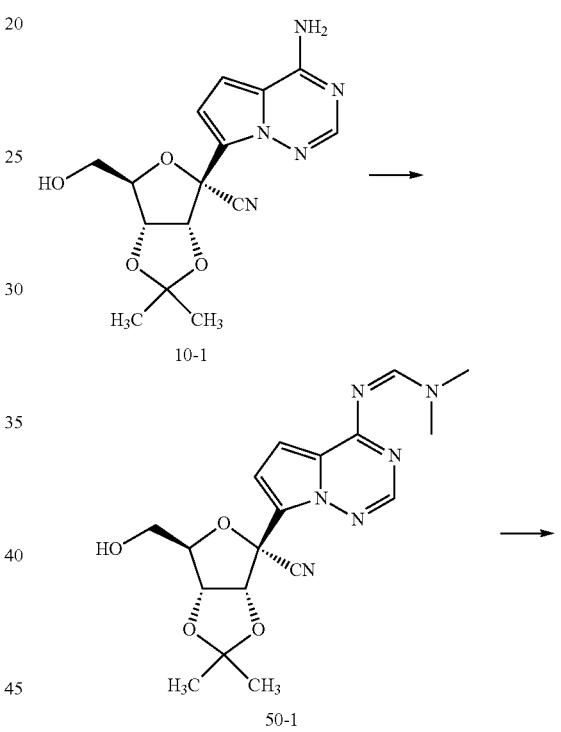

Compound 49-2 (294 mg, 0.5 mmol) was added to dichloromethane (6 mL), followed by the successive addition of triethylamine (101 mg, 1 mmol, 2 eq), DMAP (12 mg, 0.1 mmol, 0.2 eq) and isobutyryl chloride (85 mg, 0.8 mmol, 1.6 eq) at room temperature. The reaction was carried out overnight, and TLC showed the reaction was complete. Saturated aqueous sodium bicarbonate and dichloromethane were added to the reaction solution. The organic layer was separated, then dried, concentrated and purified by silica gel column chromatography to give Compound 49-3 as a white foam solid (240 mg, 72% yield).

The product 49-3 (240 mg, 0.36 mmol) obtained from the previous step was added to tetrahydrofuran (5 mL), followed by the addition of 1M tetrabutylammonium fluoride in tetrahydrofuran (0.72 mL, 0.72 mmol). After 1 hour, the reaction was complete. To the reaction solution was added water (10 mL), and extracted with ethyl acetate. The organic layer was separated. The organic phase was dried and evaporated to dryness to give an oil. The oil was added to tetrahydrofuran (6 mL), followed by the addition of water (0.5 mL) and trifluoroacetic acid (205 mg, 1.8 mmol) and the mixture was stirred overnight at room temperature. To the reaction solution was added sodium bicarbonate aqueous solution, and extracted with ethyl acetate. The organic layer

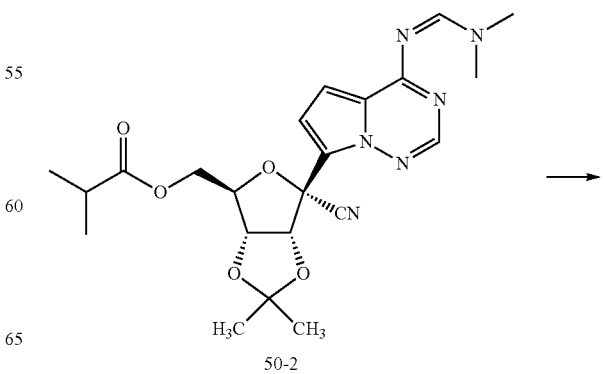

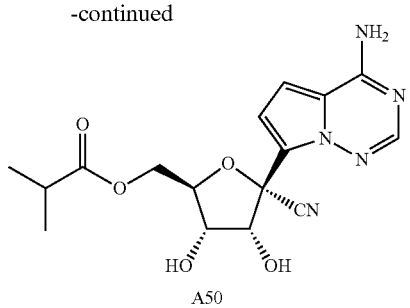

A50

Compound 10-1 (0.664 g, 2.0 mmol) was added to toluene (10 mL), followed by the addition of N,N-dimethylformamide dimethyl acetal (0.47 g, 4.0 mmol, 2.0 eq). After the addition, the reaction was carried out at 60° C. for 2-3 hours. TLC showed that the reaction was complete. The solvent was removed by evaporation to give Compound 50-1 as a yellow solid (0.65 g, 84% yield).

The product 50-1 (0.2 g, 0.52 mmol) obtained from the previous step was added to dichloromethane (10 mL), followed by the successive addition of triethylamine (0.1 g, 1.0 mmol, 2 eq), DMAP (0.012 g, 0.10 mmol, 0.2 eq) and isobutyryl chloride (0.083 g, 0.78 mmol, 1.5 eq). After the addition, the mixture was stirred at room temperature for 1-2 hours. TLC showed the reaction was complete. The reaction solution was added into 1M dilute hydrochloric acid (10 mL). The mixture was extracted with dichloromethane, and the organic phase was separated. The organic phase was washed with saturated sodium bicarbonate (20 mL), dried and concentrated to give Compound 50-2 as an off-white solid (0.2 g, 84% yield).

Compound 50-2 (0.1 g, 0.22 mmol) was added to tetrahydrofuran (3 mL), followed by the dropwise addition of concentrated hydrochloric acid (0.6 mL) in an ice bath. After the addition, the mixture was stirred at room temperature for 3 hours. TLC showed that a small amount of the raw material was remained. The reaction solution was added into saturated aqueous sodium bicarbonate solution (20 mL) and extracted with ethyl acetate. The organic phase was separated. The organic phase was dried, concentrated, and separated on preparative TLC plates to give Compound A50 as a white solid (13 mg, 16% yield). $^1$H NMR (500 MHz, DMSO-$d_6$) δ 8.00-7.80 (m, 3H), 6.92 (d, J=4.6 Hz, 1H), 6.82 (d, J=4.5 Hz, 1H), 6.33 (d, J=6.0 Hz, 1H), 5.39 (d, J=5.8 Hz, 1H), 4.70 (t, J=5.5 Hz, 1H), 4.32 (dd, J=12.0, 2.9 Hz, 1H), 4.27-4.21 (m, 1H), 4.18 (dd, J=12.0, 5.3 Hz, 1H), 3.99-3.94 (m, 1H), 2.57-2.52 (m, 1H), 1.07 (d, J=2.4 Hz, 3H), 1.06 (d, J=2.4 Hz, 3H). MS m/z=362.0 [M+1]$^+$.

Preparation Example 13: Synthesis of Compound A51 and A212

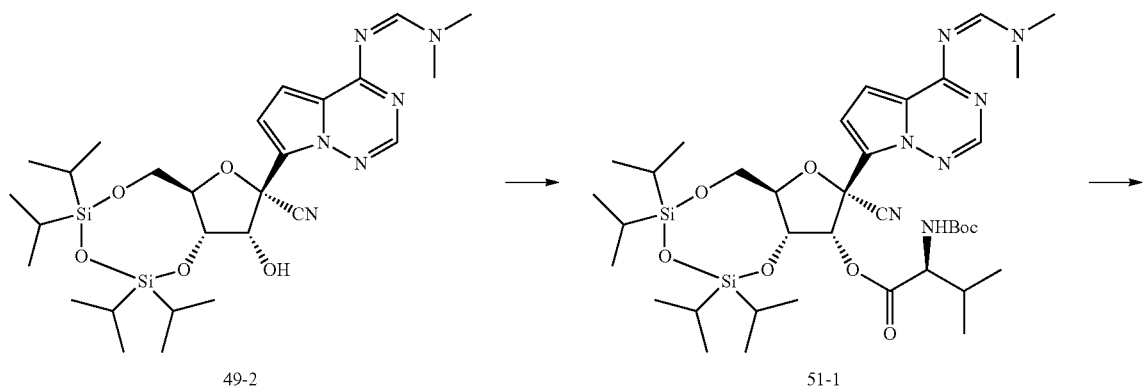

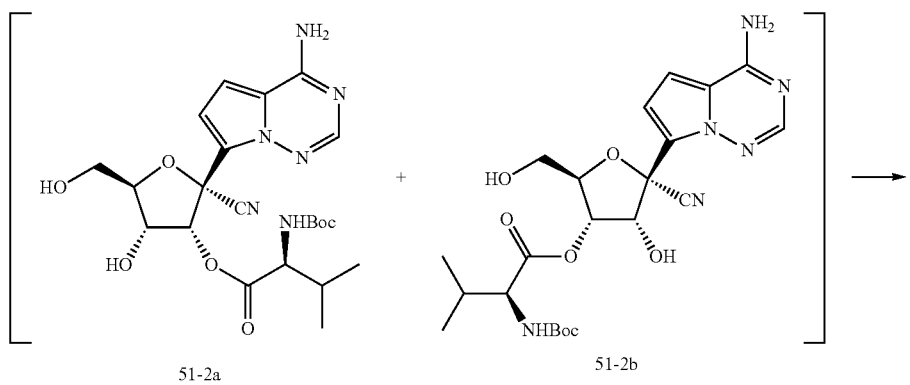

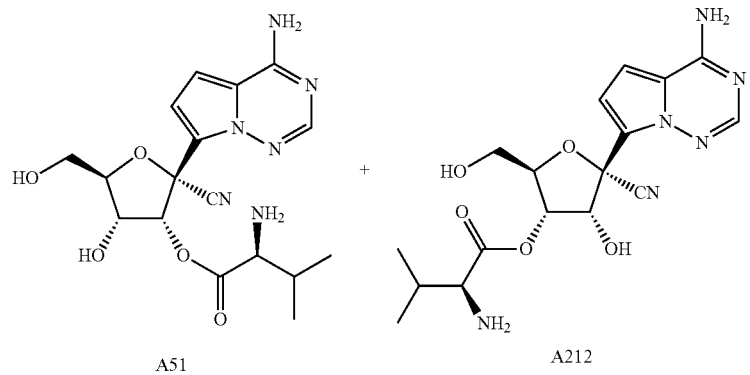

Compound 49-2 (260 mg, 0.44 mmol) and Boc-L-valine (115 mg, 0.53 mmol, 1.2 eq) were added to dichloromethane (10 mL), followed by the successive addition of HOBT (89 mg, 0.66 mmol, 1.5 eq), EDCI (169 mg, 0.88 mmol, 2 eq) and DMAP (214 mg, 1.76 mmol, 4 eq), and the mixture was stirred overnight at room temperature. To the reaction solution was added dichloromethane (20 mL) and water (20 mL). After stirring for 5 mins, the organic phase was separated, washed with saturated sodium chloride, dried, concentrated and separated by silica gel column chromatography to give Compound 51-1 as a white solid (260 mg, 75% yield). $^1$H NMR (500 MHz, DMSO-d$_6$) δ 8.98 (s, 1H), 8.15 (s, 1H), 7.23 (d, J=9.0 Hz, 1H), 6.96 (d, J=4.5 Hz, 1H), 6.85 (d, J=4.6 Hz, 1H), 5.90 (d, J=5.0 Hz, 1H), 4.57 (dd, J=9.2, 4.9 Hz, 1H), 4.27-4.17 (m, 3H), 3.95 (dd, J=13.8, 2.8 Hz, 1H), 3.27 (s, 3H), 3.21 (s, 3H), 2.30-2.19 (m, 1H), 1.45-1.34 (m, 9H), 1.10-0.86 (m, 34H).

Compound 51-1 (180 mg, 0.23 mmol) was added to tetrahydrofuran (4 mL), followed by the addition of 1M tetrabutylammonium fluoride in tetrahydrofuran (0.46 mL, 0.46 mmol) at room temperature. After 1 hour, the reaction was complete. To the reaction solution was added water (10 mL), and extracted with ethyl acetate. The organic phase was separated, dried and evaporated to dryness to give an oil. The oil was dissolved in tetrahydrofuran (6 mL), followed by the addition of water (0.5 mL) and trifluoroacetic acid (131 mg, 1.15 mmol, 5 eq), and stirred overnight at room temperature. To the reaction solution was added sodium bicarbonate aqueous solution, and extracted with ethyl acetate. The organic layer was separated, dried, concentrated and separated by silica gel column chromatography to obtain Compounds 51-2a and 51-2b. The proportion of 51-2b was more than 90%, and further recrystallization gave pure 51-2b as a white solid (70 mg, 62% yield for two steps). For the obtained Compound 51-2b: $^1$H NMR (500 MHz, DMSO-d$_6$) δ 8.08-7.87 (m, 3H), 7.06 (d, J=8.6 Hz, 1H), 6.94 (d, J=4.5 Hz, 1H), 6.91 (d, J=4.6 Hz, 1H), 6.50 (d, J=6.7 Hz, 1H), 5.19-5.14 (m, 1H), 5.10-5.05 (m, 1H), 5.03-4.98 (m, 1H), 4.26-4.20 (m, 1H), 4.10 (dd, J=8.7, 5.5 Hz, 1H), 3.66-3.53 (m, 2H), 2.31-2.22 (m, 1H), 1.45-1.35 (m, 9H), 0.93 (d, J=6.8 Hz, 3H), 0.90 (d, J=6.8 Hz, 3H).

Compound 51-2b (42 mg, 0.086 mmol) was added to saturated hydrogen chloride methanol solution (4 mL). After stirring at 35° C. for 2 hours, TLC showed that the reaction was complete. The reaction solution was concentrated, and methyl tert-butyl ether was added. The mixture was stirred and filtered to give Compound A212 as the dihydrochloride salt, white solid (45 mg, 81% yield). $^1$H NMR (500 MHz, Methanol-d$_4$) δ 8.17 (s, 1H), 7.50 (d, J=4.8 Hz, 1H), 7.21 (d, J=4.8 Hz, 1H), 5.52 (dd, J=5.8, 3.2 Hz, 1H), 5.19 (d, J=5.8 Hz, 1H), 4.54-4.48 (m, 1H), 4.16-4.10 (m, 1H), 3.83 (d, J=3.7 Hz, 2H), 2.58-2.48 (m, 1H), 1.18 (d, J=4.2 Hz, 3H), 1.17 (d, J=4.2 Hz, 3H). MS m/z=391.1 [M+1]$^+$. If the mixture of 51-2a and 51-2b (the proportion of 51-2a was 5-10%) obtained from the previous step was directly deprotected, the mixture of A51 and A212 could be obtained, and the content of A51 was about 10%.

Preparation Example 14: Synthesis of Compound A52

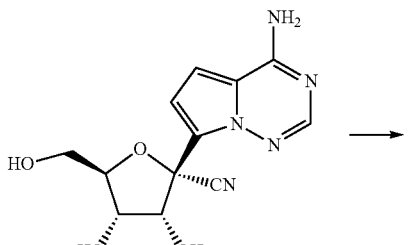

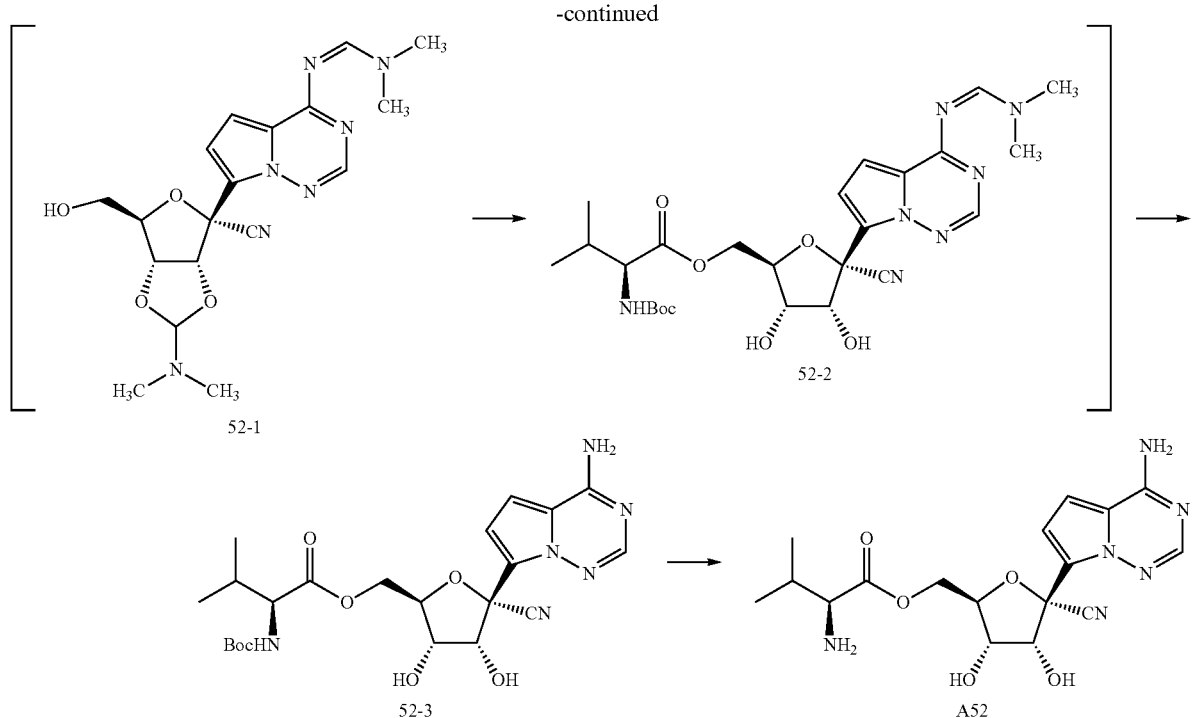

Compound 2-1 (291 mg, 1.0 mmol) was added to pyridine (8 mL), and pyridine was removed by evaporation under reduced pressure. The process was repeated once. Then, pyridine (8 mL) was added again, and N,N-dimethylformamide dimethyl acetal (477 mg, 4.0 mmol) was added at room temperature. The reaction was carried under nitrogen protection at room temperature overnight. The reaction solution was concentrated to give Compound 52-1 as an oil, which was directly used in the next step without purification.

Boc-L-valine (304 mg, 1.4 mmol), 1-hydroxybenzotriazole (203 mg, 1.5 mmol) and 1-(3-dimethylaminopropyl)-3-ethylcarbodiimide hydrochloride (422 mg, 2.2 mmol) were added to dichloromethane (10 mL). After stirring at room temperature for 15 minutes, 52-1 in dichloromethane (1 mL) obtained from the previous step and 4-dimethylaminopyridine (684 mg, 5.4 mmol) were added, and the mixture was stirred overnight at room temperature. The reaction solution was concentrated; methanol was added, and concentrated again to obtain an oil. Water was added, and the mixture was extracted with ethyl acetate. The organic phase was separated, washed with water and saturated brine successively, dried over anhydrous sodium sulfate, and concentrated to obtain crude Compound 52-2 as an oil, which can be directly used in the next step.

Compound 52-2 was dissolved in acetonitrile (10 mL), and 85% hydrazine hydrate (236 mg, 4.0 mmol) was added. After stirring at room temperature for 3 hours, the reaction solution was added into water, and extracted with ethyl acetate. The organic phase was separated, washed with saturated brine, dried over anhydrous sodium sulfate, concentrated and separated by silica gel column chromatography to give Compound 52-3 as a white solid (104 mg, 21% yield for three steps). $^1$H NMR (500 MHz, DMSO-$d_6$) δ 7.98-7.83 (m, 3H), 7.13 (d, J=8.1 Hz, 1H), 6.91 (d, J=4.5 Hz, 1H), 6.82 (d, J=4.5 Hz, 1H), 6.33 (d, J=6.0 Hz, 1H), 5.38 (d, J=5.9 Hz, 1H), 4.69 (t, J=5.4 Hz, 1H), 4.33-4.28 (m, 1H), 4.27-4.20 (m, 2H), 3.94-3.90 (m, 1H), 3.89-3.85 (m, 1H), 1.98-1.91 (m, 1H), 1.37 (s, 9H), 0.82 (t, J=6.5 Hz, 6H).

Compound 52-3 (104 mg, 0.21 mmol) was added to saturated hydrogen chloride methanol solution (5 mL). The mixture was stirred at 36° C. The reaction was complete after 1 hour. The reaction solution was concentrated, and then isopropyl ether was added. Solid was precipitated, and filtered to give Compound A52 as the dihydrochloride salt, white solid (80 mg, 82% yield). $^1$H NMR (500 MHz, Methanol-$d_4$) δ 8.15 (s, 1H), 7.49 (d, J=4.8 Hz, 1H), 7.12 (d, J=4.8 Hz, 1H), 4.74 (d, J=5.2 Hz, 1H), 4.62 (dd, J=12.1, 7.4 Hz, 1H), 4.54 (dd, J=12.1, 2.8 Hz, 1H), 4.45 (td, J=7.5, 2.7 Hz, 1H), 4.05-4.00 (m, 2H), 2.35-2.27 (m, 1H), 1.08 (d, J=1.9 Hz, 3H), 1.07 (d, J=1.8 Hz, 3H). MS m/z=391.1 [M+1]$^+$.

Preparation Example 15: Synthesis of Compound A53

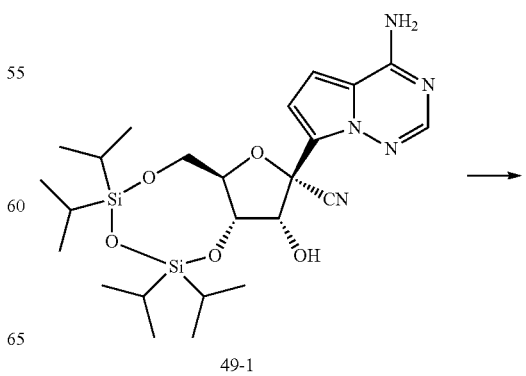

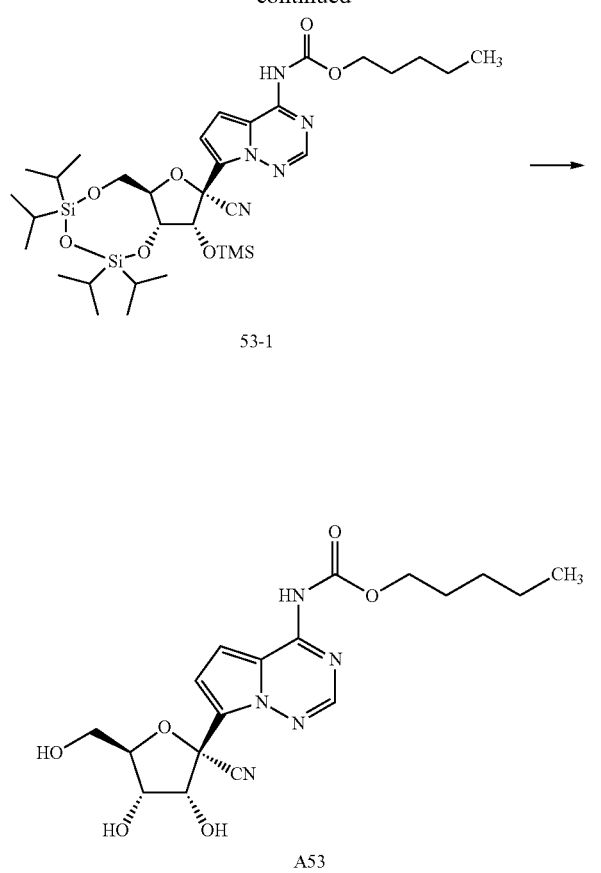

53-1

A53

Compound 49-1 (150 mg, 0.28 mmol) was dissolved in dichloromethane (2 mL), followed by the addition of pyridine (265 mg, 3.35 mmol, 12 eq), and then trimethylchlorosilane (93 mg, 0.86 mmol) was added in an ice bath. The mixture was stirred for 30 minutes, and TLC showed that the raw material was consumed completely. To the reaction solution was added n-pentyl chloroformate (120 mg, 0.8 mmol), and the mixture was further stirred for 2 hours in the ice bath. TLC showed that the reaction was complete. Dichloromethane and water were added to the reaction solution. The organic layer was separated, washed with diluted hydrochloric acid and brine successively, dried and concentrated to obtain 200 mg crude 53-1 as a colorless oil. The oil was added to tetrahydrofuran (2 mL), followed by the dropwise addition of 1M tetrabutylammonium fluoride in tetrahydrofuran (0.2 mL, 0.2 mmol) at room temperature. After the addition, the mixture was stirred at room temperature for 50 minutes, and TLC showed the reaction was complete. The reaction solution was concentrated and purified by silica gel column chromatography to obtain Compound A53 as a white solid (55 mg, 48% yield for two steps). $^1$H NMR (600 MHz, DMSO-$d_6$) δ 10.88 (s, 1H), 8.37 (s, 1H), 7.30 (d, J=4.8 Hz, 1H), 7.11 (d, J=4.8 Hz, 1H), 6.21 (d, J=6.2 Hz, 1H), 5.23 (d, J=5.5 Hz, 1H), 4.90 (t, J=5.6 Hz, 1H), 4.61 (t, J=5.7 Hz, 1H), 4.18 (t, J=6.7 Hz, 2H), 4.10-4.04 (m, 1H), 3.95 (q, J=5.5 Hz, 1H), 3.68-3.61 (m, 1H), 3.54-3.47 (m, 1H), 1.71-1.61 (p, J=6.8 Hz, 2H), 1.39-1.29 (m, 4H), 0.89 (t, J=7.0 Hz, 3H). MS m/z=406.0 [M+1]$^+$.

Preparation of Example 16: Synthesis of Compound A69 and A144

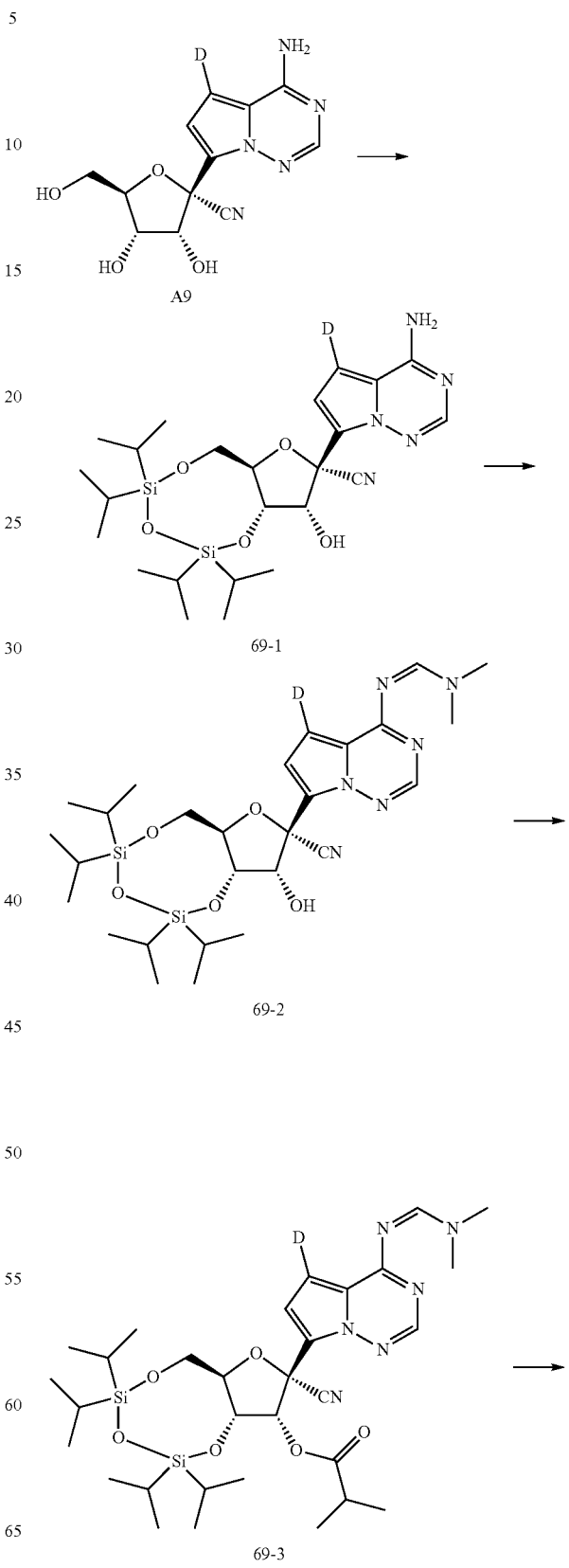

A9

69-1

69-2

69-3

-continued

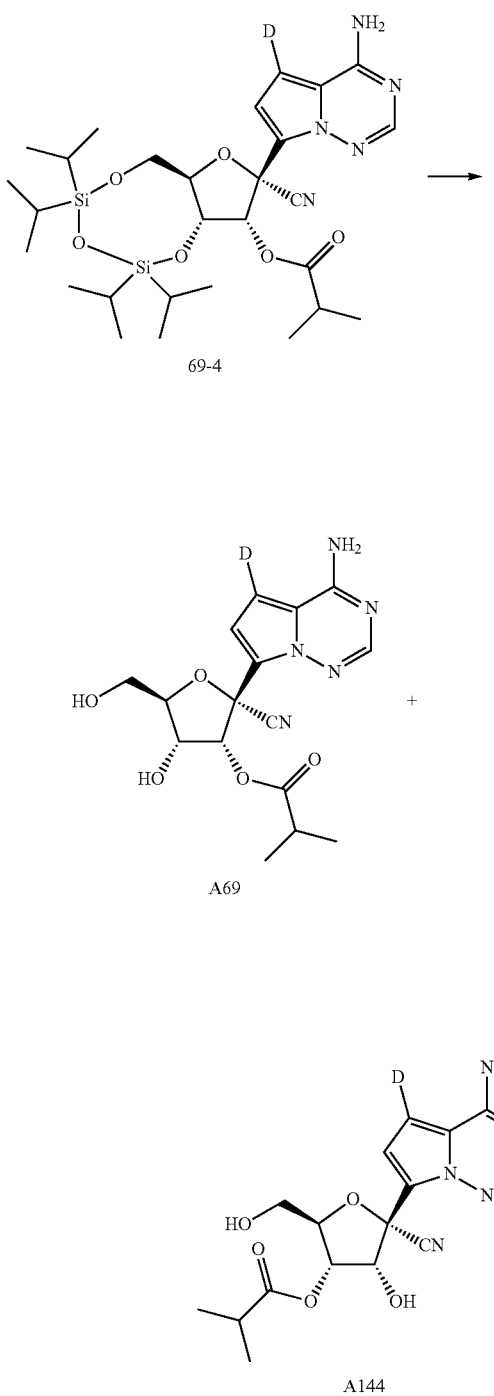

69-4

A69

A144

Compound A9 (879 mg, 3.01 mmol, with deuteration rate of no less than 97%) was added to N,N-dimethylformamide (15 mL), followed by the addition of imidazole (819 mg, 12.03 mmol, 4 eq), and then 1,3-dichloro-1,1,3,3-tetraisopropyldisiloxane (1.32 g, 4.21 mmol, 1.4 eq) was added dropwise in an ice bath. After the addition, the mixture was stirred at room temperature, and 1 hour later, the reaction was complete. The reaction solution was poured into water, and extracted with ethyl acetate. The organic layer was separated, dried, concentrated and slurried in petroleum ether to give Compound 69-1 as a white solid (1.29 g, 80% yield). $^1$H NMR (600 MHz, DMSO-$d_6$) δ 8.04-7.78 (m, 3H), 6.79 (s, 1H), 6.46 (d, J=5.7 Hz, 1H), 4.56 (t, J=5.1 Hz, 1H), 4.24-4.08 (m, 3H), 3.91 (d, J=12.0 Hz, 1H), 1.08-0.86 (m, 28H).

Compound 69-1 (1.10 g, 2.07 mmol) was added to toluene (20 mL), followed by the addition of N,N-dimethylformamide dimethyl acetal (370 mg, 3.11 mmol, 1.5 eq), and reacted at 45° C. The reaction was complete in about 30 minutes. The solvent was removed by evaporation under reduced pressure and ethyl acetate (60 mL) and water (20 mL) were added. The organic phase was separated, washed with saturated sodium chloride, dried, and evaporated to give Compound 69-2 as a white solid (1.12 g, 92% yield).

Compound 69-2 (614 mg, 1.04 mmol) was added to dichloromethane (10 mL), followed by the successive addition of triethylamine (210 mg, 2.08 mmol, 2 eq), isobutyryl chloride (166 mg, 1.56 mmol, 1.5 eq) and DMAP (127 mg, 1.04 mmol, 1 eq), and stirred at room temperature. The reaction was complete in about 1 hour. Saturated aqueous sodium bicarbonate and dichloromethane were added to the reaction solution. The organic layer was separated, dried, concentrated and purified by silica gel column chromatography to give Compound 69-3 as a white foam solid (494 mg, 72% yield).

Compound 69-3 (350 mg, 0.53 mmol) was added to acetonitrile (8 mL), followed by the addition of 85% hydrazine hydrate (125 mg, 2.12 mmol, 4 eq), and then stirred at room temperature. The reaction was complete in about 30 minutes. The reaction solution was added into water, and extracted with ethyl acetate. The organic layer was separated, washed with dilute hydrochloric acid, saturated sodium bicarbonate and saturated sodium chloride, respectively, dried and evaporated to give Compound 69-4 as a white solid (289 mg, 90% yield).

Compound 69-4 (289 mg, 0.48 mmol) was added to tetrahydrofuran (10 mL), followed by the addition of 1M tetrabutylammonium fluoride in tetrahydrofuran (0.48 mL, 0.48 mmol, 1 eq), and stirred at room temperature. The reaction was complete in about 30 mins. The reaction solution was added into water, and extracted with isopropyl acetate. The organic layer was separated, washed with saturated sodium bicarbonate and saturated sodium chloride respectively, dried and evaporated to obtain Compounds A69 and A144. The proportion of A144 in the product was more than 95%. The product was slurried in the mixture of n-heptane/isopropanol (1:1), then filtered and dried to give pure Compound A144 as a white solid (121 mg, 70% yield). For the obtained Compound A144: $^1$H NMR (600 MHz, DMSO-$d_6$) δ 8.06-7.85 (m, 3H), 6.88 (s, 1H), 6.41 (d, J=6.5 Hz, 1H), 5.21 (dd, J=5.7, 3.3 Hz, 1H), 5.08-5.04 (m, 1H), 4.99 (t, J=6.0 Hz, 1H), 4.26 (q, J=3.7 Hz, 1H), 3.64-3.52 (m, 2H), 2.67-2.58 (m, 1H), 1.17 (d, J=7.0 Hz, 3H), 1.15 (d, J=7.0 Hz, 3H). $^{13}$C NMR (126 MHz, DMSO-$d_6$) δ 175.92, 156.13, 148.45, 123.24, 117.50, 117.27, 111.60, 84.59, 78.30, 73.14, 72.69, 61.25, 33.81, 19.18, 19.08. MS m/z=363.0 [M+1]$^+$.

Preparation Example 17: Synthesis of Compound A70

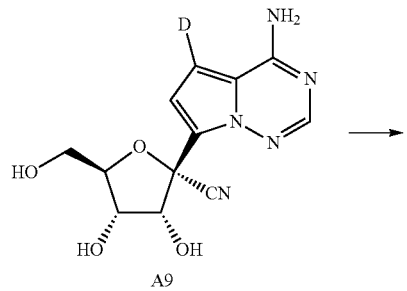

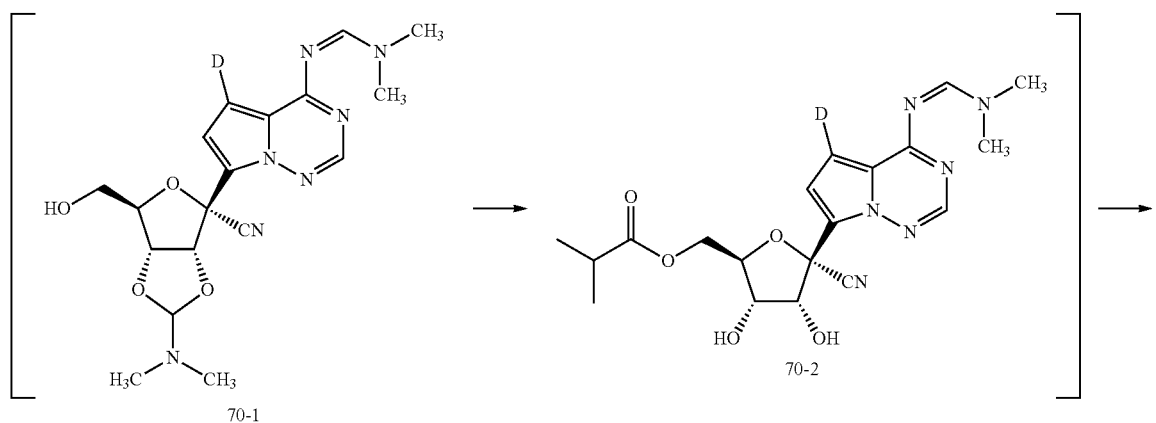

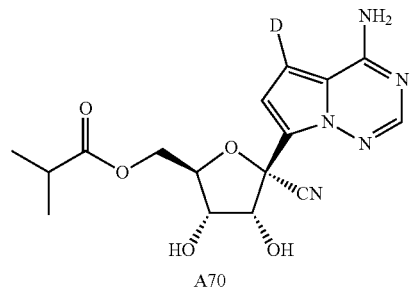

Compound A9 (145 mg, 0.5 mmol, with deuteration rate of no less than 97%) was added to pyridine (5 mL), and pyridine was removed by evaporation under reduced pressure. The process was repeated once. Then, pyridine (5 mL) was added again, and N,N-dimethylformamide dimethyl acetal (240 mg, 2.0 mmol) was added at room temperature. The reaction was carried out under nitrogen protection at room temperature overnight. The reaction solution was concentrated to obtain intermediate 70-1 as an oil, which was directly used in the next step without purification.

The intermediate 70-1 obtained from the previous step was dissolved in pyridine (5 mL), followed by the successive addition of 4-dimethylaminopyridine (6 mg, 0.05 mmol) and isobutyryl chloride (80 mg, 0.75 mmol). After 3 hours, methanol was added. The solvent was removed by evaporation to obtain intermediate 70-2 as an oil, which was directly used in the next step without purification.

The intermediate 70-2 obtained from the previous step was added to acetonitrile (5 mL), followed by the addition of hydrazine hydrate (176 mg, 3.0 mmol), and stirred overnight at room temperature. To the reaction solution was added water, and the mixture was extracted with ethyl acetate. The organic phase was separated, washed with water and saturated brine successively, dried over anhydrous sodium sulfate, concentrated and separated by silica gel column chromatography to give Compound A70 as a white solid (80 mg, 44% yield). $^1$H NMR (600 MHz, DMSO-$d_6$) δ 8.01-7.79 (m, 3H), 6.80 (s, 1H), 6.32 (d, J=6.0 Hz, 1H), 5.38 (d, J=5.8 Hz, 1H), 4.69 (t, J=5.4 Hz, 1H), 4.30 (dd, J=12.1, 2.9 Hz, 1H), 4.25-4.21 (m, 1H), 4.17 (dd, J=12.1, 5.3 Hz, 1H), 3.95 (q, J=5.9 Hz, 1H), 2.54-2.51 (m, 1H), 1.06 (d, J=2.9 Hz, 3H), 1.05 (d, J=2.9 Hz, 3H). $^{13}$C NMR (126 MHz, DMSO-$d_6$) δ 176.36, 156.06, 148.40, 123.99, 117.40, 117.00, 110.61, 81.78, 79.50, 74.49, 70.65, 63.40, 33.63, 19.19, 19.11. MS m/z=363.0 [M+1]$^+$.

Preparation Example 18: Synthesis of Compound A71 and A213

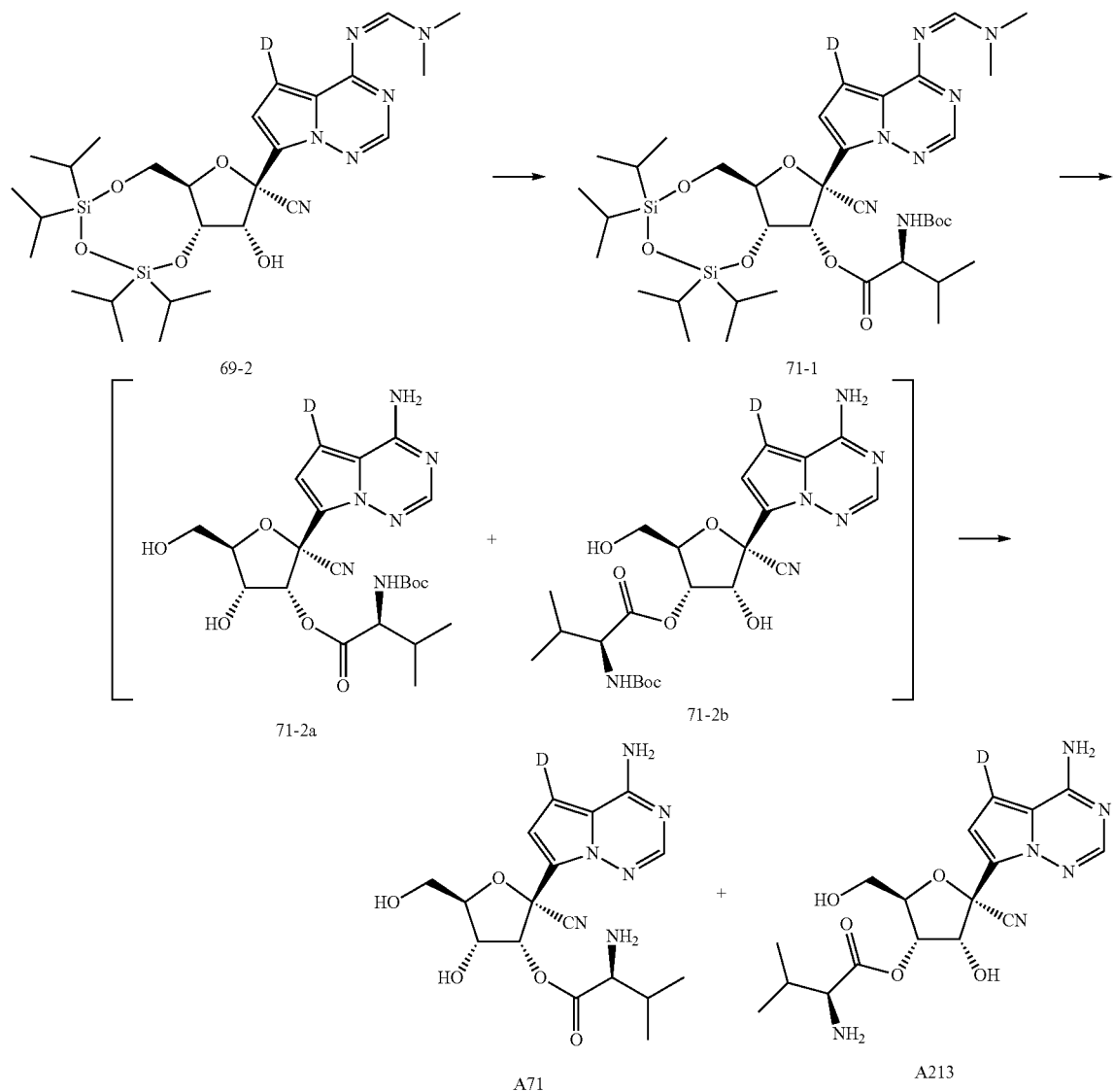

Compound 69-2 (160 mg, 0.27 mmol) was dissolved in dichloromethane (10 mL) followed by the successive addition of Boc-L-Val (82 mg, 0.38 mmol), 1-hydroxybenzotriazole (55 mg, 0.41 mmol), 1-(3-dimethylaminopropyl)-3-ethylcarbodiimide hydrochloride (113 mg, 0.59 mmol) and 4-dimethylaminopyridine (132 mg, 1.08 mmol) in an ice bath. After the addition, the reaction was carried out at room temperature overnight. The reaction solution was concentrated; water was added, and extracted with ethyl acetate. The organic phase was washed with diluted hydrochloric acid, saturated sodium bicarbonate solution and saturated brine successively, dried over anhydrous sodium sulfate, concentrated and separated by silica gel column chromatography to give Compound 71-1 as a white solid (158 mg, 740% yield).

Compound 71-1 (158 mg, 0.20 mmol) was dissolved in acetonitrile (10 mL), followed by the addition of 85% hydrazine hydrate (71 mg, 1.20 mmol) at room temperature. After stirring for 1 hour, water was added to the reaction solution, and the mixture was extracted with ethyl acetate. The organic phase was separated, washed with dilute hydrochloric acid, saturated sodium bicarbonate aqueous solution and saturated brine successively, dried over anhydrous sodium sulfate, and concentrated to obtain a white solid. The resulting white solid was added to tetrahydrofuran (8 mL), followed by the addition of acetic acid (14 mg, 0.24 mmol) and TM tetrabutylammonium fluoride in tetrahydrofuran (0.24 mL, 0.24 mmol) in an ice bath. After the addition, the mixture was stirred at room temperature. 2 hours later, TLC showed the reaction was complete. The reaction solution was concentrated, water was added, and extracted with isopropyl acetate. The organic phase was separated, washed with saturated brine, dried over anhydrous sodium sulfate, and concentrated. The resulting product was slurried in petroleum ether, filtered and dried to obtain Compounds 71-2a and 71-2b. The proportion of 71-2b was more than 90%, and further recrystallization afforded pure 71-2b as a white solid (60 mg, 61% yield for two steps). For the obtained Compound 71-2b: $^1$H NMR (500 MHz, DMSO-$d_6$) δ 8.07-7.86 (m, 3H), 7.06 (d, J=8.6 Hz, 1H), 6.91 (s, 1H), 6.50 (d, J=6.7 Hz, 1H), 5.17 (dd, J=5.8, 3.6 Hz, 1H), 5.07 (t, J=5.8 Hz, 1H), 5.01 (t, J=6.2 Hz, 1H), 4.27-4.21 (m, 1H), 4.10 (dd, J=8.6, 5.4 Hz, 1H), 3.66-3.53 (m, 2H), 2.31-2.23 (m, 1H), 1.45-1.36 (m, 9H), 0.93 (d, J=6.9 Hz, 3H), 0.90 (d, J=6.9 Hz, 3H).

Compound 71-2b (60 mg, 0.12 mmol) was added to saturated hydrogen chloride methanol solution (5 mL). The mixture was stirred at 35° C. for 2 hours, and TLC showed the reaction was complete. The reaction solution was concentrated, and the residue was slurried in methyl tert-butyl ether to give Compound A213 as the dihydrochloride, white solid (45 mg, 81% yield). $^1$H NMR (500 MHz, Methanol-$d_4$) δ 8.17 (s, 1H), 7.21 (s, 1H), 5.55-5.50 (m, 1H), 5.19 (d, J=5.8 Hz, 1H), 4.53-4.48 (m, 1H), 4.12 (d, J=4.4 Hz, 1H), 3.83 (d, J=3.7 Hz, 2H), 2.58-2.49 (m, 1H), 1.18 (d, J=4.3 Hz, 3H), 1.17 (d, J=4.3 Hz, 3H). $^{13}$C NMR (126 MHz, Methanol-$d_4$) δ 167.48, 148.78, 135.20, 128.58, 115.31, 113.58, 113.19, 84.12, 77.64, 74.29, 73.56, 60.15, 57.64, 28.91, 16.63, 16.32. MS m/z=392.1 [M+1]$^+$. If the mixture of 71-2a and 71-2b obtained from the previous step was directly deprotected, the mixture of A71 and A213 could be obtained, and the content of A71 was about 10%.

Preparation Example 19: Synthesis of Compound A72

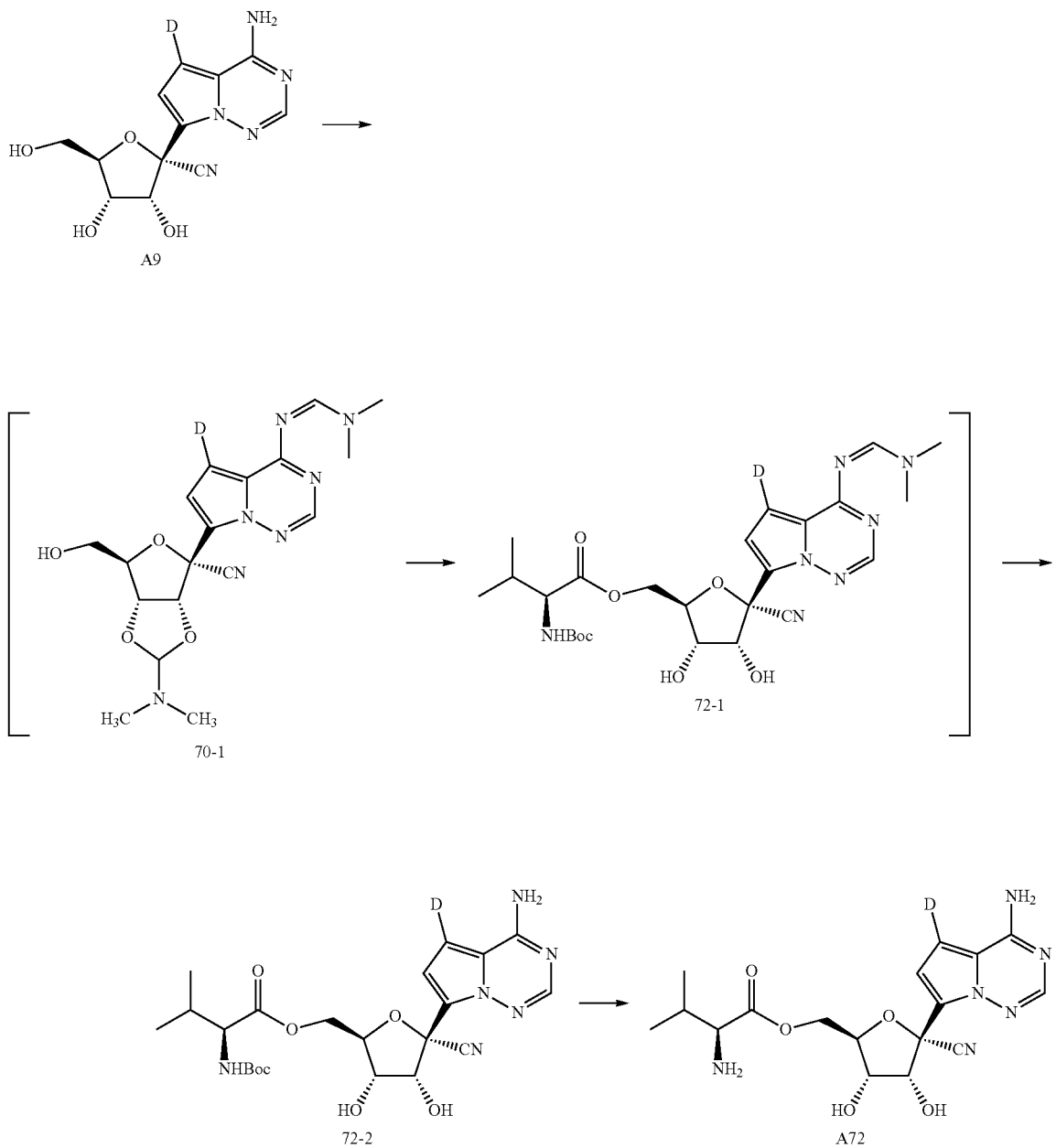

Compound A9 (350 mg, 1.2 mmol) was added to pyridine (10 mL), and pyridine was removed by evaporation under reduced pressure. The process was repeated once. Then pyridine (10 mL) was added again, and N,N-dimethylformamide dimethyl acetal (596 mg, 5.0 mmol) was added at room temperature. The reaction was carried out under nitrogen protection at room temperature overnight. The reaction solution was concentrated to give intermediate 70-1 as an oil, which was directly used in the next step without purification.

Boc-L-valine (369 mg, 1.7 mmol), 1-hydroxybenzotriazole (243 mg, 1.8 mmol) and 1-(3-dimethylaminopropyl)-3-ethylcarbodiimide hydrochloride (498 mg, 2.6 mmol) were added to dichloromethane (15 mL). After being stirred at room temperature for 15 minutes, intermediate 70-1 in dichloromethane (2 mL) obtained from the previous step and 4-dimethylaminopyridine (733 mg, 6.0 mmol) was added, and the mixture was stirred overnight at room temperature. The reaction solution was concentrated; methanol was added, and concentrated again to obtain an oil. Water was added and the mixture was extracted with ethyl acetate. The organic phase was separated, washed with water and saturated brine successively, dried over anhydrous sodium sulfate, and concentrated to obtain the crude intermediate 72-1 as an oil, which was directly used in the next step without purification.

Intermediate 72-1 was dissolved in acetonitrile (10 mL), followed by the addition of 85% hydrazine hydrate (283 mg, 4.8 mmol). After reacting at room temperature for 3 hours, the reaction solution was added into water, and extracted with ethyl acetate. The organic phase was separated, washed with saturated brine, dried over anhydrous sodium sulfate, concentrated and separated by silica gel column chromatography to give Compound 72-2 as a white solid (195 mg, 33% yield for three steps). $^1$H NMR (600 MHz, DMSO-$d_6$) δ 8.01-7.80 (m, 3H), 7.14 (d, J=8.2 Hz, 1H), 6.82 (s, 1H), 6.33 (d, J=6.0 Hz, 1H), 5.38 (d, J=5.9 Hz, 1H), 4.69 (t, J=5.4 Hz, 1H), 4.34-4.28 (m, 1H), 4.26-4.21 (m, 2H), 3.95-3.90 (m, 1H), 3.89-3.85 (m, 1H), 1.99-1.92 (m, 1H), 1.40-1.28 (m, 9H), 0.81 (t, J=7.1 Hz, 6H).

Compound 72-2 (100 mg, 0.2 mmol) was added to saturated hydrogen chloride methanol solution (5 mL). The mixture was stirred at 36° C. for 1 hour, and the reaction was complete. The reaction solution was concentrated, and isopropyl ether was added. Solid was precipitated, and filtered to give Compound A72 as the hydrochloride, white solid (74 mg, 80% yield). $^1$H NMR (600 MHz, Methanol-$d_4$) δ 8.15 (s, 1H), 7.12 (s, 1H), 4.75 (d, J=5.2 Hz, 1H), 4.62 (dd, J=12.1, 7.4 Hz, 1H), 4.54 (dd, J=12.1, 2.8 Hz, 1H), 4.45 (td, J=7.5, 2.8 Hz, 1H), 4.05-4.01 (m, 2H), 2.34-2.28 (m, 1H), 1.08 (d, J=2.4 Hz, 3H), 1.07 (d, J=2.3 Hz, 3H). $^{13}$C NMR (151 MHz, Methanol-$d_4$) δ 168.15, 148.61, 135.04, 129.77, 114.70, 113.28, 112.57, 80.77, 79.53, 74.42, 70.17, 64.81, 57.56, 29.19, 16.48, 16.32. MS m/z=392.0 [M+1]$^+$.

Preparation Example 20: Synthesis of Compound A74 and A164

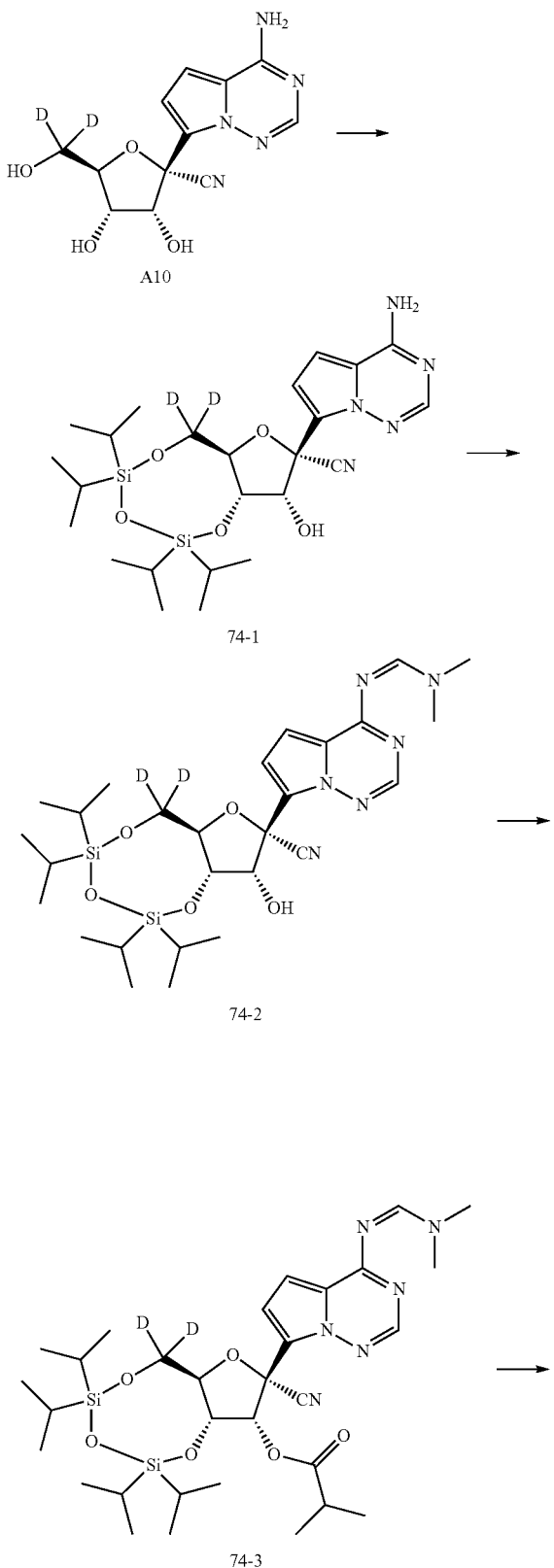

141
-continued

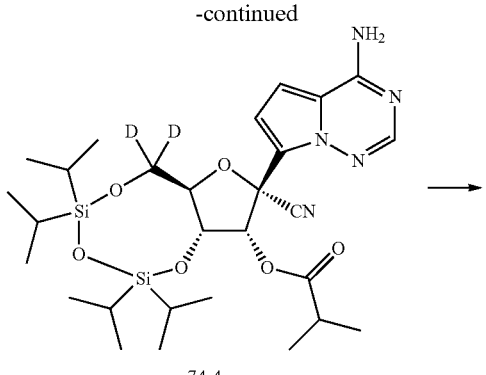

74-4

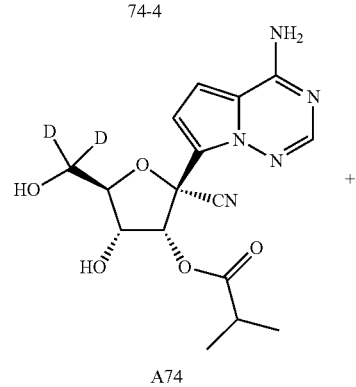

A74

+

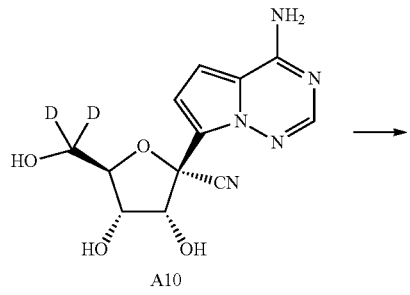

A10

142
-continued

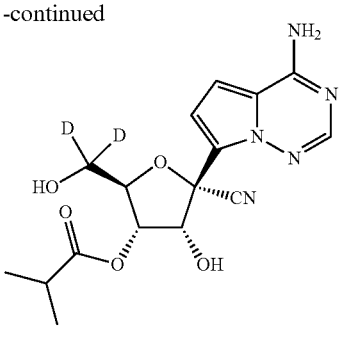

A164

According to the synthesis method for Compound A144, with A10 (176 mg, 0.6 mmol, with a deuteration rate of 99%) as the starting material, Compound A74 and A164 were synthesized over five steps, and further recrystallization afforded pure A164 as a white solid (139 mg, total yield of 64%). For Compound A164: $^1$H NMR (600 MHz, DMSO-$d_6$) δ 8.07-7.83 (m, 3H), 6.92 (d, J=4.6 Hz, 1H), 6.88 (d, J=4.6 Hz, 1H), 6.41 (d, J=6.6 Hz, 1H), 5.21 (dd, J=5.7, 3.3 Hz, 1H), 5.02 (s, 1H), 5.01-4.97 (m, 1H), 4.25 (d, J=3.2 Hz, 1H), 2.66-2.58 (m, 1H), 1.17 (d, J=7.0 Hz, 3H), 1.15 (d, J=6.9 Hz, 3H). MS m/z=364.0 [M+1]$^+$.

Preparation Example 21: Synthesis of Compound A75

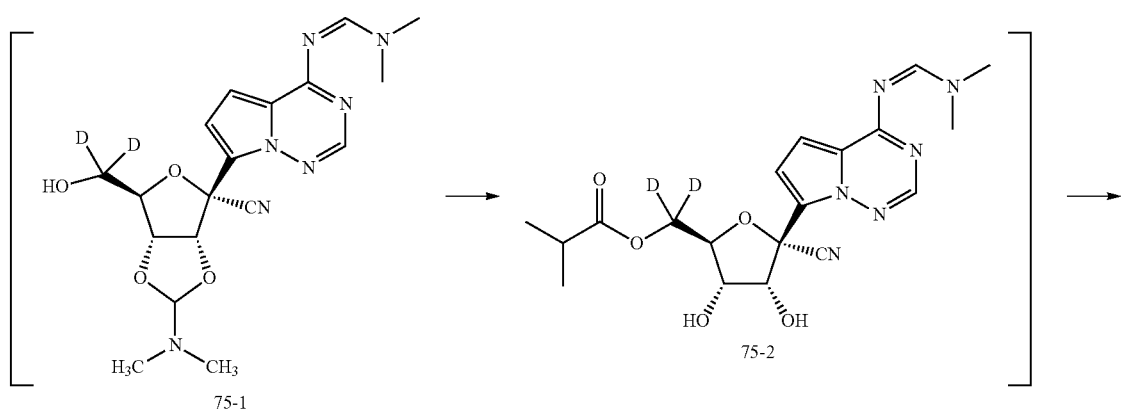

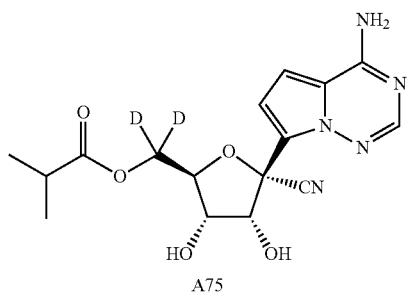
A75
According to the synthesis method for Compound A70, with A10 (176 mg, 0.6 mmol) as the starting material, Compound A75 was obtained over three steps, as a white solid (109 mg, total yield of 50%). $^1$H NMR (500 MHz, DMSO-$d_6$) δ 8.03-7.82 (m, 3H), 6.92 (d, J=4.5 Hz, 1H), 6.82 (d, J=4.5 Hz, 1H), 6.33 (d, J=6.0 Hz, 1H), 5.39 (d, J=5.8 Hz, 1H), 4.71 (t, J=5.5 Hz, 1H), 4.24 (d, J=6.6 Hz, 1H), 3.97 (q, J=5.8 Hz, 1H), 2.57-2.53 (m, 1H), 1.07 (d, J=2.5 Hz, 3H), 1.06 (d, J=2.5 Hz, 3H). MS m/z=364.0 [M+1]$^+$.
Preparation Example 22: Synthesis of Compound A76 and A214
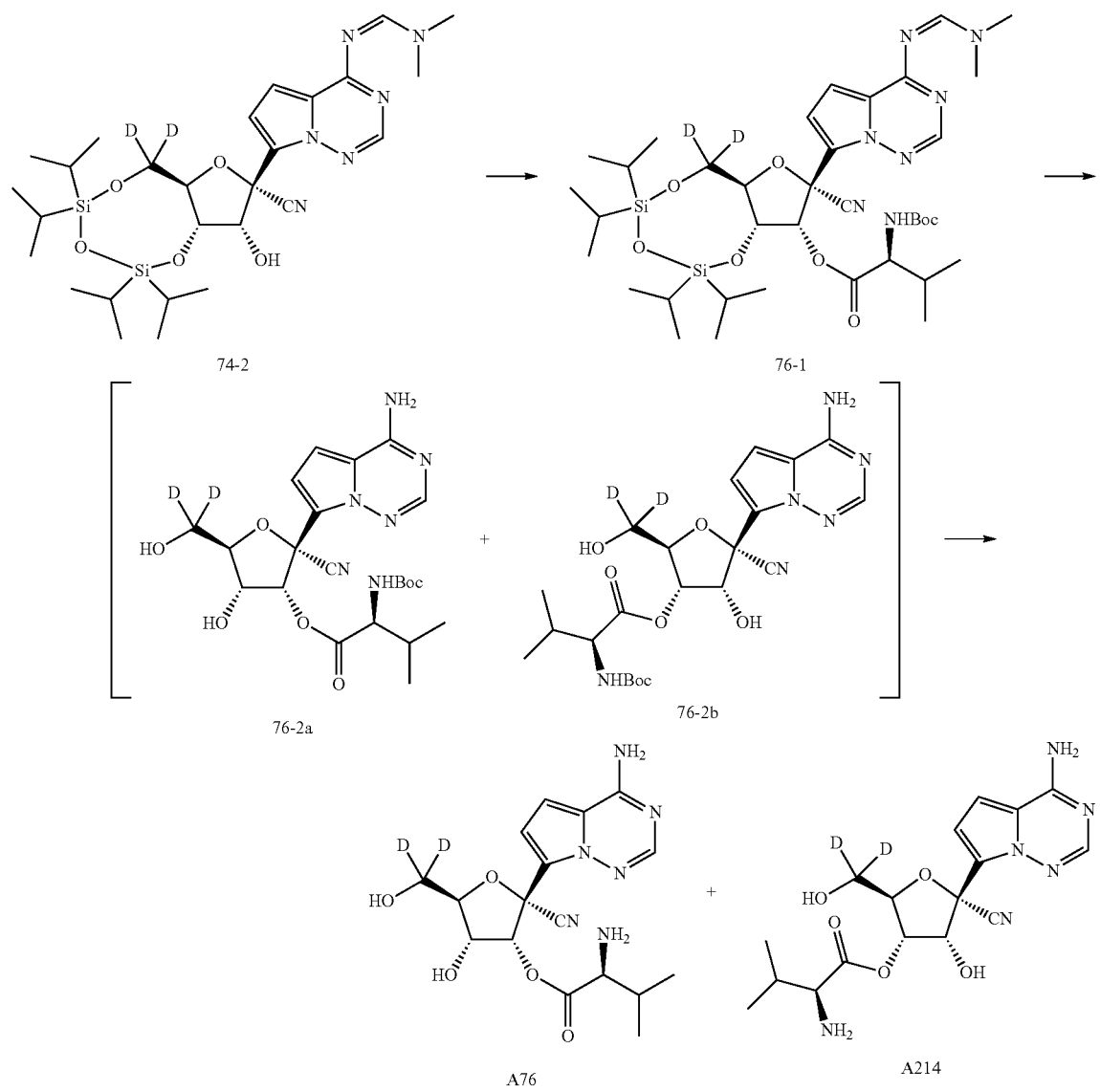

According to the synthesis method for Compound A213, with 74-2 (295 mg, 0.5 mmol) as the starting material, Compound A214 was obtained over three steps, as the dihydrochloride salt, white solid (97 mg, total yield of 42%). ¹H NMR (500 MHz, Methanol-d₄) δ 8.17 (s, 1H), 7.49 (d, J=4.8 Hz, 1H), 7.21 (d, J=4.9 Hz, 1H), 5.53 (dd, J=5.8, 3.1 Hz, 1H), 5.19 (d, J=5.8 Hz, 1H), 4.50 (d, J=3.1 Hz, 1H), 4.13 (d, J=4.5 Hz, 1H), 2.58-2.50 (m, 1H), 1.18 (d, J=4.6 Hz, 3H), 1.17 (d, J=4.6 Hz, 3H). MS m/z=393.0 [M+1]⁺.

If the mixture of 76-2a and 76-2b obtained from the second step was directly deprotected, the mixture of A76 and A214 could be obtained, and the content of A76 was about 10%.

Preparation Example 23: Synthesis of Compound A77

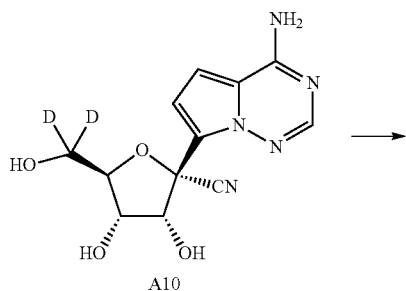

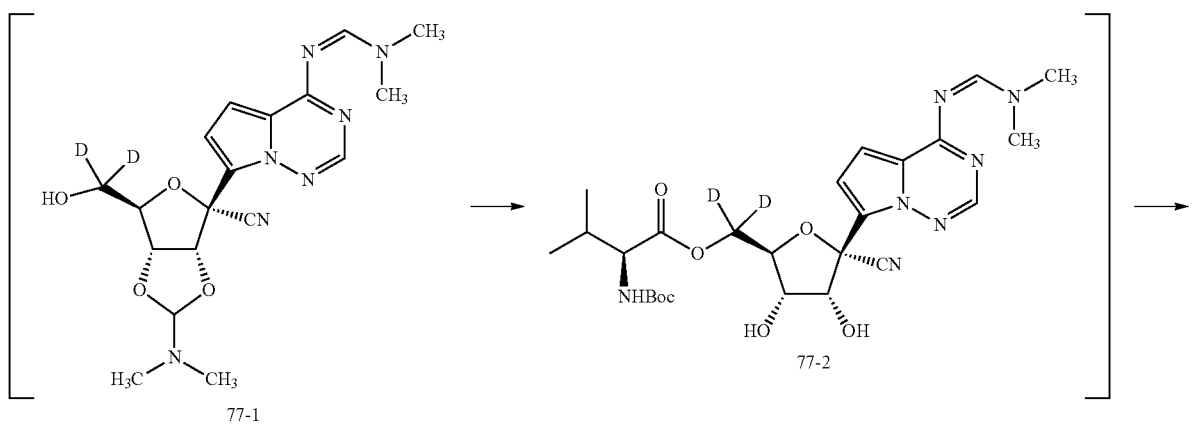

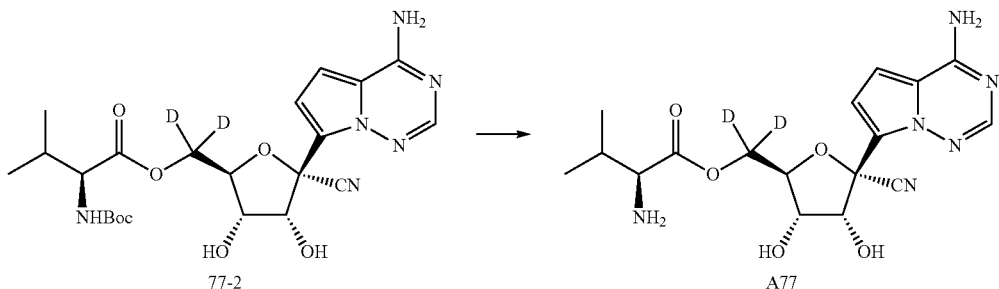

According to the synthesis method for Compound A72, with A10 (1.0 mmol, 293 mg) as the starting material, Compound A77 was obtained over four steps, as the dihydrochloride salt, white solid (107 mg, total yield of 23%). MS m/z=393.0 [M+1]⁺.

Preparation Example 24: Synthesis of Compound A84

Compound A1 (49 mg, 0.16 mmol) was added to acetone (3 mL), followed by successive addition of 2,2-dimethoxypropane (83 mg, 0.8 mmol, 5 eq) and p-toluenesulfonic acid monohydrate (30 mg, 0.16 mmol, 1 eq). After the addition, the mixture was warmed to 40° C., stirred for 2 hours, and TLC showed the reaction was complete. The reaction solution was added into saturated aqueous sodium bicarbonate solution (20 mL) and extracted with ethyl acetate. The organic phase was separated, dried, concentrated, and sepa-

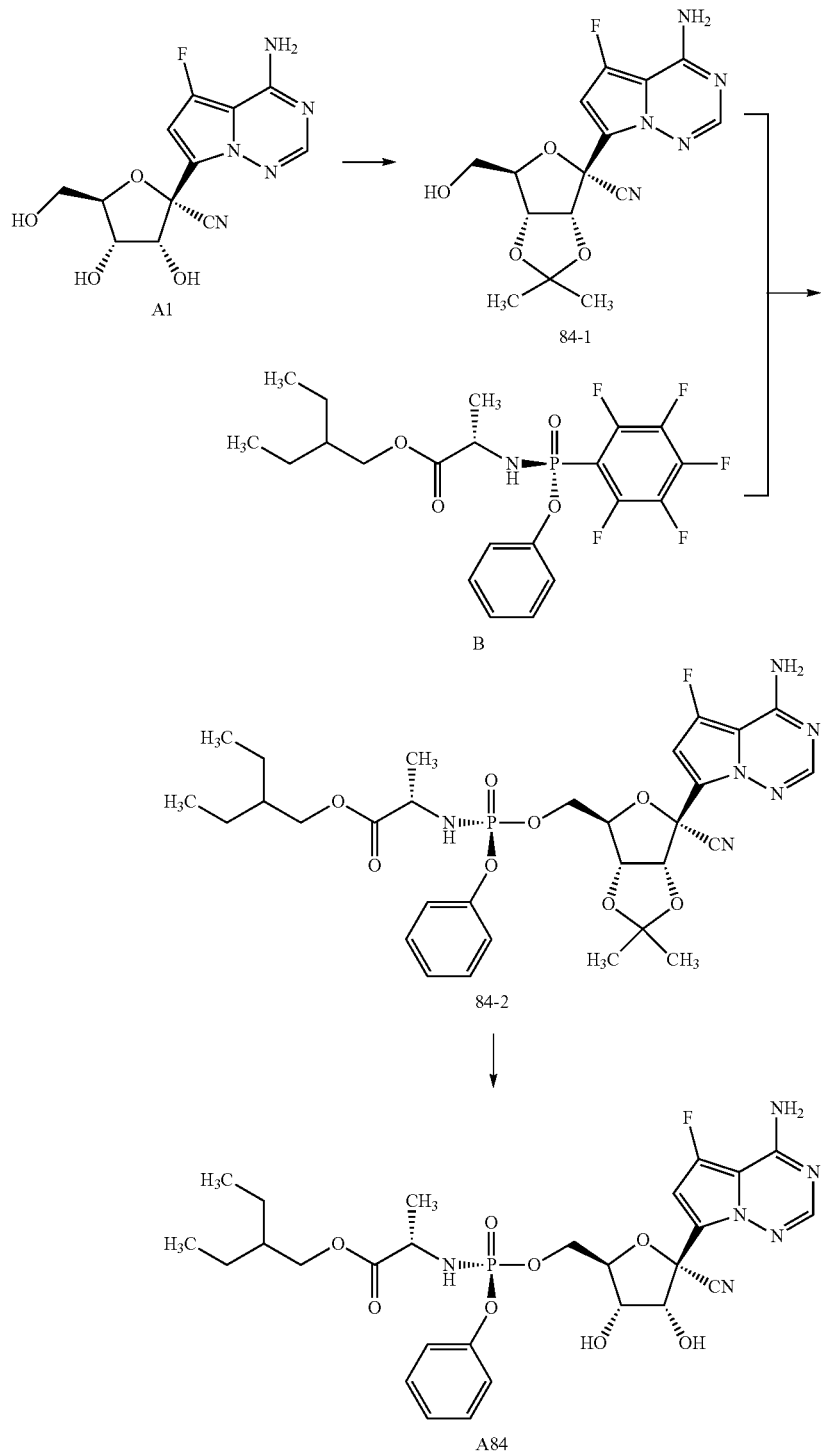

rated by preparative TLC chromatography to give Compound 84-1 as a white solid (27 mg, 48% yield).

Compound 84-1 (27 mg, 0.077 mmol) was added to anhydrous tetrahydrofuran (3 mL), followed by the dropwise addition of 3M methylmagnesium bromide in 2-methyltetrahydrofuran (0.05 mL, 0.15 mmol, 2 eq) in an ice bath. After the addition, the mixture was stirred for 5 minutes; and compound B (57 mg, 0.12 mmol, 1.5 eq) in anhydrous tetrahydrofuran (1 mL) was added dropwise. After the addition, the reaction was carried out at room temperature for 2 hours, and TLC showed that the reaction was complete. The reaction solution was added into saturated ammonium chloride solution (20 mL), and extracted with ethyl acetate. The organic layer was separated, dried and concentrated to give Compound 84-2 as an oil which was directly used in the next step.

The product obtained from the previous step was added to tetrahydrofuran (2 mL), followed by the dropwise addition of concentrated hydrochloric acid (0.4 mL) in an ice bath. Upon complete addition, the mixture was stirred at room temperature until the reaction was complete. The reaction solution was added into saturated aqueous sodium bicarbonate solution (20 mL) and extracted with ethyl acetate. The organic phase was separated, dried, concentrated, and separated on preparative TLC plates to give Compound A84 as a white solid (10 mg, 21% yield). $^1$H NMR (500 MHz, DMSO-$d_6$) δ 8.12 (brs, 1H), 7.88 (s, 1H), 7.42 (brs, 1H), 7.36 (t, J=7.7 Hz, 2H), 7.24-7.14 (m, 3H), 6.73 (s, 1H), 6.45 (d, J=6.0 Hz, 1H), 6.12-6.02 (m, 1H), 5.39 (d, J=6.0 Hz, 1H), 4.56 (t, J=5.2 Hz, 1H), 4.31-4.19 (m, 2H), 4.16-4.06 (m, 1H), 4.01-3.77 (m, 4H), 1.45-1.38 (m, 1H), 1.28-1.20 (m, 7H), 0.80 (t, J=7.4 Hz, 6H). $^1$H NMR (500 MHz, Methanol-$d_4$) δ 7.82 (s, 1H), 7.34 (t, J=7.9 Hz, 2H), 7.27-7.16 (m, 3H), 6.72 (s, 1H), 4.73 (d, J=5.2 Hz, 1H), 4.46-4.35 (m, 2H), 4.33-4.27 (m, 1H), 4.15 (t, J=5.7 Hz, 1H), 4.06 (dd, J=11.0, 5.8 Hz, 1H), 4.01-3.90 (m, 2H), 1.53-1.45 (m, 1H), 1.38-1.30 (m, 7H), 0.89 (t, J=7.5 Hz, 6H).

Preparation Example 25: Synthesis of Compound A102

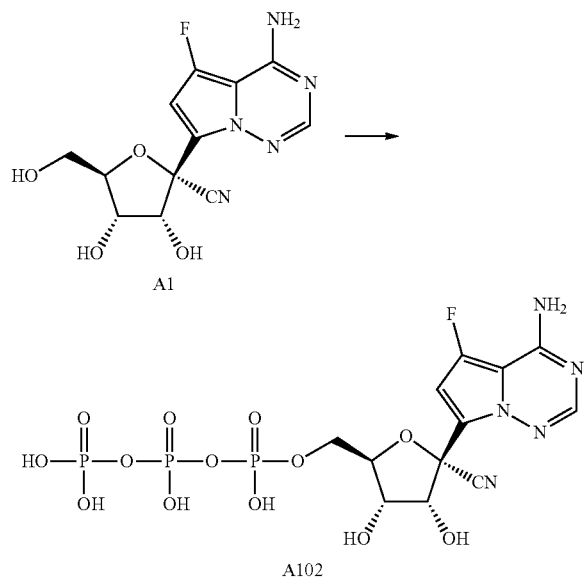

Compound A1 (62 mg, 0.2 mmol) and 1,8-bis(dimethylamino)naphthalene (56 mg, 0.26 mmol, 1.3 eq) were added to trimethyl phosphate (3 mL), and stirred in an ice bath. Phosphorus oxychloride (153 mg, 1.0 mmol, 5 eq) was added slowly. About 3 hours, TLC showed that the raw material was almost completely consumed. A solution of tributylammonium pyrophosphate (549 mg, 1.0 mmol, 5 eq) in DMF (3 mL) was added to the above mentioned solution, followed by the addition of tri-n-butylamine (222 mg, 1.2 mmol, 6 eq). After stirring in an ice bath for 10 minutes, the reaction solution was naturally warmed up. The reaction was monitored by TLC until the amount of the product was no longer increased. To the reaction solution was added 0.5M aqueous solution of triethylammonium bicarbonate to adjust the pH to 7.5, then deionized water (5 mL) was added, and extracted with dichloromethane and ethyl acetate, respectively. The organic phase was discarded. The aqueous phase was separated on a gel column to obtain crude A102, which was further purified by reversed-phase column chromatography to obtain A102 as the di-triethylamine salt, foam solid (44 mg, 29% yield). $^1$H NMR (500 MHz, D$_2$O) δ 7.88 (s, 1H), 6.87 (s, 1H), 4.76 (d, J=5.2 Hz, 1H), 4.45-4.41 (m, 1H), 4.38 (t, J=4.8 Hz, 1H), 4.17-4.10 (m, 2H), 3.12 (q, J=7.3 Hz, 12H), 1.19 (t, J=7.3 Hz, 18H). $^{31}$P NMR (202 MHz, D$_2$O) δ-10.89 (d), −11.46 (d), −23.19 (t). MS m/z=548.0 [M−1]$^-$.

Preparation Example 26: Synthesis of Compound A106

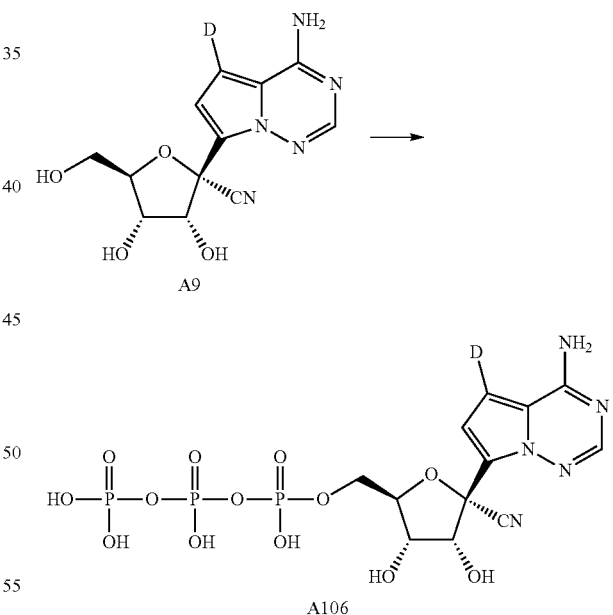

According to the synthesis method for Compound A102, with A9 (58 mg, 0.2 mmol, with a deuteration rate of no less than 97%) as the starting material, A106 was obtained in the form of tri-triethylamine salt, foam solid (55 mg, 33% yield). $^1$H NMR (500 MHz, D$_2$O) δ7.92 (s, 1H), 7.02 (s, 1H), 4.92 (d, J=4.4 Hz, 1H), 4.50-4.42 (m, 2H), 4.16-4.10 (m, 1H), 4.09-4.01 (m, 1H), 3.11 (q, J=7.3 Hz, 18H), 1.19 (t, J=7.2 Hz, 27H). $^{31}$P NMR (202 MHz, D$_2$O) δ-10.90 (d), −11.52 (d), −23.29 (t). MS m/z=531.0 [M−1]$^-$.

Preparation Example 27: Synthesis of Compound A107

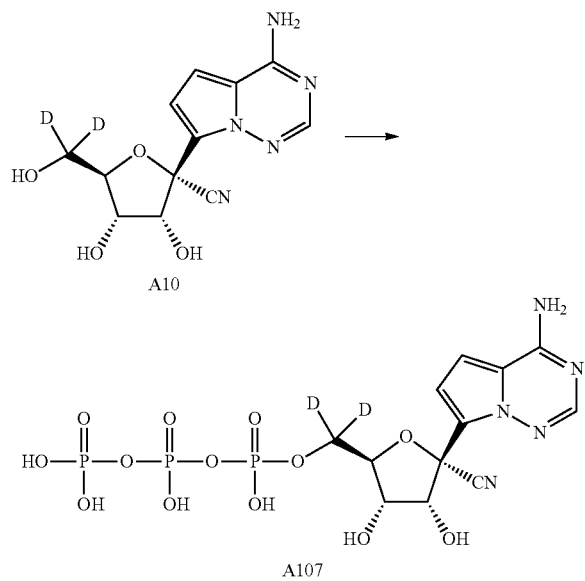

According to the synthesis method for Compound A102, with A10 (59 mg, 0.2 mmol, with a deuteration rate of 99%) as the starting material, product A107 was obtained in the form of tetra-triethylamine salt, foam solid (54 mg, 29% yield). $^1$H NMR (500 MHz, D$_2$O) δ 7.97 (s, 1H), 7.17 (d, J=4.9 Hz, 1H), 7.07 (d, J=4.8 Hz, 1H), 4.87 (d, J=5.0 Hz, 1H), 4.48-4.40 (m, 2H), 3.12 (q, J=7.3 Hz, 24H), 1.20 (t, J=7.3 Hz, 36H). $^{31}$P NMR (202 MHz, D$_2$O) δ-10.92 (d), −11.45 (d), −23.29 (t). MS m/z=532.0 [M−1]$^-$.

Preparation Example 28: Synthesis of Compound A109

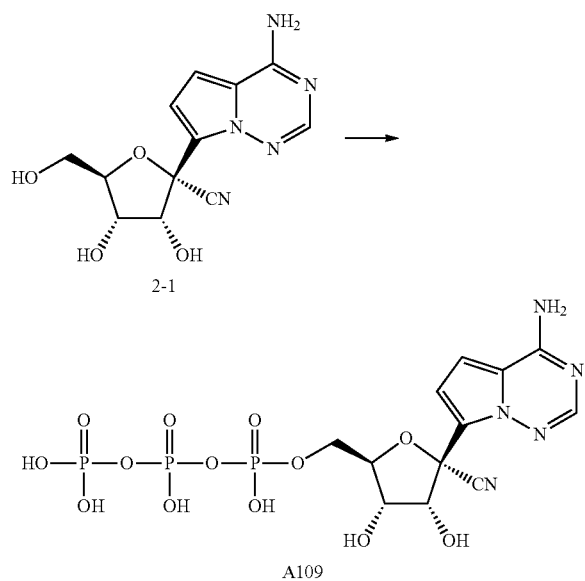

Compound 2-1 (145 mg, 0.5 mmol) was added to trimethyl phosphate (2 mL), followed by the addition of phosphorus oxychloride (153 mg, 1 mmol, 2 eq) in an ice bath. After stirring for 3-4 hours, TLC showed that a large amount of the raw material was still remained. Additional phosphorus oxychloride (80 mg) was added, and the mixture was further stirred for 2 hours in the ice bath. To the reaction solution, a suspension of tributylammonium pyrophosphate (1.1 g, 2 mmol, 4 eq) in acetonitrile (2 mL) and tri-n-butyl amine (741 mg, 4 mmol, 8 eq) were added, and the mixture continued to be stirred for 2 hours. 1M aqueous solution of triethyl ammonium bicarbonate (8 mL) was added into the reaction solution, followed by the addition of distilled water (8 mL) and then stirred. The mixture was extracted with ethyl acetate, and the organic phase was discarded. The aqueous phase was lyophilized and separated by preparative liquid chromatography to give Compound A109 as the tri-tri-n-butylamine salt, white solid (55 mg, 10% yield). $^1$H NMR (400 MHz, D$_2$O) δ 7.85 (s, 1H), 7.00-6.91 (m, 2H), 4.89-4.83 (m, 1H), 4.43-4.36 (m, 2H), 4.13-4.04 (m, 1H), 4.03-3.94 (m, 1H), 3.04-2.93 (m, 18H), 1.60-1.47 (m, 18H), 1.29-1.17 (m, 18H), 0.79 (t, J=7.4 Hz, 27H). MS m/z=530.0 [M−1]$^-$.

Preparation Example 29: Synthesis of Compound A112

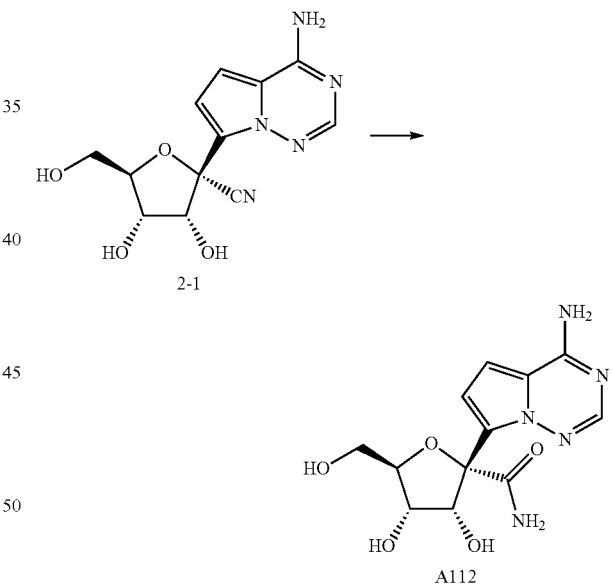

Compound 2-1 (291 mg, 1.0 mmol) was added to tetrahydrofuran (6 mL), followed by the addition of concentrated hydrochloric acid (3 mL), and the mixture was stirred at 45° C. The reaction was monitored by TLC until it was complete. The solvent was evaporated, and separated by silica gel column chromatography to obtain Compound A112 as a white solid (168 mg, 54% yield). $^1$H NMR (500 MHz, DMSO-d$_6$) δ 7.77 (s, 1H), 7.72 (brs, 2H), 7.49 (s, 1H), 7.44 (s, 1H), 6.83 (d, J=4.5 Hz, 1H), 6.62 (d, J=4.5 Hz, 1H), 5.58 (s, 1H), 4.93 (s, 1H), 4.85 (d, J=4.4 Hz, 1H), 4.68 (s, 1H), 4.08-3.98 (m, 2H), 3.52 (d, J=12.0 Hz, 1H), 3.34-3.29 (m, 1H). MS m/z=310.1 [M+1]$^+$.

Preparation Example 30: Synthesis of Compound A173 and A188

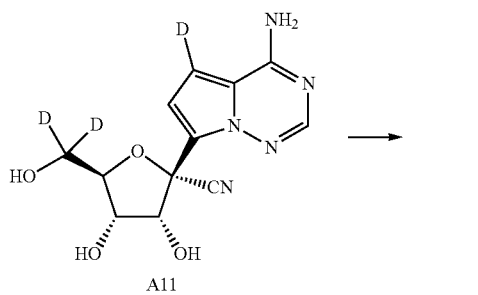

A11

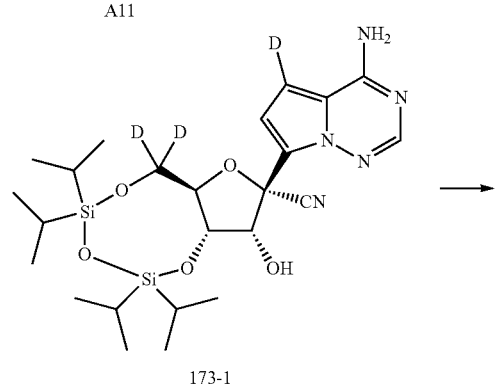

173-1

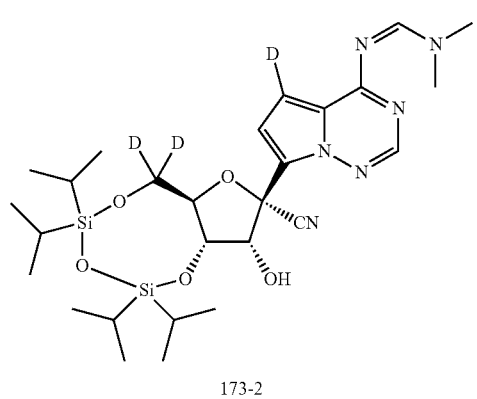

173-2

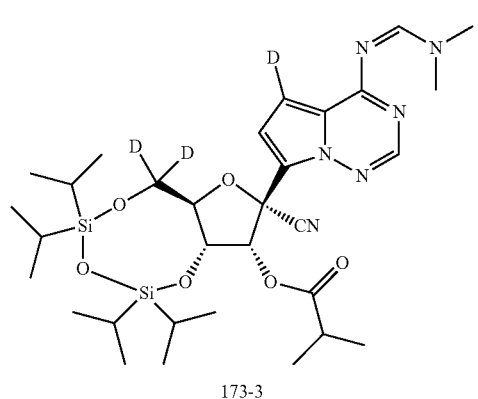

173-3

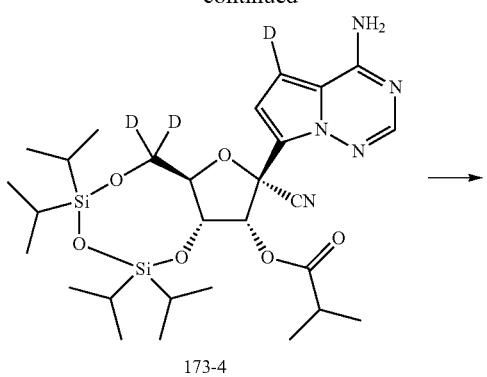

173-4

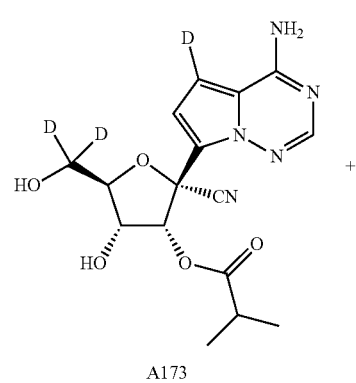

A173

+

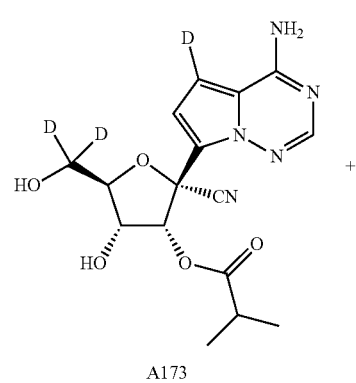

A188

According to the synthesis method for Compound A144, with A11 (294 mg, 1.0 mmol) as the starting material, Compound A173 and A188 were obtained over five steps, and further recrystallization afforded pure A188 as a white solid (91 mg, total yield of 25%). For Compound A188: $^1$H NMR (600 MHz, DMSO-$d_6$) δ 8.07-7.83 (m, 3H), 6.88 (s, 1H), 6.41 (d, J=6.6 Hz, 1H), 5.21 (dd, J=5.7, 3.3 Hz, 1H), 5.02 (s, 1H), 5.01-4.97 (m, 1H), 4.25 (d, J=3.2 Hz, 1H), 2.66-2.58 (m, 1H), 1.17 (d, J=7.0 Hz, 3H), 1.15 (d, J=6.9 Hz, 3H). MS m/z=365.0 [M+1]$^+$.

Preparation Example 31: Synthesis of Compound A180
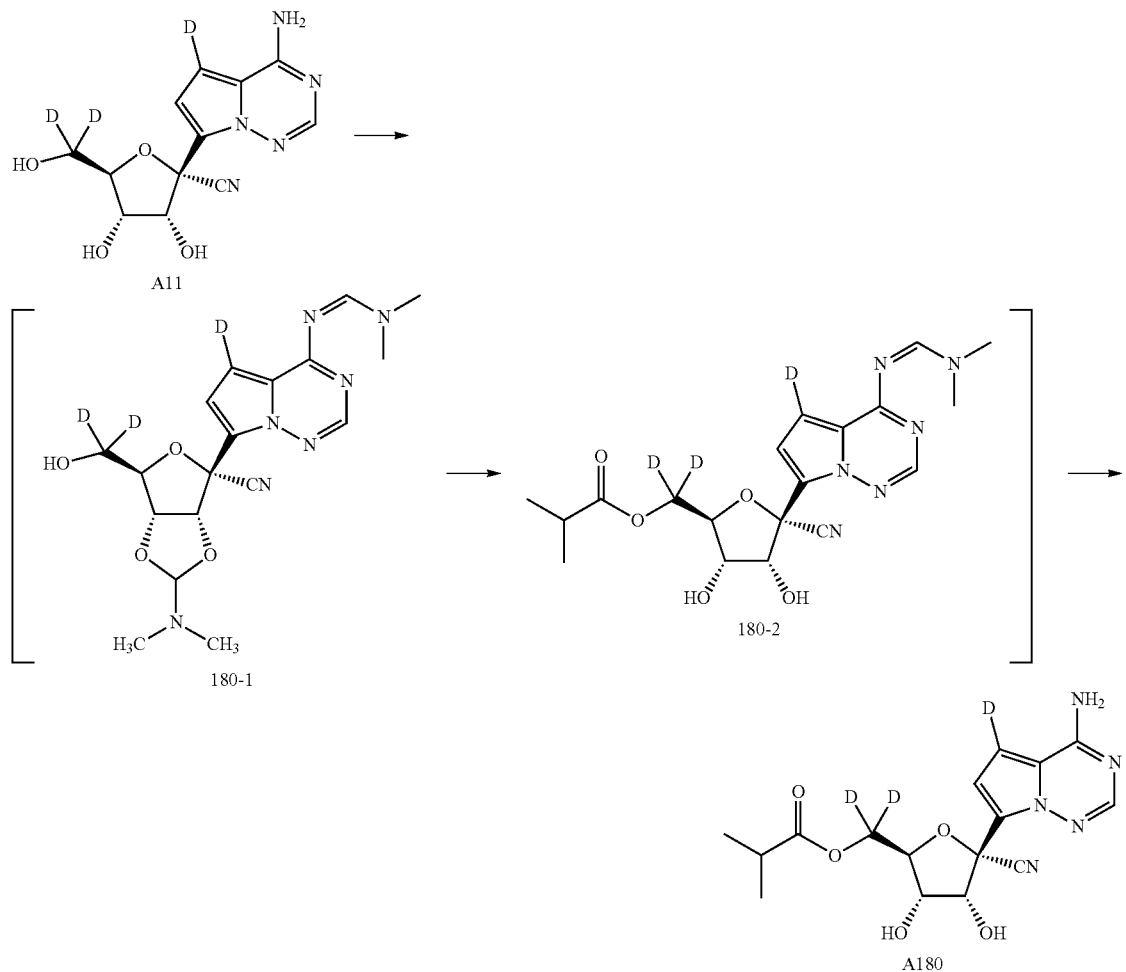
According to the synthesis method for Compound A70, with A11 (147 mg, 0.5 mmol) as the starting material, Compound A180 was obtained over three steps as a white solid (80 mg, total yield of 44%). ¹H NMR (500 MHz, DMSO-d$_6$) δ 8.03-7.83 (m, 3H), 6.82 (s, 1H), 6.32 (d, J=6.1 Hz, 1H), 5.39 (d, J=5.8 Hz, 1H), 4.71 (t, J=5.5 Hz, 1H), 4.23 (d, J=6.6 Hz, 1H), 3.97 (q, J=5.8 Hz, 1H), 2.57-2.53 (m, 1H), 1.10-1.01 (m, 6H). MS m/z=365.0 [M+1]$^+$.
Preparation Example 32: Synthesis of Compound A174 and A215
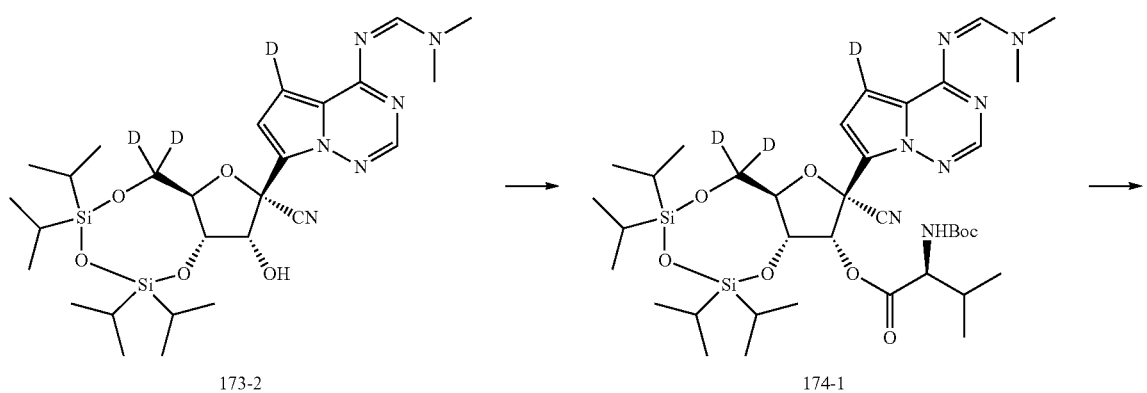

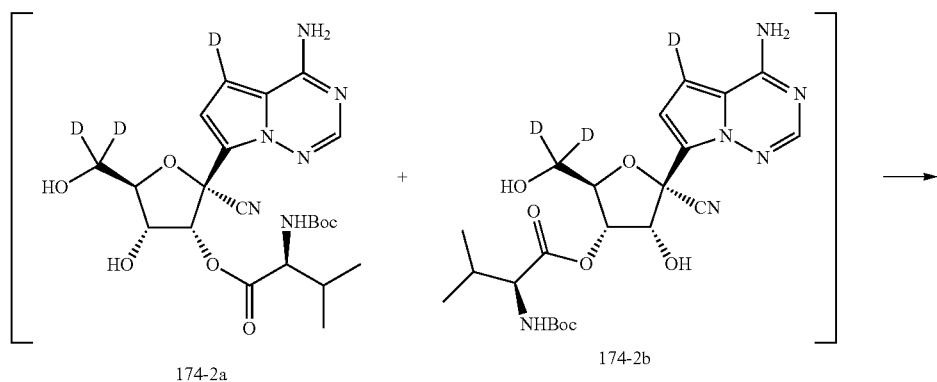

174-2a  174-2b

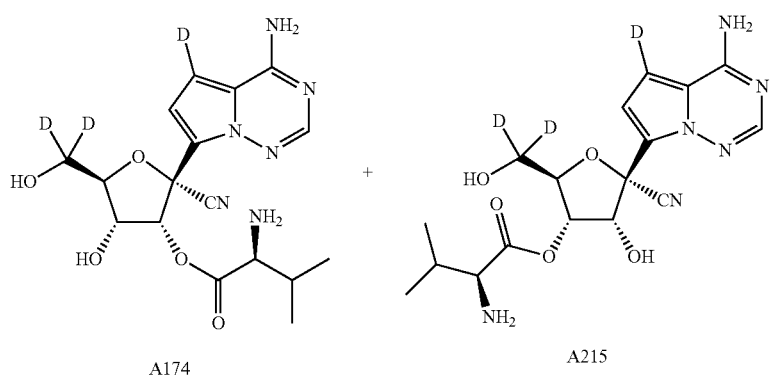

A174  A215

According to the synthesis method for Compound A213, with 173-2 (296 mg, 0.5 mmol) as the starting material, Compound A215 was obtained over three steps as the dihydrochloride salt, white solid (93 mg, 40% yield). H NMR (500 MHz, Methanol-$d_4$) δ 8.17 (s, TH), 7.21 (s, TH), 5.53 (dd, J=5.8, 3.1 Hz, TH), 5.19 (d, J=5.8 Hz, TH), 4.50 (d, J=3.1 Hz, TH), 4.13 (d, J=4.5 Hz, TH), 2.58-2.50 (m, TH), 1.18 (d, J=4.6 Hz, 3H), 1.17 (d, J=4.6 Hz, 3H). MS m/z=394.0 [M+1]$^+$. If the mixture 174-2a and 174-2b obtained from the second step were directly deprotected, the mixture of A174 and A215 could be obtained, and the content of A174 was about 10%.

Preparation Example 33: Synthesis of Compound A181

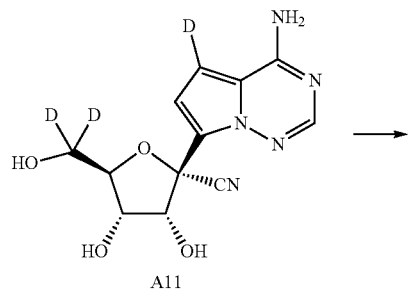

A11

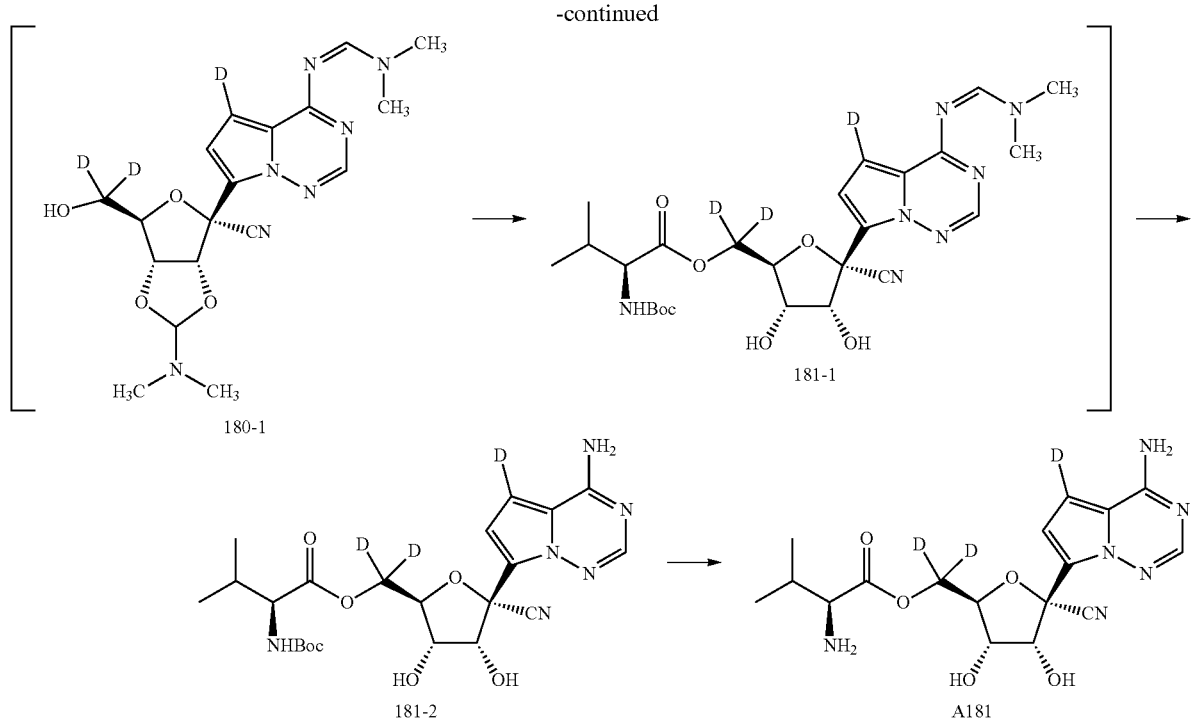

180-1

181-1

181-2

A181

According to the synthesis method for Compound A72, with A11 (147 mg, 0.5 mmol) as the starting material, Compound A181 was obtained over four steps as the dihydrochloride salt, white solid (75 mg, 32% yield). $^1$H NMR (600 MHz, Methanol-$d_4$) δ 8.15 (s, 1H), 7.12 (s, 1H), 4.75 (d, J=5.2 Hz, 1H), 4.62 (dd, J=12.1, 7.4 Hz, 1H), 4.54 (dd, J=12.1, 2.8 Hz, 1H), 4.45 (td, J=7.5, 2.8 Hz, 1H), 2.35-2.28 (m, 1H), 1.08 (d, J=2.4 Hz, 3H), 1.07 (d, J=2.3 Hz, 3H). MS m/z=394.0 [M+1]$^+$.

Preparation Example 34: Synthesis of Compound A198

According to the synthesis method for Compound A102, with A11 (59 mg, 0.2 mmol) as the starting material, A198 was obtained in the form of tri-triethylamine salt, foam solid (59 mg, 35% yield). $^1$H NMR (500 MHz, D$_2$O) δ 7.90 (s, 1H), 7.00 (s, 1H), 4.84 (d, J=4.6 Hz, 1H), 4.42-4.38 (m, 2H), 3.07 (q, J=7.3 Hz, 18H), 1.15 (t, J=7.3 Hz, 27H). $^{31}$P NMR (202 MHz, D$_2$O) δ-10.93 (d), −11.46 (d), −23.31 (t). MS m/z=533.0 [M−1]$^-$.

Preparation Example 35: Synthesis of Compound A131

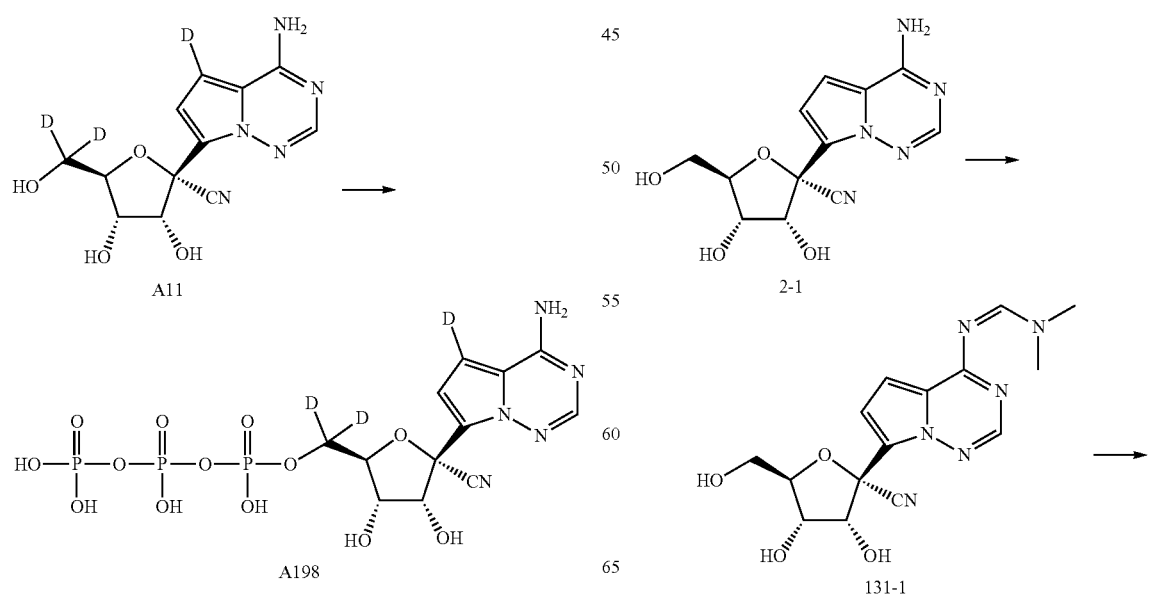

A11

2-1

A198

131-1

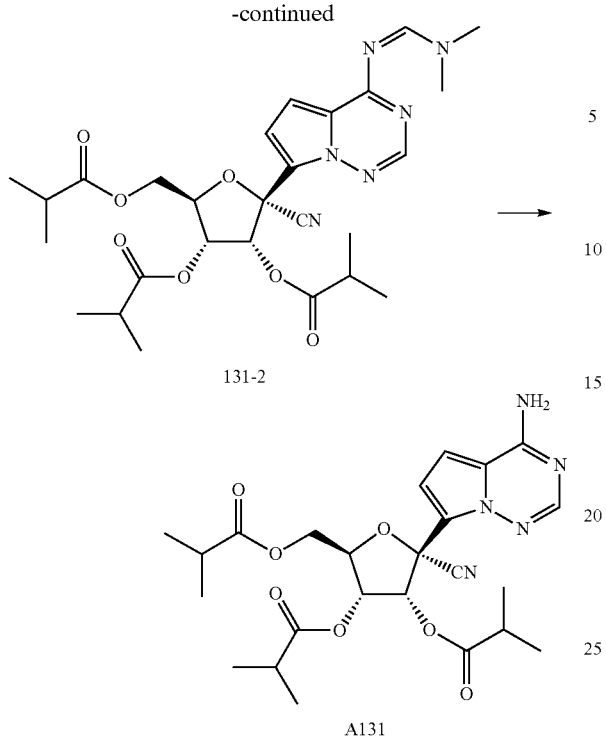

131-2

A131

Compound 2-1 (58 mg, 0.2 mmol) was added to N,N-dimethylformamide (3 mL), followed by the addition of N,N-dimethylformamide dimethyl acetal (160 mg, 1.34 mmol, 6.7 eq). After the addition, the reaction was carried out at room temperature, and 1 hour later, the reaction was complete. Methanol was added, and the reaction solution was concentrated. The residue was slurried in isopropanol and toluene to give Compound 131-1 as a white solid (59 mg, 85% yield).

Compound 131-1 (59 mg, 0.17 mmol) was added to dichloromethane (5 mL), followed by the successive addition of triethylamine (138 mg, 1.36 mmol, 8 eq), DMAP (62 mg, 0.51 mmol, 3 eq) and isobutyryl chloride (72 mg, 0.68 mmol, 4 eq) at room temperature, and reacted overnight. The reaction solution was concentrated, followed by the addition of ethyl acetate (30 mL) and water (10 mL). The organic phase was separated, washed with diluted hydrochloric acid, saturated sodium bicarbonate and saturated sodium chloride respectively, dried, and evaporated to give Compound 131-2 as a white solid (85 mg, 90% yield).

Compound 131-2 (85 mg, 0.15 mmol) was added to acetonitrile (10 mL), followed by the addition of hydrazine hydrate (30 mg, 0.60 mmol, 4 eq), and after the addition, the reaction was complete in about 30 minutes. The reaction solution was added into water, and extracted with ethyl acetate. The organic layer was separated, washed with diluted hydrochloric acid, saturated sodium bicarbonate and saturated sodium chloride, respectively, dried and evaporated to dryness. The residue was separated by silica gel column chromatography to give Compound A131 as a white solid (70 mg, 93% yield). $^1$H NMR (600 MHz, DMSO-$d_6$) δ 8.04 (br, 1H), 7.96 (br, 1H), 7.93 (s, 1H), 6.93 (d, J=4.6 Hz, 1H), 6.75 (d, J=4.6 Hz, 1H), 6.08 (d, J=5.7 Hz, 1H), 5.44 (dd, J=5.7, 3.7 Hz, 1H), 4.63 (q, J=3.7 Hz, 1H), 4.33 (dd, J=12.4, 3.3 Hz, 1H), 4.28 (dd, J=12.4, 4.1 Hz, 1H), 2.66-2.57 (m, 2H), 2.50-2.46 (m, 1H), 1.17 (d, J=7.0 Hz, 3H), 1.15 (d, J=6.9 Hz, 3H), 1.12-1.09 (m, 6H), 1.05 (d, J=7.0 Hz, 3H), 1.02 (d, J=7.0 Hz, 3H). MS m/z=502.0 [M+1]$^+$.

Preparation Example 36: Synthesis of Compound A151

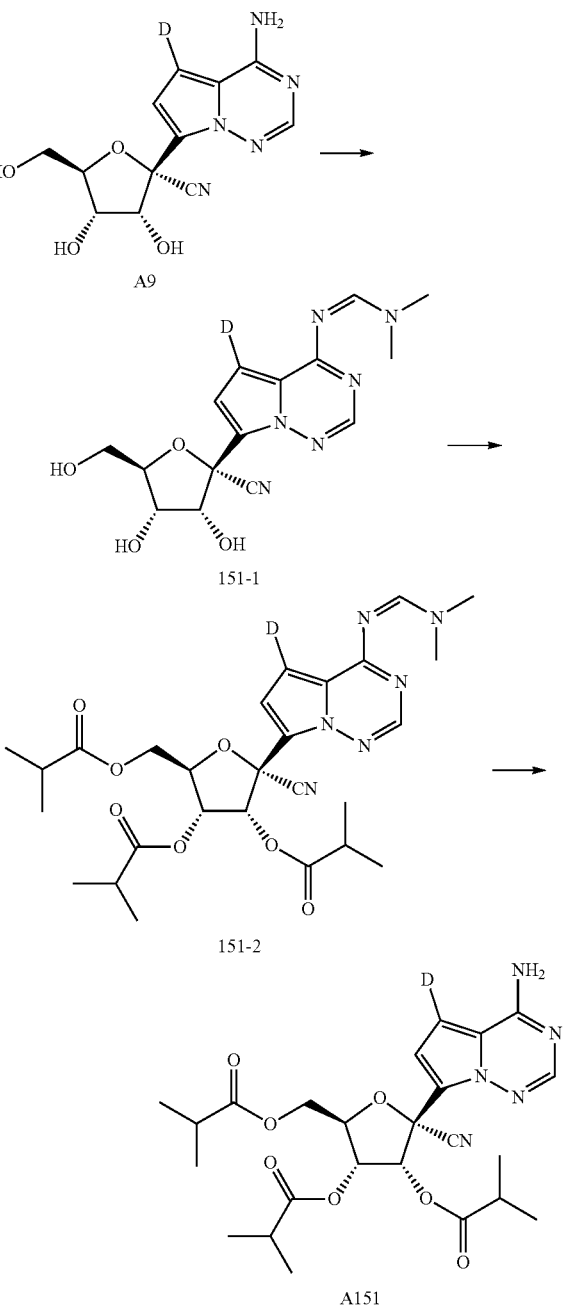

According to the synthesis method for Compound A131, with A9 (58 mg, 0.2 mmol) as the starting material, Compound A151 was obtained over three steps as a white solid (69 mg, total yield of 68%). $^1$H NMR (600 MHz, DMSO-$d_6$) δ 8.04 (br, 1H), 7.96 (br, 1H), 7.93 (s, 1H), 6.75 (s, 1H), 6.08 (d, J=5.7 Hz, 1H), 5.44 (dd, J=5.7, 3.7 Hz, 1H), 4.63 (q, J=3.7 Hz, 1H), 4.33 (dd, J=12.4, 3.3 Hz, 1H), 4.28 (dd, J=12.4, 4.1 Hz, 1H), 2.66-2.57 (m, 2H), 2.49-2.46 (m, 1H), 1.17 (d, J=7.0 Hz, 3H), 1.15 (d, J=6.9 Hz, 3H), 1.12-1.09 (m, 6H), 1.05 (d, J=7.0 Hz, 3H), 1.02 (d, J=7.0 Hz, 3H). $^{13}$C NMR (126 MHz, DMSO-d$_6$) δ 175.53, 174.90, 174.13, 155.58, 148.12, 120.98, 117.17, 115.44, 110.30, 81.25, 75.81, 72.05, 70.30, 62.46, 33.20, 33.16, 33.09, 18.55, 18.46, 18.40, 18.35, 18.33, 18.18. MS m/z=503.0 [M+1]$^+$.

Preparation Example 37: Synthesis of Compound A171

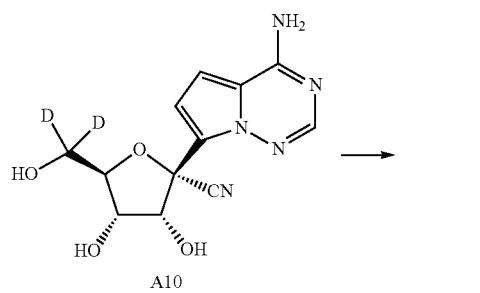

A10

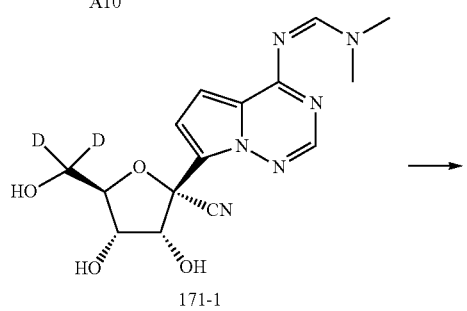

171-1

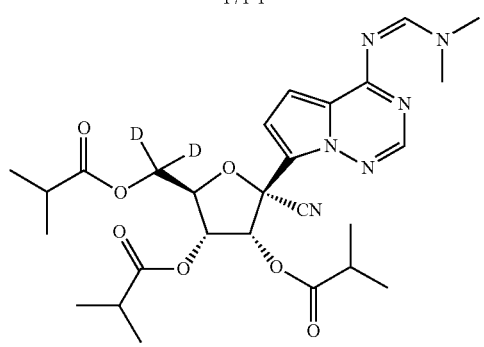

171-2

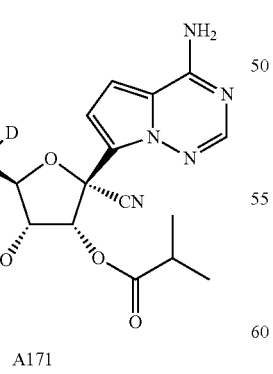

A171

According to the synthesis method for Compound A131, with A10 (59 mg, 0.2 mmol) as the starting material, Compound A171 was obtained over three steps as a white solid (70 mg, total yield of 69%). MS m/z=504.0 [M+1]$^+$.

Preparation Example 38: Synthesis of Compound A196

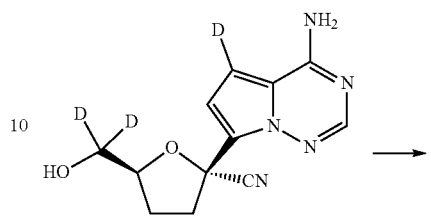

A11

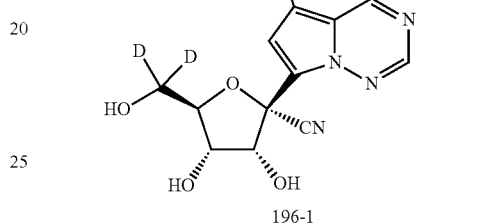

196-1

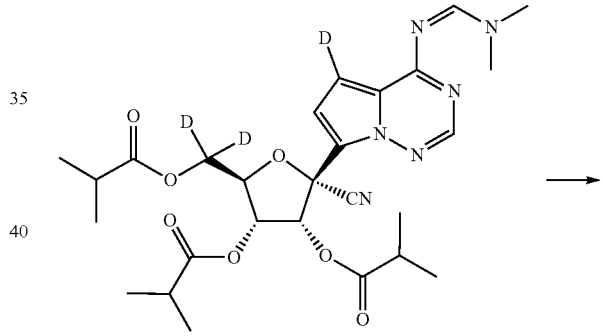

196-2

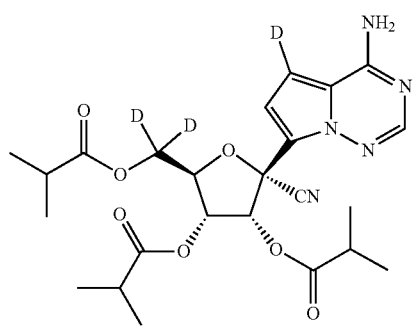

A196

According to the synthesis method for Compound A131, with A11 (59 mg, 0.2 mmol) as the starting material, Compound A196 was obtained over three steps as a white solid (59 mg, total yield of 58%). MS m/z=505.0 [M+1]$^+$.

Preparation Example 39: Synthesis of Compound A209

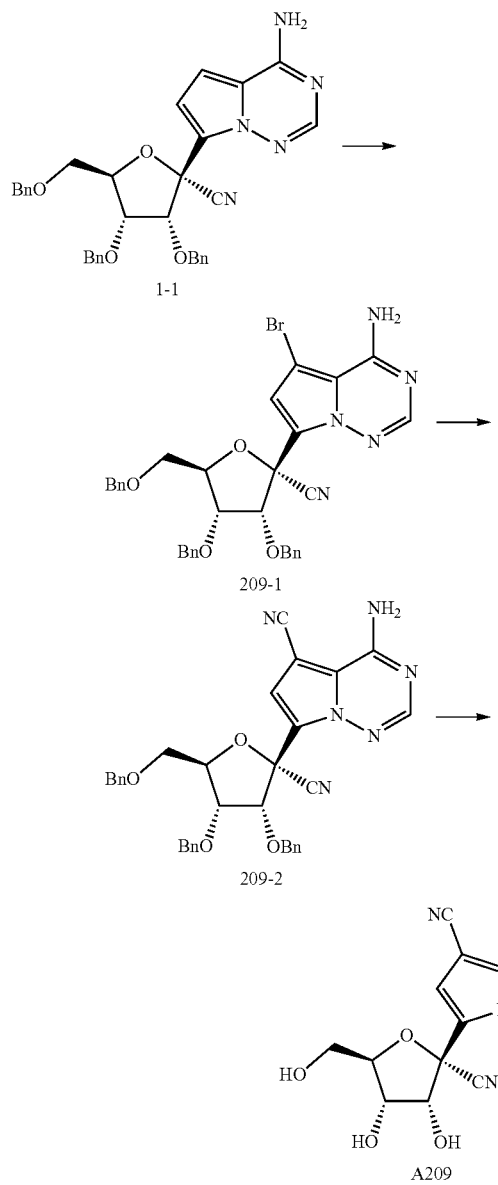

Compound 1-1 (0.5 g, 0.89 mmol) was added to DMF (9 mL), followed by the addition of NBS (0.16 g, 0.89 mmol, 1.0 eq), and stirred at room temperature for 3-4 hours. TLC showed that the reaction was complete. To the reaction solution was added saturated sodium thiosulfate (10 mL) solution, then stirred, and extracted with ethyl acetate. The aqueous layer was extracted with ethyl acetate (20 mL) again. The organic layers were combined, dried, concentrated and separated by column chromatography to obtain Compound 209-1 as a white solid (0.5 g, 87% yield).

Compound 209-1 (0.15 g, 0.23 mmol) was added to N,N-dimethylacetamide (5 mL), followed by the successive addition of Zn (2 mg, 0.031 mmol, 0.13 eq), Zn(CN)$_2$ (0.06 g, 0.51 mmol, 2.2 eq), NiCl$_2$(dppf) (0.03 g, 0.043 mmol, 0.2 eq) and Pd$_2$(dba)$_3$ (0.02 g, 0.02 mmol, 0.1 eq). After the addition, the reaction was carried out at 140° C. overnight. TLC showed that the reaction was complete. The reaction solution was poured into ethyl acetate/water (20 mL/20 mL), the layers were separated, and the aqueous layer was extracted with ethyl acetate (20 mL) again. The organic layers were combined, dried, concentrated and separated on preparative TLC plates to obtain Compound 209-2 as a white solid (0.1 g, 74% yield).

Compound 209-2 (0.1 g, 0.17 mmol) was added to dichloromethane (3 mL), and 1M boron trichloride in dichloromethane (0.7 mL, 4.1 eq) was added dropwise at −30° C. After the addition, the mixture was stirred at the same temperature for 1-2 hours. TLC showed that the reaction was complete. To the reaction solution was added methanol (0.5 mL) and triethylamine (0.3 mL) successively. The resulting solution was evaporated to dryness, and separated on preparative TLC plates to obtain Compound A209 as a white solid (15 mg, 28% yield). $^1$H NMR (500 MHz, DMSO-d$_6$) δ 8.23 (s, 1H), 7.50 (s, 1H), 6.30 (d, J=6.1 Hz, 1H), 5.22 (d, J=5.9 Hz, 1H), 4.93 (t, J=5.7 Hz, 1H), 4.55 (t, J=5.5 Hz, 1H), 4.11-4.03 (m, 1H), 3.94 (q, J=5.8 Hz, 1H), 3.73-3.65 (m, 1H), 3.57-3.49 (m, 1H). MS m/z=317.1 [M+1]$^+$.

Preparation Example 40: Synthesis of Compound A87

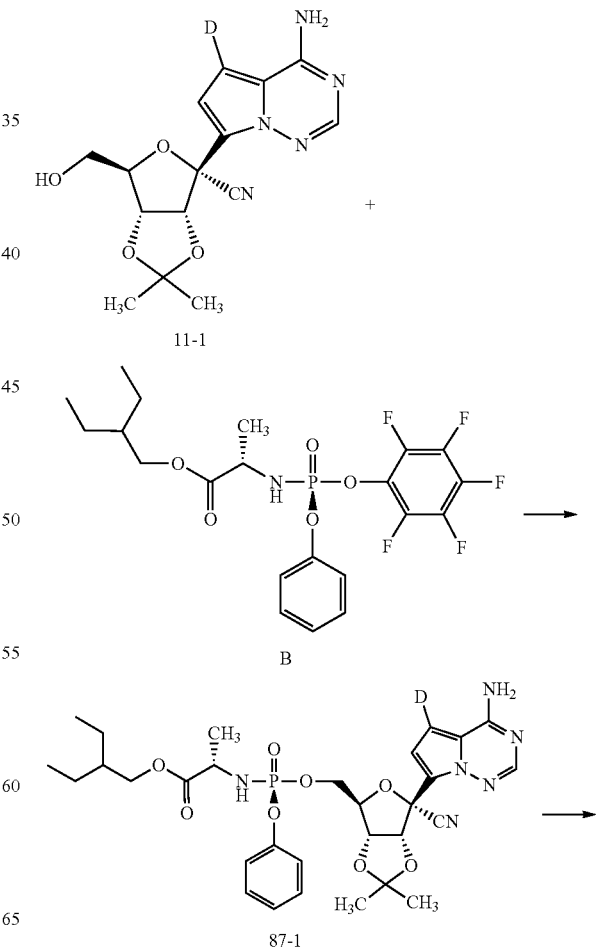

-continued

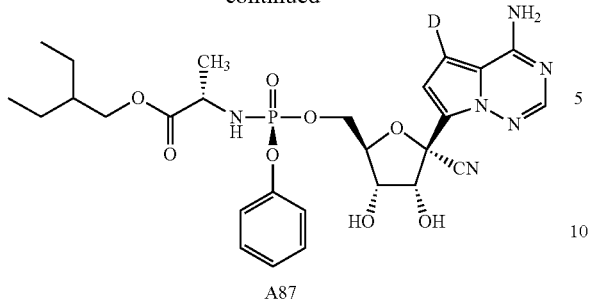

A87

Compound 11-1 (0.05 g, 0.15 mmol) was added to tetrahydrofuran (3 mL), followed by the dropwise addition of 3M methylmagnesium bromide in 2-methyltetrahydrofuran (0.1 mL, 0.3 mmol) in an ice bath. After the addition, the mixture was stirred for 5 minutes, and then the solution of compound B (0.1 g, 0.23 mmol) in tetrahydrofuran (1 mL) was added dropwise. After that, the mixture was stirred at room temperature for 2 hours. TLC showed that the reaction was complete. The reaction solution was added into saturated ammonium chloride solution (10 mL), and extracted with ethyl acetate. The organic layer was separated, dried and concentrated to give crude Compound 87-1, which was directly used in the next step.

The product obtained from the previous step was added to tetrahydrofuran (2 mL), followed by the addition of concentrated hydrochloric acid (0.4 mL) in an ice bath. Upon addition, the mixture was stirred at room temperature until the reaction was complete. The reaction solution was added into saturated sodium bicarbonate solution (10 mL) and extracted with ethyl acetate. The organic phase was separated, dried, concentrated, and separated by silica gel column chromatography to give Compound A87 as a white solid (0.03 g, 33% yield). $^1$H NMR (500 MHz, Methanol-$d_4$) δ 7.89 (s, 1H), 7.36-7.30 (m, 2H), 7.24-7.15 (m, 3H), 6.94 (s, 1H), 4.82 (d, J=5.4 Hz, 1H), 4.46-4.37 (m, 2H), 4.35-4.28 (m, 1H), 4.20 (t, J=5.6 Hz, 1H), 4.05 (dd, J=10.9, 5.8 Hz, 1H), 3.98-3.88 (m, 2H), 1.51-1.44 (m, 1H), 1.37-1.30 (m, 7H), 0.88 (t, J=7.5 Hz, 6H). MS m/z=604.1 [M+1]$^+$.

Preparation Example 41: Synthesis of Compound A138

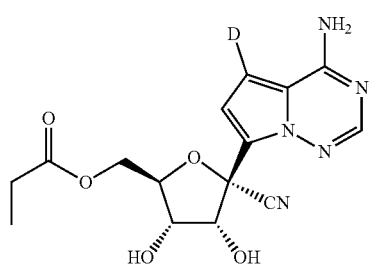

A138

According to the synthesis method for Compound A70, with A9 (147 mg, 0.5 mmol) as the starting material, Compound A138 was obtained over three steps as a white solid (65 mg, total yield of 37%). $^1$H NMR (400 MHz, DMSO-$d_6$) δ 7.99-7.83 (m, 3H), 6.80 (s, 1H), 6.32 (d, J=6.1 Hz, 1H), 5.38 (d, J=5.8 Hz, 1H), 4.71-4.65 (m, 1H), 4.33 (dd, J=12.0, 2.8 Hz, 1H), 4.25-4.19 (m, 1H), 4.15 (dd, J=12.0, 5.5 Hz, 1H), 3.97-3.90 (m, 1H), 2.30 (q, J=7.5 Hz, 2H), 1.00 (t, J=7.5 Hz, 3H). MS m/z=349.2 [M+1]$^+$.

Preparation Example 42: Synthesis of Compound A140

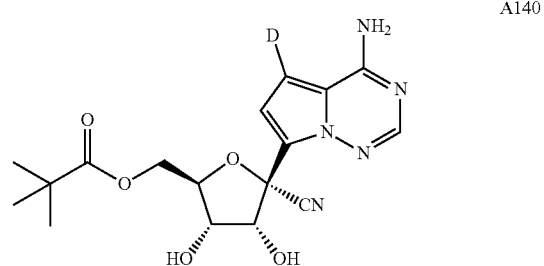

A140

According to the synthesis method for A70, with A9 (147 mg, 0.5 mmol) as the starting material, Compound A140 was obtained over three steps as a white solid (77 mg, total yield of 41%). $^1$H NMR (500 MHz, DMSO-$d_6$) δ 8.03-7.80 (m, 3H), 6.80 (s, 1H), 6.32 (d, J=6.1 Hz, 1H), 5.37 (d, J=5.7 Hz, 1H), 4.70 (t, J=5.3 Hz, 1H), 4.30-4.22 (m, 2H), 4.21-4.14 (m, 1H), 4.01-3.94 (m, 1H), 1.09 (s, 9H). MS m/z=377.2 [M+1]$^+$.

Preparation of Example 43: Synthesis of Compound A146

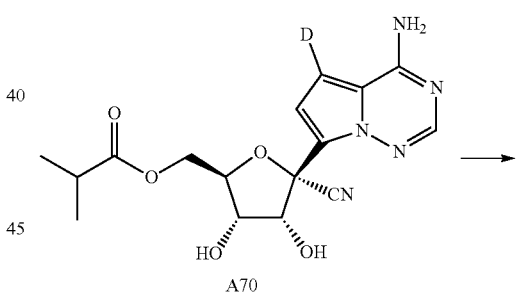

A70

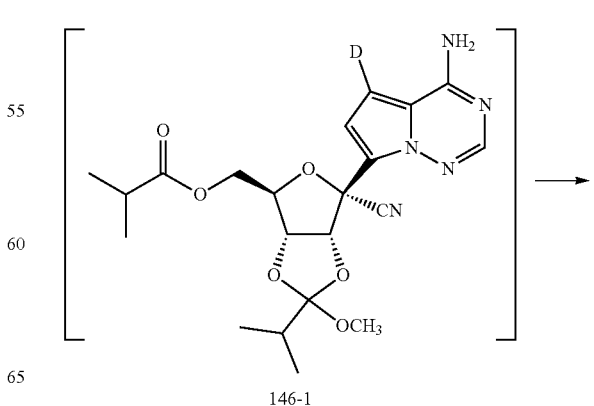

146-1

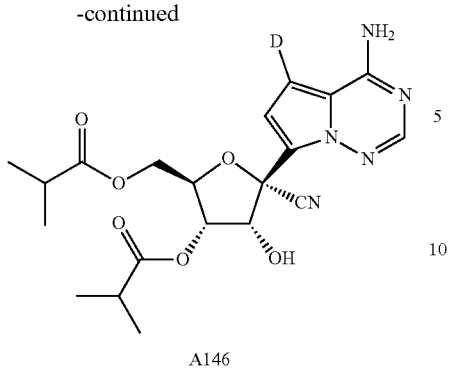

A146

Compound A70 (0.18 g, 0.5 mmol) was added to acetic acid (3 mL), then trimethyl orthoisobutyrate (0.37 g, 2.5 mmol) was added, and the mixture was stirred at 50° C. until the reaction was complete. The solvent was removed by evaporation to obtain an unstable intermediate 146-1. The intermediate was dissolved in tetrahydrofuran (6 mL), followed by the addition of 1M diluted hydrochloric acid (0.5 mL), and stirred at room temperature. The reaction was complete in about 1 hour. To the reaction solution was added saturated sodium bicarbonate aqueous solution until the pH was neutral, and extracted with ethyl acetate. The organic phase was dried and evaporated to dryness to obtain crude Compound A146. The crude product was recrystallized in isopropanol/water to obtain a white solid (0.18 g, 82% yield). $^1$H NMR (600 MHz, DMSO-$d_6$) δ 8.05-7.83 (m, 3H), 6.85 (s, 1H), 6.56 (d, J=6.5 Hz, 1H), 5.16 (dd, J=5.6, 4.1 Hz, 1H), 5.09 (t, J=6.1 Hz, 1H), 4.46 (q, J=4.3 Hz, 1H), 4.27 (dd, J=12.2, 4.0 Hz, 1H), 4.23 (dd, J=12.2, 4.8 Hz, 1H), 2.67-2.58 (m, 1H), 2.55-2.49 (m, 1H), 1.16 (d, J=7.0 Hz, 3H), 1.15 (d, J=7.0 Hz, 3H), 1.05 (d, J=7.0 Hz, 3H), 1.03 (d, J=7.2 Hz, 3H). MS m/z=433.2 [M+1]$^+$.

Preparation Example 44: Synthesis of Compound A147

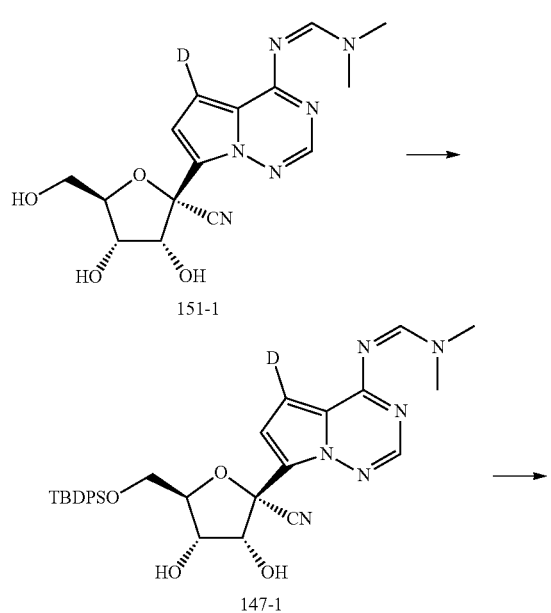

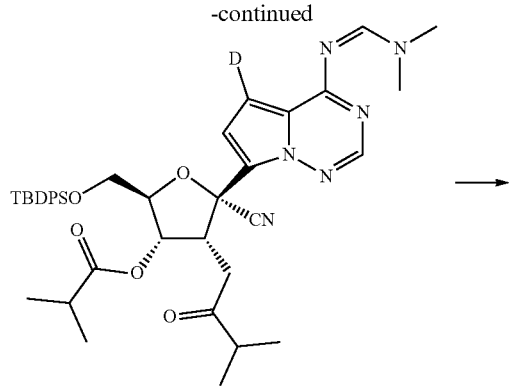

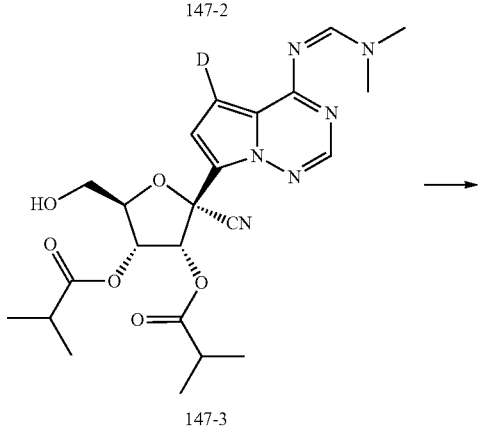

A147

Compound 151-1 (1.51 g, 4.34 mmol) was added to N,N-dimethylformamide (15 mL), followed by the addition of tert-butyldiphenylchlorosilane (2.39 g, 8.69 mmol) and imidazole (1.18 g, 17.37 mmol) in an ice bath, and stirred at room temperature for 5 hours. Water and ethyl acetate were added to the reaction solution. The organic phase was separated, washed with diluted hydrochloric acid, saturated sodium bicarbonate aqueous solution and saturated brine successively, dried over anhydrous sodium sulfate, concentrated, and separated by silica gel column chromatography to give 2.05 g Compound 147-1 as a foam solid.

Compound 147-1 (2.05 g, 3.50 mmol) was added to dichloromethane (30 mL), followed by the addition of triethylamine (1.24 g, 12.26 mmol), DMAP (0.21 g, 1.75 mmol) and isobutyric anhydride (1.39 g, 8.76 mmol) at room temperature, and reacted for 1 hour under nitrogen protection at room temperature. The reaction solution was concentrated, and water and ethyl acetate were added. The organic phase was separated, washed with diluted hydrochloric acid, saturated sodium bicarbonate aqueous solution and saturated brine successively, dried over anhydrous sodium sulfate, and concentrated to obtain crude Compound 147-2 as an oil, which was directly used in the next reaction without purification.

The product obtained from the previous step was added to tetrahydrofuran (30 mL), followed by the addition of acetic acid (0.11 g, 1.75 mmol) and 1M tetrabutylammonium fluoride (3.5 mL, 3.5 mmol) in tetrahydrofuran, and stirred at room temperature for 2 hours. Water and ethyl acetate were added into the reaction solution. The organic phase was separated, washed with saturated sodium bicarbonate aqueous solution and saturated brine successively, dried over anhydrous sodium sulfate, and concentrated to obtain crude Compound 147-3 as an oil.

The crude 147-3 obtained from the previous step was added to ethanol (20 mL), followed by the addition of acetic acid (4.2 g, 70 mmol) at room temperature, and stirred overnight at 50° C. under nitrogen protection. The reaction solution was concentrated, and then water and ethyl acetate were added. The organic phase was separated, washed with saturated sodium bicarbonate and saturated brine successively, dried over anhydrous sodium sulfate, concentrated and separated by silica gel column chromatography to give Compound A147 as a white solid (0.85 g, 56% yield for 3 steps). $^1$H NMR (500 MHz, DMSO-d$_6$) δ 8.15-7.89 (m, 3H), 6.80 (s, 1H), 6.01 (d, J=5.7 Hz, 1H), 5.44 (dd, J=5.7, 3.1 Hz, 1H), 5.18 (dd, J=6.1, 5.2 Hz, 1H), 4.41 (q, J=3.4 Hz, 1H), 3.71-3.60 (m, 2H), 2.69-2.54 (m, 2H), 1.19 (d, J=7.0 Hz, 3H), 1.16 (d, J=7.0 Hz, 3H), 1.11 (d, J=2.4 Hz, 3H), 1.09 (d, J=2.4 Hz, 3H). MS m/z=433.2 [M+1]$^+$.

Preparation Example 45: Synthesis of Compound A216

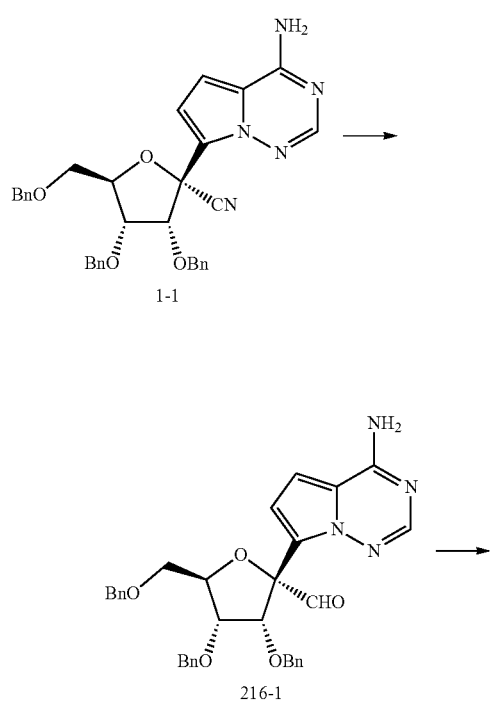

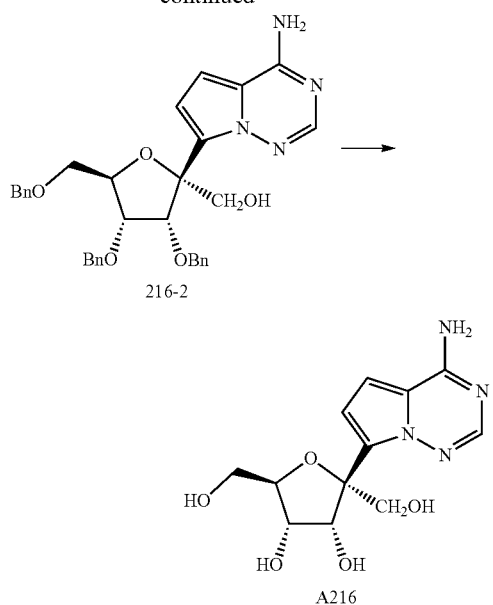

Compound 1-1 (0.2 g, 0.36 mmol) was added to dichloromethane (2 mL), followed by the slow addition of 1.2M diisobutyl aluminum hydride in toluene (0.9 mL, 1.08 mmol) at 78° C. After the addition, the reaction was stirred at the same temperature for 3-4 hours. TLC showed that the reaction was complete. Ethyl acetate (3 mL) was added to the reaction solution dropwise. After the addition, the mixture was warmed up naturally to room temperature, then 20% sodium potassium tartrate aqueous solution (5 mL) was added, and the mixture was stirred at room temperature overnight. The reaction solution was added into water (15 mL), and extracted with ethyl acetate. The organic layer was separated, dried and concentrated to give Compound 216-1.

Compound 216-1 (0.6 g, 1.06 mmol) was added to a mixture of ethanol (10 mL) and dichloromethane (10 mL), and NaBH$_4$ (0.1 g, 2.6 mmol) was added portionwise in an ice bath. After the addition, the mixture was stirred at room temperature for 2-3 hours. TLC showed the reaction was complete. Acetic acid was added into the reaction solution dropwise until no bubbles were generated. Water (30 mL) was added, and the mixture was extracted with ethyl acetate. The organic layer was separated, washed with saturated sodium bicarbonate, dried, concentrated, and separated by silica gel column chromatography to give Compound 216-2 as a white solid (0.48 g, 80% yield).

Compound 216-2 (0.48 g, 0.85 mmol), formic acid (2 mL) and 10% palladium carbon (0.06 g) were successively added to methanol (6 mL), and the mixture was pumped with hydrogen at room temperature and stirred at normal pressure for 16 hours, the mixture was filtered, concentrated, and separated by reversed-phase column chromatography to obtain Compound A216 as a white solid (0.05 g, 20% yield). $^1$H NMR (500 MHz, DMSO-d$_6$) δ 7.80 (s, 1H), 7.61 (s, 2H), 6.81 (d, J=4.4 Hz, 1H), 6.73 (d, J=4.4 Hz, 1H), 5.18 (d, J=4.7 Hz, 1H), 4.89 (d, J=6.9 Hz, 1H), 4.79 (t, J=5.8 Hz, 1H), 4.51-4.38 (m, 2H), 4.16 (dd, J=11.6, 6.7 Hz, 1H), 3.99 (dd, J=11.6, 4.7 Hz, 1H), 3.94-3.83 (m, 1H), 3.78-3.69 (m, 1H), 3.70-3.59 (m, 1H), 3.56-3.47 (m, 1H). MS m/z=297.1 [M+1]$^+$.

Preparation Example 46: Synthesis of Compound A28

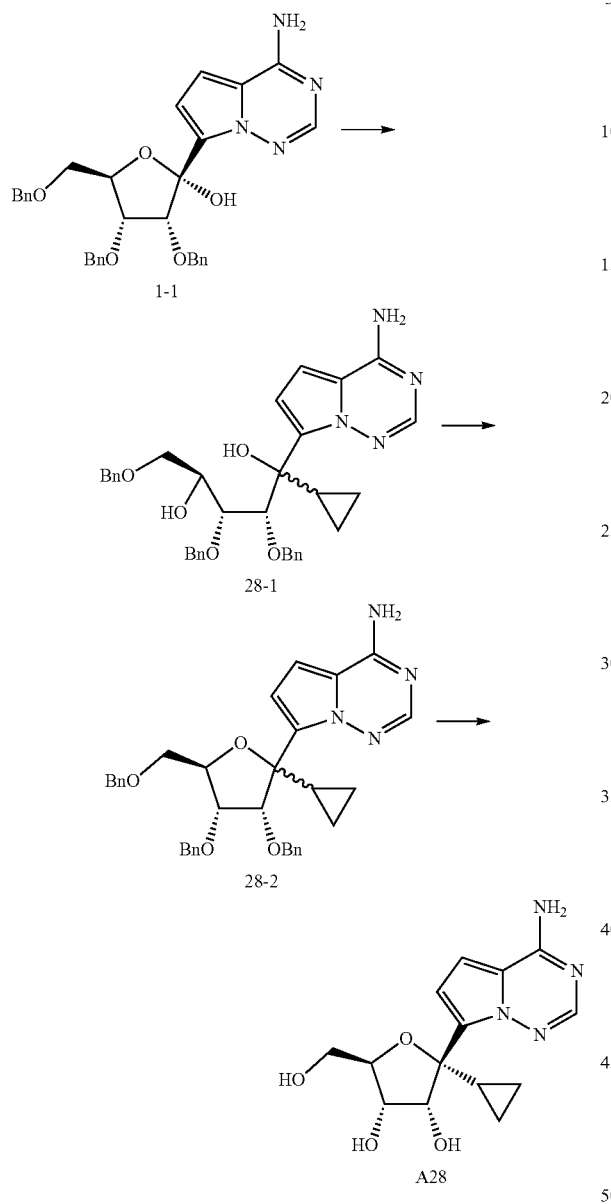

A solution of 0.5M cyclopropyl magnesium bromide in tetrahydrofuran (18 mL, 9 mmol) was added dropwise to Compound 1-1 (0.5 g, 0.9 mmol) in an ice bath and stirred overnight at room temperature upon addition. The reaction solution was added saturated ammonium chloride solution (10 mL) dropwise in an ice bath. Then, water (50 mL) was added, and the mixture was extracted with ethyl acetate. The organic layer was separated, dried, concentrated, and separated by silica gel column chromatography to obtain Compound 28-1 as a white solid (0.2 g, 37% yield).

Compound 28-1 (0.2 g, 0.34 mmol) was added to dichloromethane (4 mL), and methane sulfonic acid (0.1 g, 1.04 mmol) was added dropwise in an ice bath. Upon complete addition, the mixture was stirred at room temperature for 10-12 hours. TLC showed the reaction was complete. Saturated sodium bicarbonate solution (10 mL) was added to the reaction solution until the pH was neutral. Then water (15 mL) was added, and the mixture was extracted with ethyl acetate. The organic phase was separated, dried, concentrated, and separated by silica gel column chromatography to give Compound 28-2 as a white solid (0.1 g, 51% yield).

Compound 28-2 (0.24 g, 0.42 mmol), formic acid (1 mL) and 10% palladium carbon (0.03 g) were successively added to methanol (3 mL), and was pumped with hydrogen and stirred under atmospheric pressure for 16 hours at room temperature. TLC showed that the reaction was complete. The mixture was filtered, concentrated, and separated by silica gel column chromatography to obtain Compound A28 as a white solid (13 mg, 10% yield). $^1$H NMR (500 MHz, Methanol-$d_4$) δ 7.78 (s, 1H), 6.85 (d, J=4.5 Hz, 1H), 6.79 (d, J=4.5 Hz, 1H), 4.78 (d, J=5.1 Hz, 1H), 4.01-3.95 (m, 1H), 3.95-3.89 (m, 1H), 3.81 (dd, J=11.9, 2.8 Hz, 1H), 3.68 (dd, J=11.8, 5.5 Hz, 1H), 2.02-1.92 (m, 1H), 0.68-0.52 (m, 2H), 0.28-0.19 (m, 1H), 0.19-0.08 (m, 1H). MS m/z=307.1 [M+1]$^+$.

Preparation Example 47: Synthesis of Compound A218

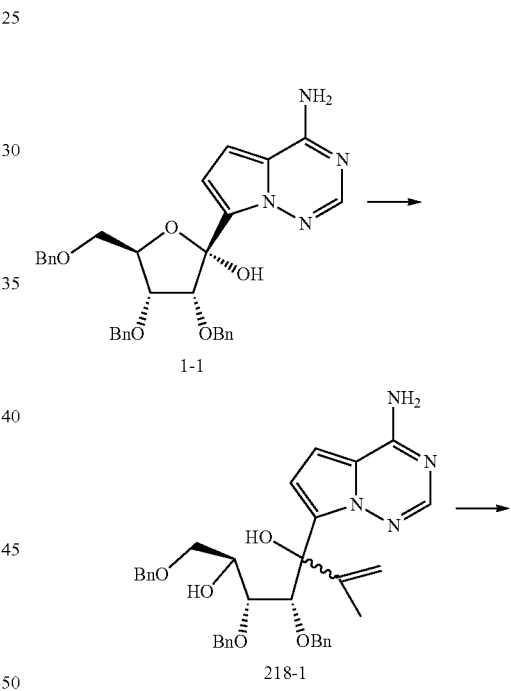

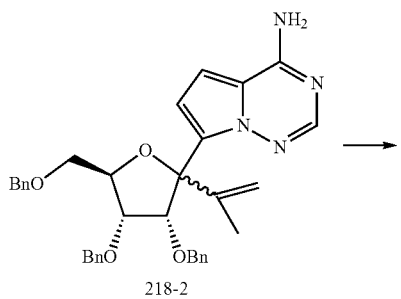

-continued

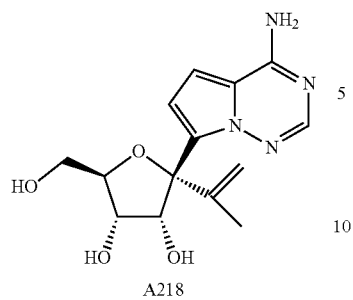

A218

A solution of 1.0M isopropenyl magnesium bromide in tetrahydrofuran (40 mL, 40 mmol) was added dropwise to Compound 1-1 (2.2 g, 3.98 mmol) in an ice bath, and stirred overnight at room temperature after addition. Saturated ammonium chloride solution (10 mL) was slowly added into the reaction solution. After addition, water (40 mL) was added, and the mixture was extracted with ethyl acetate. The organic layer was separated, dried, concentrated, and separated by silica gel column chromatography to obtain intermediate 218-1 as a white solid (1.6 g, 68% yield).

Intermediate 218-1 (1.6 g, 2.69 mmol) was added to dichloromethane (30 mL), and methane sulfonic acid (0.77 g, 8.01 mmol) was slowly added. Upon addition, the mixture was stirred at room temperature overnight. TLC showed that the reaction was complete. Saturated sodium bicarbonate solution was added dropwise into the reaction solution in an ice bath until the pH was neutral. Water (40 mL) was added, and the mixture was extracted with dichloromethane. The organic layer was separated, dried, concentrated, and separated by silica gel column chromatography to obtain intermediate 218-2 as a yellow oil (0.7 g, 45% yield).

According to the method for the debenzylation step in Example 5, intermediate 218-2 (0.7 g, 1.21 mmol) was reacted with a solution of 1.0M BCl$_3$ in dichloromethane (6.0 mL, 6.0 mol) to give the product that was separated by column chromatography to give 0.025 g Compound A218 as a white solid. $^1$H NMR (600 MHz, DMSO-d$_6$) δ 7.74 (s, 1H), 7.55 (s, 2H), 6.82 (d, J=4.5 Hz, 1H), 6.58 (d, J=4.4 Hz, 1H), 5.03 (s, 1H), 4.83-4.73 (m, 3H), 4.72-4.64 (m, 2H), 4.05-3.94 (m, 1H), 3.84-3.76 (m, 1H), 3.70-3.60 (m, 1H), 3.51-3.42 (m, 1H), 1.59 (s, 3H). m/z=307.2 [M+1]$^+$.

Preparation Example 48: Synthesis of Compound A219

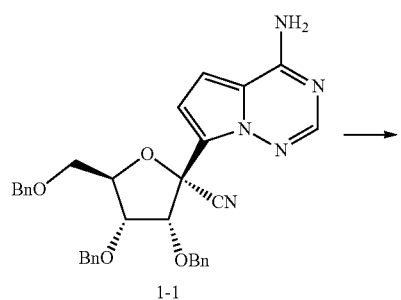

1-1

-continued

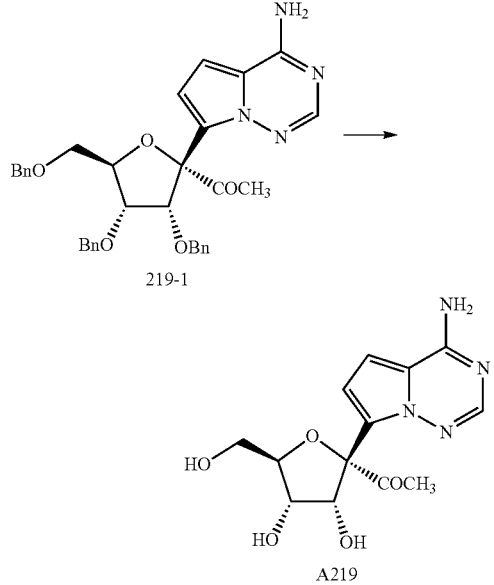

219-1

A219

Compound 1-1 (0.56 g, 1.0 mmol) was added to tetrahydrofuran (5 mL), followed by the dropwise addition of 3M methyl magnesium bromide in tetrahydrofuran (1.7 mL, 5.1 mmol) in an ice bath under nitrogen protection. After the addition, the mixture was stirred at 60° C. for 2-3 hours. TLC showed that the reaction was complete. Saturated ammonium chloride solution (1.0 mL) was added dropwise in an ice bath. Water (10 mL) was added, and the mixture was extracted with ethyl acetate. The organic layer was separated, dried, concentrated, and separated by column chromatography to obtain Compound 219-1 as a white solid (0.38 g, 66% yield).

According to the method for the debenzylation step in Example 5, intermediate 219-1 (0.2 g, 0.345 mmol) was reacted with a solution of 1.0M BCl$_3$ in dichloromethane (1.7 mL, 1.7 mmol) to give the product that was separated by silica gel column chromatography to give Compound A219 as a white solid (0.05 g, 47% yield). $^1$H NMR (600 MHz, DMSO-d$_6$) δ 7.99-7.43 (m, 3H), 6.79 (s, 1H), 6.62 (s, 1H), 5.49 (s, 1H), 5.10-4.93 (m, 1H), 4.83-4.67 (m, 1H), 4.60-4.40 (m, 1H), 4.19-3.96 (m, 2H), 3.59-3.44 (m, 1H), 3.27-3.16 (m, 1H), 2.30 (s, 3H). MS m/z=309.2[M+1]$^+$.

Preparation Example 49: Synthesis of Compound A221

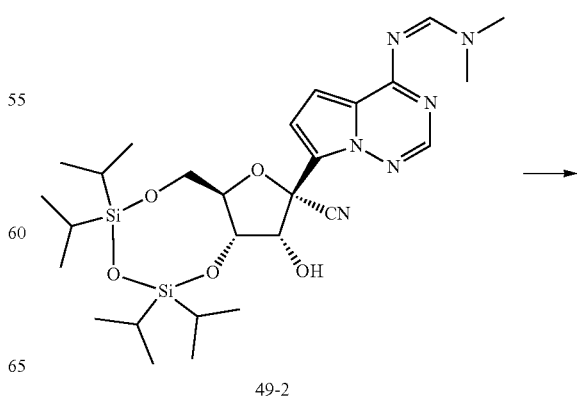

49-2

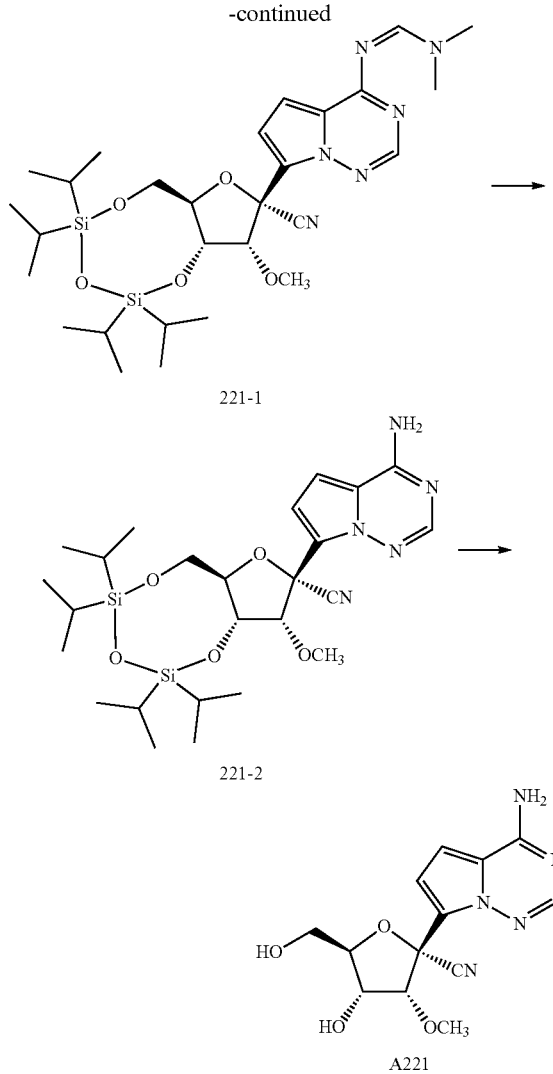

221-1

221-2

A221

Compound 49-2 (0.6 g, 1 mmol) was added to DMF (10 mL), followed by the successive addition of methyl iodide (0.28 g, 2.0 mmol) and 60% sodium hydride (0.014 g, 2.0 mmol) in an ice bath. After stirring for 15 minutes, TLC showed the reaction was complete. The reaction solution was added into saturated ammonium chloride aqueous solution (15 mL), and extracted with ethyl acetate. The organic layer was separated, dried, concentrated and evaporated to dryness to give Compound 221-1. This intermediate was used in the next step without purification.

Intermediate 221-1 obtained from the previous step was added to acetonitrile (2 mL), followed by the addition of 85% hydrazine hydrate (0.24 g, 4.0 mmol), and stirred at room temperature for 1 hour. TLC showed the reaction was complete. The reaction solution was added into water (15 mL), and the mixture was extracted with ethyl acetate. The organic layer was separated, dried, concentrated and separated by column chromatography to give Compound 221-2 as a white solid (0.2 g, 37% yield for two steps).

Compound 221-2 (0.2 g, 0.36 mmol) was added to tetrahydrofuran (2 mL), followed by the addition of 1M tetrabutylammonium fluoride in tetrahydrofuran (0.4 mL, 0.4 mmol), and stirred at room temperature for 2 hours. TLC showed the reaction was complete. The reaction solution was concentrated, and separated on preparative TLC plates to give Compound A221 as a white solid (0.045 g, 41% yield). $^1$H NMR (500 MHz, DMSO-$d_6$) δ 8.07-7.78 (m, 3H), 6.87 (s, 1H), 5.30 (d, J=5.4 Hz, 1H), 4.94 (t, J=5.8 Hz, 1H), 4.37 (d, J=4.9 Hz, 1H), 4.11 (q, J=5.4 Hz, 1H), 4.08-4.02 (m, 1H), 3.71-3.62 (m, 1H), 3.55 (s, 3H), 3.54-3.48 (m, 1H). MS m/z=306.0[M+1]$^+$.

Preparation Example 50: Synthesis of Compound A36

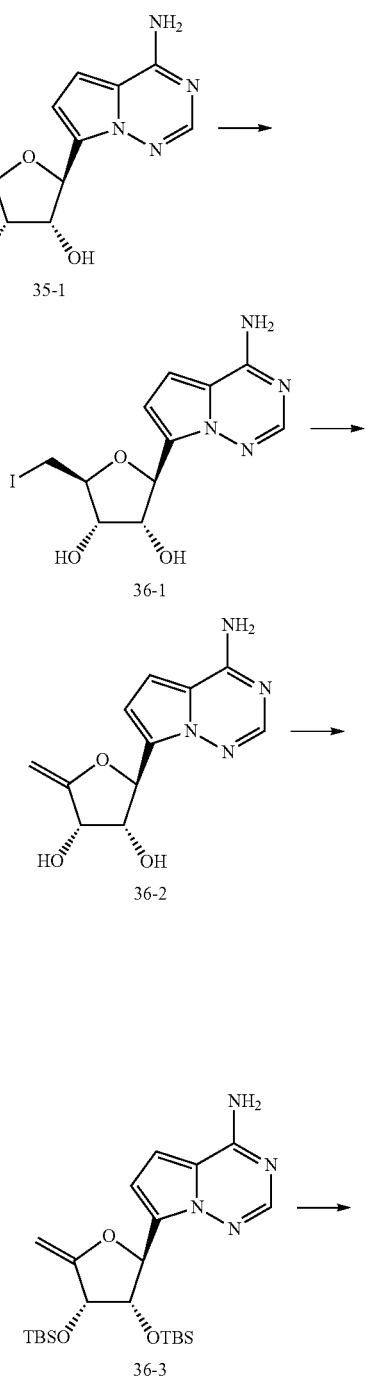

35-1

36-1

36-2

36-3

-continued

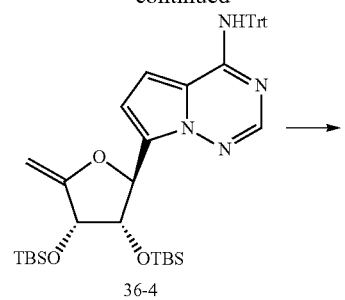
36-4

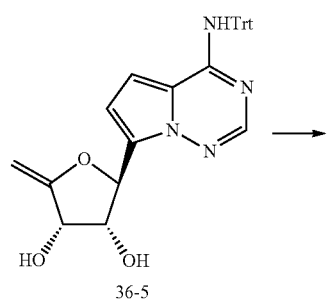
36-5

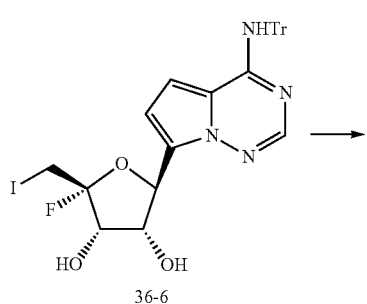
36-6

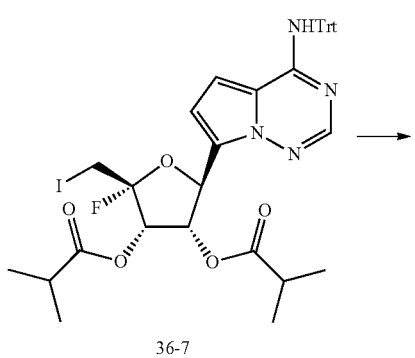
36-7

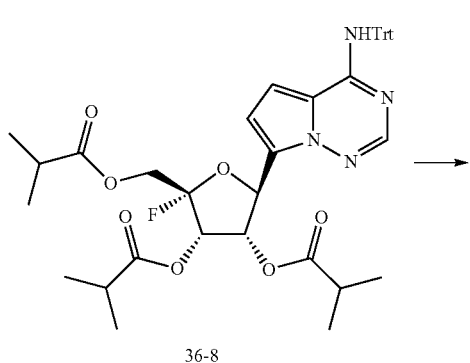
36-8

-continued

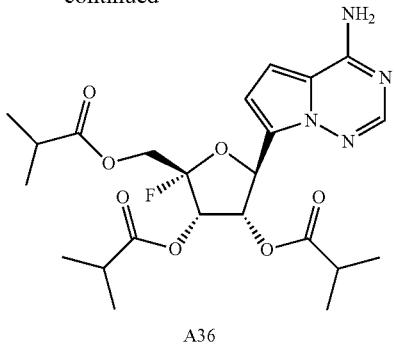
A36

Compound 35-1 (8.4 g, 31.5 mmol) was dissolved in pyridine (85 mL), followed by the addition of triphenylphosphine (33.1 g, 126.2 mmol), then warmed up to 30° C. under nitrogen protection, and iodine (32.0 g, 126.2 mmol) was added portionwise at the temperature of below 40° C. The mixture was stirred for 1 hour, and TLC showed that the reaction was complete. Saturated sodium thiosulfate solution was added, and the mixture was separated by silica gel column chromatography (DCM:MeOH=100: 1-10:1) to give Compound 36-1 (8.5 g, 72% yield).

Compound 36-1 (3.0 g, 8.0 mmol) was dissolved in acetonitrile (60 mL), followed by the addition of DBU (2.4 g, 16.0 mmol), and stirred at 40° C. for 3 h. TLC showed that the reaction was complete. The mixture was separated by silica gel column chromatography (DCM:MeOH=50:1-10:1) to give Compound 36-2 (600 mg, 30% yield).

Compound 36-2 (200 mg, 0.8 mmol) was added to THF (5 mL), followed by the addition of DBU (731 mg, 4.8 mmol) and TBSCl (543 mg, 3.6 mmol), and stirred at room temperature for 2 hours. TLC showed that the reaction was complete. Methanol (1 mL) and saturated citric acid aqueous solution (4 mL) were added, stirred, and extracted with ethyl acetate. The organic layer was washed with saturated brine and saturated sodium bicarbonate solution, dried over anhydrous sodium sulfate, and concentrated to obtain crude Compound 36-3.

Crude Compound 36-3 was added to dichloromethane (10 mL), followed by the addition of 2,4,6-trimethylpyridine (194 mg, 1.6 mmol), silver nitrate (272 mg, 1.6 mmol), and triphenylchloromethane (374 mg, 1.2 mmol). After reacting at room temperature for 2 hours, methanol was added. The reaction solution was concentrated, and ethyl acetate was added. The solution was washed with saturated copper sulfate and saturated sodium chloride, respectively, dried over anhydrous sodium sulfate, and concentrated to give crude Compound 36-4;

Crude Compound 36-4 was added into THF (5 mL), followed by the addition of tetrabutylammonium fluoride hydrate (508 mg, 1.6 mmol) in tetrahydrofuran. The mixture was stirred for 1 hour, then additional tetrabutylammonium fluoride hydrate (508 mg, 1.6 mmol) in tetrahydrofuran was added, and the mixture continued to be stirred for 1 hour. Then water was added, and the mixture was extracted with ethyl acetate. The organic layer was concentrated and separated by silica gel column chromatography to obtain Compound 36-5 as a white solid (84 mg, 22% yield for three steps);

Compound 36-5 (70 mg, 0.14 mmol) was added to acetonitrile (2 mL), cooled to −5° C. in an ice salt bath, and triethylamine trihydrofluoride (35 mg, 0.21 mmol) and iodosuccinimide (36 mg, 0.15 mmol) were added. The reaction was carried out at the same temperature for 2 hours, then the mixture was warmed to room temperature, and reacted for 2 hours. A mixed solution of saturated sodium bicarbonate and saturated sodium thiosulfate was added. The mixture was extracted with ethyl acetate, and the organic layer was washed with saturated sodium chloride, dried over anhydrous sodium sulfate, and concentrated to obtain crude Compound 36-6;

Crude Compound 36-6 was added to dichloromethane (5 mL), followed by the successive addition of pyridine (114 mg, 1.4 mmol), isobutyric anhydride (162 mg, 1.0 mmol) and DMAP (5 mg). The reaction was carried out at room temperature for 2 hours. Methanol was added, then concentrated, and ethyl acetate was added. The resulting solution was washed with saturated copper sulfate solution and saturated sodium chloride solution, respectively, then concentrated, and separated by silica gel column chromatography (PE:EA=20: 1-10:1) to give Compound 36-7 as a light-yellow solid (28 mg, 20% yield).

Compound 36-7 (28 mg, 0.036 mmol) was added to DMF (2 mL), followed by the addition of 18-crown-6 (26 mg) and sodium isobutyrate (35 mg, 0.32 mmol). The reaction was carried out at 110° C. for 18 hours. Water was added, and the mixture was extracted with ethyl acetate. The organic layer was washed with saturated sodium chloride, and separated by silica gel column chromatography (PE:EA=20: 1-10:1) to obtain 20 mg Compound 36-8 as a light-yellow solid.

Compound 36-8 (100 mg, 0.14 mmol) was added to acetic acid (3 mL) and water (1 mL). The mixture was heated to 85° C., and after reacting for 10 mins, the raw material was disappeared. To the reaction solution saturated sodium bicarbonate solution was added, and extracted with ethyl acetate. The organic layer was concentrated, and separated by silica gel column chromatography (DCM:MeOH=100:1-50:1) to obtain 50 mg Compound A36 as a light-yellow solid. MS m/z=495.2[M+1]$^+$.

Preparation Example 51: Synthesis of Nucleoside Analogs

Compounds A5, A6, A8, A13, A14, A28, A30, A37, A54, A55, A57, A58, A63, A73, A78, A79, A80, A81, A86, A88, A89, A91, A95, A97, A99, A101, A105, A113, A114, A115, A116, A117, A118, A119, A120, A121, A122, A123, A125, A126, A127, A128, A129, A130, A132, A133, A134, A135, A136, A137, A139, A141, A142, A143, A145, A148, A149, A150, A152, A153, A154, A155, A156, A157, A158, A159, A160, A161, A162, A163, A165, A166, A167, A168, A169, A170, A172, A175, A176, A177, A179, A182, A183, A184, A185, A186, A187, A189, A190, A191, A192, A193, A194, A195, A197, A199, A200, A201, A202, A203, A204, A205, A206, A207, A208, A210, A211 were obtained according to the method of Preparation Examples 1-50, differing in using different raw material compounds.

Test Example 1: Study on the Inhibitory Effect of Compounds on the Replication of Novel Coronavirus Determining the inhibitory activity of compounds of the present invention on the replication of 2019 novel coronavirus (SARS-CoV-2): Vero E6 cells were purchased from ATCC, and SARS-CoV-2 virus was derived from Microbiological Culture Collection Center of National Virus Resource Center. Vero E6 cells were cultured overnight at a density of $5\times10^4$ cells/well in a 48-well cell culture plate. The cells were pretreated with different concentrations of the compound of the invention for 1 hour. Then, the virus was added at multiplicity of infection (MOI) of 0.05. One hour later, the mixture of virus and compound was removed, and cells were treated with fresh medium containing the compound of the invention. At 24 h p.i., cell supernatant was collected and lysed in lysis buffer. Virus copy number in cell supernatant was quantitatively determined by quantitative real-time RT-PCR (qRT-PCR).

The results showed that at the concentration of 10 μM or 5 μM, many compounds significantly inhibited the replication of SARS-CoV-2 compared with the control group, with the inhibition rate was >99N against novel coronavirus. The EC$_{50}$ values of some compounds were at a low micromolar level, and their antiviral activities were significantly better than that of the control compound, remdesivir.

The EC$_{50}$ values and the inhibition rates of some preferred compounds are listed in Table 1.

TABLE 1

The inhibitory activities on the replication of the 2019 novel coronavirus (SARS-CoV-2)

| Compound Number | Structure (free state) | Inhibition Rate (10 μM) | Inhibition Rate (5 μM) | EC$_{50}$ (μM) |
| --- | --- | --- | --- | --- |
| A1 | 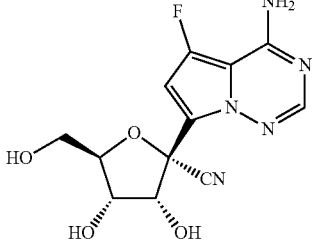 | 97% | 80% | / |

TABLE 1-continued

The inhibitory activities on the replication of the 2019 novel coronavirus (SARS-CoV-2)

| Compound Number | Structure (free state) | Inhibition Rate (10 μM) | Inhibition Rate (5 μM) | EC$_{50}$ (μM) |
| --- | --- | --- | --- | --- |
| A2 | | <50% | / | / |
| A3 | | <50% | / | / |
| A4 | | <50% | / | / |
| A9 | | / | 99% | 0.44 |
| A10 | | / | 99% | 0.43 |

TABLE 1-continued

The inhibitory activities on the replication of the 2019 novel coronavirus (SARS-CoV-2)

| Compound Number | Structure (free state) | Inhibition Rate (10 μM) | Inhibition Rate (5 μM) | EC$_{50}$ (μM) |
|---|---|---|---|---|
| A11 | | / | 99% | / |
| A12 | | / | 98% | / |
| A35 | | / | / | / |
| A124 | | 99% | 99% | 0.25 |
| A50 | | 99% | 99% | 0.23 |

TABLE 1-continued

The inhibitory activities on the replication of the 2019 novel coronavirus (SARS-CoV-2)

| Compound Number | Structure (free state) | Inhibition Rate (10 μM) | Inhibition Rate (5 μM) | EC$_{50}$ (μM) |
|---|---|---|---|---|
| A212 | | 99% | 99% | 0.11 |
| A52 | | / | 99% | / |
| A53 | | 65% | / | / |
| A144 | | / | 99% | 0.24 |
| A70 | | / | 99% | / |

TABLE 1-continued

The inhibitory activities on the replication of the 2019 novel coronavirus (SARS-CoV-2)

| Compound Number | Structure (free state) | Inhibition Rate (10 μM) | Inhibition Rate (5 μM) | $EC_{50}$ (μM) |
|---|---|---|---|---|
| A213 | | / | 99% | 0.10 |
| A72 | | / | 99% | |
| A164 | | / | 99% | 0.27 |
| A75 | | / | 99% | / |

TABLE 1-continued
The inhibitory activities on the replication of the 2019 novel coronavirus (SARS-CoV-2)
| Compound Number | Structure (free state) | Inhibition Rate (10 μM) | Inhibition Rate (5 μM) | $EC_{50}$ (μM) |
|---|---|---|---|---|
| A214 | 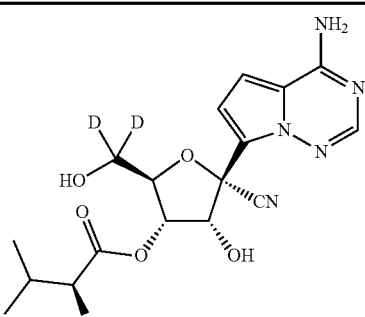 | / | 99% | 0.11 |
| A77 | 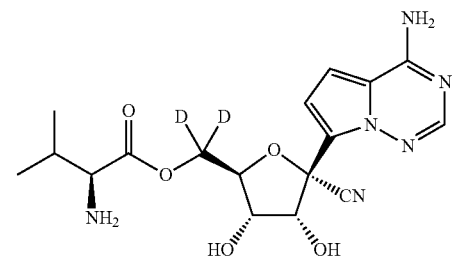 | / | 99% | / |
| A84 | 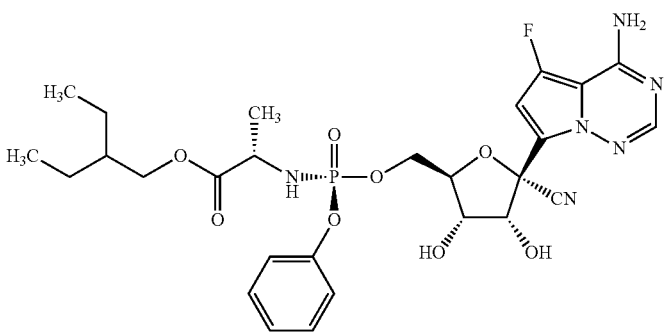 | 82% | / | / |
| A109 | 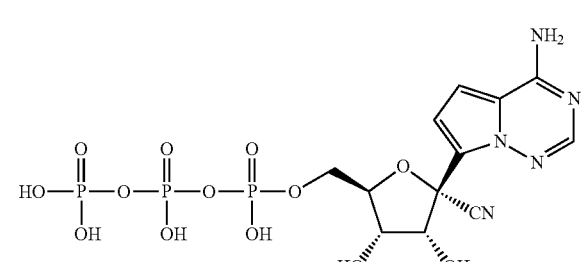 | 99% | 99% | 0.58 |
| A112 | 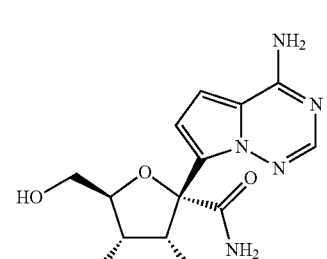 | <50% | / | / |

TABLE 1-continued

The inhibitory activities on the replication of the 2019 novel coronavirus (SARS-CoV-2)

| Compound Number | Structure (free state) | Inhibition Rate (10 μM) | Inhibition Rate (5 μM) | EC$_{50}$ (μM) |
| --- | --- | --- | --- | --- |
| A131 | | / | 99% | / |
| A151 | | / | 99% | 0.31 |
| A171 | | / | 99% | / |
| A188 | | / | 99% | / |

TABLE 1-continued

The inhibitory activities on the replication of the 2019 novel coronavirus (SARS-CoV-2)

| Compound Number | Structure (free state) | Inhibition Rate (10 μM) | Inhibition Rate (5 μM) | EC$_{50}$ (μM) |
|---|---|---|---|---|
| A180 | | / | 99% | / |
| A215 | | / | 99% | / |
| A181 | | / | 99% | / |
| A196 | | / | 99% | / |

TABLE 1-continued

The inhibitory activities on the replication of the 2019 novel coronavirus (SARS-CoV-2)

| Compound Number | Structure (free state) | Inhibition Rate (10 μM) | Inhibition Rate (5 μM) | $EC_{50}$ (μM) |
|---|---|---|---|---|
| A209 | (structure) | / | / | / |
| GS-441524 | (structure) | / | 99% | 0.48 |
| Remdesivir | (structure) | 99% | 65% | 2.0 |
| Favipiravir | (structure) | <20% | 0% | / |

Note:
"/" means undetermined.

Test Example 2: Determination of Half Toxic Concentration of Compounds

In this Example, half toxic concentration ($CC_{50}$) of the compounds of the present invention (each compound in Table 1) on Vero E6 cells was determined and analyzed using CCK8 assay kit.

The results showed that the test compounds had no cytotoxic effect on Vero E6 cells at the highest concentration (10 μM), which suggested that the $CC_{50}$ of the compounds of the present invention are much higher than 10 μM.

Test Example 3: Study of the Inhibitory Effect of Compounds on the RNA-Dependent RNA Polymerase (RdRp) of Novel Coronavirus According to the method reported in the literature (Virus Genes, 2015, 50:498-504), the inhibitory activity of the compound of the invention on RNA-dependent RNA polymerase (RdRp) of 2019 novel coronavirus (SARS-CoV-2) was determined using the fluorescence method: after the solution of the novel coronavirus RdRp, substrate, compound solution, buffer solution, etc were co-incubated for 1 hour, fluorescent DNA binding dye was added. 10 minutes later, data collection was carried out and the inhibitory activities of the compounds on RdRp were determined.

The results showed that some compounds had significant inhibitory activities on RdRp, as shown in Table 2.

TABLE 2

Inhibitory activity of compounds on RdRp of 2019 novel coronavirus

| Compound Number | Structure (free state) | IC$_{50}$ (μM) |
|---|---|---|
| A102 | | B |
| A106 | | A |
| A107 | | A |
| A108 | | / |
| A198 | | A |

A: <1 μM;
B: 1 μM~10 μM;
C: >1 μM;
"/" means undetermined.

Test Example 4. Study of the Inhibitory Effect of Compounds on the Replication of Other Viruses The inhibitory effects of compounds on the replication of respiratory syncytial virus (RSV), human coronavirus OC43, influenza A virus, Zika virus (Zika) were tested using cytopathic effect (CPE) assay.

Cytopathic Effect (CPE) Assay

Experimental cells were inoculated in 96-well cell culture plate at a certain cell density, and cultured in an incubator (5% $CO_2$, 37° C.) overnight. Compounds and viruses were added on the second day. Cells were cultured in an incubator for 3-7 days under a condition of 5% $CO_2$, and 33° C. or 37° C., which varied depending on the virus tested, until 80-95% cytopathic effect was observed in the virus infection control well (without compound). Then cell viability of each well was detected using Cell Titer-Glo or CCK-8. If the cell viability of the well containing the compound was higher than that of the virus infection control well, i.e. the CPE was reduced, indicating that the compound had inhibitory effect against the tested virus. The cytotoxicity test method was the same as the corresponding antiviral test method without virus infection.

The antiviral activity and cytotoxicity of the compounds are respectively indicated by the inhibition rate (%) of compounds on virus-induced cellular viral effects and cell viability (%). Calculating formulas are as follows:

Inhibition rate (%)=(reading value of test well—average value of virus control)/(average value of cell control—average value of virus control)×100;

Cell viability (%)=(reading value of test well—average value of medium control)/(average value of cell control—average value of medium control)×100;

$EC_{50}$ and $CC_{50}$ value are calculated by Prism software, and the inhibition curve fitting method is "log (inhibitor) vs. response—Variable slope".

Dengue Virus Plaque Reduction Test

Vero cells were inoculated in 6-well cell culture plate at a density of 600,000 cells per well, and cultured in an incubator (5% $CO_2$, 37° C.) overnight. Compounds and viruses (40-50 PFU/well) were added on the second day. Cells were incubated in an incubator under a condition of 5% $CO_2$ and 37° C. for 2 h, then the supernatant was sucked off, and low melting point agarose medium containing corresponding concentration of compounds was added. Cells were cultured in an incubator for 6-7 days under a condition of 5% $CO_2$, and 33° C. or 37° C. until obvious virus plaque could be observed microscopically in the virus infection control well (without compound). Cells were fixed with 4% paraformaldehyde and stained with crystal violet. The number of plaques in each well was calculated.

Cytotoxicity experiment was carried out in parallel with antiviral experiment. Vero cells were inoculated in 96-well cell culture plate at a density of 20,000 cells per well, and cultured in an incubator (5% $CO_2$, 37° C.) overnight. The compounds (1-5 concentration points, single point) were added the next day. Cells were cultured in an incubator for 6-7 days under a condition of 5% $CO_2$, and 33° C. or 37° C. Then cell viability of each well was detected using CCK-8.

The antiviral activity ($EC_{50}$ or inhibition rate) and cytotoxicity ($CC_{50}$) of compounds were calculated by the same method as described above.

Anti-Porcine Epidemic Diarrhea Virus (PEDV) Activity Test

Vero cells were digested and passaged. The cell density was adjusted to $1\times10^5$/mL using cell growth media. The cells were inoculated in 96-well plate, 100 μL/well, and cultured in an incubator (37° C., 5% $CO_2$) for 24 hours. The 96-well plate was taken out; the culture medium in the well was discarded, and washed with 1×PBS for three times. After spin-drying, the mixture of compound (10 concentration points) and virus (0.01 MOI per well) was added to each well with 8 duplicates for each concentration, and cultured in an incubator at 37° C. and 5% $CO_2$. The virus control and cell control were set at the same time. After 36 h, cell samples were collected, and the changes of virus content in different treatment groups were determined using fluorescence quantitative PCR. The $EC_{50}$ of the compound was calculated.

The results showed that many compounds have significant antiviral activities against respiratory syncytial virus (RSV), human coronavirus OC43 (HCoV OC43), porcine epidemic diarrhea virus (PEDV), Zika virus (Zika) and dengue virus (DENV). Compared with GS-441524, the deuterated derivatives have stronger antiviral effect. The $EC_{50}$ values of some preferred compounds were listed in Table 3 and Table 4.

TABLE 3

Inhibitory activity on the replication of respiratory syncytial virus (RSV), human coronavirus OC43 (HCoV OC43)

| Compound Number | Structure (free state) | RSV (HEp-2) | | HCoV OC43 (Huh7) | |
| --- | --- | --- | --- | --- | --- |
| | | $EC_{50}$ (μM) | $CC_{50}$ (μM) | $EC_{50}$ (μM) | $CC_{50}$ (μM) |
| A1 | 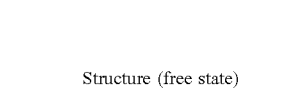 | / | / | / | / |

TABLE 3-continued

Inhibitory activity on the replication of respiratory syncytial virus (RSV), human coronavirus OC43 (HCoV OC43)

| Compound Number | Structure (free state) | RSV (HEp-2) EC$_{50}$ (μM) | CC$_{50}$ (μM) | HCoV OC43 (Huh7) EC$_{50}$ (μM) | CC$_{50}$ (μM) |
|---|---|---|---|---|---|
| A9 | | 0.56 | >10 | 1.77 | >10 |
| A10 | | 0.63 | >10 | 1.98 | >10 |
| A11 | | 0.66 | >10 | 1.99 | >10 |
| A144 | | 0.47 | >10 | 1.88 | >10 |
| A70 | | 0.58 | >10 | 1.90 | >10 |

TABLE 3-continued

Inhibitory activity on the replication of respiratory syncytial virus (RSV), human coronavirus OC43 (HCoV OC43)

| Compound Number | Structure (free state) | RSV (HEp-2) | | HCoV OC43 (Huh7) | |
|---|---|---|---|---|---|
| | | EC$_{50}$ (μM) | CC$_{50}$ (μM) | EC$_{50}$ (μM) | CC$_{50}$ (μM) |
| A213 | | 0.76 | >10 | 1.97 | >10 |
| A72 | | 0.77 | >10 | / | / |
| A164 | | / | / | / | / |
| A75 | | 0.49 | >10 | / | / |
| A214 | | / | / | / | / |

TABLE 3-continued

Inhibitory activity on the replication of respiratory syncytial virus (RSV), human coronavirus OC43 (HCoV OC43)

| Compound Number | Structure (free state) | RSV (HEp-2) | | HCoV OC43 (Huh7) | |
|---|---|---|---|---|---|
| | | EC$_{50}$ (μM) | CC$_{50}$ (μM) | EC$_{50}$ (μM) | CC$_{50}$ (μM) |
| A77 | | / | / | / | / |
| A84 | | / | / | / | / |
| A131 | | / | / | / | / |
| A151 | | 0.63 | >10 | 1.99 | / |

TABLE 3-continued
Inhibitory activity on the replication of respiratory syncytial virus (RSV), human coronavirus OC43 (HCoV OC43)
| Compound Number | Structure (free state) | RSV (HEp-2) | | HCoV OC43 (Huh7) | |
|---|---|---|---|---|---|
| | | $EC_{50}$ (μM) | $CC_{50}$ (μM) | $EC_{50}$ (μM) | $CC_{50}$ (μM) |
| A173 | 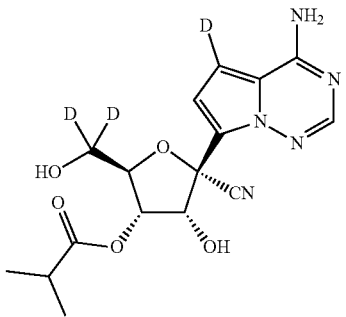 [SMILES: [2H]c1cc([C@]2(C#N)O[C@H](C([2H])([2H])O)[C@@H](OC(=O)C(C)C)[C@H]2O)n2ncnc(N)c12] | 0.46 | >10 | / | / |
| A180 | 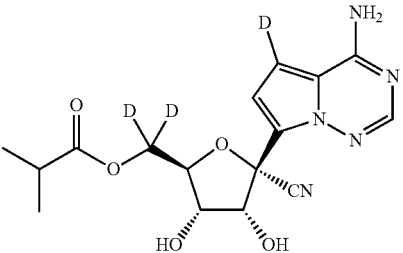 [SMILES: [2H]c1cc([C@]2(C#N)O[C@H](C([2H])([2H])OC(=O)C(C)C)[C@@H](O)[C@H]2O)n2ncnc(N)c12] | / | / | / | / |
| GS-441524 | 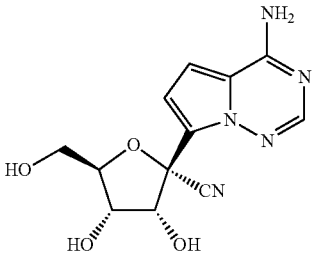 [SMILES: N#C[C@@]1(c2ccc3c(N)ncnn23)O[C@H](CO)[C@@H](O)[C@H]1O] | 0.73 | >10 | 1.88 | >10 |
| Remdesivir | 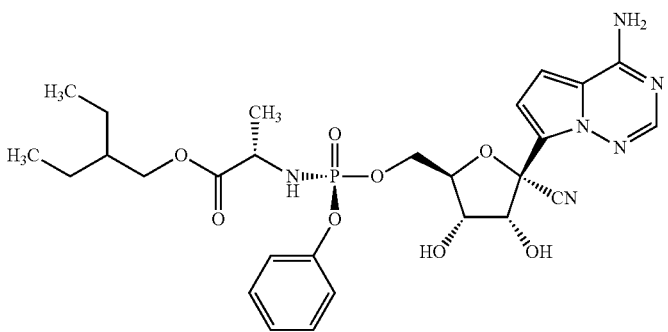 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1] | / | / | 0.021 | 25.7 |
Note:
"/" means undetermined.

TABLE 4

Inhibitory activity on the replication of porcine epidemic diarrhea virus (PEDV),
Zika virus (Zika), dengue fever virus (DENV)

| Compound Number | Structure | PEDV (Vero) EC$_{50}$ (μM) | Zika (Huh7) EC$_{50}$ (μM) | DENV (Vero) 5 μM |
|---|---|---|---|---|
| A9 | 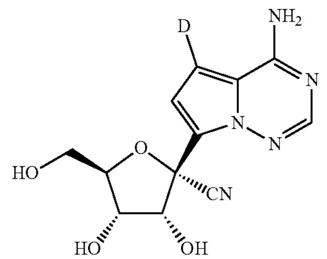 [SMILES: [2H]c1cc([C@]2(C#N)O[C@H](CO)[C@@H](O)[C@H]2O)n2ncnc(N)c12] | 0.016 | 12 | 100% |
| A10 | 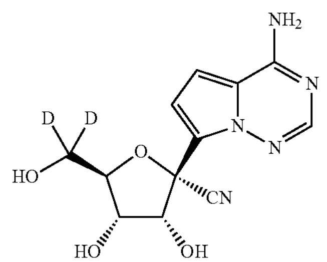 [SMILES: [2H]C([2H])(O)[C@H]1O[C@@](C#N)(c2ccc3c(N)ncnn23)[C@H](O)[C@@H]1O] | 0.006 | / | / |
| A11 | 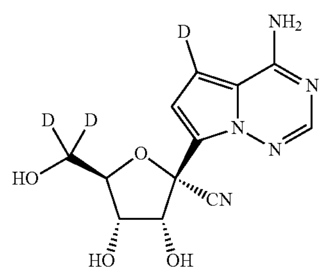 [SMILES: [2H]c1cc([C@]2(C#N)O[C@H](C([2H])([2H])O)[C@@H](O)[C@H]2O)n2ncnc(N)c12] | 0.005 | / | / |
| A50 | 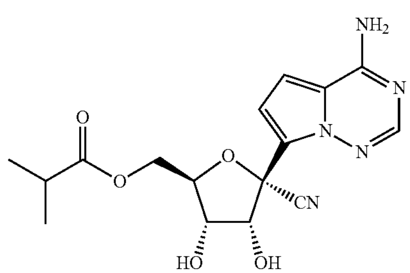 [SMILES: CC(C)C(=O)OC[C@H]1O[C@@](C#N)(c2ccc3c(N)ncnn23)[C@H](O)[C@@H]1O] | 0.002 | / | / |
| A144 | 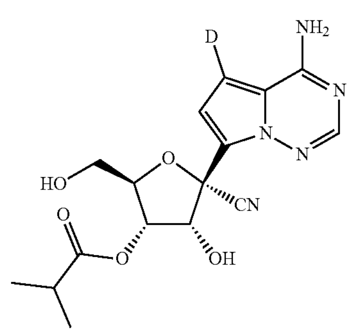 [SMILES: [2H]c1cc([C@]2(C#N)O[C@H](CO)[C@@H](OC(=O)C(C)C)[C@H]2O)n2ncnc(N)c12] | <0.1 | / | / |

TABLE 4-continued

Inhibitory activity on the replication of porcine epidemic diarrhea virus (PEDV), Zika virus (Zika), dengue fever virus (DENV)

| Compound Number | Structure | PEDV (Vero) EC$_{50}$ (μM) | Zika (Huh7) EC$_{50}$ (μM) | DENV (Vero) 5 μM |
|---|---|---|---|---|
| A70 | 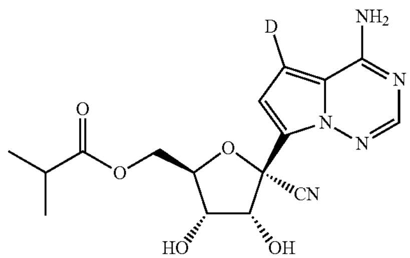 [SMILES: [2H]c1cc([C@]2(C#N)O[C@H](COC(=O)C(C)C)[C@@H](O)[C@H]2O)n2ncnc(N)c12] | 0.002 | ~27%, 5 μM | / |
| A164 | 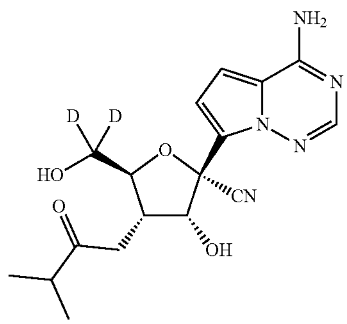 [SMILES: [2H]C([2H])(O)[C@H]1O[C@@](C#N)(c2ccc3c(N)ncnn23)[C@H](O)[C@@H]1CC(=O)C(C)C] | / | / | / |
| A75 | 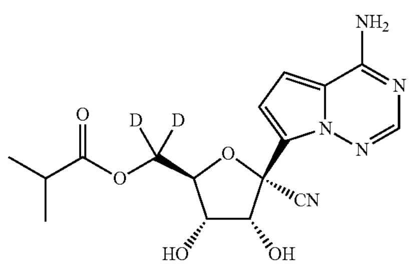 [SMILES: [2H]C([2H])(OC(=O)C(C)C)[C@H]1O[C@@](C#N)(c2ccc3c(N)ncnn23)[C@H](O)[C@@H]1O] | / | / | / |
| A131 | 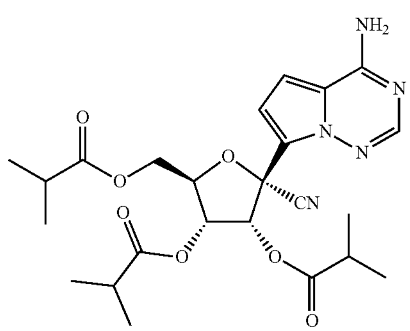 [SMILES: CC(C)C(=O)OC[C@H]1O[C@@](C#N)(c2ccc3c(N)ncnn23)[C@H](OC(=O)C(C)C)[C@@H]1OC(=O)C(C)C] | <0.1 | / | / |
| A151 | 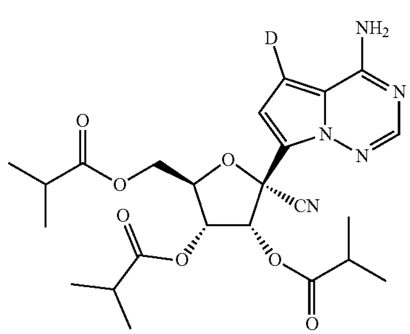 [SMILES: [2H]c1cc([C@]2(C#N)O[C@H](COC(=O)C(C)C)[C@@H](OC(=O)C(C)C)[C@H]2OC(=O)C(C)C)n2ncnc(N)c12] | <0.1 | / | / |

TABLE 4-continued

Inhibitory activity on the replication of porcine epidemic diarrhea virus (PEDV), Zika virus (Zika), dengue fever virus (DENV)

| Compound Number | Structure | PEDV (Vero) EC$_{50}$ (μM) | Zika (Huh7) EC$_{50}$ (μM) | DENV (Vero) 5 μM |
|---|---|---|---|---|
| A180 | 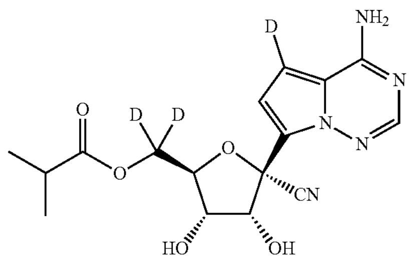 [SMILES: [2H]c1cc([C@]2(C#N)O[C@H](C([2H])([2H])OC(=O)C(C)C)[C@@H](O)[C@H]2O)n2ncnc(N)c12] | / | / | / |
| A216 | 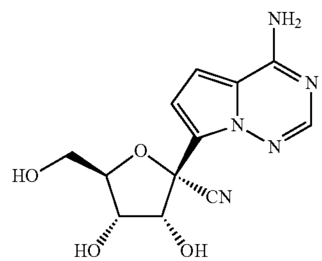 [SMILES: N#C[C@@]1(c2ccc3c(N)ncnn23)O[C@H](CO)[C@@H](O)[C@H]1O] | 1.92 | / | 24% |
| A28 | 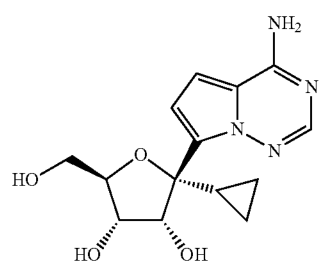 [SMILES: Nc1ncnn2c([C@]3(C4CC4)O[C@H](CO)[C@@H](O)[C@H]3O)ccc12] | 1.10 | / | 6% |
| A221 | 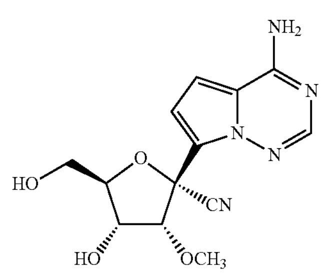 [SMILES: CO[C@@H]1[C@H](O)[C@@H](CO)O[C@@]1(C#N)c1ccc2c(N)ncnn12] | 1.35 | / | 51% |
| GS-441524 | 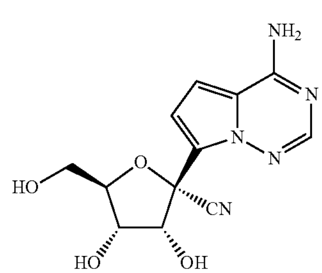 [SMILES: N#C[C@@]1(c2ccc3c(N)ncnn23)O[C@H](CO)[C@@H](O)[C@H]1O] | 0.026 | 15 | / |

TABLE 4-continued

Inhibitory activity on the replication of porcine epidemic diarrhea virus (PEDV),
Zika virus (Zika), dengue fever virus (DENV)

| Compound Number | Structure | PEDV (Vero) EC$_{50}$ (μM) | Zika (Huh7) EC$_{50}$ (μM) | DENV (Vero) 5 μM |
|---|---|---|---|---|
| Remdesivir | 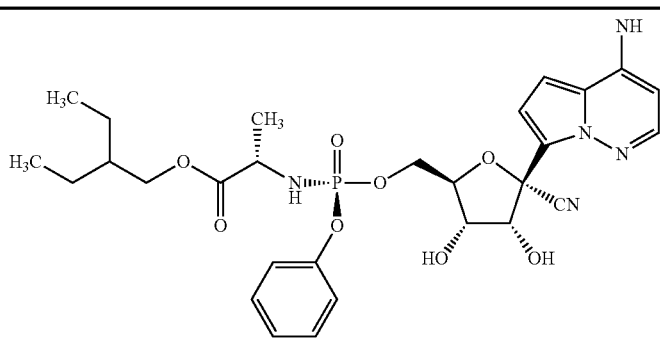 | / | / | 100% |
| Ribavirin | | / | / | 17.4 |

Note:
"/" means undetermined.

Test Example 5: Pharmacokinetic Evaluation in Mice

Experimental Method 15 male CD-1 mice were randomly divided into 5 groups, with 3 mice for each group. Before the experiment, they were fasted for 12 hours and allowed to drink water. 2 hours after dosing, the animals were fed. Among them, 4 groups were intragastrically administered with 50 mg/kg of GS-441524, A9, A10 and A11, respectively, and 30 μL of blood sample was collected from femoral vein into heparin anticoagulant tube at 0.25, 0.5, 1, 2, 4, 8 and 24 hours post administration. 20 μL whole blood was immediately and accurately sucked into a centrifuge tube containing 2 μL PhosSTOP and 7 μL DTNB (0.5M), then mixed evenly, and centrifuged at 4° C. 10 μL plasma was taken into a centrifuge tube containing 100 μL precipitant (methanol:acetonitrile, 1:1, v/v), mixed evenly, centrifuged at 4° C., then placed in dry ice for temporary storage and transportation, and frozen at −80° C. to be measured. The remaining group was administered with GS-441524 (25 mg/kg) intravenously, and blood sample was collected from femoral vein at 5 min, 0.25, 0.5, 1, 2, 4, 8, 24 h post administration, and placed in heparin anticoagulant tube. The processing method was the same as described above.

The concentrations of GS-441524, A9, A10 and A11 in plasma were determined using LC-MS-MS method. 20 μL supernatant was mixed with 20 μL deionized water, and then the sample was injected for analysis. Samples were separated by Waters HSS T3 (2.1*50 mm, 1.8 μm) chromatographic column, and then detected by multi-reaction monitoring mode under positive ion condition using electrospray ionization source. The linear range of samples was 10-30000 ng/ml.

TABLE 5

Pharmacokinetic parameters of Compounds
GS-441524, A9, A10 and A11 in mice

| | Compounds | | | | |
|---|---|---|---|---|---|
| PK parameters | GS-441524 (p.o.) | GS-441524 (i.v.) | A9 (p.o.) | A10 (p.o.) | A11 (p.o.) |
| T$_{max}$ (h) | 0.8 | — | 1.2 | 0.8 | 0.7 |
| C$_{max}$ (ng/mL) | 1826 | — | 3227 | 1764 | 2117 |
| T$_{1/2}$ (h) | 1.2 | 1.0 | 1.0 | 1.3 | 1.9 |
| AUC(0-t) (h * ng/mL) | 4556 | 14513 | 5982 | 4551 | 5684 |
| AUC(0-∞) (h * ng/mL) | 4616 | 14581 | 6013 | 4619 | 5754 |
| F % | 15.7% | | | | |

Test Example 6: Pharmacokinetic Evaluation in Rats

Experimental Method 18 male SD rats were randomly divided into 6 groups, with 3 rats for each group. Before the experiment, they were fasted for 12 hours (not for the intravenous experiment group) and allowed to drink water. 4 hours after dosing, the animals were fed. Among them, 3 groups were intragastrically administered with 10 mg/kg of A9, A146 and A151, respectively, and the remaining 3 groups were intravenously administered with 2 mg/kg of A9, A146 and A151, respectively. The vehicle for administration was DMSO/EtOH/PEG300/0.9% NaCl (5/5/40/50, v/v/v/v).

5 min (intravenous only), 0.25, 0.5, 1.0, 2.0, 4.0, 6.0, 8.0 and 24 h post administration, 0.2 mL of blood sample was collected from jugular vein into EDTA-K2 tubes, and centrifuged at 11000 rpm for 5 min. The plasma was separated, and frozen in a refrigerator at −70° C. for testing. The operation was conducted in an ice water bath. The concentration of A9 in plasma was determined by LC-MS-MS, and the pharmacokinetic parameters were calculated.

TABLE 6

Pharmacokinetic parameters of Compounds A9, A146, and A151 in rats

| PK parameters | Compounds | | | | | |
|---|---|---|---|---|---|---|
| | A9 (po-10 mpk) | A9 (iv-2 mpk) | A146 (po-10 mpk) | A146 (iv-2 mpk) | A151 (po-10 mpk) | A151 (iv-2 mpk) |
| $T_{max}$ (h) | 3.0 | 0.08 | 0.25 | 0.08 | 0.5 | 0.1 |
| $C_{max}$ (ng/mL) | 221 | 1260 | 576 | 770 | 498 | 513 |
| $T_{1/2}$ (h) | 3.4 | 2.3 | 2.5 | 1.4 | 2.6 | 1.5 |
| AUC(0-t) (h * ng/mL) | 1336 | 1257 | 1888 | 779 | 1886 | 665 |
| AUC(0-∞) (h * ng/mL) | 1726 | 1283 | 1998 | 821 | 1998 | 700 |
| F % | 21.3% | | 48.5% | | 56.7% | |

Test Example 7: Tissue Distribution Test

Experimental Method:

16 male CD-1 mice were randomly divided into 4 groups, with 4 mice for each group. Before the experiment, they were fasted for 12 hours and allowed to drink water. 2 hours after dosing, the animals were fed. The 4 groups were given 200 mg/kg A151 (dissolved in DMSO-enthanol-PEG300-saline, volume ratio: 5/5/40/50) by intragastric administration. At 1 h, 2 h, 4 h and 8 h after administration, the mice were anesthetized; blood sample was collected by heart puncture, and tissues of liver, kidney, heart and lung were harvested. The distribution profile of A9 in the tissues was determined by HPLC-MS/MS.

TABLE 7

Tissue distribution of metabolite A9 after oral administration of A151 (200 mg/kg) in mice

| | Organs | | | | |
|---|---|---|---|---|---|
| Time | Whole blood nM | Liver nMol/kg | Kidney nMol/kg | Lung nMol/kg | Heart nMol/kg |
| 1 h | 30820 | 30853 | 47166 | 31441 | 25648 |
| 2 h | 18261 | 14281 | 26719 | 12830 | 12927 |
| 4 h | 8754 | 6289 | 11059 | 5705 | 6256 |
| 8 h | 549 | 639 | 1220 | 1032 | 749 |

Test Example 8: In Vivo Efficacy Test Against SARS-CoV-2

Experiment 8.1

Figure 2:
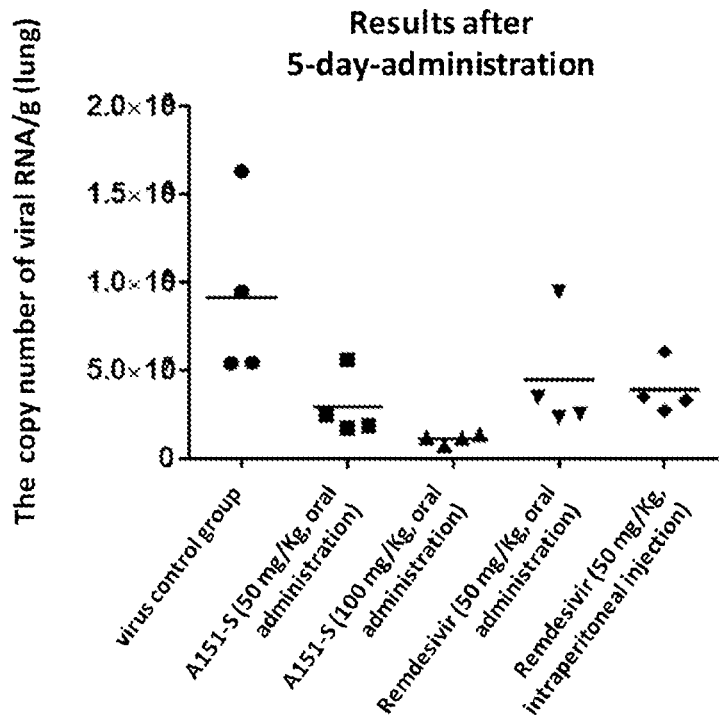
FIG. 2 shows the status of viral RNA replication after administration for 5 days in the examples of the present invention, wherein virus control group, 50 mg/kg oral A151-S group, 100 mg/kg oral A151-S group, 50 mg/kg oral Remdesivir group, and 50 mg/kg intraperitoneal injection Remdesivir group are set.

8-week-old Balb/c mice were divided into 5 groups: virus control group (vehicle: 40% PEG400+10% HS 15+50% ultrapure water), A151 hydrobromide salt (A151-S) oral group (50 mg/kg, 100 mg/kg), Remdesivir oral group (50 mg/kg), Remdesivir intraperitoneal group (50 mg/kg). Animals in each group were transduced with adenovirus carrying human ACE2 gene, and infected with novel coronavirus 5 days after transduction. At 1 hour post infection, the vehicle, A151-S and the control drug Remdesivir were administered once daily by gavage or intraperitoneal injection, respectively. The mice were sacrificed on the 2nd and 5th day post infection, and the lung tissues of mice were taken to measure the copy number of viral RNA in the lung tissues of mice. The viral RNA copies after administration for 2 days and 5 days were shown in FIG. 1 and FIG. 2, respectively.

The results showed that oral administration of compound A151-S at 50 mg/kg and 100 mg/kg could effectively reduce the amount of viral RNA in mouse lung tissue in a certain dose-dependent manner. After administration for 2 days at a dose of 50 mg/kg, the antiviral effect of A151-S oral administration was better than that of Remdesivir oral administration group, and after administration for 5 days, the antiviral effect of A151-S oral administration was better than that of Remdesivir intraperitoneal injection group.

Experiment 8.2

Figure 3:
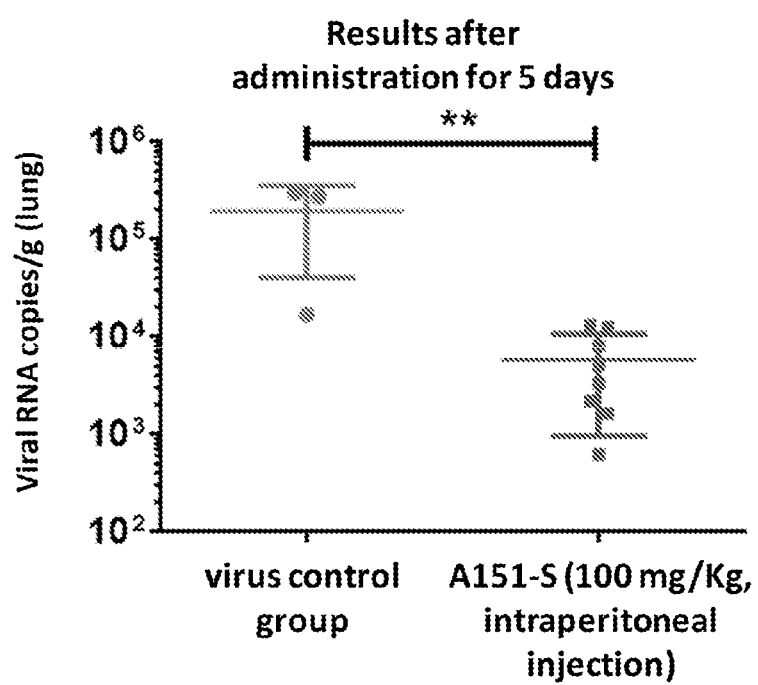
FIG. 3 shows the status of viral RNA replication after administration for 5 days in the examples of the present invention, wherein virus control group and 100 mg/kg intraperitoneal injection A151-S group are set.

8-week-old Balb/c mice were divided into two groups: virus control group (vehicle: 5% DMSO+5% SolutolHS15+90% Saline) and A151-S intraperitoneal injection group (100 mg/kg). Animals of the two groups were transduced with adenovirus carrying human ACE2 gene. A151-S was given one day before the novel coronavirus infection and administered once a day by intraperitoneal injection from the day of infection to the 4th day post infection. The control group was treated in the same way. The mice were killed at the 4th day post infection, and the lung tissues of mice were taken to detect the copy number of viral RNA in the lung tissues of mice. The results were shown in FIG. 3.

The results showed that Compound A151-S given by intraperitoneal injection can significantly reduce the amount of viral RNA in mouse lung tissue, and the viral load was decreased by more than 30 times compared with the control group.

DISCUSSION

The compound of formula (I) of the invention has remarkable anti-SARS-CoV-2 activity. In virus-infected Vero E6 cells, representative Compounds A9 (Example 6), A10 (Example 7), A124 (Example 11), A50 (Example 12), A212 (Example 13), A144 (Example 16), A213 (Example 18), A164 (Example 20), A214 (Example 22), A151 (Example 36) can significantly inhibit the replication of virus. $EC_{50}$ thereof are 0.44 μM, 0.43 μM, 0.25 μM, 0.23 μM, 0.11 μM, 0.24 μM, 0.10 μM, 0.27 μM, 0.11 μM and 0.31 μM, respectively, which are significantly superior to the control compound Remdesivir ($EC_{50}$=2.0 μM). In addition, A11, A12, A52, A70, A72, A75, A77, A131, A171, A180, A181, A188, A196, A215 and the like can significantly inhibit the replication of virus at the concentration of 5 μM, with an inhibition rate of over 98%, which are significantly higher than that (65%) of Remdesivir at the same concentration.

A102, A106, A107 and A198 can significantly inhibit the activity of RdRp of novel coronavirus, which indicates that these compounds exert their antiviral effect by targeting RdRp.

The compounds of formula (I) of the present invention can also efficiently inhibit the replication of other viruses including respiratory syncytial virus (RSV), human coronavirus OC43 (HCoV OC43), porcine epidemic diarrhea virus (PEDV), Zika virus (Zika), dengue fever virus (DENV). It is worth to be noted that the antiviral effect of deuterated compounds is more obvious.

PK test in mice showed that after oral administration of the deuterated compounds A9 and A11, their plasma exposure was higher than that of GS-441524, and were 1.3 times and 1.2 times of that of GS-441524, respectively; The oral bioavailability of A9 in rats was 21.3%, and the oral bioavailabilities of A146 and A151 were 48.5% and 56.7%, respectively, which were significantly higher than that of A9.

Tissue distribution test in mice showed that after oral administration of A151 for 1 hour, the concentration of metabolite A9 in liver, kidney, lung and heart was the highest, and A9 was evenly distributed, without accumulation in liver or kidney.

A151 hydrobromide salt (A151-S) can reduce the viral load in mouse lungs in a dose-dependent manner administered orally once a day in a mouse model transduced with adenovirus expressing the novel coronavirus receptor human ACE2, and the anti-Novel Coronavirus effect of A151-S is better than that of Remdesivir at the same dose (50 mg/Kg). The above data show that A151-S has significant anti-SARS-CoV-2 effect and has an advantage for oral use. Based on the above data, it can be suggested that the compounds of the present invention have a good application prospect as antiviral agents, especially agents against the Novel Coronavirus (SARS-CoV-2).

All documents mentioned in the present invention are cited as references in this application, just as each document is individually cited as a reference. In addition, it should be understood that, after reading the above teaching content of the present invention, those skilled in the art can make various changes or modifications to the present invention, and these equivalent forms also fall within the scope defined by the appended claims of the present application.

The invention claimed is:

1. A compound of formula (I), or a pharmaceutically acceptable salt thereof or a crystalline hydrate thereof or a solvate thereof:

(I)

wherein, $R_1$ is cyano;

$R_2$ is $OR_3$;

one of $R_3$ in formula (I), the $R_3$ in the definition of $R_2$, and $R_5$ is selected from the group consisting of —C(O)—$C_{3-6}$cycloalkyl, $C_{1-20}$alkanoyl, and amino$C_{1-20}$alkanoyl; and the rest of the $R_3$ in formula (I), the $R_3$ in the definition of $R_2$, and $R_5$ are each independently selected from the group consisting of hydrogen, —C(O)—$C_{3-6}$cycloalkyl, $C_{1-20}$alkanoyl, and amino$C_{1-20}$alkanoyl;

$R_4$ is hydrogen, deuterium, and halogen;

$R_6$ is amino;

$R_7$ is hydrogen;

$R_8$ is selected from the group consisting of hydrogen, deuterium, and halogen; and X is —$CH_2$—, or —$CD_2$—.

2. The compound of formula (I) of claim 1, or the pharmaceutically acceptable salt thereof or the crystalline hydrate thereof or the solvate thereof, wherein, the $R_3$ in formula (I) is selected from the group consisting of —C(O)—$C_{3-6}$cycloalkyl, $C_{1-20}$alkanoyl, and amino$C_{1-20}$alkanoyl;

the $R_3$ in the definition of $R_2$ is selected from the group consisting of hydrogen, —C(O)—$C_{3-6}$cycloalkyl, $C_{1-20}$alkanoyl, and amino$C_{1-20}$alkanoyl; and $R_5$ is selected from the group consisting of hydrogen, —C(O)—$C_{3-6}$cycloalkyl, $C_{1-20}$alkanoyl, and amino$C_{1-20}$alkanoyl.

3. A method for (a) inhibiting viral replication; and/or (b) treating, preventing, and/or alleviating a disease associated with a viral infection or a related disease caused by the virus, the method comprising administrating to a subject in need thereof a safe and effective amount of an active ingredient or a formulation containing an active ingredient, wherein the active ingredient is the compound of formula (I) according to claim 1 or the pharmaceutically acceptable salt thereof or the crystalline hydrate thereof or the solvate thereof.

4. The method of claim 3, wherein the virus is coronavirus, influenza virus, respiratory syncytial virus, flaviviridae virus, filoviridae virus or porcine epidemic diarrhea virus (PEDV).

5. The method of claim 3, wherein the virus is selected from the group consisting of:
(1) coronavirus infecting human: severe acute respiratory syndrome coronavirus (SARS-COV), 2019 novel coronavirus (2019-nCOV or SARS-COV-2), Middle East respiratory syndrome coronavirus (MERS-COV);
(2) coronavirus causing the common cold: the coronavirus causing the common cold is selected from the group consisting of: Human coronavirus OC43, Human coronvirus 229E, Human coronvirus NL63, and Human coronvirus HKUL;
(3) human respiratory syncytial virus (RSV);
(4) human influenza virus: influenza A virus, influenza B virus and influenza C virus;
(5) flaviviridae virus: hepatitis C virus (HCV), dengue virus (DENV), Zika virus (Zika);
(6) filoviridae virus: Marburg virus (MBV) and Ebola virus (EBV); and
(7) coronavirus infecting other mammals: porcine epidemic diarrhea virus (PEDV).

6. The method of claim 3, wherein the related disease caused by the virus is selected from the group consisting of
(D1) common cold, high-risk symptom infection, respiratory tract infection, pneumonia and the complications thereof caused by human coronavirus infection;
(D2) common cold, high-risk symptom infection, respiratory tract infection, pneumonia and the complications thereof caused by human respiratory syncytial virus (RSV) infection;
(D3) common cold, high-risk symptom infection, respiratory tract infection, pneumonia and the complications thereof caused by human influenza virus infection;
(D4) chronic hepatitis C and the complications thereof caused by hepatitis C virus (HCV);
(D5) dengue fever and the complications thereof caused by dengue virus (DENV);
(D6) infection and the complications thereof caused by Zika virus (Zika);
(D7) hemorrhagic fever and the complications thereof caused by Marburg virus (MBV) and Ebola virus (EBV);
(D8) novel coronavirus pneumonia (Corona Virus Disease 2019, COVID-19) caused by SARS-COV-2 (COVID-19);

(D9) Porcine epidemic diarrhea caused by porcine epidemic diarrhea virus (PEDV); and
(D10) any combination of the above diseases.

7. The method of claim 3, wherein
the $R_3$ in formula (I) is selected from the group consisting of —C(O)—$C_{3-6}$cycloalkyl, $C_{1-20}$alkanoyl, and amino$C_{1-20}$alkanoyl;
the $R_3$ in the definition of $R_2$ is selected from the group consisting of hydrogen, —C(O)—$C_{3-6}$cycloalkyl, $C_{1-20}$alkanoyl, and amino$C_{1-20}$alkanoyl; and
$R_5$ is selected from the group consisting of hydrogen, —C(O)—$C_{3-6}$cycloalkyl, $C_{1-20}$alkanoyl, and amino$C_{1-20}$alkanoyl.

8. A pharmaceutical composition comprising
(a) the compound of formula (I) according to claim 1, or the pharmaceutically acceptable salt thereof or the crystalline hydrate thereof or the solvate thereof;
and (b) one or more pharmaceutically acceptable carriers.

9. The pharmaceutical composition of claim 8, wherein
the $R_3$ in formula (i) is selected from the group consisting of —C(O)—$C_{3-6}$cycloalkyl, $C_{1-20}$alkanoyl, and amino$C_{1-20}$alkanoyl;
the $R_3$ in the definition of $R_2$ is selected from the group consisting of hydrogen, —C(O)—$C_{3-6}$cycloalkyl, $C_{1-20}$alkanoyl, and amino$C_{1-20}$alkanoyl; and
$R_5$ is selected from the group consisting of hydrogen, —C(O)—$C_{3-6}$cycloalkyl, $C_{1-20}$alkanoyl, and amino$C_{1-20}$alkanoyl.

10. The compound of formula (I) of claim 1, or the pharmaceutically acceptable salt thereof or the crystalline hydrate thereof or the solvate thereof, wherein
one of the $R_3$ in formula (I), the $R_3$ in the definition of $R_2$, and $R_5$ is —C(O)—$C_{3-6}$cycloalkyl, or $C_{3-20}$alkanoyl; and
the rest of the $R_3$ in formula (I), the $R_3$ in the definition of $R_2$, and $R_5$ are each independently selected from the group consisting of hydrogen, —C(O)—$C_{3-6}$cycloalkyl, $C_{1-20}$alkanoyl, and amino$C_{1-20}$alkanoyl.

11. The compound of formula (I) of claim 1, or the pharmaceutically acceptable salt thereof or the crystalline hydrate thereof or the solvate thereof, wherein
the $R_3$ in formula (I) is —C(O)—$C_{3-6}$cycloalkyl, or $C_{3-20}$alkanoyl.

12. The compound of formula (I) of claim 1, or the pharmaceutically acceptable salt thereof or the crystalline hydrate thereof or the solvate thereof, wherein
one of the $R_3$ in formula (I), the $R_3$ in the definition of $R_2$, and $R_5$ is selected from the group consisting of formyl, acetyl, propionyl, butyryl, isobutyryl, valeroyl, pivaloyl, hexanoyl, cyclopropanecarbonyl, α-aminoisovaleryl, 2-ethylbutanoyl, and 3,3-dimethylbutanoyl; and
the rest of the $R_3$ in formula (I), the $R_3$ in the definition of $R_2$, and $R_5$ are selected from the group consisting of formyl, acetyl, propionyl, butyryl, isobutyryl, valeroyl, pivaloyl, hexanoyl, cyclopropanecarbonyl, α-aminoisovaleryl, 2-ethylbutanoyl, and 3,3-dimethylbutanoyl.

13. The compound of formula (I) of claim 1, or the pharmaceutically acceptable salt thereof or the crystalline hydrate thereof or the solvate thereof, wherein
the $R_3$ in formula (I) is selected from the group consisting of formyl, acetyl, propionyl, butyryl, isobutyryl, valeroyl, pivaloyl, hexanoyl, cyclopropanecarbony, α-aminoisovaleryl, 2-ethylbutanoyl, and 3,3-dimethylbutanoyl;
the $R_3$ in the definition of $R_2$ is selected from the group consisting of hydrogen, formyl, acetyl, propionyl, butyryl, isobutyryl, valeroyl, pivaloyl, hexanoyl, cyclopropanecarbonyl, α-aminoisovaleryl, 2-ethylbutanoyl, and 3,3-dimethylbutanoyl; and
$R_5$ are selected from the group consisting of hydrogen, formyl, acetyl, propionyl, butyryl, isobutyryl, valeroyl, pivaloyl, hexanoyl, cyclopropanecarbonyl, α-aminoisovaleryl, 2-ethylbutanoyl, and 3,3-dimethylbutanoyl.

14. The compound of formula (I) of claim 1, or the pharmaceutically acceptable salt thereof or the crystalline hydrate thereof or the solvate thereof, wherein
$R_8$ is deuterium.

15. The method of claim 3, wherein the $R_3$ in formula (I) is —C(O)—$C_{3-6}$cycloalkyl, or $C_{3-20}$alkanoyl.

16. The method of claim 3, wherein
one of the $R_3$ in formula (I), the $R_3$ in the definition of $R_2$, and $R_5$ is selected from the group consisting of formyl, acetyl, propionyl, butyryl, isobutyryl, valeroyl, pivaloyl, hexanoyl, cyclopropanecarbonyl, α-aminoisovaleryl, 2-ethylbutanoyl, and 3,3-dimethylbutanoyl; and
the rest of the $R_3$ in formula (I), the $R_3$ in the definition of $R_2$, and $R_5$ are selected from the group consisting of hydrogen, formyl, acetyl, propionyl, butyryl, isobutyryl, valeroyl, pivaloyl, hexanoyl, cyclopropanecarbonyl, α-aminoisovaleryl, 2-ethylbutanoyl, and 3,3-dimethylbutanoyl.

17. The method of claim 3, wherein
the compound of formula (I) is selected from the group consisting of:

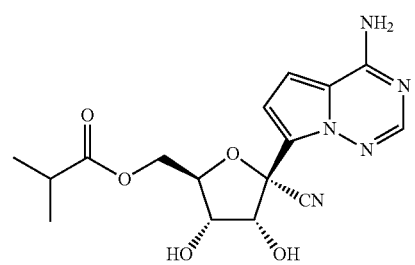

A50

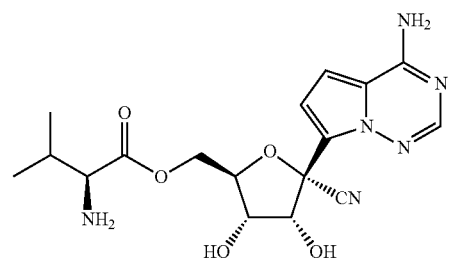

A52

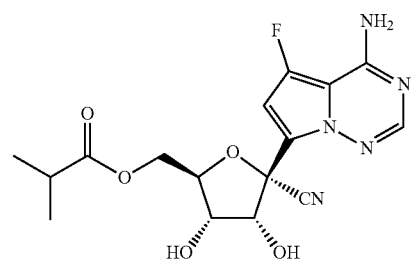

A55

225
-continued
A57
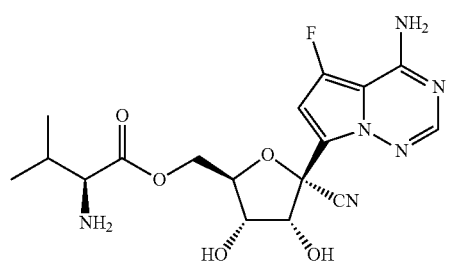
A70
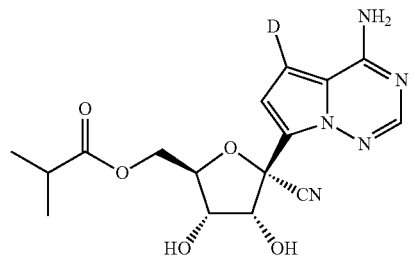
A72
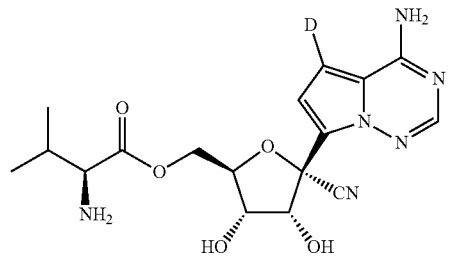
A75
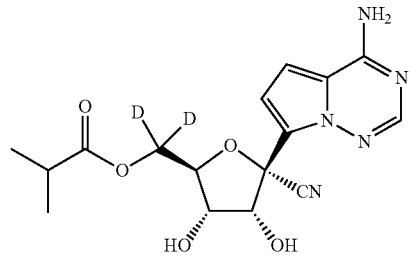
A77
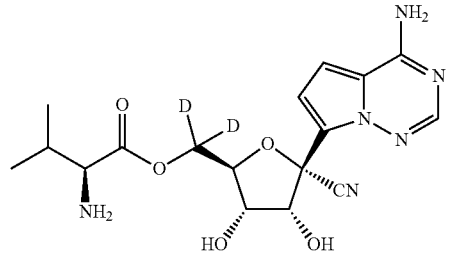
A118
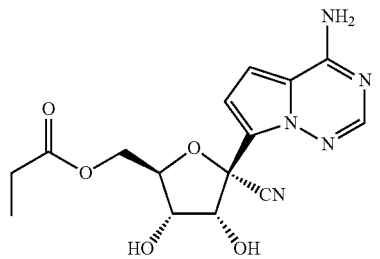
226
-continued
A119
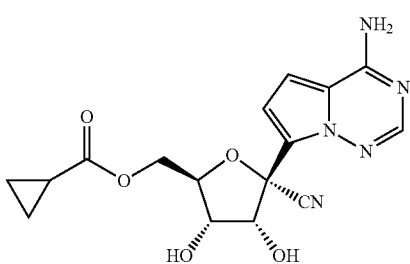
A120
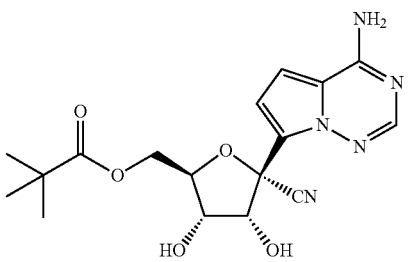
A121
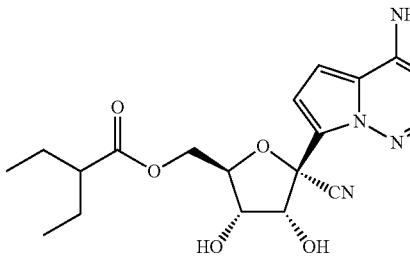
A122
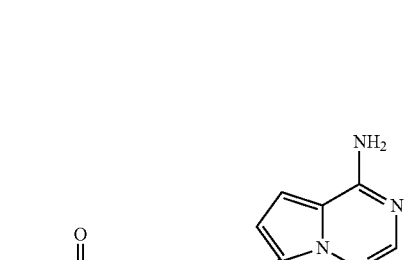
A124
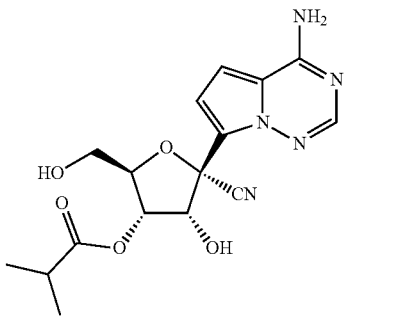

A126 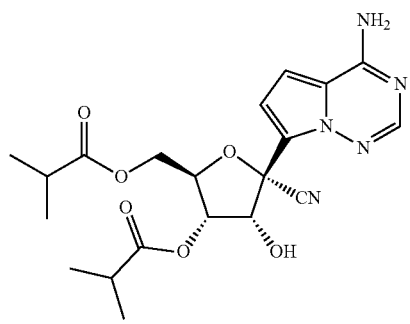
A127 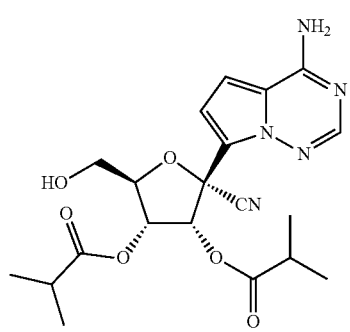
A128 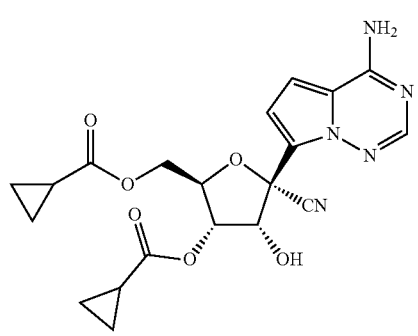
A130 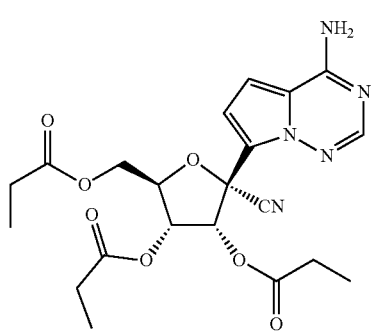
A131 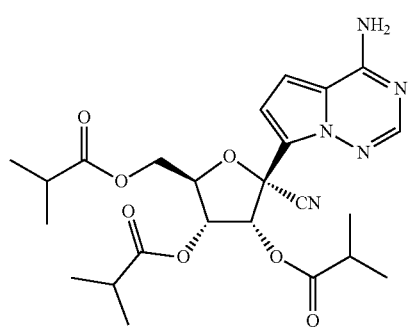
A132 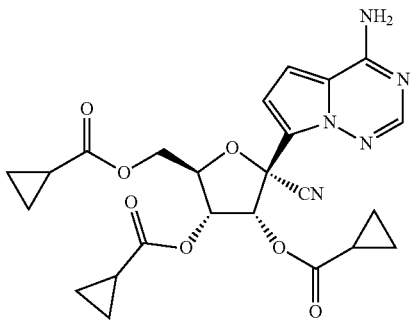
A138 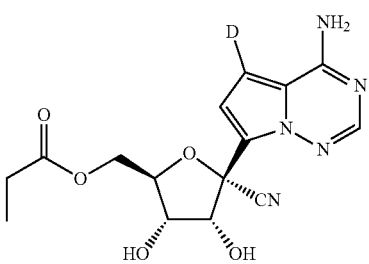
A139 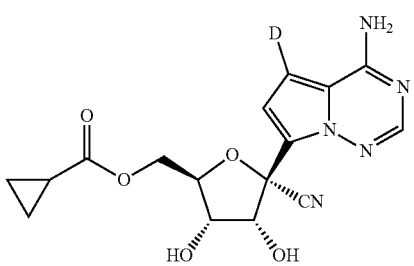
A140 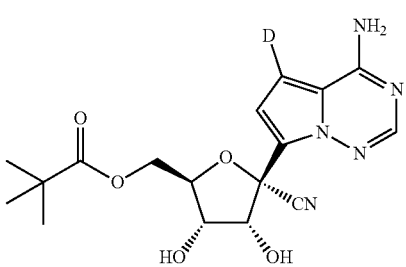
A141 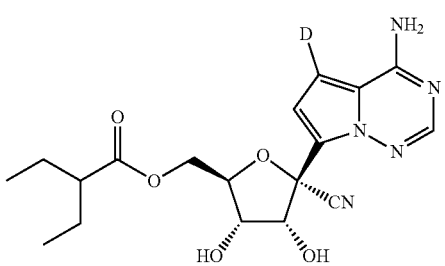
A142 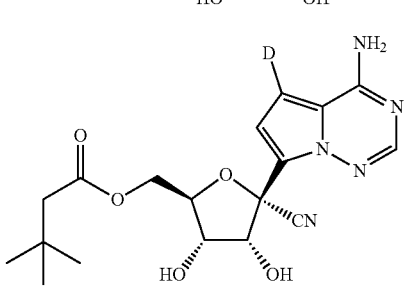

A143 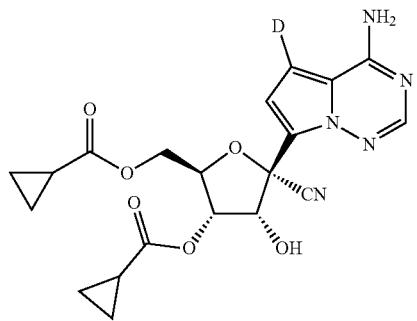
A144 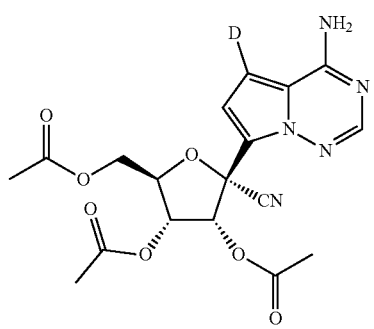
A145 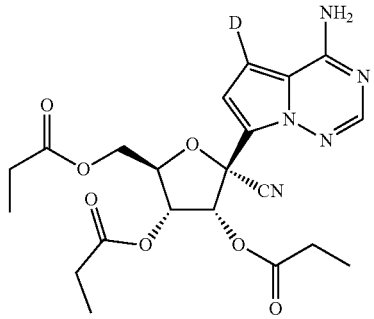
A146 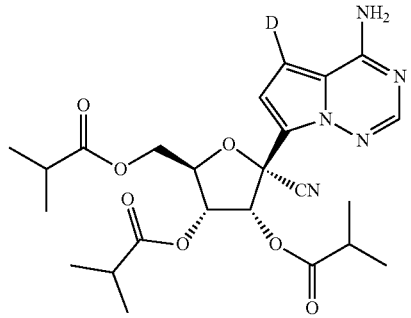
A147 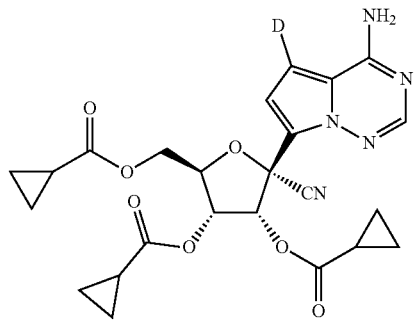
A148 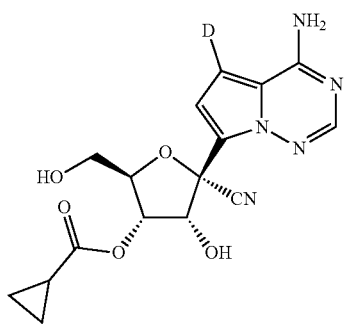
A149 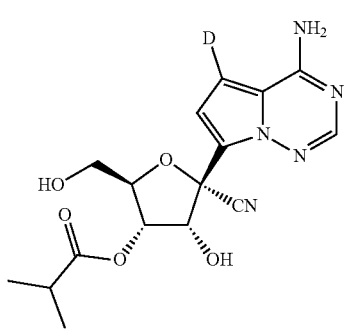
A150 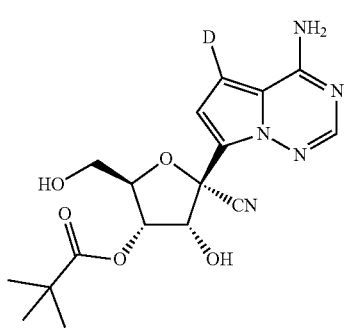
A151 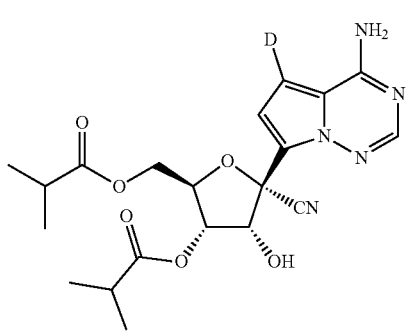
A152 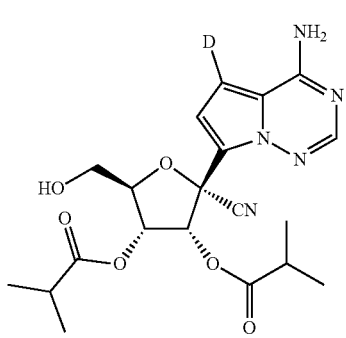

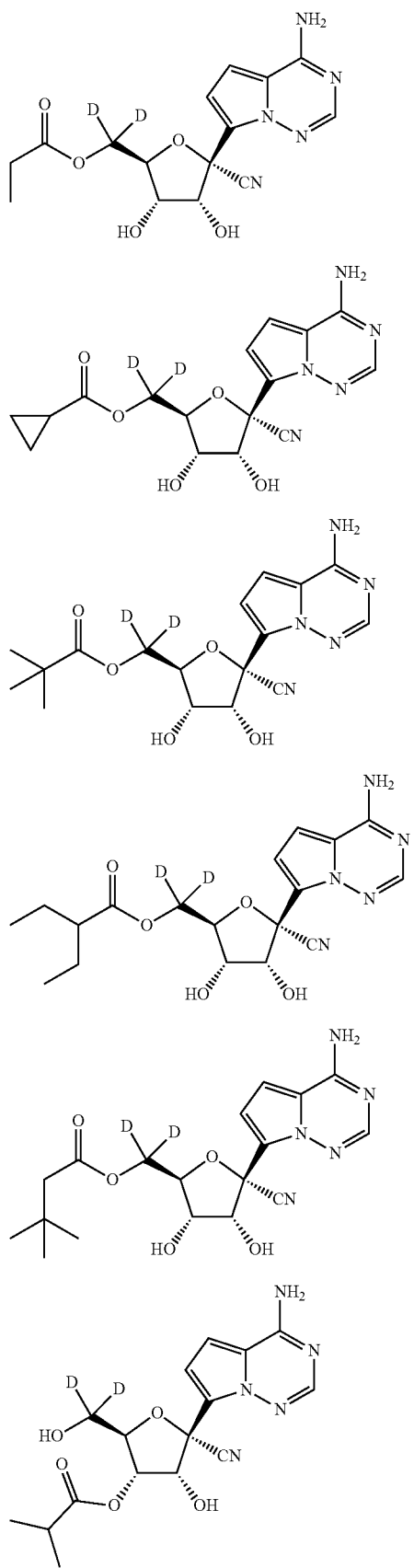
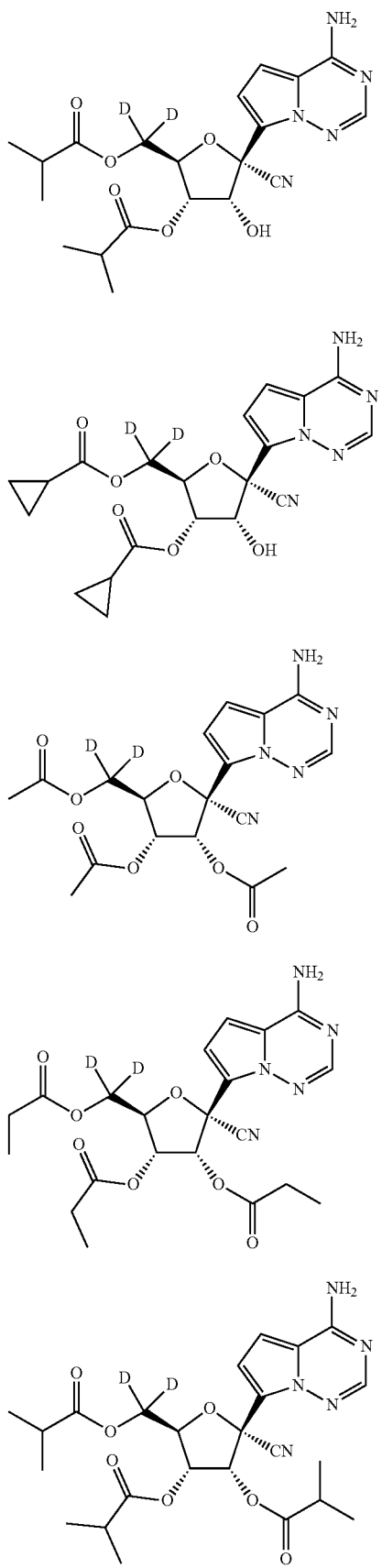

A172
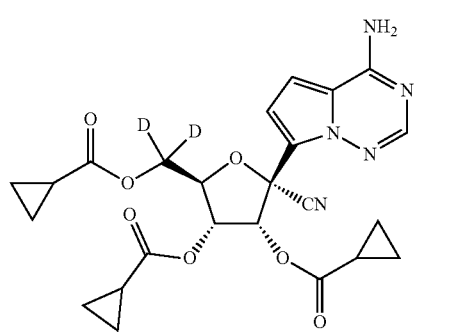
A180
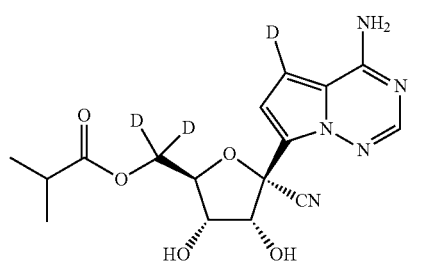
A181
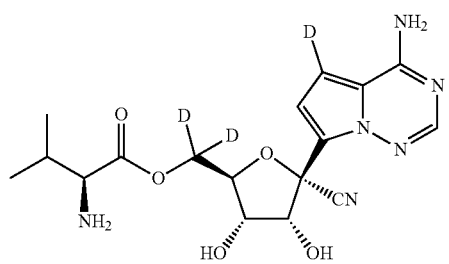
A182
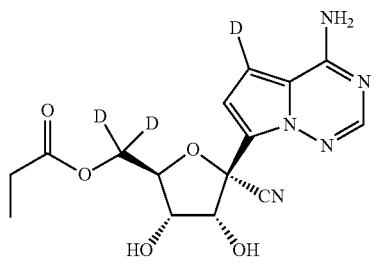
A183
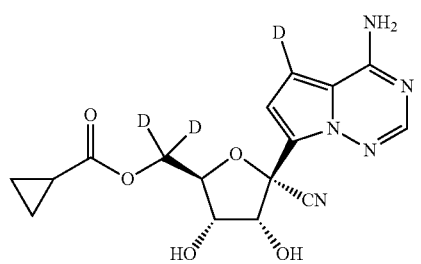
A184
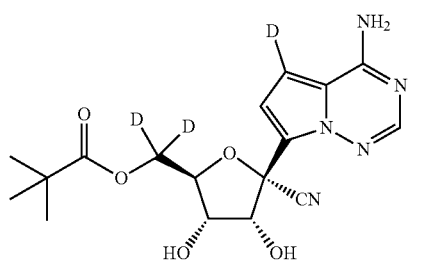
A185
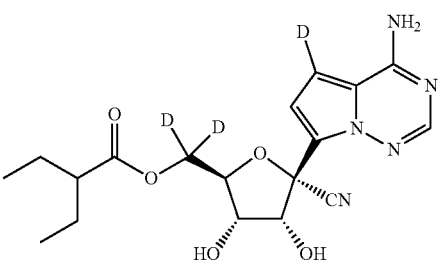
A186
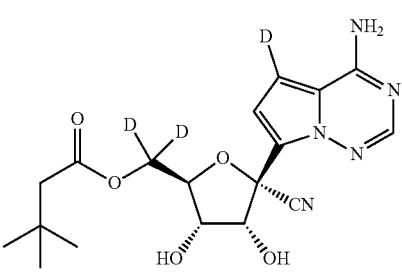
A187
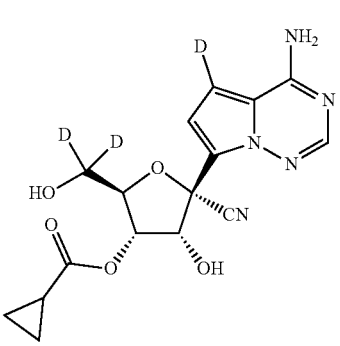
A188
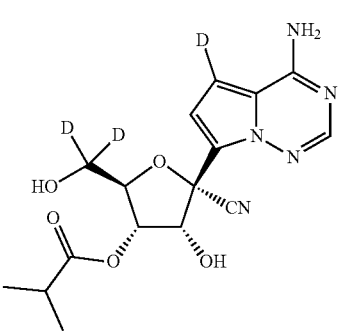
A189
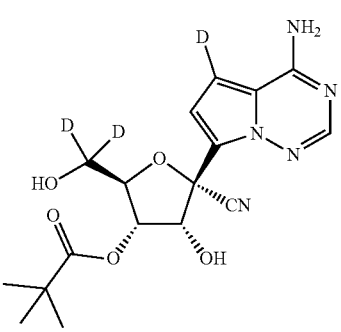

235
-continued
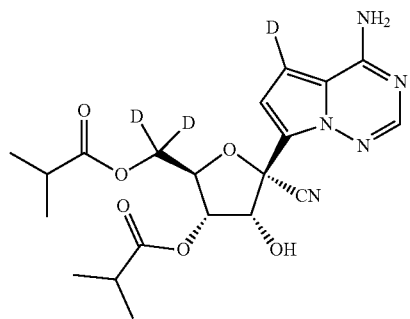
A190
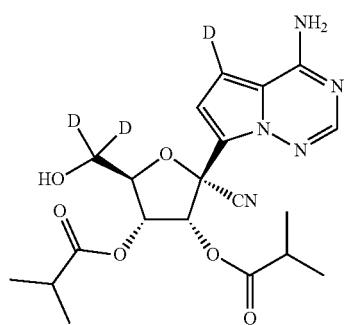
A191
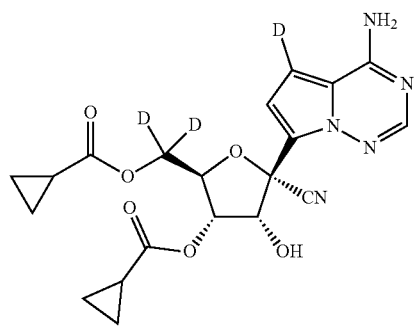
A193
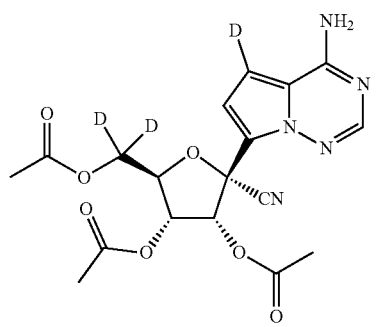
A194
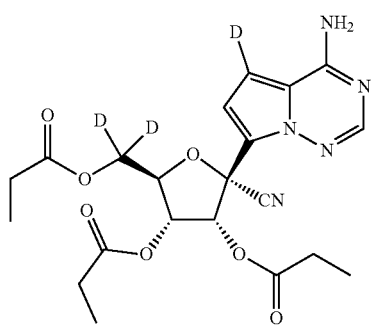
A195
236
-continued
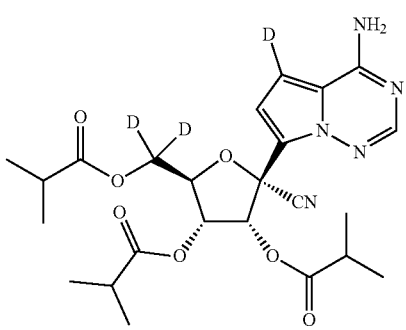
A196
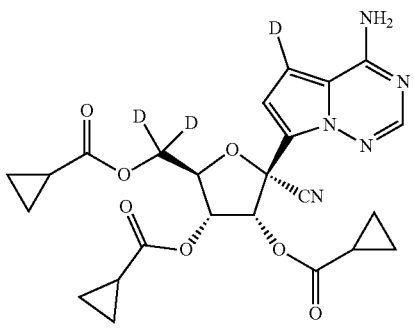
A197
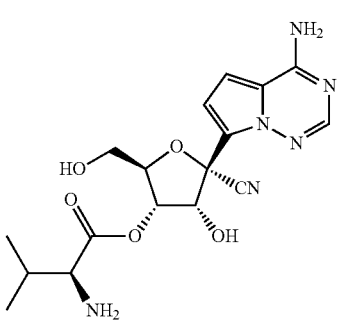
A212
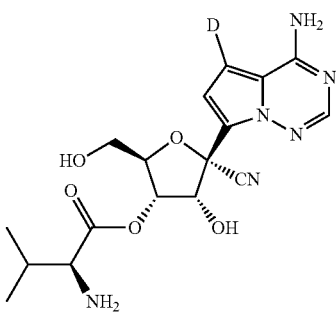
A213
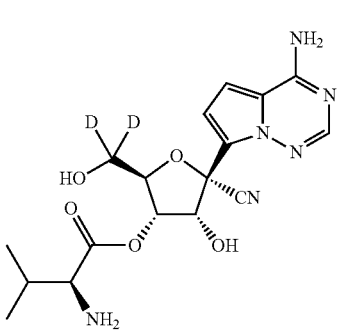
A214

-continued

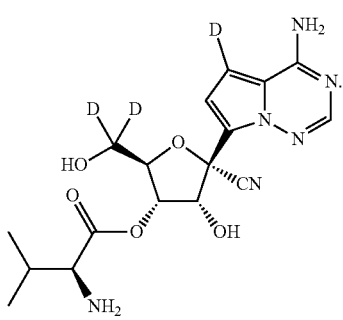

A215

18. The pharmaceutical composition of claim 8, wherein the $R_3$ in formula (I) is —C(O)—$C_{3-6}$cycloalkyl, or $C_{3-20}$alkanoyl.

19. The pharmaceutical composition of claim 8, wherein one of the $R_3$ in formula (I), the $R_3$ in the definition of $R_2$, and $R_5$ is selected from the group consisting of formyl, acetyl, propionyl, butyryl, isobutyryl, valeroyl, pivaloyl, hexanoyl, cyclopropanecarbonyl, α-aminoisovaleryl, 2-ethylbutanoyl, and 3,3-dimethylbutanoyl; and the rest of the $R_3$ in formula (I), the $R_3$ in the definition of $R_2$, and $R_5$ are selected from the group consisting of hydrogen, formyl, acetyl, propionyl, butyryl, isobutyryl, valeroyl, pivaloyl, hexanoyl, cyclopropanecarbonyl, α-aminoisovaleryl, 2-ethylbutanoyl, and 3,3-dimethylbutanoyl.

\* \* \* \* \*